United States Patent
Solomon et al.

(10) Patent No.: US 12,065,641 B2
(45) Date of Patent: Aug. 20, 2024

(54) NgAgo-BASED GENE-EDITING METHOD AND THE USES THEREOF

(71) Applicant: Purdue Research Foundation, West Lafayette, IN (US)

(72) Inventors: Kevin V. Solomon, Lafayette, IN (US); Kok Zhi Lee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 529 days.

(21) Appl. No.: 16/354,415

(22) Filed: Mar. 15, 2019

(65) Prior Publication Data

US 2019/0284547 A1 Sep. 19, 2019

Related U.S. Application Data

(60) Provisional application No. 62/643,814, filed on Mar. 16, 2018.

(51) Int. Cl.
| | |
|---|---|
| *C12N 9/22* | (2006.01) |
| *C12N 15/10* | (2006.01) |
| *C12N 15/11* | (2006.01) |

(52) U.S. Cl.
CPC ............. *C12N 15/102* (2013.01); *C12N 9/22* (2013.01); *C12N 15/11* (2013.01); *C12N 2800/80* (2013.01)

(58) Field of Classification Search
None
See application file for complete search history.

(56) References Cited

U.S. PATENT DOCUMENTS

2017/0367280 A1 12/2017 Hummel

FOREIGN PATENT DOCUMENTS

WO WO2017139264 A1 8/2017

OTHER PUBLICATIONS

Qin et al., NgAgo-based fabp11a gene knockdown causes eye developmental defects in zebrafish. Cell Research (2016) 26: 1349-1352 (Year: 2016).*
Burgess et al., Questions about NgAgo. Protein Cell (2016), 7(12): 913-915 (Year: 2016).*
Javidi-Parsijani et al., No evidence of genome editing activity from Natronobacterium gregoryi Argonaute (NgAgo) in human cells. PLOS One (2017), 12(5): e0177444 (Year: 2017).*
Wu et al., NgAgo-gDNA system efficiently suppresses hepatitis B virus replication through accelerating decay of pregenomic RNA. Antiviral Research (2017), 145: 20-23 (Year: 2017).*
Gao et al., DNA-guided genome editing using the Natronobacterium gregoryi Argonaute. Nature Biotechnology (2016), 34(7): 768- 773 (Year: 2016).*
Menouni et al., Bacterial genome remodeling through bacteriophage recombination. FEMS Microbiology Letters (2015), 362: 1-10 (Year: 2015).*
Pyne et al., Coupling the CRISPR/Cas9 System with Lambda Red Recombineering Enables Simplified Chromosomal Gene Replacement in *Escherichia coli*. Applied and Environmental Microbiology (2015), 81(15): 5103-5114 (Year: 2015).*
Lee et al., NgAgo possesses guided DNA nicking activity. Nucleic Acids Res. (2021), 49(17): 9926-9937 (Year: 2021).*
Lee, S. H. et al. Failure to detect DNA-guided genome editing using Natronobacterium gregoryi Argonaute. Nature Biotechnol. 35, 17-18 (2017) (Year: 2017).*
Qi, J. et al. NgAgo-based fabp11a gene knockdown causes eye developmental defects in zebrafish. Cell Res. 26, 1349-1352 (2016) (Year: 2016).*
Javidi-Parsijani, P. et al. No evidence of genome editing activity from Natronobacterium gregoryi Argonaute (NgAgo) in human cells. PLOS One 12, e0177444 (2017) (Year: 2017).*
Robinson et al., Growth Kinetics of Extremely Halophilic Archaea (Family Halobacteriaceae) as Revealed by Arrhenius Plots, Journal of Bacteriology (2005), 187: 923-929. (Year: 2005).*
Mougiakos et al., Characterizing a thermostable Cas9 for bacterial genome editing and silencing. Nature Communications (2017), 8:1647 (Year: 2017).*
Swarts, D., et al., "The evolutionary journey of Argonaute proteins", Nature structural & molecular biology 21, 2014, pp. 743-753.
Swarts, D., et al., "DNA-guided DNA interference by a prokaryotic Argonaute", Nature 507, 2014, pp. 258-261.
Kaya, E., et al., "A bacterial Argonaute with noncanonical guide RNA specificity", Proceedings of the National Academy of Sciences 113, 2016, pp. 4057-4062.
Hegge, J., et al., "Prokaryotic Argonaute proteins: novel genome-editing tools?", Nature Reviews Microbiology 16, 5, 2018, pp. 5-11.
Willkomm, S, et al., "Structural and mechanistic insights into an archaeal DNA-guided Argonaute protein", Nature Microbiology 2, 17035, 2017, pp. 1-7.
Zander, A. et al., "Guide-independent DNA cleavage by archaeal Argonaute from Methanocaldococcus jannaschii", Nature Microbiology 2, 17034, 2017, pp. 1-10.

(Continued)

*Primary Examiner* — Celine X Qian
*Assistant Examiner* — Catherine Konopka
(74) *Attorney, Agent, or Firm* — Reichel Stohry Dean LLP; Natalie J. Dean

(57) ABSTRACT

This invention relates to a method to produce gene alterations in the genomes of a eukaryotic and prokaryotic host cell. The method comprises utilizing Argonaute from Natronobacterium gregoryi (NgAgo) or a mutant thereof, and complementary 5' phosphorylated single-stranded DNA that target the enzyme to cleave specific regions of the chromosome. Additionally, N-terminal truncations (deletion of the repA domain; N-del), or its mutants including N-del/E598A, N-del/D601P, and N-del/E602P reduces random cleavage and can be used for targeted gene editing with a guide DNA. An expression system or a host cell and method of creating thereof are also in the scope of this application.

17 Claims, 23 Drawing Sheets

Specification includes a Sequence Listing.

(56) References Cited

OTHER PUBLICATIONS

Swarts, D., et al., "Autonomous Generation and Loading of DNA Guides by Bacterial Argonaute", Molecular Cell, 2017, pp. 985-988.

Javidi-Parsijani, P. et al., "No evidence of genome editing activity from Natronobacterium gregoryi Argonaute (NgAgo) in human cells", Plos One 12, 14, 2017, pp. 14.

Wu, Z. et al., "NgAgo-gDNA system efficiently suppresses hepatitis B virus replication through accelerating decay of pregenomic RNA", Antiviral Research, 2017, pp. 20-23.

Burgess, S., et al., "Questions about NgAgo", Protein & Cell 7, 2016, pp. 913-915.

Khin, N., et al., "No evidence for genome editing in mouse zygotes and HEK293T human cell line using the DNA-guided Natronobacterium gregoryi Argonaute (NgAgo)", PloS one 12, 2017, pp. 1-10.

Qin, Y., et al., "NgAgo-based fabp11a gene knockdown causes eye developmental defects in zebrafish", Cell Research 26, 2016, pp. 1349-1352.

Sunghyeok, Y., et al., "DNA-dependent RNA cleavage by the Natronobacterium gregoryi Argonaute", BioRxiv, 101923, 2017, pp. 9.

Tas, H., et al., "An integrated system for precise genome modification in *Escherichia coli*", PloS one 10, 2015, pp. 19.

Kelley, L., et al., "The Phyre2 web portal for protein modeling, prediction and analysis.", Nature protocols 10, 2015 pp. 845-858.

Lee, S. H. et al., "Failure to detect DNA-guided genome editing using Natronobacterium gregoryi Argonaute", Nature biotechnology 35, 2017, pp. 17-18.

Hunt, E., et al.,. "Single-stranded binding proteins and helicase enhance the activity of prokaryotic argonautes in vitro", PloS one 13, 2018, pp. 20.

Cyranoski, News In Focus: Gene-editing row escalates, Nature 540: 20 (2016), Macmillan Publishers Limited, US.

Cyranoski, News: Authors retract controversial NgAgo gene-editing study, Nature (2017); doi: 10.1038/nature.2017.22412, Macmillan Publishers Limited, US.

\* cited by examiner

FIG. 1C
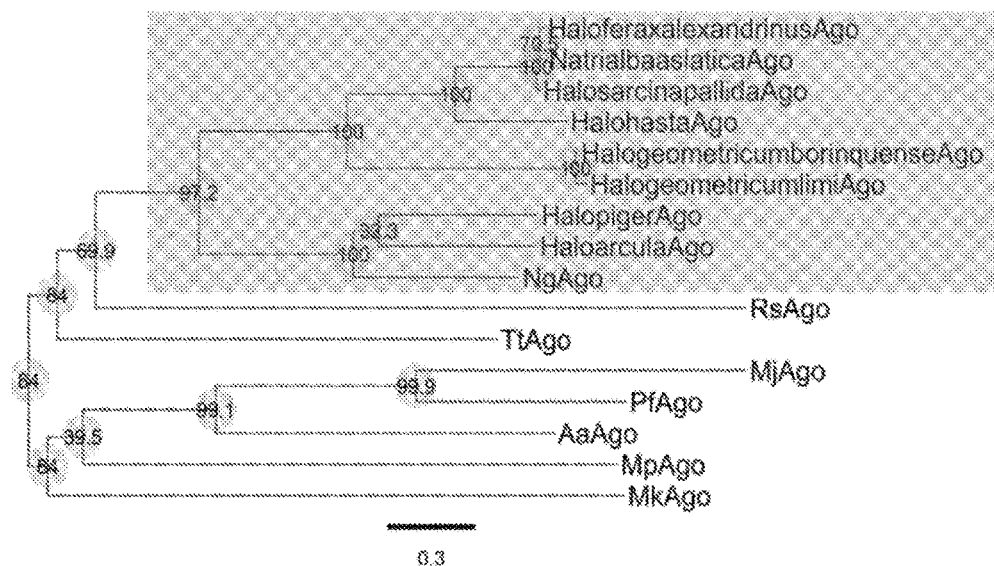
FIG. 1D
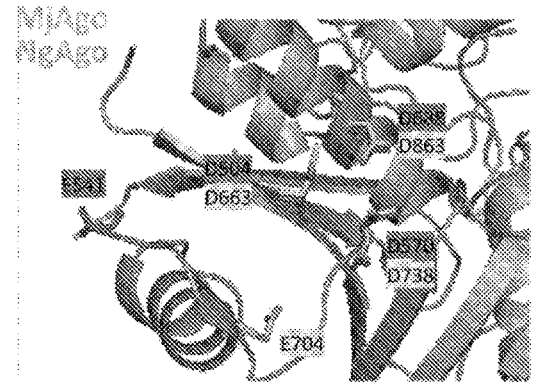
FIG. 1E

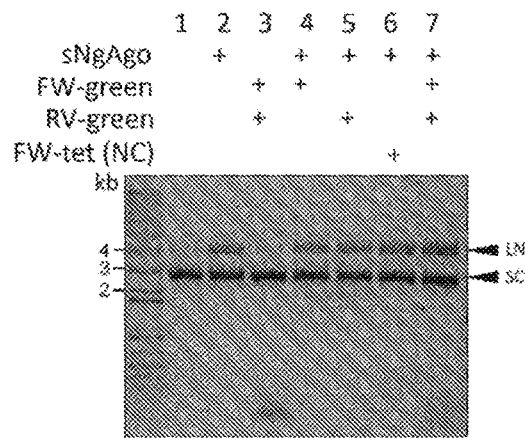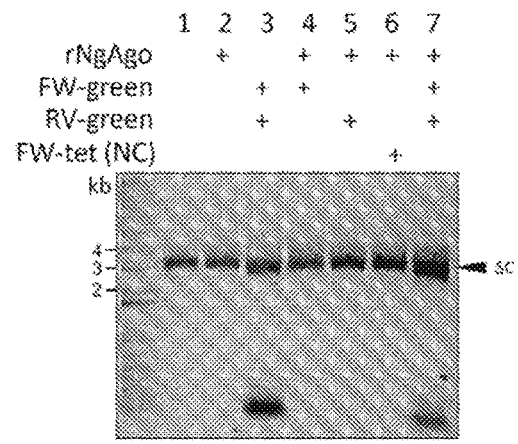
FIG. 3A  FIG. 3B
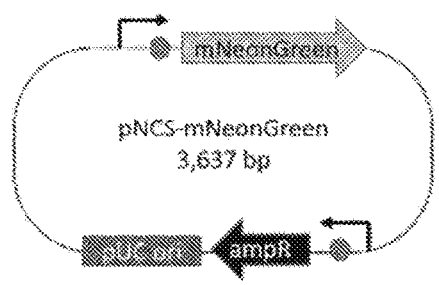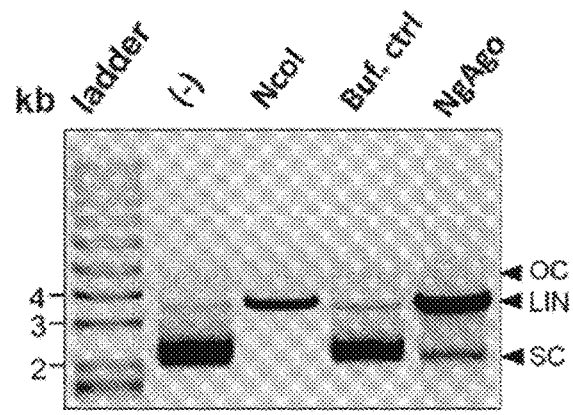
FIG. 3C  FIG. 3D

NgAgo-BASED GENE-EDITING METHOD AND THE USES THEREOF

CROSS REFERENCE TO RELATED APPLICATIONS

This present patent application relates to and claims the priority benefit of U.S. Provisional Application Ser. No. 62/643,814, filed Mar. 16, 2018, the content of which is hereby incorporated herein by reference in its entirety.

TECHNICAL FIELD

The present application relates generally to a method of gene editing, and specifically to a gene editing method using Argonaute from Natronbacterium gregoryi (NgAgo), or its mutants, with its repA domain removed, to cleave and edit specific regions of a chromosome and an extrachromosomal genetic material.

STATEMENT OF SEQUENCE LISTING

The contents of the electronic sequence listing (68167_02_Seq_Listingnew_ST25_supplemental_f04202021.txt; file size: 181,648 bytes; date of creation: Apr. 20, 2021) is herein incorporated by reference in its entirety. The content of the computer-readable form referenced above is the same and the information recorded in computer readable form is identical to the written sequence listings provided herein.

BACKGROUND

This section introduces aspects that may help facilitate a better understanding of the disclosure. Accordingly, these statements are to be read in this light and are not to be understood as admissions about what is or is not prior art.

Genome engineering can refer to altering the genome by deleting, inserting, mutating, or substituting specific nucleic acid sequences. The altering can be gene or location specific. Genome engineering can use Argonaute proteins to cut a nucleic acid thereby generating a site for the alteration. Prokaryotic Argonautes are prokaryotic homologs of eukaryotic Argonaute proteins, which are key enzymes in RNA interference pathways. An Argonaute can bind and cleave a target nucleic acid by forming a complex with a designed nucleic acid-targeting nucleic acid. Cleavage can introduce double stranded breaks in the target nucleic acid. A nucleic acid can be repaired e.g. by endogenous non-homologous end joining (NHEJ) machinery. A piece of nucleic acid can be inserted. Engineering of non-genomic nucleic acid is also contemplated. Modifications of designed nucleic acid-targeting nucleic acids and Argonautes can introduce new functions to be used for genome engineering.

The ability to precisely modify genetic material in cells enables a wide range of high value applications in agriculture, medical research, pharmaceutical industry and biotechnology, and other basic researches important to the welfare of human society. Fundamentally, this requires using genome engineering to introduce predefined genetic variation at specific locations by deleting, inserting, mutating, or substitution specific nucleic acid sequences in both prokaryotic and eukaryotic cell systems (Jinek, et al., Science, 2012, 337, 816-821; Swarts, et al., *Nature Structural and Molecular Biology*, 2014, 21, 743-753).

Several methods are currently available for gene-editing (Church, G M, et al., WO 2017/139264; Hummel, US 2017/0367280). For example, Church et al, disclosed methods and compositions of altering a eukaryotic cell using a guide DNA sequence complementary to a target nucleic acid sequence and an Ago enzyme or a nuclease (WO 2017/139264). Previously, Zhang, et al., disclosed a gene-editing method named a Clustered Regularly Interspersed Short Palindromic Repeats (CRISPR)-CRISPR associated (CAS) (CRISPR-Cas) system. The invention provides for systems, methods, and compositions for manipulation of sequences and/or activities of target sequences (US 20140242664A1). However, this technology enables gene-editing at programmable target sites adjacent to sequence-specific motifs called Protospacer adjacent motif (PAM). PAM is a 2-6 base pair DNA sequence immediately following the DNA sequence targeted by the Cas9 nuclease in the CRISPR bacterial adaptive immune system (Shah S A, et al., RNA Biology 2013, 10 (5): 891-899). PAM is a component of the invading virus or plasmid, but is not a component of the bacterial CRISPR locus. Cas9 will not successfully bind to or cleave the target DNA sequence if it is not followed by the PAM sequence. This sequence-specific motif requirement limits choices of target sites and may be problematic in genomes with biased GC-content. There are still unmet needs for more flexible gene editing tools.

SUMMARY OF THE INVENTION

The invention is a method to produce gene alterations in the genomes of eukaryotic and prokaryotic cells (gene editing). The method consists of Argonaute from Natronobacterium gregoryi, NgAgo or its mutants, and complementary 5' phosphorylated single-stranded DNA that target the enzyme to cleave specific regions of the chromosome. NgAgo-based gene-editing tools are more flexible than conventional Clustered Regularly Interspaced Short Palindromic Repeats (CRISPR) technology as it is not restricted to targeting regions adjacent to a specific motif. The 5' phosphate DNA guides are designed as but not limited to 24 nucleotides complementary to a gene of interest. NgAgo consists of repA, N-terminal, PAZ, MID and PIWI domains. NgAgo in isolation randomly cleaves DNA and may be used for random mutagenesis. N-terminal truncations (deletion of repA domain; N-del) reduces random cleavage and may be used for targeted gene editing with guide DNA as described above. Other mutants including N-del/E598A, N-del/D601P, and N-del/E602P were found to have reduced random DNA cleaving abilities and may serve as alternative mutants for gene editing.

In some illustrative embodiments, the present invention relates to a method for modifying a chromosomal or an extrachromosomal genetic material of a prokaryotic host cell, comprising:
  a) introducing a NgAgo or a mutant thereof to a prokaryotic host cell in a DNA expression cassette form, a RNA form or a protein form; and
  b) introducing a plurality of 5'-phosphorylated guide nucleic acid sequences, each comprising about 15-30 nucleotides complementary to at least one target nucleic acid sequence of interest within the chromosomal or the extrachromosomal genetic material, wherein said NgAgo or a mutant thereof forms a complex with the 5'phosphorylated guide nucleic acid sequence, directing the complex to bind to the complementary target nucleic acid sequence and cleave it; and
  wherein the plurality of guide nucleic acid sequences are targeted to different regions of said target nucleic acid sequence in a site-specific manner.

In some illustrative embodiments, the present invention relates to a method for modifying a chromosomal or an extrachromosomal genetic material of a prokaryotic host cell as disclosed herein, wherein said DNA expression cassette further comprises p15-kanR-PtetRed, SEQ ID NO: 37.

In some illustrative embodiments, the present invention relates to a method for modifying a chromosomal or an extrachromosomal genetic material of a prokaryotic host cell as disclosed herein, the method further comprises a donor DNA, wherein said donor DNA comprises at least 20 nucleotides of homology to the flanking regions of the target nucleic acid so that the donor DNA may recombine with the cleaved nucleic acids flanking regions to replace or edit the chromosomal or extrachromosomal genetic material.

In some illustrative embodiments, the present invention relates to a method for modifying a chromosomal or an extrachromosomal genetic material of a prokaryotic host cell as disclosed herein, wherein the donor DNA is used to introduce new sequences, delete sequences, create point mutations, or promote a general DNA rearrangement.

In some illustrative embodiments, the present invention relates to a method for modifying a chromosomal or an extrachromosomal genetic material of a prokaryotic host cell as disclosed herein, wherein the prokaryotic host cell is an *Escherichia Coli*.

In some illustrative embodiments, the present invention relates to a method for modifying a chromosomal or an extrachromosomal genetic material of a prokaryotic host cell as disclosed herein, wherein the prokaryotic host cell is a bacterial cell containing one or more vectors comprising
  a) a lambda red recombinase system including exo, gam, and beta, or other recombinase systems driven by an inducible promoter that is sufficient to induce homologous recombination;
  b) a donor DNA;
  c) a regulatory sequence linked to the nucleotide sequence of NgAgo fused with additional sequences as needed; and
  d) an inducible promoter to drive efficient expression of said regulatory sequence linked to the nucleotide sequence of NgAgo.

In some illustrative embodiments, the present invention relates to a method for modifying a chromosomal or an extrachromosomal genetic material of a prokaryotic host cell as disclosed herein, wherein said NgAgo is a full-length NgAgo, a repA-deletion NgAgo (N-del) or a mutant thereof.

In some illustrative embodiments, the present invention relates to a method for modifying a chromosomal or an extrachromosomal genetic material of a prokaryotic host cell as disclosed herein, wherein said mutant of N-del is a mutant of N-del/E598A, N-del/D601P or N-del/E602P.

In some other illustrative embodiments, the present invention relates to a gene editing system in a host cell comprising:
  a designed DNA sequence of about 24 nucleotides with 5' phosphorylation, wherein said DNA sequence is complementary to a gene of interest in the cell; a lambda red recombinase system including exo, gam, and beta, or other recombinase systems driven by an inducible promoter that is sufficient to induce homologous recombination; and an NgAgo enzyme or a mutant thereof, wherein said NgAgo enzyme specifically interact with said designed DNA and nick the gene of interest in the cell through the guidance of said designed DNA.

In some illustrative embodiments, the present invention relates to a gene editing system in a host cell as disclosed herein, wherein the gene editing system further comprises a donor DNA wherein said donor DNA comprises at least 20 nucleotides of homology to the flanking regions of the gene of interest so that the donor DNA may recombine with the flanking regions of the gene of interest to replace or edit the cleaved gene of interest.

In some illustrative embodiments, the present invention relates to a gene editing system in a host cell as disclosed herein, wherein said NgAgo enzyme is a full-length NgAgo, a repA-deletion NgAgo (N-del) or a mutant thereof, in the form of DNA expression cassette, messenger RNA or a protein product thereof.

In some illustrative embodiments, the present invention relates to a gene editing system in a host cell as disclosed herein, wherein said NgAgo enzyme is a full-length NgAgo, a repA-deletion NgAgo (N-del) or a mutant thereof, in the form of DNA expression cassette, messenger RNA or a protein product thereof.

In some illustrative embodiments, the present invention relates to a gene editing system in a host cell as disclosed herein, wherein said N-Del mutant is N-del/E598A, N-del/E601P, or N-del D602P.

In some illustrative embodiments, the present invention relates to a gene editing system in a host cell as disclosed herein, wherein said host cell is a prokaryotic cell.

In some illustrative embodiments, the present invention relates to a gene editing system in a host cell as disclosed herein, wherein said prokaryotic cell is *Escherichia Coli*.

In some illustrative embodiments, the present invention relates to a method for modifying a chromosomal or an extrachromosomal genetic material of a host cell, comprising:
  a) introducing NgAgo or a mutant thereof to a host cell in a DNA expression cassette form, a RNA form or a protein form; and
  b) introducing a plurality of 5'-phosphorylated guide nucleic acid sequences, each comprising about 15-30 nucleotides complementary to at least one target nucleic acid sequence of interest within the chromosomal or the extrachromosomal genetic material, wherein said NgAgo or a mutant thereof forms a complex with the 5'phosphorylated guide nucleic acid sequence, directing the complex to bind to the complementary target nucleic acid sequence and cleave it; and wherein the plurality of guide nucleic acid sequences are targeted to different regions of said target nucleic acid sequence in a site-specific manner.

In some other embodiments, the present invention relates to a gene editing system in a host cell disclosed herein, wherein the host cell is a prokaryotic cell or a eukaryotic cell.

These and other features, aspects and advantages of the present invention will become better understood with reference to the following figures, descriptions and claims.

BRIEF DESCRIPTION OF THE DRAWINGS

The objects, features, and advantages of the present invention will become more apparent when taken in conjunction with the following description and drawings, wherein:

FIG. 1C shows phylogenetic analysis of repA-containing pAgos (blue shaded) found from blastP against all isolates via JGI-IMG portal and other characterized pAgos; FIG. 1D shows that the catalytic tetrad, DEDD, is well conserved in both structure alignment of NgAgo and MjAgo; and FIG. 1E shows the sequence alignment of catalytically active pAgos (see, e.g., SEQ ID NOS: 52-71).

FIGS. 3A-3G demonstrate that soluble NgAgo but not refolded NgAgo cut DNA guide-independently. FIG. 3A shows soluble NgAgo, sNgAgo, or FIG. 3B shows refolded NgAgo, rNgAgo, were mixed with a combination of guide DNA and plasmid at 37° C. for 30 minutes and subsequently mixed with pNCS-mNeonGreen plasmid to see if NgAgo cuts or nicks DNA guide-dependently at 37°C for an hour to see if NgAgo cuts or nicks DNA guide-dependently. NgAgo guide-independently cuts related pNCS-mNeonGreen, and unrelated plasmid DNA, p15-KanR (FIGS. 3C-3F) and E. coli genomic DNA from MG1655 (FIG. 3G).

FIG. 5A shows NgAgo variants used in the in vitro assay to identify which domain is essential for nicking and cleavage activity. FIG. 5B shows WT and D663A/D738A nick plasmids DNA while repA and N-del nick and cleave plasmids DNA. N-del/D663A/D738A loses the ability to nick and cleave. I-SceI is used to linearize the plasmids while I-SCEI K223I is used to nick the plasmids. OC, open circular; LN, linear; SC, supercoiled. Two hundreds of pBSI-SceI (E/H) plasmids were incubated with 5 µg of each NgAgo variant for an hour at 37° C. in the buffer (20 mM Tris-Cl, 250 uM MgCl2, 2 mM DTT, and 300 mM NaCl) in 50 µl reaction. Total 0.8 unit of proteinase K was added to each sample and incubated at 37°C for 5 minutes. Samples were then cleaned-up and ran on a 0.7% agarose gel with loading dye containing SDS.

FIG. 9A depicts RNA polymerase subunit, rpoz, was successfully amplified with cDNA from BL21 (DE3) harboring pIncw-Green, indicating successful reverse transcription. mNeonGreen-integrated genomic DNA and wildtype genomic DNA were used as positive control to amplify mNeonGreen. FIG. 9B shows that mNeonGreen (~800 bp) was amplified with cDNA from BL21 (DE3) harboring pIncw-Green, pNCS-mNeonGreen plasmid DNA, and wild-type genomic DNA. mNeonGreen expression was not detected in BL21 (DE3) harboring pIncw-mNeonGreen.

FIG. 11 (Supplementary FIG. 5.) SDS-PAGE analysis of His-tag purified wildtype NgAgo and repA.

FIG. 17A shows SDS-PAGE analysis of purified WT NgAgo from soluble fraction (sNgAgo). FIG. 17B shows SDS-PAGE analysis of purified WT NgAgo from insoluble fraction after refolding (rNgAgo). FIG. 17C shows SDS-PAGE analysis of purified repA.

FIG. 18A shows SDS-PAGE analysis of GST-tag purified WT NgAgo. FIG. 18B shows SDS-PAGE analysis of GST-tag purified D663A/D738A. FIG. 18C shows SDS-PAGE analysis of GST-tag purified N-del. FIG. 18D shows SDS-PAGE analysis of GST-tag purified N-del/D663A/D738A. Lane #1: whole cell lysate; Lane #2: soluble fraction; Lane #3: unbound soluble fraction; Lane #4 washed fraction; Lanes #5-8: eluted fraction 1-4.

DETAILED DESCRIPTION

Figure 1A:
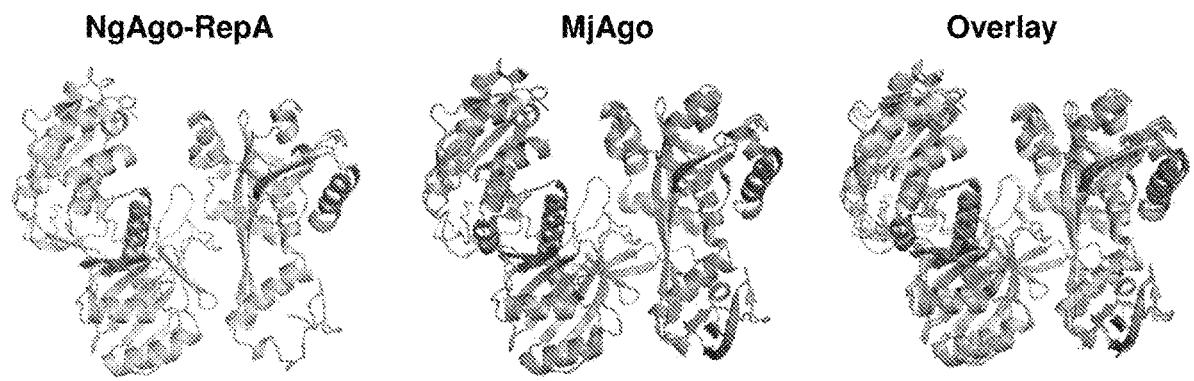
FIG. 1A shows an uncharacterized repA domain is located at the N-terminal of NgAgo and a Phyre 2 simulation 3D structure based on MjAgo structure (PDB: 5G5T)

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

In the present disclosure the term "about" can allow for a degree of variability in a value or range, for example, within 20%, within 10%, within 5%, or within 1% of a stated value or of a stated limit of a range.

In the present disclosure the term "substantial" or "substantially" can allow for a degree of variability in a value or range, for example, within 80%, within 90%, within 95%, or within 99% of a stated value or of a stated limit of a range.

Definitions. It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythyuridine. A nucleic acid can comprise nucleo-tides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g., rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourine, dihydrouridine, queuosine, and wyosine.

As used herein, the terms "Argonaute" or "Argonaute endonuclease" can be used interchangeably. An Argonaute can refer to any modified (e.g., shortened, mutated, lengthened) polypeptide sequence or homologue of the Argonaute, including variant, modified, fusion (as defined herein), and/or enzymatically inactive forms of the Argonaute. An Argonaute can be codon optimized. An Argonaute can be a codon-optimized homologue of an Argonaute. An Argonaute can be enzymatically inactive, partially active, constitutively active, fully active, inducibly active, active at different temperatures, and/or more active (e.g., more than the wild type homologue of the protein or polypeptide). In some instances, the Argonaute (e.g., variant, mutated, and/or enzymatically inactive Argonaute) can target a target nucleic acid. The Argonaute (e.g., variant, mutated, and/or enzymatically inactive) can target double-stranded or single-stranded DNA or RNA. The Argonaute can associate with a short targeting or guide nucleic acid that provides specificity for a target nucleic acid to be cleaved by the protein's endonuclease activity. The Argonaute can be provided separately or in a complex wherein it is pre-associated with the targeting or guide nucleic acid. In some instances, the Argonaute can be a fusion as described herein.

As used herein, the terms "Natronobacterium gregoryi Argonaute" or "NgAgo" are used interchangeably to refer to a DNA-guided endonuclease isolated from *N. gregoryi* that is suitable for genome editing. NgAgo binds 5' phosphorylated single-stranded guide DNA of at least 10 to about 30 nucleotides in length, preferably at least 20 to about 30 nucleotides, and efficiently creates site-specific DNA double-strand breaks when loaded with the guide-DNA. The NgAgo-guide-DNA system does not require a protospacer-adjacent motif (PAM), as does Cas9, and has a low tolerance to guide-target nucleic acid mismatches and high efficiency in editing (G+C)-rich genomic targets. The NgAgo is active at temperatures that are suitable for genome engineering in a host cell, preferably a prokaryotic host cell, more preferably an *E. Coli*.

As used herein, "nucleic acid-targeting nucleic acid" or "nucleic acid-targeting guide nucleic acid" or "guide-DNA" or "guide-RNA" are used interchangeably and can refer to a nucleic acid that can bind an Argonaute protein of the disclosure and hybridize with a target nucleic acid. A nucleic acid-targeting nucleic acid can be RNA or DNA, including, without limitation, single-stranded RNA, double-stranded RNA, single-stranded DNA, and double-stranded DNA. The nucleic acid-targeting nucleic acid can bind to a target nucleic acid site-specifically. A portion of the nucleic acid-targeting nucleic acid can be complementary to a portion of a target nucleic acid. A nucleic acid-targeting nucleic acid can comprise a segment that can be referred to as a "nucleic acid-targeting segment." A nucleic acid-targeting nucleic acid can comprise a segment that can be referred to as a "protein-binding segment." The nucleic acid-targeting segment and the protein-binding segment can be the same segment of the nucleic acid-targeting nucleic acid. The nucleic acid-targeting nucleic acid may contain modified nucleotides, a modified backbone, or both. The nucleic acid-targeting nucleic acid may comprise a peptide nucleic acid (PNA).

As used herein, "donor polynucleotide" can refer to a nucleic acid that can be integrated into a site during genome engineering, target nucleic acid engineering, or during any other method of the disclosure.

As used herein, "fusion" can refer to a protein and/or nucleic acid comprising one or more non-native sequences (e.g., moieties). A fusion can be at the N-terminal or C-terminal end of the modified protein, or both. A fusion can be a transcriptional and/or translational fusion. A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the Argonaute (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify, such as His-tag. In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent reporter or fluorescent protein; a quantum dot; and the like. A fusion can comprise a member of a FRET pair, or a fluorophore/quantum dot donor/acceptor pair.

A fusion can comprise an enzyme. Suitable enzymes can include, but are not limited to, horse radish peroxidase, luciferase, beta-galactosidase, and the like. A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*) any of a variety of fluorescent and colored proteins.

As used herein, "target nucleic acid" or "target site" can generally refer to a target nucleic acid to be targeted in the methods of the disclosure. A target nucleic acid can refer to a nuclear chromosomal/genomic sequence or an extrachromosomal sequence, (e.g., an episomal sequence, a minicircle sequence, a mitochondrial sequence, a chloroplast sequence, a protoplast sequence, a plastid sequence, etc.). A target nucleic acid can be DNA. A target nucleic acid can be single-stranded DNA. A target nucleic acid can be double-stranded DNA. A target nucleic acid can be single-stranded or double-stranded RNA. A target nucleic acid can herein be used interchangeably with "target nucleotide sequence" and/or "target polynucleotide".

As used herein, "sequence identity" or "identity" in the context of nucleic acid or polypeptide sequences refers to the nucleic acid bases or amino acid residues in two sequences that are the same when aligned for maximum correspondence over a specified comparison window.

As used herein, the term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 60%, 70%, 80%, 90% or 95%, or any integer percentage from 50% to 100%.

As used herein, the terms "plasmid", "vector" and "cassette" refer to an extra-chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

Argonaute may introduce double-stranded breaks or single-stranded breaks in the target nucleic acid, (e.g. genomic DNA). The double-stranded break can stimulate a cell's endogenous DNA-repair pathways (e.g., HR, NHEJ, A-NHEJ, or MMEJ). NHEJ can repair cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by an Argonaute, the site of cleavage can be destroyed (e.g., the site may not be accessible for another round of cleavage with the original nucleic acid-targeting nucleic acid and Argonaute).

Argonaute proteins which can function as endonucleases can comprise three key functional domains: a PIWI endonuclease domain, a PAZ domain, and a MID domain. The PIWI domain may resemble a nuclease. The nuclease may be an RNase H or a DNA-guided ribonuclease. The PIWI domain may share a divalent cation-binding motif for catalysis exhibited by other nucleases that can cleave RNA and DNA. The divalent cation-binding motif may contain four negatively charged, evolutionary conserved amino acids. The four negatively charged evolutionary conserved amino acids may be aspartate-glutamate-aspartate-aspartate (DEDD). The four negatively charged evolutionary conserved amino acids may form a catalytic tetrad that binds two Mg2+ ions and cleaves a target nucleic acid into products bearing a 3' hydroxyl and 5' phosphate group. The PIWI domain may further comprise one or more amino acids selected from a basic residue. The PIWI domain may further comprise one or more amino acids selected from histidine, arginine, lysine and a combination thereof. The histidine, arginine and/or lysine may play an important role in catalysis and/or cleavage. Cleavage of the target nucleic acid by Argonaute can occur at a single phosphodiester bond.

In some instances, one or more magnesium and/or manganese cations can facilitate target nucleic acid cleavage, wherein a first cation can nucleophilically attack and activate a water molecule and a second cation can stabilize the transition state and leaving group.

The MID domain can bind the 5' phosphate and first nucleotide of the designed nucleic acid-targeting nucleic acid. The PAZ domain can use its oligonucleotide-binding fold to secure the 3' end of the designed nucleic acid-targeting nucleic acid.

The Argonaute protein may comprise one or more domains. The Argonaute protein may comprise a domain selected from a PAZ domain, a MID domain, and a PIWI domain or any combination thereof. The Argonaute protein may comprise a domain architecture of N-PAZ-MID-PIWI-C. The PAZ domain may comprise an oligonucleotide-binding fold to secure a 3' end of a nucleic acid-targeting nucleic acid. Release of the 3'-end of the nucleic acid-targeting nucleic acid from the PAZ domain may facilitate the transitioning of the Argonaute ternary complex into a cleavage active conformation. The MID domain may bind a 5' phosphate and a first nucleotide of the nucleic acid-targeting nucleic acid. The target nucleic acid can remain bound to the Argonaute through many rounds of cleavage by means of anchorage of the 5' phosphate in the MID domain.

This invention is a method to produce gene alterations in the genomes of eukaryotic and prokaryotic cells (gene editing). The method consists of Argonaute from Natronobacterium gregoryi, NgAgo or its mutants and complementary 5' phosphorylated single-stranded DNA that target the enzyme to cleave specific regions of the chromosome. NgAgo-based gene editing tools are more flexible than conventional Clustered Regularly Interspaced Short Palindromic Repeats (CRISPR) technology as it is not restricted to targeting regions adjacent to a specific motif. The 5' phosphate DNA guides are designed as but not limited to 24 nucleotides complementary to a gene of interest. NgAgo consists of an N-terminal repA, PAZ, MID and PIWI domains. NgAgo in isolation randomly cleaves DNA and may be used for random mutagenesis. N-terminal truncations (deletion of the repA domain; N-del) reduces random cleavage and may be used for targeted gene editing with a guide DNA as described above. Other mutants including N-del/E598A, N-del/D601P, and N-del/E602P were found to have reduced random DNA cleaving abilities, and may serve as alternative mutants for gene editing.

In some illustrative embodiments, the present invention relates to a method for modifying a chromosomal or an extrachromosomal genetic material of a prokaryotic host cell, comprising:
a) introducing a NgAgo or a mutant thereof to a prokaryotic host cell in a DNA expression cassette form, a RNA form or a protein form; and
b) introducing a plurality of 5'-phosphorylated guide nucleic acid sequences, each comprising about 15-30 nucleotides complementary to at least one target nucleic acid sequence of interest within the chromosomal or the extrachromosomal genetic material, wherein said NgAgo or a mutant thereof forms a complex with the 5'phosphorylated guide nucleic acid sequence, directing the complex to bind to the complementary target nucleic acid sequence and cleave it; and wherein the plurality of guide nucleic acid sequences are targeted to different regions of said target nucleic acid sequence in a site-specific manner.

In some illustrative embodiments, the present invention relates to a method for modifying a chromosomal or an extrachromosomal genetic material of a prokaryotic host cell as disclosed herein, wherein said DNA expression cassette further comprises p15-kanR-PtetRed, SEQ ID NO: 37.

In some illustrative embodiments, the present invention relates to a method for modifying a chromosomal or an extrachromosomal genetic material of a prokaryotic host cell as disclosed herein, the method further comprises a donor DNA, wherein said donor DNA comprises at least 20 nucleotides of homology to the flanking regions of the target nucleic acid so that the donor DNA may recombine with the cleaved nucleic acids flanking regions to replace or edit the chromosomal or extrachromosomal genetic material.

In some illustrative embodiments, the present invention relates to a method for modifying a chromosomal or an extrachromosomal genetic material of a prokaryotic host cell as disclosed herein, wherein the donor DNA is used to introduce new sequences, delete sequences, create point mutations, or promote a general DNA rearrangement.

In some illustrative embodiments, the present invention relates to a method for modifying a chromosomal or an extrachromosomal genetic material of a prokaryotic host cell as disclosed herein, wherein the prokaryotic host cell is an *Escherichia Coli*.

In some illustrative embodiments, the present invention relates to a method for modifying a chromosomal or an extrachromosomal genetic material of a prokaryotic host cell as disclosed herein, wherein the prokaryotic host cell is a bacterial cell containing one or more vectors comprising a) a lambda red recombinase system including exo, gam, and beta, or other recombinase systems driven by an inducible promoter that is sufficient to induce homologous recombination;
b) a donor DNA;
c) a regulatory sequence linked to the nucleotide sequence of NgAgo fused with additional sequences as needed; and
d) an inducible promoter to drive efficient expression of said regulatory sequence linked to the nucleotide sequence of NgAgo.

In some illustrative embodiments, the present invention relates to a method for modifying a chromosomal or an extrachromosomal genetic material of a prokaryotic host cell as disclosed herein, wherein said NgAgo is a full-length NgAgo, a repA-deletion NgAgo (N-del) or a mutant thereof.

In some illustrative embodiments, the present invention relates to a method for modifying a chromosomal or an extrachromosomal genetic material of a prokaryotic host cell as disclosed herein, wherein said mutant of N-del is a mutant of N-del/E598A, N-del/D601P or N-del/E602P.

In some other illustrative embodiments, the present invention relates to a gene editing system in a host cell comprising:
a designed DNA sequence of about 24 nucleotides with 5' phosphorylation, wherein said DNA sequence is complementary to a gene of interest in the cell; a lambda red recombinase system including exo, gam, and beta, or other recombinase systems driven by an inducible promoter that is sufficient to induce homologous recombination; and
an NgAgo enzyme or a mutant thereof, wherein said NgAgo enzyme specifically interact with said designed DNA and nick the gene of interest in the cell through the guidance of said designed DNA.

In some illustrative embodiments, the present invention relates to a gene editing system in a host cell as disclosed herein, wherein the gene editing system further comprises a donor DNA wherein said donor DNA comprises at least 20 nucleotides of homology to the flanking regions of the gene of interest so that the donor DNA may recombine with the flanking regions of the gene of interest to replace or edit the cleaved gene of interest.

In some illustrative embodiments, the present invention relates to a gene editing system in a host cell as disclosed herein, wherein said NgAgo enzyme is a full-length NgAgo, a repA-deletion NgAgo (N-del) or a mutant thereof, in the form of DNA expression cassette, messenger RNA or a protein product thereof.

In some illustrative embodiments, the present invention relates to a gene editing system in a host cell as disclosed herein, wherein said NgAgo enzyme is a full-length NgAgo, a repA-deletion NgAgo (N-del) or a mutant thereof, in the form of DNA expression cassette, messenger RNA or a protein product thereof.

In some illustrative embodiments, the present invention relates to a gene editing system in a host cell as disclosed herein, wherein said N-Del mutant is N-del/E598A, N-del/E601P, or N-del D602P.

In some illustrative embodiments, the present invention relates to a gene editing system in a host cell as disclosed herein, wherein said host cell is a prokaryotic cell.

In some illustrative embodiments, the present invention relates to a gene editing system in a host cell as disclosed herein, wherein said prokaryotic cell is *Escherichia Coli*.

In some illustrative embodiments, the present invention relates to a method for modifying a chromosomal or an extrachromosomal genetic material of a host cell, comprising:
- a) introducing NgAgo or a mutant thereof to a host cell in a DNA expression cassette form, a RNA form or a protein form; and
- b) introducing a plurality of 5'-phosphorylated guide nucleic acid sequences, each comprising about 15-30 nucleotides complementary to at least one target nucleic acid sequence of interest within the chromosomal or the extrachromosomal genetic material, wherein said NgAgo or a mutant thereof forms a complex with the 5'phosphorylated guide nucleic acid sequence, directing the complex to bind to the complementary target nucleic acid sequence and cleave it; and wherein the plurality of guide nucleic acid sequences are targeted to different regions of said target nucleic acid sequence in a site-specific manner.

In some illustrative embodiments, the present invention relates to a method for modifying a chromosomal or an extrachromosomal genetic material of a host cell as disclosed herein, the method further comprises a donor DNA, wherein said donor DNA comprises at least 20 nucleotides of homology to the flanking regions of the target nucleic acid so that the donor DNA may recombine with the cleaved nucleic acids flanking regions to replace or edit the chromosomal or extrachromosomal genetic material.

In some illustrative embodiments, the present invention relates to a method for modifying a chromosomal or an extrachromosomal genetic material of a host cell as disclosed herein, wherein the donor DNA is used to introduce new sequences, delete sequences, create point mutations, or promote a general DNA rearrangement.

In some illustrative embodiments, the present invention relates to a method for modifying a chromosomal or an extrachromosomal genetic material of a host cell as disclosed herein, wherein said host cell is a prokaryotic cell.

In some illustrative embodiments, the present invention relates to a method for modifying a chromosomal or an extrachromosomal genetic material of a host cell as disclosed herein, wherein said NgAgo is a whole length of NbAgo, a repA-deletion NgAgo (N-del) or a mutant thereof.

In some illustrative embodiments, the present invention relates to a method for modifying a chromosomal or an extrachromosomal genetic material of a host cell as disclosed herein, wherein the host cell is a bacterial cell containing one or more vectors comprising
- a) a lambda red recombinase system including exo, gam, and beta, or other recombinase systems driven by an inducible promoter that is sufficient to induce homologous recombination;
- b) a donor DNA;
- c) a regulatory sequence linked to the nucleotide sequence of NgAgo or a mutant thereof fused with additional sequences as needed; and
- d) an inducible promoter to drive efficient expression of said regulatory sequence linked to the nucleotide sequence of NgAgo.

In some other embodiments, the present invention relates to a gene editing system in a host cell disclosed herein, wherein the host cell is a prokaryotic cell or a eukaryotic cell.

These and other features, aspects and advantages of the present invention will become better understood with reference to the following descriptions and claims.

Argonautes belong to PIWI protein superfamily, featuring with an N (N-terminal) domain, a PAZ (PIWI-Argonaute-Zwille) domain and a MID (middle) domain. Eukaryotic Argonautes (eAgos) have four domains, involving in RNA interference (RNAi) mechanisms, while prokaryotic Argonautes (pAgos) have diverse domain architectures. Depending on the presence of the domains, pAgos are grouped into four categories, including long pAgos, long pAgos with associated proteins, short pAgos with associated proteins, and PIWI-RE with associated proteins. Long pAgos have all four domains. The nucleic acid cleavage activity relies on a complete catalytic tetrad. Incomplete catalytic tetrad of long pAgos may associate with other nuclease, assisting target nucleic acids cleavage activity, making up of long pAgos with associated proteins category. Short pAgos with associated proteins and PIWI-RE with associated proteins only have a MID domain and a PIWI domain. The difference is that the former has an analogue of PAZ (APAZ) domain fused to a nuclease domain and latter has a cluster on operons with both helicase and a predicted nuclease.

Despite diversity of pAgos, they all were predicted to serve as a form of defense mechanism to protect prokaryotic hosts from invading nucleic acids. So far, only long pAgos have been shown to cleave nucleic acids without adjacent motif. By using a single-stranded DNA and/or RNA as a guide, long pAgos cleave complementary target DNA, RNA, or both via the well-conserved catalytic tetrad, DEDX (D: aspartate, E: glutamate, X: histidine, aspartate or asparagine) (Swarts, D C, et al., *Nature Structural & Molecular Biology*, 2014, 21, 743-753). For double stranded DNA, long pAgos require two guides to create a double stranded break.

Although DNA cleavage activity of long pAgos including TtAgo, MpAgo, PfAgo and MjAgo isolated from thermophile is well-characterized in vitro, how guides are generated in vivo remains unclear (Swarts, D C, et al., *Nature*, 2014, 507, 258-262; Kaya, E., et al., *PNAS*, 2016, 113, 4057-4062; Willkomm, S. et al., *Nature Microbiology*, 2017, 2, 17035). Recent studies of MjAgo and TtAgo proposed that apo-pAgos randomly chop foreign DNA to create the guide nucleic acids. These fragments can then be used for subsequent guide-dependent cleavage activity (Zander A., et al., *Nature Microbiology*, 2017, 2, 17034; Swarts, D C, et al., *Molecular Cell*, 2017, 65, 985-998). From a gene-editing prospective, guide-independent cleavage activity may cause off-target effects, interfering with the specific gene-editing ability.

Despite the presence of potential off-target effects, motif-less cleavage ability of pAgos may serve as a more flexible gene-editing tool compared to the popular, Clustered Regularly Interspaced Short Palindromic Repeats (CRISPRs)-based gene-editing tools, which require a protoadjacent motif (PAM) to cleave the target DNA. This characteristic of pAgos allows scientists to target any sequence without bias. Despite the advantage of pAgos for gene-editing tool development, current thermophilic pAgos targeting DNA work at a very high temperature (>55°) C., making them inappropriate for use in human cells and other model organisms (Swarts, D C, et al., *Nature*, 2014, 507, 258-262; Kaya, E., et al., *PNAS*, 2016, 113, 4057-4062; Willkomm, S. et al., *Nature Microbiology*, 2017, 2, 17035).

Recently, a mesophilic long pAgo, NgAgo, isolated from Natronobacterium gregoryi, was claimed to edit genes in human cell lines (Cyranoski, D, 2017, Nature News). However, subsequent studies failed to replicate the gene-editing ability in human cell lines, mouse cell lines, mouse embryos, or zebrafish, but did observe down-regulation of targeted genes (Javidi-Parsijani, P. et al., *PloS One*, 2017, 12, 14; Wu, Z. et al., *Antiviral Research* 2017; Burgess, S, et al., *Protein & Cell*, 2016, 7, 913-915; Khin, N C, et al., *PloS One* 2017, 12, e0178768; Qin, Y Y, et al., *Cell Research*, 2016, 26, 1349-1352). In vitro studies by Sunghyeok et al. showed that NgAgo protein cleaves RNA but not DNA, which is a proposed mechanism for the down-regulation observed in previous studies (Sunhyeok, T. et al., *BioRxiv*, 2017, 101923). However, in all cases NgAgo expression was poor with most protein needing to be refolded before assays. This poor expression is consistent with other halophilic proteins that adapt to high salt conditions with high surface charges, which makes the protein unstable when expressed in low salt conditions. Results from Sunghyeok et al., however, are less than conclusive as the catalytic tetrad mutant still cleave target nucleic acids, which is inconsistent with other catalytically active pAgos (Swarts, D C, et al., *Nature Structural & Molecular Biology*, 2014, 21, 743-753).

Due to inconsistent results in the literature, we have revisited several key questions in understanding the function of NgAgo. We asked whether NgAgo interacts with DNA or RNA, and if it does, whether this interaction is binding only or cleavage. First, we established that NgAgo interacts with DNA, not RNA in vivo, with a targeted functional assay in *E. coli*. Second, we purified NgAgo from the soluble fraction, not from the insoluble fraction, to establish nucleic acid cleavage activity, along with *E. coli* in vivo experiments. Third, we completed homology domain analysis to identify an N-terminal repA domain and the conserved catalytic tetrad. By deletion and site-directed mutagenesis, we showed the repA domain degrades plasmid DNA and the catalytic tetrad is required for DNA cleavage activity. We also edit loci in *E. coli* and human cells with repA-deletion NgAgo mutant. In total, we demonstrate that heterogously expressed NgAgo has programmable DNA cleavage, and identify key protein domains for engineering as a precise gene-editing tool.

An Uncharacterized repA Domain is Present at the N-Terminal of NgAgo

Figure 1B:
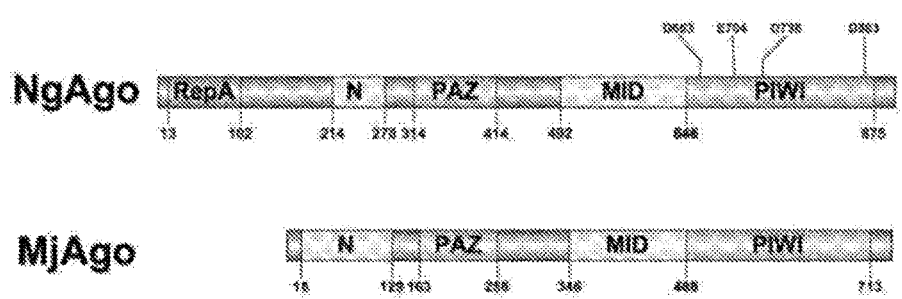
FIG. 1B shows domains architectures of NgAgo and MjAgo.

We analyzed the NgAgo protein for by harnessing the ability of homology detection and structure prediction of Phyre 2 and HHpred (Kelley, L A, et al., *Nature Protocols*, 2015, 10, 845-858). Phyre 2 analysis found that NgAgo matches many catalytically active pAgos and eukaryotic Argonautes (eAgos) including MjAgo, PfAgo, and RsAgo (Table 3). Overall, the predicted 3D structure of NgAgo is very similar to long pAgos such as MjAgo with PAZ domain, MID domain, and PIWI domain, except for the truncated N-terminal domain of NgAgo (FIGS. 1A and 1B). Both Phyre 2 and HHpred also identified an uncharacterized oligonucleotide/oligosaccharide-binding (OB) fold domain essential to proteins such as replication protein A (repA), single stranded-binding protein, and SOSS complex at the N-terminus of NgAgo with high confidence (FIG. 1B; Tables 5 and 6). Since both Phyre 2 and HHpred both identify the repA domain as most likely (probabilities of Phyre 2 and HHpred are 95.2 and 92.46, respectively), hereafter we refer to this domain as a repA. Since this repA domain is absent in all characterized pAgos, we then used IMG server to BLAST full-length NgAgo against all isolates in the database. We found 138 homologs of NgAgo. Twelve out of 138 NgAgo homologs contain the repA domain with the full-length Argonautes while three out of 138 have matched repA domain without full-length of Argonautes. Phylogenetic analysis showed that the repA domain-containing pAgos were from halophilic Archaea, which forms a clade that is distant from that of the current well-characterized pAgos (FIG. 1C). This monophyletic group of repA-containing pAgos may represent a new class of pAgos that is currently unrecognized in the literature (Swarts, D C, et al., *Nature Structural & Molecular Biology*, 2014, 21, 743-753). Interestingly, all the repA domain-containing pAgos come from halophilic Archaea, suggesting the repA domain may be required for function in high salt environments.

NgAgo has an Intact DEDD Catalytic Tetrad

The critical residues for Argonaute cleavage lie within the well-conserved catalytic tetrad, DEDX (X: H, D or N. Swarts, D C, et al., *Nature Structural & Molecular Biology*, 2014, 21, 743-753). We used structural alignment and sequence alignment to check if NgAgo has an intact catalytic tetrad. From the sequence alignment with catalytically active pAgos, including MjAgo, PfAgo, MpAgo, and TtAgo, the catalytic tetrad (D663, E704, D738, and D863) is conserved in NgAgo. Perhaps more specifically, FIG. 1E shows the sequence alignment, for example, of D663 (NgAgo SEQ ID NO: 52, MjAgo SEQ ID NO: 56, PfAgo SEQ ID NO: 60, MpAgo SEQ ID NO: 64, and TtAgo SEQ ID NO: 68), E704 (NgAgo SEQ ID NO: 53, MjAgo SEQ ID NO: 57, PfAgo SEQ ID NO: 61, MpAgo SEQ ID NO: 65, and TtAgo SEQ ID NO: 69), D738 (NgAgo SEQ ID NO: 54, MjAgo SEQ ID NO: 58, PfAgo SEQ ID NO: 62, MpAgo SEQ ID NO: 66, and TtAgo SEQ ID NO: 70), and D863 (NgAgo SEQ ID NO: 55, MjAgo SEQ ID NO: 59, PfAgo SEQ ID NO: 63, MpAgo SEQ ID NO: 67, and TtAgo SEQ ID NO: 71). We then used structural alignment to further confirm whether those catalytic residues are structurally close together. All the catalytic residues including D663, D738, and D683 of NgAgo except E704 structurally colocalize with the catalytic tetrad of MjAgo (D504, D570, and D688) (FIG. 1D), suggesting the presence of cleavage activity. Retaining nucleic acid cleavage activity of catalytic mutant in the previous study (Sunghyeok, Y, et al., 2017) contradicts to the fact that catalytic mutant of pAgos loses nucleic acids cleavage activity (Olovnikov, I, et al., *Molecular Cell*, 2013, 51, 594-605). This prompted us to revisit the cleavage activity in later experiments.

Figure 2A:
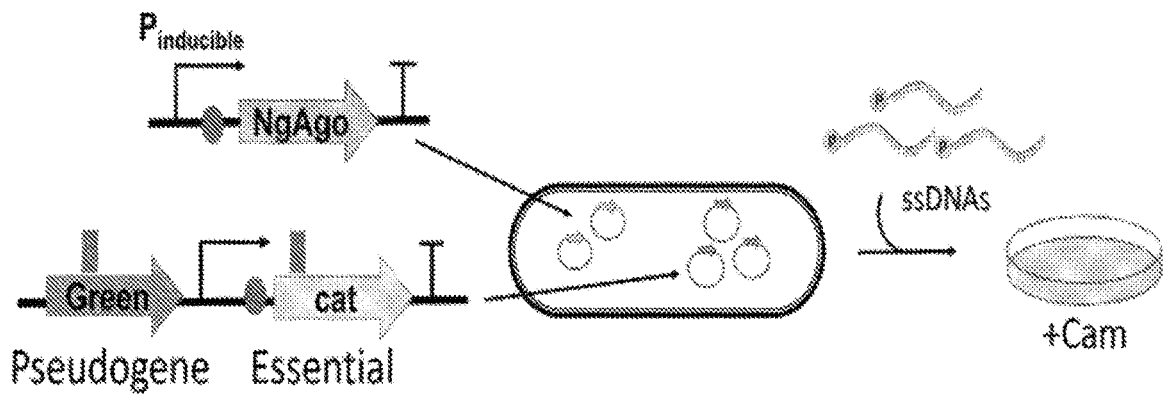
FIG. 2A shows workflow of testing NgAgo function in BL21 (DE3) E. coli. Two plasmids system used to test the function of NgAgo. One plasmid harbors NgAgo driven by T7 inducible promoter while the other low-copy plasmid serves as the targets of NgAgo, including a non-transcribed pseudogene, mNeonGreen, and an essential gene, cat.
Figure 2B:
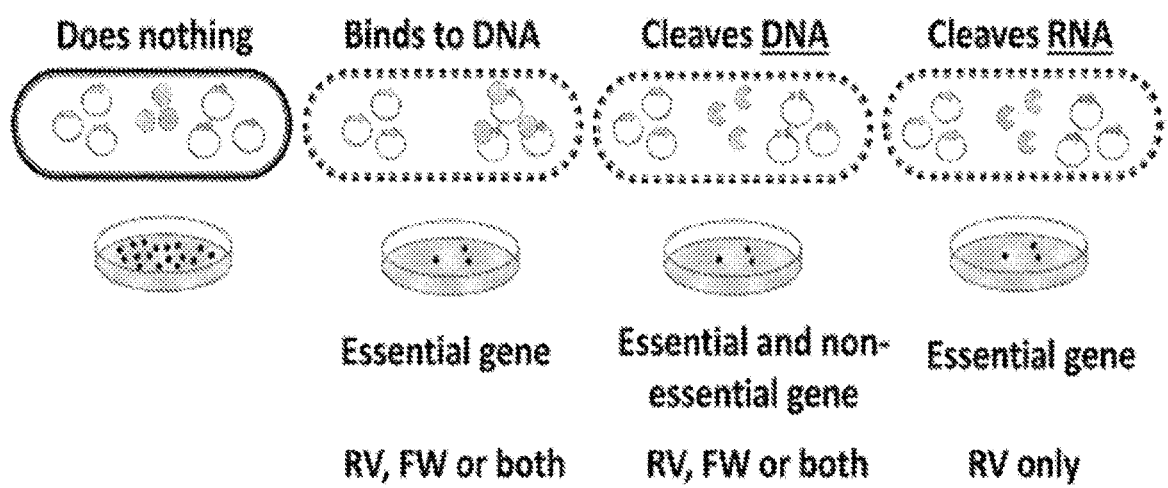
FIG. 2B shows the four possible outcomes that reveal the function of NgAgo.
Figure 2C:
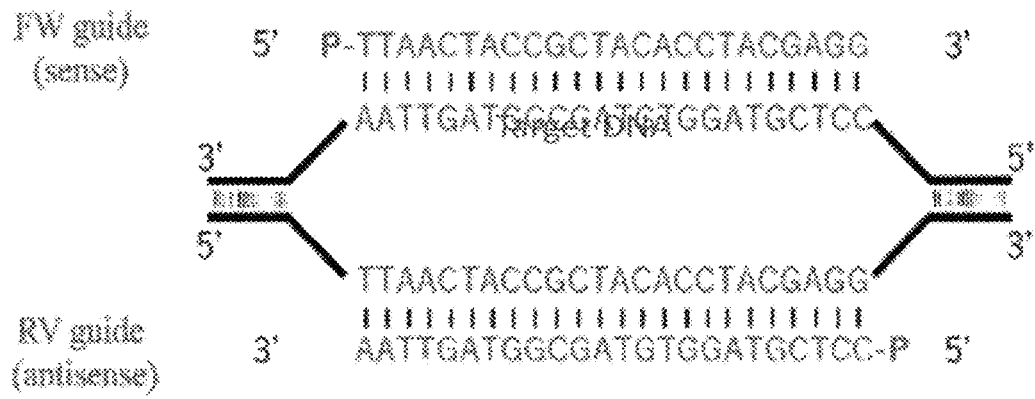
FIG. 2C shows NgAgo targets DNA region (blue color) of the target plasmid pIncW-mNeonGreen, mNeon-Green (see, e.g., SEQ ID NOS: 72 and 73), and the DNA guide (red color) in E. coli (see, e.g., SEQ ID NOS: 22 and 23)

FIGS. 2A-2C describe NgAgo targeting DNA in *E. coli*. FIG. 2A shows the workflow of testing NgAgo function in *E. coli*. Two plasmids system used to test the function of NgAgo. One plasmid harbors NgAgo driven by T7 inducible promoter while the other low-copy plasmid serves as the targets of NgAgo, including a non-transcribed pseudogene, mNeonGreen, and an essential gene, cat. Four possible outcomes reveal the function of NgAgo (see FIG. 2B). If NgAgo cuts DNA, targeting either the essential genes (cat and dnaA) or the non-essential genes (mNeonGreen and arpB) would reduce survival. DNA Double-strand breaks are lethal in *E. coli* due to inefficient non-homologous end joining (NHEJ) repair mechanisms. If NgAgo cuts or binds to RNA, only targeting the essential genes (cat and dnaA) would reduce survival. This would only be true when using guide nucleic acids complementary to target RNA. If NgAgo binds to DNA, only targeting the essential genes (cat and dnaA) would reduce survival. This is true when target with both forward and reverse guides. If NgAgo does nothing, there would be no reduced survival. Competent cells with two-plasmid system were transformed with total of one microgram of forward (for example, SEQ ID NO: 23), reverse (for example, SEQ ID NO: 22), both, or no guides, individually, and plated on agar plates with ampicillin, chloramphenicol, and 0.1 mM IPTG at 37° ° C. for 16-20 hours.

FIG. 2C shows target region of the target plasmid pIncW-mNeonGreen, mNeonGreen (SEQ ID NOS: 72 and 73).

Figure 2D:
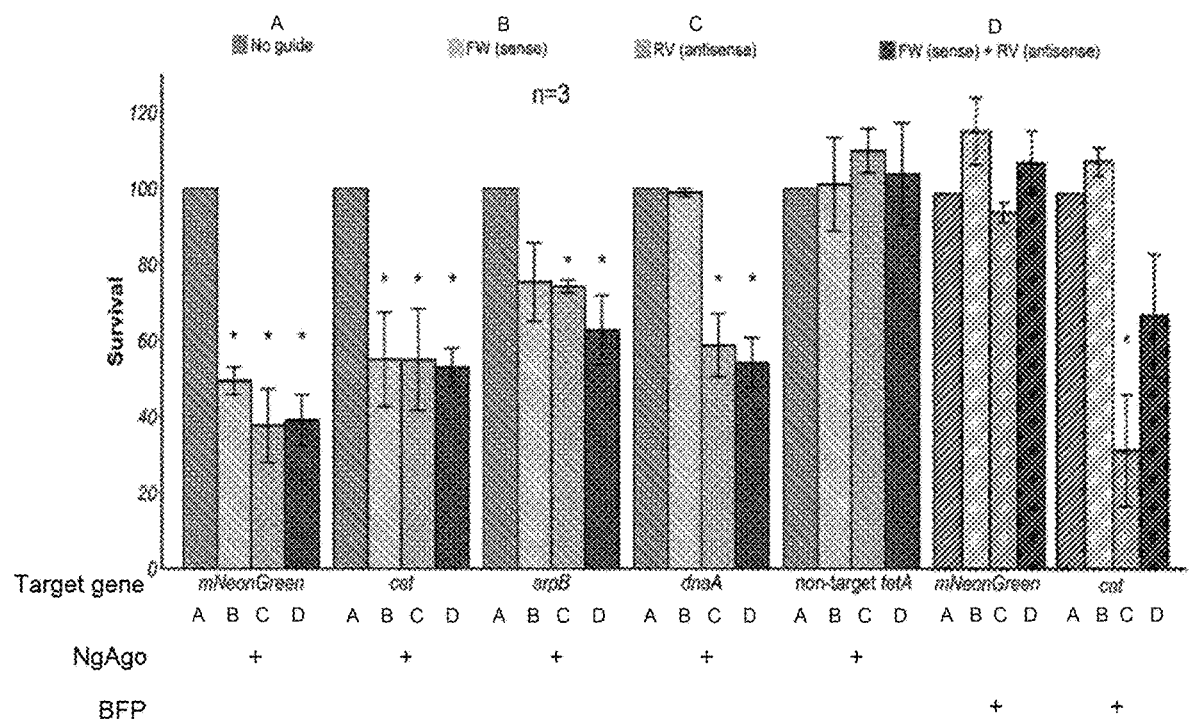
FIG. 2D shows the survival rate targeting a pseudogene (mNeonGreen) and an essential gene (cat) on the plasmid or targeting a nonessential gene (arpB) and an essential gene (DnaA) at the NgAgo genome in E. coli.

FIGS. 2C and 2D depict the survival rate targeting a pseudogene (mNeonGreen) and an essential gene (cat) on the plasmid or targeting a nonessential gene (arpB) and an essential gene (DnaA) at the genome.

NgAgo Inhibits Plasmid Replication Via an Uncharacterized DNA Interaction

Figure 9A:
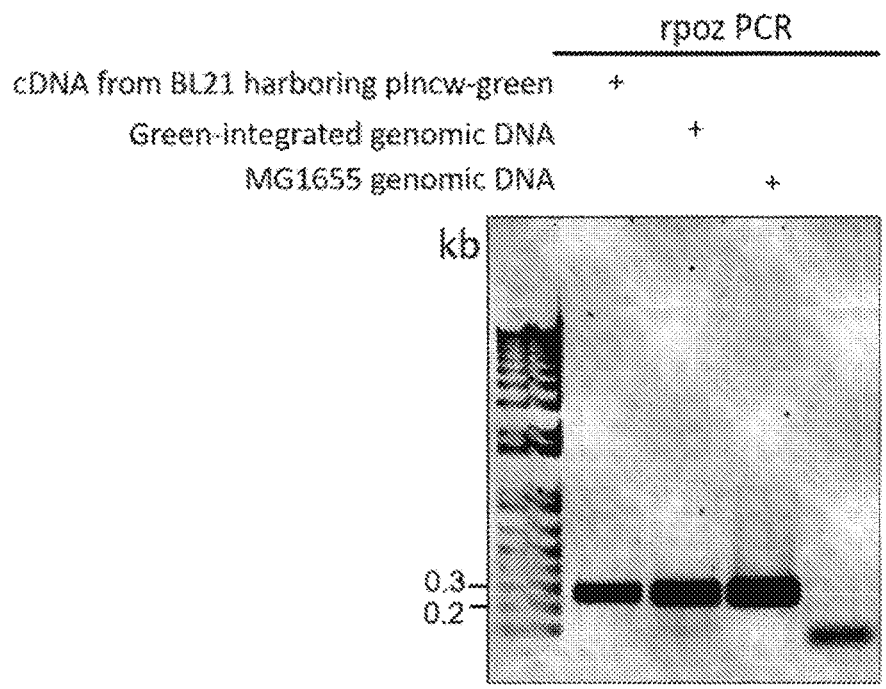
FIGS. 9A-9B demonstrates that mNeonGreen of pIncw-green does not express. RNA from BL21 (DE3) harboring pIncw-green was extracted and reverse transcribed and tested to see if mNeonGreen from pIncw-green is expressed.
Figure 9B:
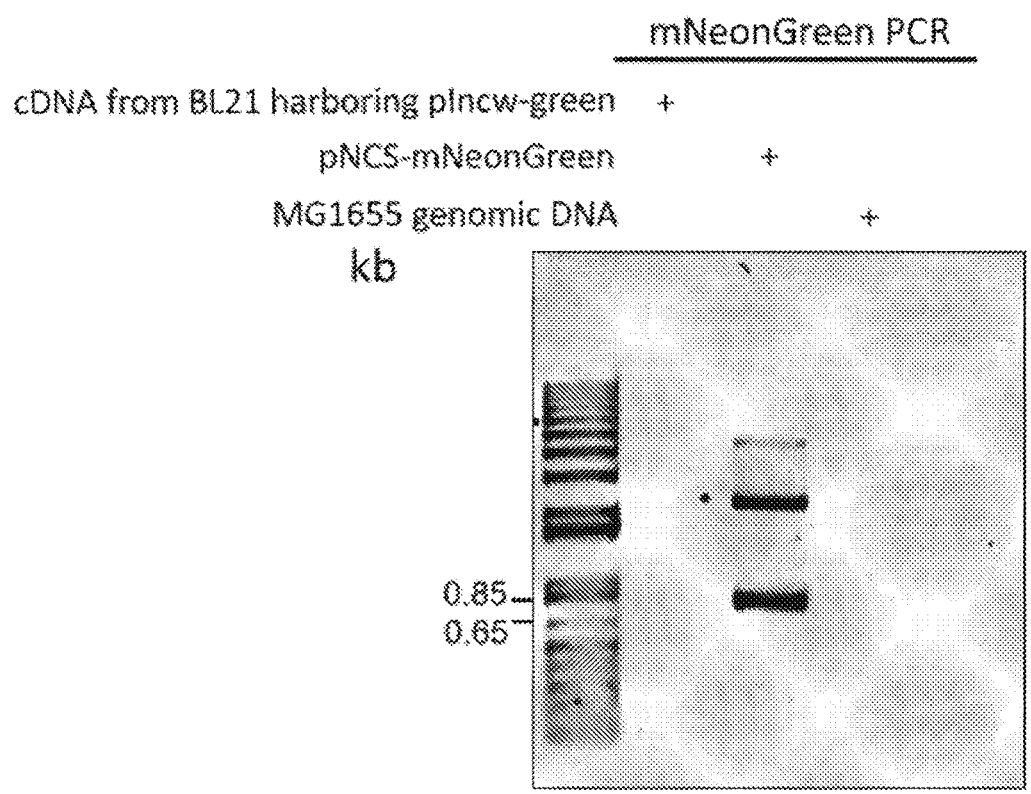

Since NgAgo is similar to long pAgos architecture except for the extra repA domain, indicating the nucleic acids interaction could be either binding or cleavage. Although the initial report claims that NgAgo may cleave DNA for gene-editing, studies have refuted this claim. Researchers have confirmed the ability of NgAgo to reduce gene expression and demonstrate in vitro RNA cleavage as a possible mechanism. However, this cleavage did not rely on the catalytic tetrad. We sought to replicate these findings and establish whether NgAgo interacted with DNA, RNA, or both. Three mechanisms that could explain these conflicting reports are that NgAgo cuts DNA, binds tightly to DNA or cleaves RNA. To distinguish between these three outcomes, we created a two-plasmid system: one harbors an inducible NgAgo expression cassette; the other serves as a targeted plasmid, harboring an essential chloramphenicol resistance gene target, cat, and a transcriptionally idle pseudogene target, mNeonGreen (FIG. 2A and FIGS. 9A and 9B). E. coli harboring the two-plasmid system were transformed with different strands of phosphorylated guide ssDNA (P-ssDNA), including reverse (RV, antisense; SEQ ID NO: 22), forward (FW, sense; SEQ ID NO: 23) (FIG. 2C), both RV and FW or without a guide, and streaked on an agar plate selecting for the two-plasmid system (FIG. 2A).

Figure 7:
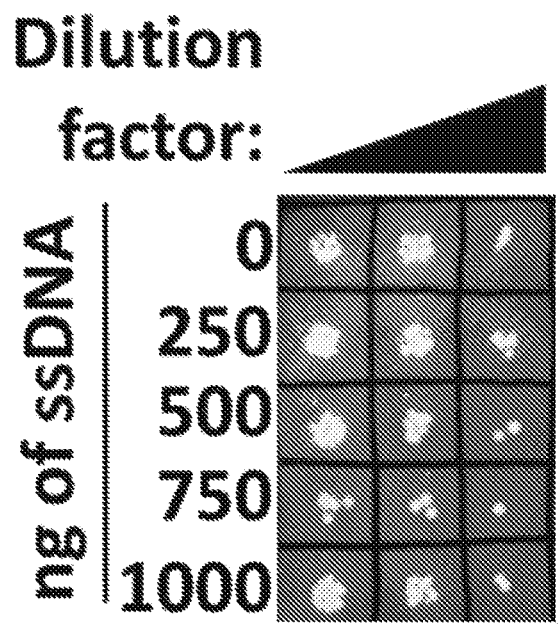
FIG. 7 shows exogenously introduction of one microgram of ssDNA is nontoxic to the E. coli. Different concentration (250 ng, 500 ng, 750 ng, and 1000 ng) of ssDNAs are transformed to BL21 (DE3) by electroporation and plated on LB plate with different dilution factors (1000×, 2000× and 5000×) at 37° ° C. for 16-20 hours.
Figure 8A:
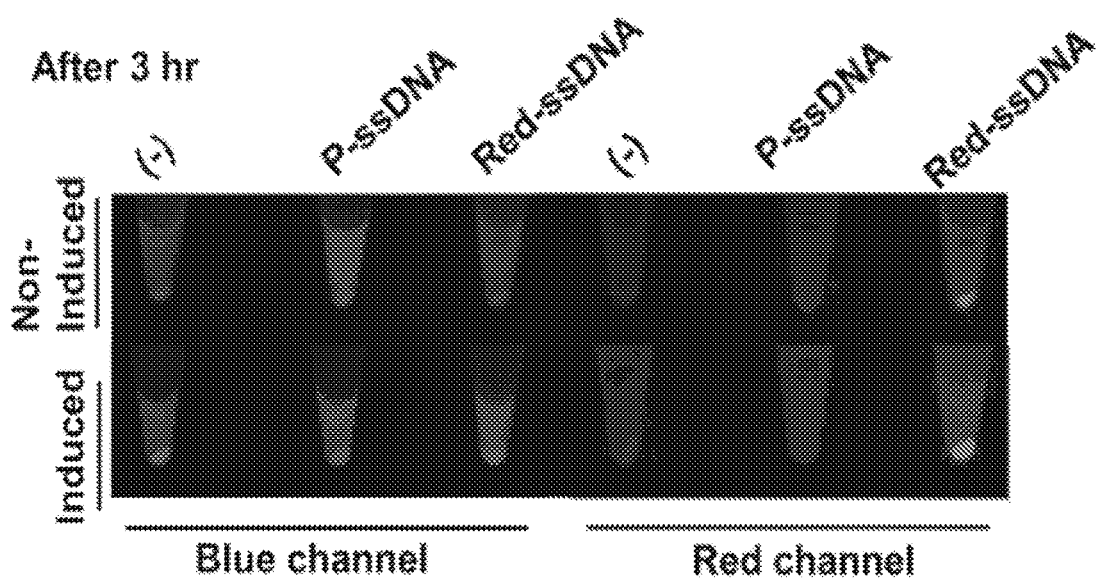
FIG. 8A shows BL21 (DE3) harboring inducible BFP expression plasmid was made electrocompetent and transformed with D4PA-labelled Red-ssDNA. After transformation, cells were resuspended in SOC in the presence of 0.1 mM IPTG and 100 µg/ml ampicillin at 37° C. BFP expression is observed after 3 hr transformation. Red-ssDNA is still present after three hours transformation.
Figure 8B:
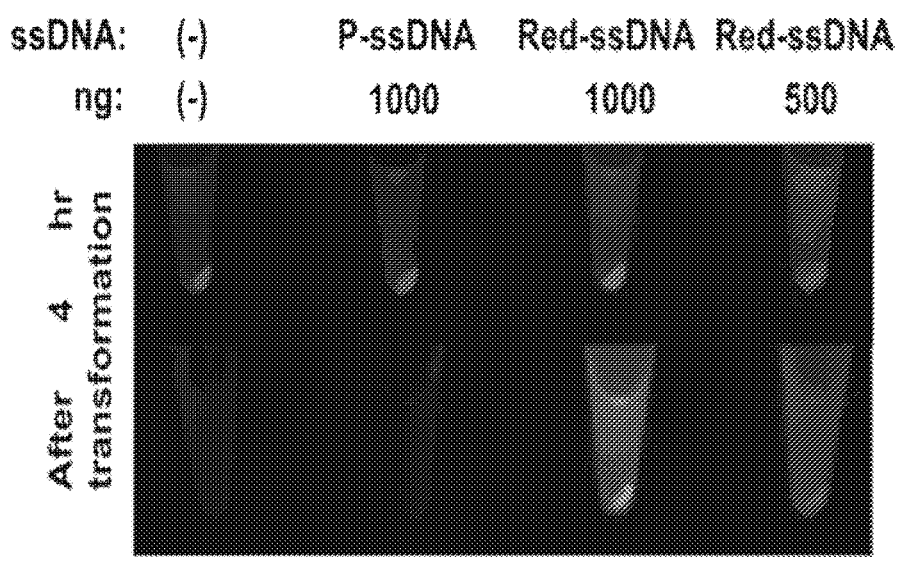
FIG. 8B depicts BL21 (DE3) harboring inducible BFP expression was induced with 0.1 mM IPTG before it made to electrocompetent cells at 37° C. After transformation with either 500 ng or 1000 ng Red-ssDNA, Red-ssDNA still present in the cells.
Figure 8C:
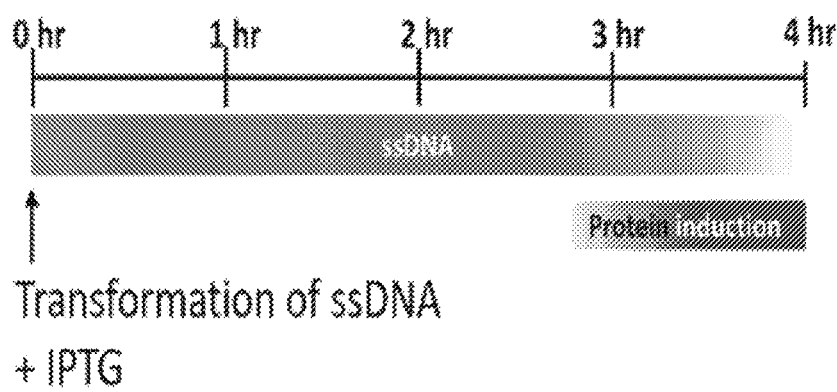
FIG. 8C shows the timeline of ssDNA stability and protein expression at 37°C.

We first demonstrated that transformation with one microgram of ssDNA did not reduce survival (FIG. 7) and that ssDNA could survive long enough to form a complex with NgAgo without reducing the survival (FIGS. 8A-8C). If NgAgo cleaves DNA, targeting the essential gene or the pseudogene will linearize the plasmid, causing loss of the targeted plasmid and subsequent reduction in colonies formed on chloramphenicol selective plates. Similarly, if the NgAgo/P-ssDNA complex binds to the DNA of the essential gene target, preventing transcription, or cleaves the essential gene mRNA to disrupt translation, survival on chloramphenicol selective media decreases; however, targeting the pseudogene should not have an impact on cell survival. If NgAgo acts at the RNA level, it should operate in a strand-specific manner with only RV guide DNA (antisense) capable of interacting with the single-stranded mRNA (FIG. 2A).

Our results showed that NgAgo reduces survival when targeted to a gene (cat or mNeonGreen) and does nothing when targeted to a region absent in the host (tet), indicating that NgAgo interacts with nucleic acids in a programmable manner in E. coli. We observed reduction of the survival when the essential gene, cat, was targeted with either FW or RV guide. As this behavior is strand independent, RNA cleavage is unlikely the primary mechanism of action. Targeting the pseudogene, mNeonGreen, also resulted in a reduction of survival, suggesting that NgAgo inhibits plasmid replication via an uncharacterized interaction, either by direct DNA cleavage or tight DNA binding which blocks the DNA replication machinery.

To confirm the reduced survival is caused by NgAgo/P-ssDNA complex, we used tetA P-ssDNA as a non-target control. Without any target on the plasmid or on the genome, NgAgo does not affect survival (FIG. 2C). We also replaced NgAgo with BFP as a protein control in the two-plasmid system. There was no reduction of survival with transformed E. coli harboring the BFP-modified two-plasmid system with mNeonGreen P-ssDNA targeting the pseudogene, (FIG. 2C), confirming the survival reduction effect requires NgAgo expression. Collectively, we showed that the reduction of survival resulted from the NgAgo/P-ssDNA complex, not from the NgAgo protein or P-ssDNA itself.

RNase H May Contribute to DNA Guide-Mediated Gene Repression In Vivo

In the previous in vitro study, Sunghyeok and colleagues showed that purified NgAgo cleaves RNAs in a programmable manner (14). Reviewer has argued that RNaseH may contribute to the cleavage because it cleaves RNA when hybridized with DNA (14). To determine if RNaseH contributes to target gene down-regulation in vivo, we introduced either FW, RV or both guide targeting the essential gene, cat, into BL21 harboring a BFP expression cassette/target plasmid and checked the survival. Our results showed that targeting with the RV guide reduces survival guide while FW has no impact on survival, suggesting RNaseH may contribute to target gene down-regulation in vivo. This guide strand specific effect was not observed in NgAgo-mediated cat gene down-regulation, further confirming that NgAgo/guide DNA interacts with DNA. Although an Rnase H-mediated effect may contribute to our results with the transcriptionally active gene, it cannot explain our observation with pseudogenes and non-essential genes. Thus, there must be DNA interaction between NgAgo/ssDNA complex and DNA. Due to the essentiality of RNaseH in E. coli, we did not knockout Rnase H to study whether NgAgo targets RNA in the absence of Rnase H.

NgAgo Reduced Survival by Targeting Programmable Loci on the Genome

To confirm that the reduced survival is not limited to targets on the plasmid, we targeted an essential gene, dnaA and a non-essential pseudogene, arpB on the genome. Our results showed that targeting dnaA with either FW guide or both FW and RV guides resulted in a reduction of survival. Using both guides has a more severe effect on lethality (FIG. 2C). We also observed that the RV guide does not effectively reduce the survival rate when targeting the genes at the genome. We hypothesize that this could result from the sequence specific differences in targeting efficiency in guide DNA, as seen in a previous TtAgo study (Swarts, D C et al., Nature, 2014, 507, 258-261).

To clarify whether NgAgo targets DNA, we chose a non-essential pseudogene that was interrupted by a stop codon, arpB. Since arpB RNA is not required for survival (i.e., the arpB mutant is nonlethal), RNA cleavage would not reduce survival. However, targeting arpB did reduce survival (FIG. 2C), suggesting NgAgo interacts with DNA, consistent with the previous result targeting a pseudogene on a plasmid.

Collectively, targeting both essential and non-essential genes either on a plasmid or on the genome reduces survival. Targeting essential genes is guide-independent, suggesting RNA cleavage is not the primary mechanism of action while targeting pseudogenes at both plasmid and genome suggested an uncharacterized DNA interaction by NgAgo.

Figure 3E:
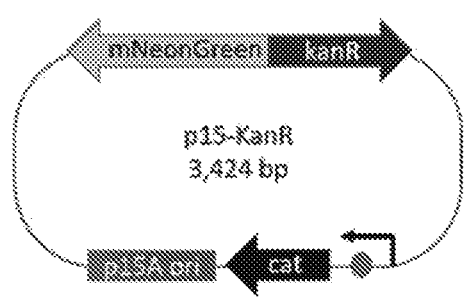
Figure 3F:
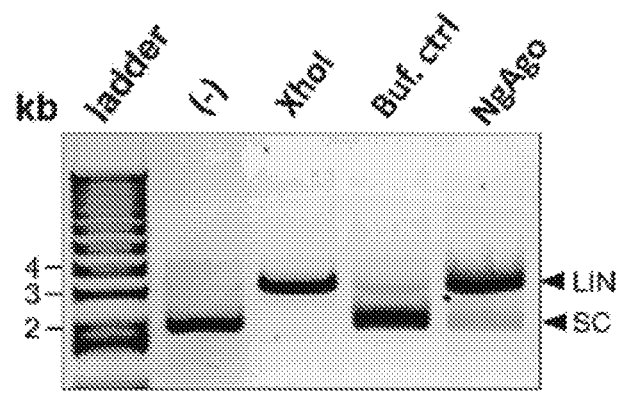
Figure 3G:
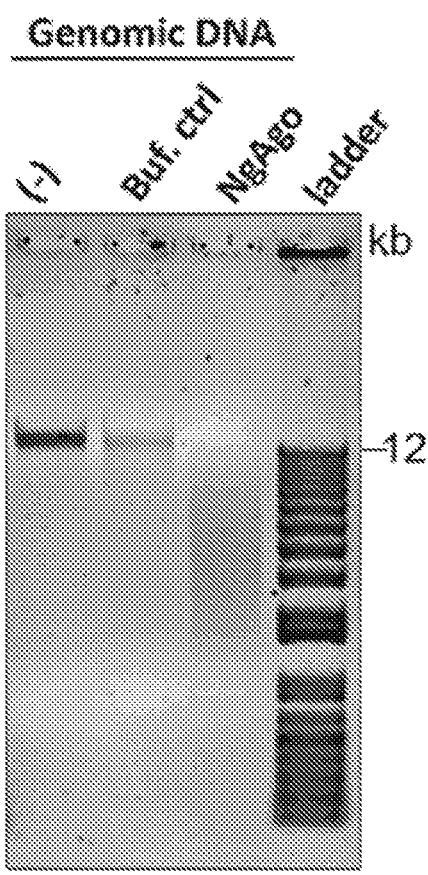

FIGS. 3A-3G demonstrate that soluble NgAgo but not refolded NgAgo cuts DNA guide-independently. Soluble NgAgo, sNgAgo (FIG. 3A), or refolded NgAgo, rNgAgo (FIG. 3B), were mixed with a combination of guide DNA and plasmid to see if NgAgo cuts or nicks DNA guide-dependently. NgAgo guide-independently cuts related and unrelated plasmid DNA (FIGS. 3C-3F) and E. coli genomic DNA (FIG. 3G).

NgAgo Cuts/Nicks DNA In Vitro and In Vivo

Figure 10:
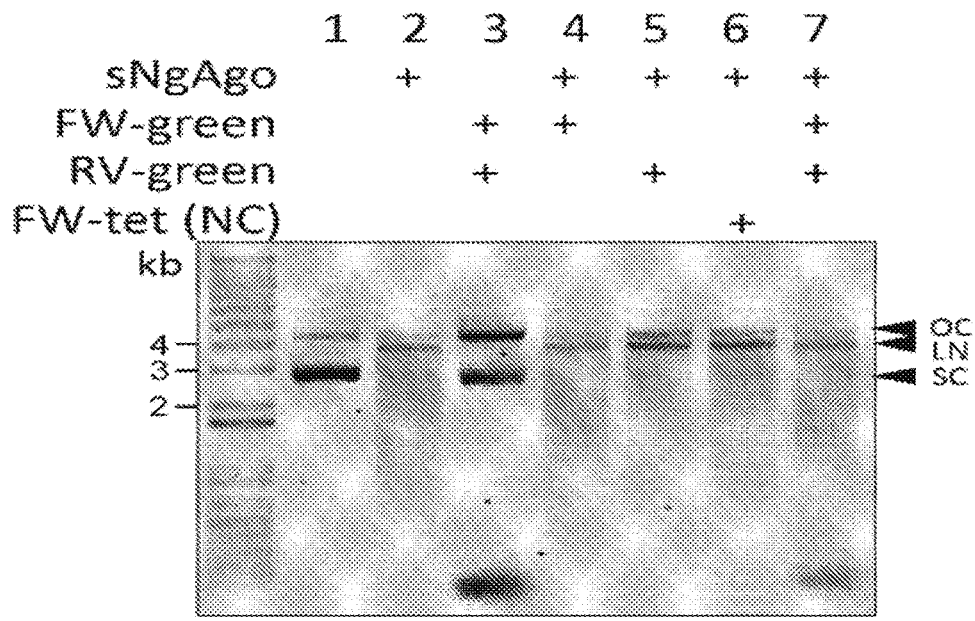
FIG. 10 shows soluble NgAgo nicks/cuts plasmid by using Han's protocol. Five micrograms of soluble NgAgo was incubated with 300 ng of guides at 55° C. for an hour and subsequent incubated with 400 ng of pNCS-mNeonGreen plasmid for 2 hours with 50 µl final volume (working concentration: 20 mM Tris-Cl, 300 mM KCl, 500 µM MgCl$_2$, and 2 mM DTT). Total 0.8 unit of Proteinase K was added to the samples to digest the protein for 5 minutes at 37° C. The nucleic acids were then cleaned up and loaded with loading dye containing SDS for gel electrophoresis.

To check if NgAgo cuts DNA, we purified N-terminal His-tagged NgAgo and conducted in vitro activity assay. With different combination of NgAgo and guide DNA, we tested if NgAgo cleaves DNA guide-dependently. In contrast to the Han study (24), our result showed that purified NgAgo from the soluble cell lysate fraction (sNgAgo) cuts plasmid DNA, independently of guide (FIG. 3A), as evidenced by the presence of the linearized form of plasmid. However, purified refolded NgAgo from the insoluble lysate fraction (rNgAgo) has little or no activity (FIG. 3B), consistent with a study by Sunghyeok colleagues cited above. We hypothesized that NgAgo co-purifies with loaded DNA guides from in vivo DNA chopping. Thus, we attempted to dissociate with these guides with reloading protocol by incubating at high temperature (50°) C. Our results showed that NgAgo still exhibits guide-independent cleavage activity, as evidenced by the presence of open circular form, linearized plasmid DNA and smearing (FIG. 10). Hereafter, we used soluble NgAgo to study its function in vitro unless stated explicitly. To further confirm the phenomenon that NgAgo randomly cleaves DNA, we used a related plasmid DNA, pNCS-mNeonGreen (FIG. 3C), and unrelated plasmid DNA, p15-KanR (FIG. 3E), to test the guide-independent cleavage activity. Unrelated plasmid, p15-KanR, shares no DNA parts with NgAgo expression plasmid while related plasmid, pNCS-mNeonGreen, has the same ampicillin resistance gene. Previous studies showed that TtAgo can obtain guide from the expression plasmid DNA. To exclude the possibility that NgAgo is using guides obtained from the expression plasmid, we used a nonrelated plasmid as a substrate. NgAgo cleaves both related and unrelated plasmids without guide DNA (FIGS. 3D and 3F), as evidenced by the presence of linearized DNA, indicating the guide-independent cleavage activity of our purified NgAgo does not rely on pre-loaded DNA, as demonstrated in TtAgo (7). Incubation of NgAgo with MG1655 genomic DNA also showed smearing (FIG. 3G), suggesting NgAgo guide-independently cuts genomic DNA. To exclude DNase contamination, we checked the in vitro activity by using the size-exclusion fast protein liquid chromatography (FPLC)-purified NgAgo after His-tagged purification. FPLC-purified NgAgo also exhibits cleavage activity, suggesting the cleavage is not due to DNase contamination.

To demonstrate that guide-independent cleavage activity is also present in vivo, we checked plasmid integrity after NgAgo expression. To visualize plasmid integrity, plasmid DNA purified from an NgAgo-induced strain was linearized by a restriction enzyme and analyzed by gel electrophoresis. Our result showed that NgAgo expression degrades the expression plasmid DNA (FIG. 4C), as evidenced by the smearing on the gel.

Collectively, our results demonstrated that soluble NgAgo, but not the refolded NgAgo, guide-independently cuts plasmid DNA, consistent with the previous in vitro study by Sunghyeok, Y (2017), suggesting that refolded NgAgo may not be fully functional. Additionally, the guide-independent cleavage activity of NgAgo may explain why there is no specific DNA cleavage activity detected in earlier studies (Javidi-Parsijani, P., et al., *Plos One*, 2017, 12, 14).

RepA Domain Contributes to Guide-Independent Cleavage Activity

To test the requirement of the repA domain for cleavage activity, we constructed a repA deletion mutant, which named as N-del. We miniprepped the plasmid DNA after N-del mutant expression in *E. coli* and performed agarose gel electrophoresis to check the integrity of the plasmid with the same amount of DNA loading. Our results showed that deletion of the repA domain significantly reduced plasmid degradation compared to wild-type NgAgo (FIG. 4C). Although it is unknown whether host factors participate in the process, our results suggest that the repA domain contributes to the guide-independent cleavage activity in *E. coli*. Interestingly, expression of repA domain alone also induces plasmid degradation (FIG. 4C). RT-PCR showed that expression of repA domain induced recBCD-mediated DNA repair pathway in *E. coli*.

To understand the impact of the repA domain, we analyzed the global gene expression by RNAseq. RNAseq analysis showed that repA induced several critical genes.

Canonical Catalytic Tetrad Contributes to Guide-Independent Cleavage Activity

To study whether catalytic tetrad contributes to DNA cleavage ability, we constructed the double mutant (D663A/D738A) with and without repA domain, which eliminates the degradation ability contributed by repA. Since double mutant of TtAgo (D478A/D546A) loses guide binding ability and DNA cleavage activity, we hypothesized that mutations corresponding to NgAgo may also lose cleavage activity. Indeed, plasmid integrity assay with gel electrophoresis showed that double mutant has more intact plasmid DNA compared to wild-type and combining the repA deletion with double mutant retains even more intact DNA, indicating catalytic tetrad of NgAgo is required for guide-independent cleavage activity. We also observed there is still some degradation when we expressed the N-del/double mutant. Further research is needed for investigating this phenomenon.

RepA Domain Induces DNA Arrangement in *E. coli*

Figure 6A:
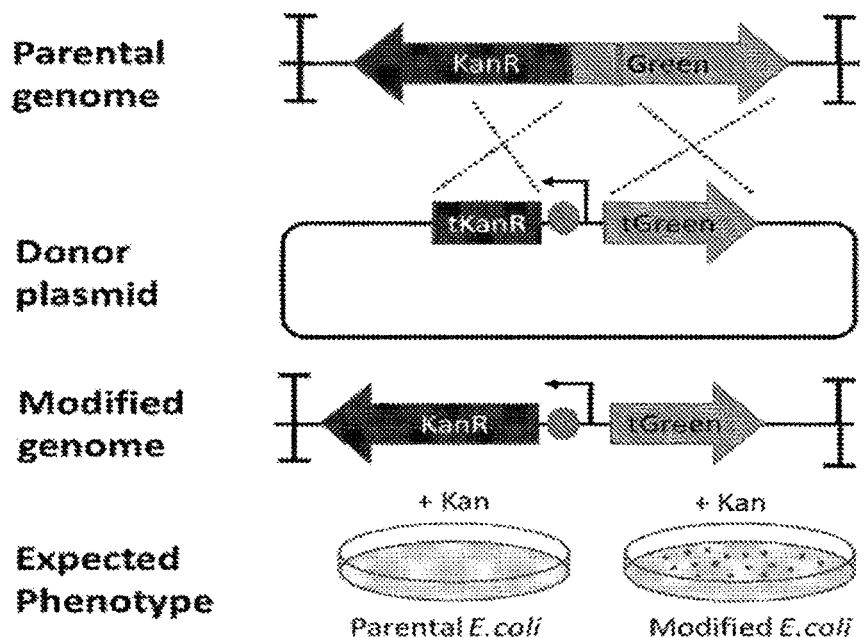
FIGS. 6A-6C demonstrate the detailed process of DNA editing in E. coli using NgAgo or its mutants, revealing a modest level of gene editing efficiency of NgAgo variants in E. coli. NgAgo variants were transformed to BL21 (DE3) harboring the donor plasmid, p15-kanR-Ptetred, and streaked on LB agar plate containing 100 µg/ml ampicillin and 25 µg/ml chloramphenicol at 37° C for 16 hours. Single colony was inoculated in LB containing ampicillin and chloramphenicol at 37° C for 16 hours. Liquid culture were expanded with 100-fold dilution in LB containing ampicillin and chloramphenicol at 37° C. until OD600 reach 0.5. Cells were made electro-competent and transformed with FW, RV, both or no guides and resuspended in LB for an hour containing ampicillin, chloramphenicol, and 0.1 mM IPTG at 37° C. Cultures were diluted 10-fold in LB containing ampicillin, chloramphenicol, 0.1 mM IPTG, and 50 µg/ml anhydrotetracycline at 37° C for 2 hours. Cells were then plated without and with 50 µg/ml kanamycin on LB agar plate and incubated at 37° C for 16 hours. Colonies were counted. Unguided control was set to 100% while FW, RV, and both guides were normalized with the unguided control. To further confirm the gene-editing ability of the N-del mutant, we targeted the endogenous lacZ and provided a donor template with a frameshifted lacZ as to repair (FIG. 6C).

We tested if the N-del mutant retains guide-dependent cleavage activity because repA domain alone contributes to plasmid DNA degradation, which may hinder site-specific gene modification. We created BL21 (DE3) strain harboring a cassette to perform a gene-editing assay. The cassette is composed of a KanR gene and a mNeonGreen gene without RBS and promoter, flanked by two double terminators (FIG. 6A). This arrangement prevents any KanR/mNeonGreen expression from readthrough, transcription, and translation. Since DNA breaks in *E. coli* are lethal, only correct recombinants will survive on kanamycin plates when provided with donor plasmid, which harbors a truncated mNeonGreen, a constitutive promoter, an RBS and a truncated KanR (FIG. 6A). Our results showed that without the guide, wild-type NgAgo decreased the survival dramatically compared to the N-del mutant, even only with an hour recovery with IPTG induction in LB broth. We also observed GFP-expressing cells in wild-type NgAgo transformants but not N-del mutant transformants, indicating DNA rearrangement because the mNeonGreen gene does not have a promoter and an RBS either before or after recombination event. We also observed more colonies of N-del mutant compare to the wild-type NgAgo, consistent with the results of previous experiment (FIG. 4A), supporting the notion that N-del mutant has less plasmid degradation ability.

Figure 6B:
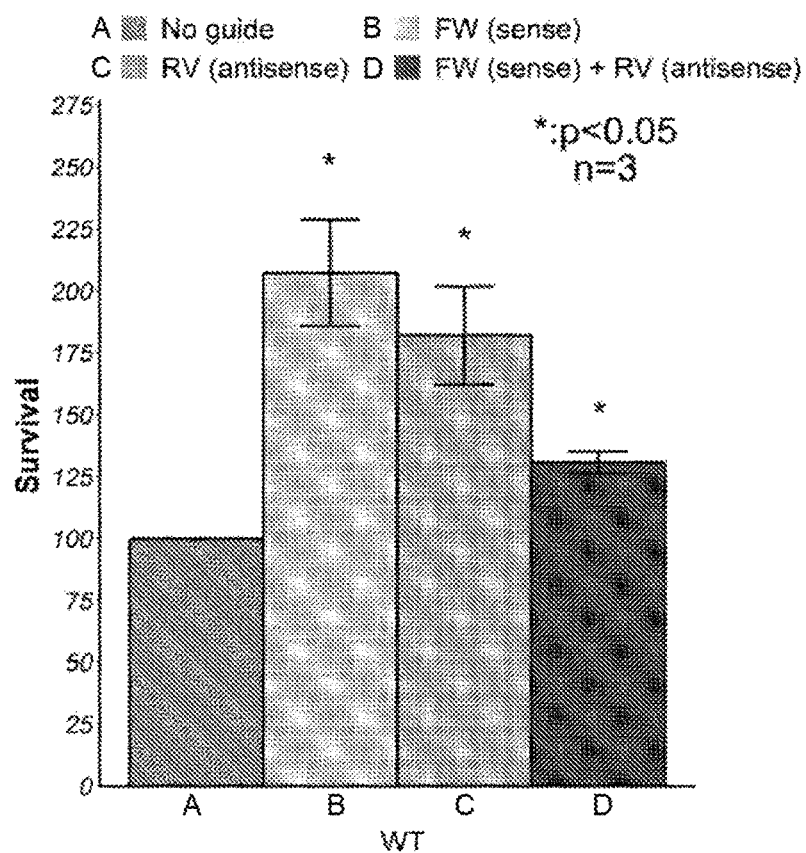
Figure 6C:
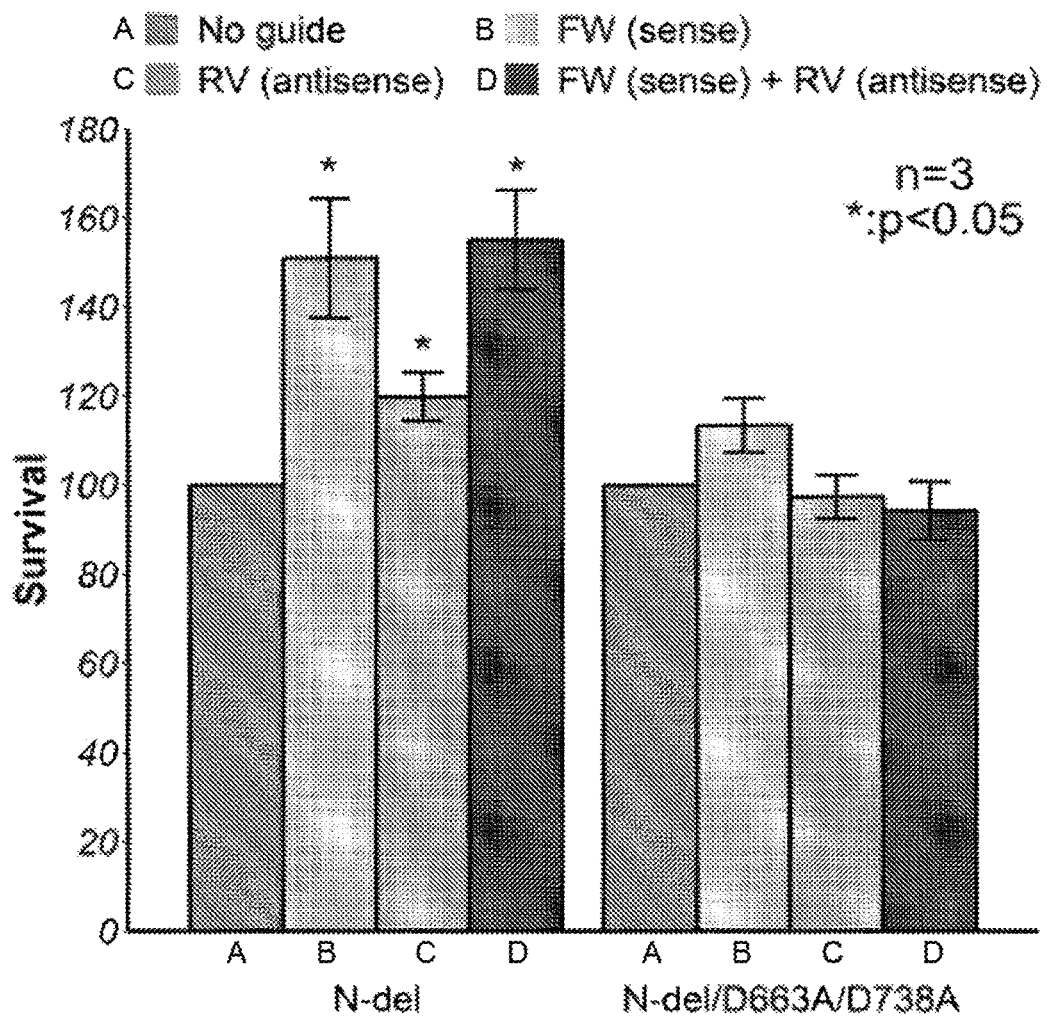

As demonstrated by FIGS. 6A-6C, Lambda recombinase comprises of gamma, beta, and exo proteins. Bacteria like *E. coli* don't have these homologous proteins. During DNA double-stranded break, *E. coli* is likely to die if there is no DNA repair. DNA repair happens when there is donor DNA and lambda red recombinase. Long story short, lambda recombinase repair the DNA lesion using donor plasmid as a template via a mechanism called homologous recombination. Without either donor DNA or the lambda recombinase, repair and subsequent gene editing would fail.

Lambda red system has previously been used to help homologous recombination in bacteria. In our system, we used NgAgo to create a specific cut in the GFP. Donor plasmid with homologous sequence serves as a template to repair the DNA lesion with the help of recombinase. As you can see in the genome, KanR does not have the arrow/oval shape, which indicates the sequences required for gene expression. Without KanR expression, cells with this DNA cassette can't grow on kanamycin plate. For the donor plasmid, truncated KanR has the arrow/oval shape, which drives the expression of truncated KanR. However, as KanR is truncated, it is not functional. So, cells only with correct modification of KanR by repair mechanism helped by donor plasmid and lambda red can grow on kanamycin plate.

FIG. 7 shows exogenously introduction of one microgram of ssDNA is nontoxic to the *E. coli*. Different concentration (250 ng, 500 ng, 750 ng, and 1000 ng) of ssDNAs are transformed to BL21 (DE3) by electroporation and plated on LB plate with different dilution factors (1000×, 2000× and 5000×) at 37° ° C. for 16-20 hours.

FIG. 8A shows BL21 (DE3) harboring inducible BFP expression plasmid was made electrocompetent and transformed with D4PA-labelled Red-ssDNA. After transformation, cells were resuspended in SOC in the presence of 0.1 mM IPTG and 100 µg/ml ampicillin at 37° C. BFP expression is observed after 3 hr transformation. Red-ssDNA is still present after three hours transformation. FIG. 8B depicts BL21 (DE3) harboring inducible BFP expression was induced with 0.1 mM IPTG before it made to electrocompetent cells at 37° C. After transformation with either 500 ng or 1000 ng Red-ssDNA, Red-ssDNA still present in the cells. FIG. 8C shows the timeline of ssDNA stability and protein expression at 37° C.

FIGS. 9A-9B demonstrates that mNeonGreen of pIncw-green does not express. RNA from BL21 (DE3) harboring pIncw-green was extracted and reverse transcribed and tested to see if mNeonGreen from pIncw-green is expressed. FIG. 9A depicts RNA polymerase subunit, rpoz, was successfully amplified with cDNA from BL21 (DE3) harboring pIncw-Green, indicating successful reverse transcription. mNeonGreen-integrated genomic DNA and wildtype genomic DNA were used as positive control to amplify mNeonGreen. FIG. 9B shows that mNeonGreen (~800 bp) was amplified with cDNA from BL21 (DE3) harboring pIncw-Green, pNCS-mNeonGreen plasmid DNA, and wildtype genomic DNA. mNeonGreen expression was not detected in BL21 (DE3) harboring pIncw-mNeonGreen.

FIG. 10 shows soluble NgAgo nicks/cuts plasmid by using Han's protocol. Five micrograms of soluble NgAgo was incubated with 300 ng of guides at 55° C. for an hour and subsequent incubated with 400 ng of pNCS-mNeon-Green plasmid for 2 hours with 50 µl final volume (working concentration: 20 mM Tris-Cl, 300 mM KCl, 500 µM MgCl$_2$, and 2 mM DTT). Total 0.8 unit of Proteinase K was added to the samples to digest the protein for 5 minutes at 37° C. The nucleic acids were then cleaned up and loaded with loading dye containing SDS for gel electrophoresis.

Figure 11A:
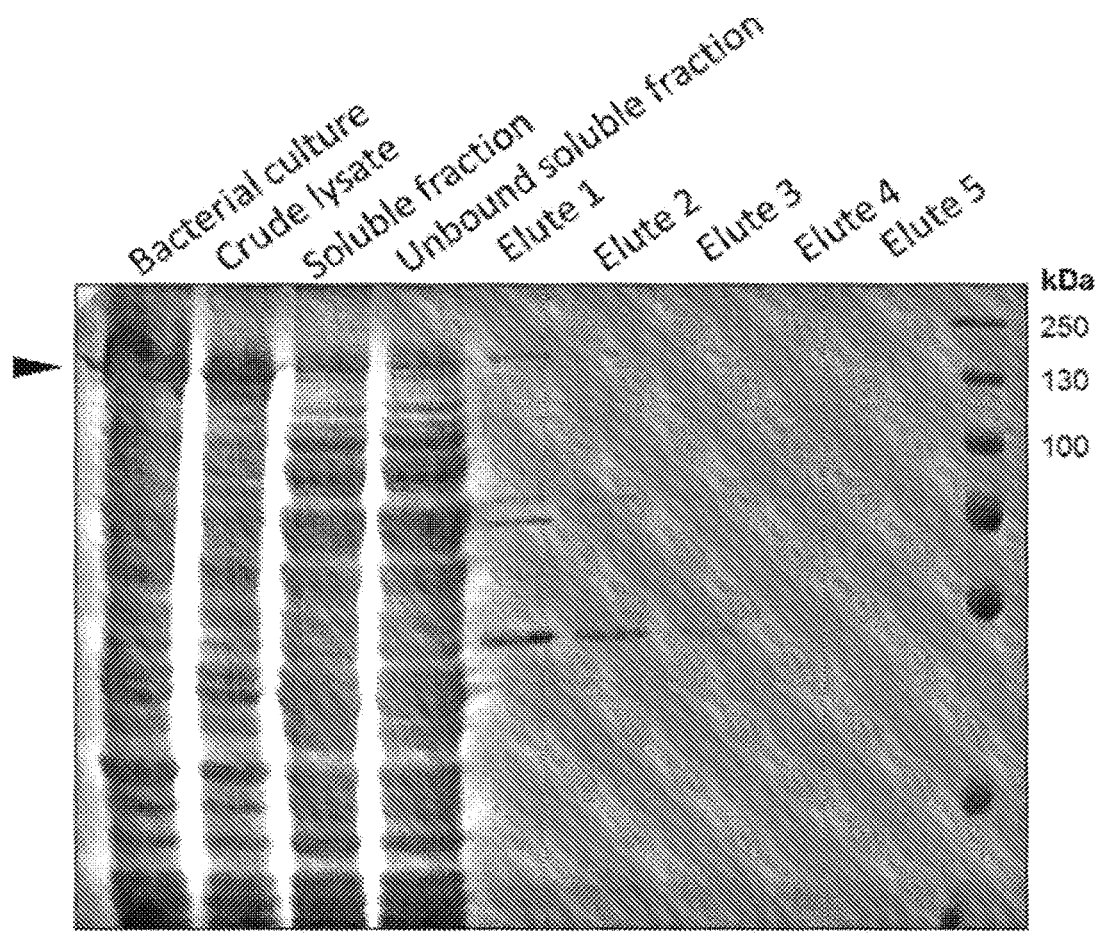
FIG. 11A shows SDS-PAGE analysis of purified wildtype NgAgo from soluble fraction (sNgAgo)
Figure 11B:
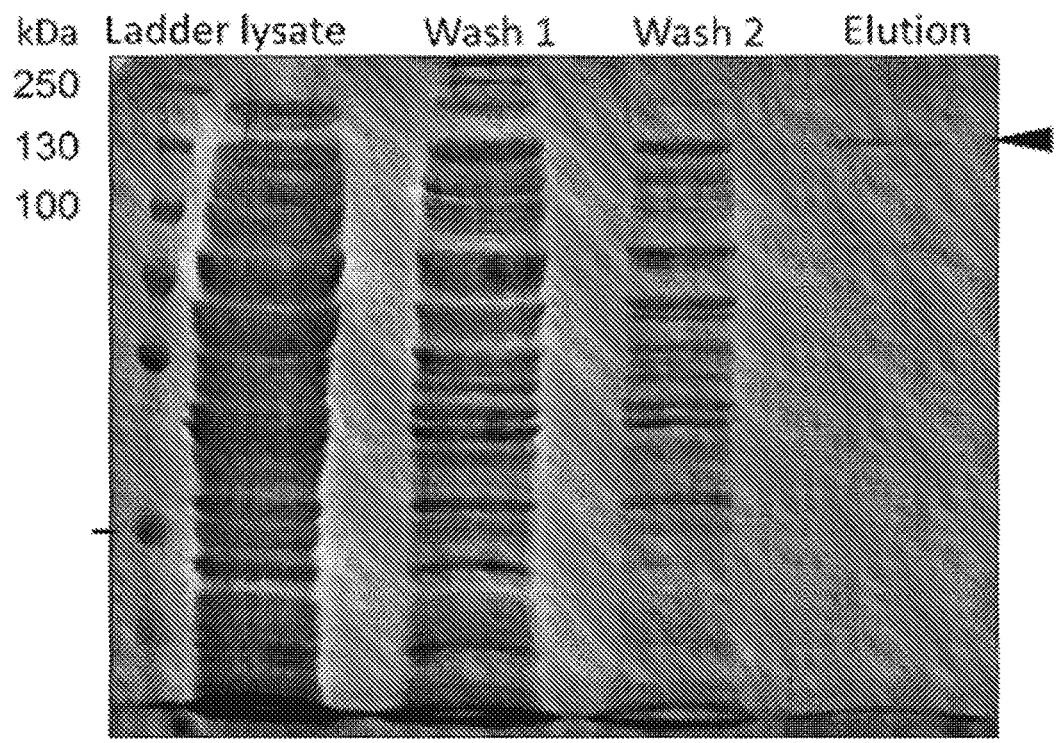
FIG. 11B shows SDS-PAGE analysis of purified wildtype NgAgo from insoluble fraction after refolding (rNgAgo)
Figure 11C:
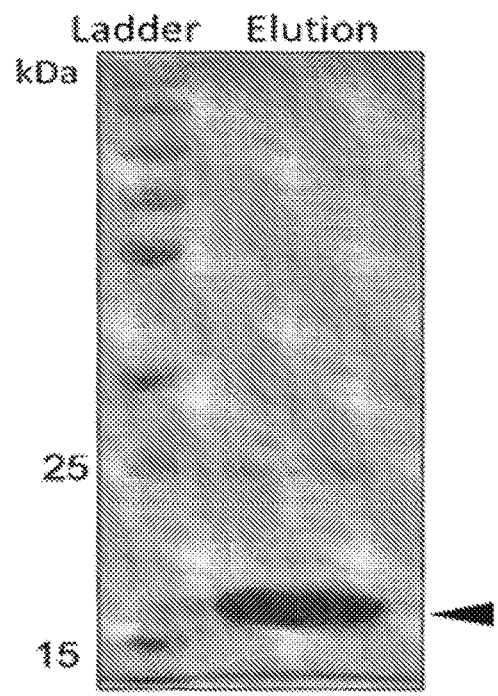
FIG. 11C shows SDS-PAGE analysis of purified repA. Soluble repA was purified similarly to the soluble NgAgo. His-tagged NgAgo (pET-His-Ago) was transformed into BL21 (DE3) electrocompetent cells and was plated on agar plates containing ampicillin (100 μg/ml). A single colony was inoculated in LB with ampicillin for 16 hours and then cultured in 100 ml of LB containing ampicillin for 16 hours. Liquid culture was diluted to 100-fold in LB containing ampicillin. IPTG was added to the liquid culture when the OD600 reached 0.5 with 0.1 mM final concentration. After 4 hours incubation at 37° C., cells were collected by centrifuge 7500 rpm at 4° C. for 5 minutes. Pellet was resuspended in TN buffer (10 mM Tris and 100 mM NaCl, pH 7.5). Sonication was carried out with power of 5 for 5 cycles of ten seconds rest and ten seconds sonication to lyse the cells. Cell lysates were centrifuged 12000 rpm at 4° C. for 30 minutes. The supernatant was collected as a soluble protein fraction and purified via His-IDA nickel column (Clontech Laboratories, Mountain View, CA. Cat. No: 635657) according to the manufacturer instructions, particularly Gravity-Flow Column purification protocol, generating fractions used in (a). Guanidium chloride (6M) was used in the denaturing protocol provided by the manufacturer, and the protein was refolded on the column with buffer containing 50 mM sodium phosphate, 300 mM sodium chloride, 40 mM imidazole, and 1M NaCl (pH 7.4). Then the protein was washed with the wash buffer (50 mM sodium phosphate, 300 mM sodium chloride, 40 mM imidazole; pH 7.4) prior to elution with buffer containing 50 mM sodium phosphate, 300 mM sodium chloride, and 300 mM imidazole (pH 7.4). Fractions generated from denaturing protocol were analyzed by SDS-PAGE.

SDS-PAGE analysis of His-tag purified wildtype NgAgo and repA. FIG. 11A shows SDS-PAGE analysis of purified wildtype NgAgo from soluble fraction (sNgAgo); FIG. 11B shows SDS-PAGE analysis of purified wildtype NgAgo from insoluble fraction after refolding (rNgAgo); and FIG. 11C shows SDS-PAGE analysis of purified repA. Soluble repA was purified similarly to the soluble NgAgo. His-tagged NgAgo (pET-His-Ago) was transformed into BL21 (DE3) electrocompetent cells and was plated on agar plates containing ampicillin (100 µg/ml). A single colony was inoculated in LB with ampicillin for 16 hours and then cultured in 100 ml of LB containing ampicillin for 16 hours. Liquid culture was diluted to 100-fold in LB containing ampicillin. IPTG was added to the liquid culture when the OD600 reached 0.5 with 0.1 mM final concentration. After 4 hours incubation at 37° C., cells were collected by centrifuge 7500 rpm at 4° C. for 5 minutes. Pellet was resuspended in TN buffer (10 mM Tris and 100 mM NaCl, pH 7.5). Sonication was carried out with power of 5 for 5 cycles of ten seconds rest and ten seconds sonication to lyse the cells. Cell lysates were centrifuged 12000 rpm at 4° C. for 30 minutes. The supernatant was collected as a soluble protein fraction and purified via His-IDA nickel column (Clontech Laboratories, Mountain View, CA. Cat. No: 635657) according to the manufacturer instructions, particularly Gravity-Flow Column purification protocol, generating fractions used in (a). Guanidium chloride (6M) was used in the denaturing protocol provided by the manufacturer, and the protein was refolded on the column with buffer containing 50 mM sodium phosphate, 300 mM sodium chloride, 40 mM imidazole, and 1M NaCl (pH 7.4). Then the protein was washed with the wash buffer (50 mM sodium phosphate, 300 mM sodium chloride, 40 mM imidazole; pH 7.4) prior to elution with buffer containing 50 mM sodium phosphate, 300 mM sodium chloride, and 300 mM imidazole (pH 7.4). Fractions generated from denaturing protocol were analyzed by SDS-PAGE.

Figure 12A:
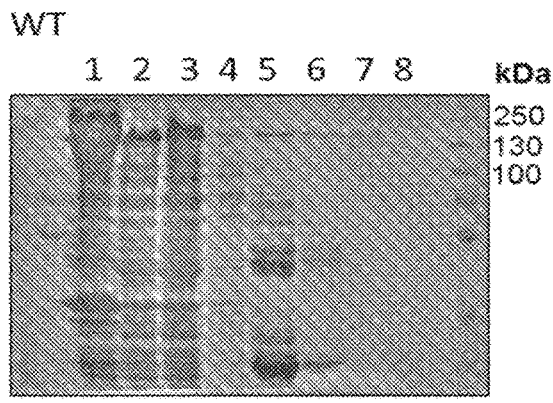
FIG. 12A shows SDS-PAGE analysis of GST-tag purified wildtype NgAgo.
Figure 12B:
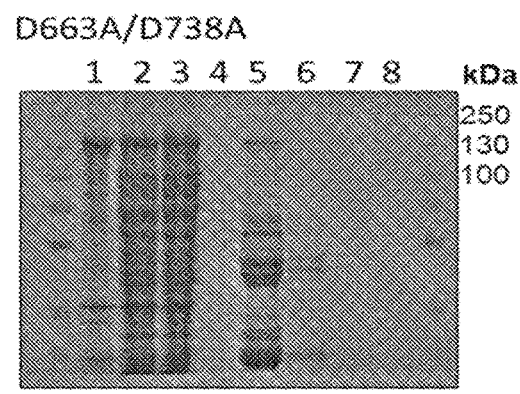
FIG. 12B shows SDS-PAGE analysis of GST-tag purified D663A/D738A.
Figure 12C:
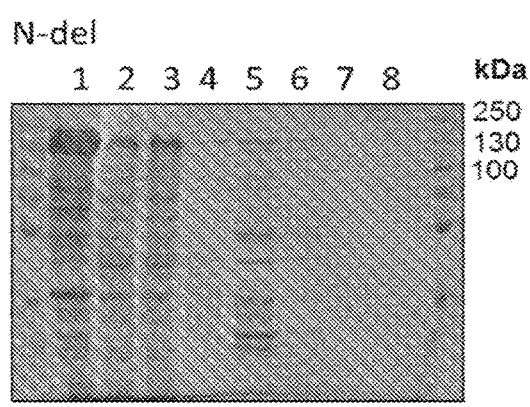
FIG. 12C shows SDS-PAGE analysis of GST-tag purified N-del.
Figure 12D:
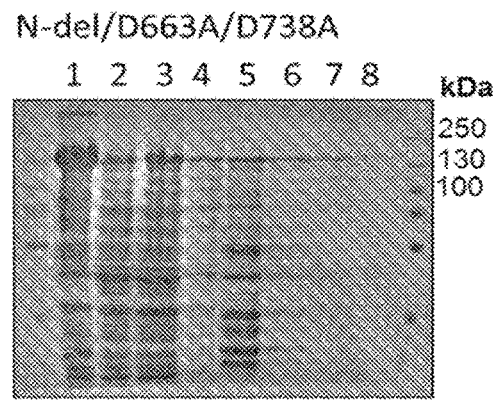
FIG. 12D shows SDS-PAGE analysis of GST-tag purified N-del/D663A/D738A. For FIGS. 12A-12D of SDS-PAGE analysis of GST-tag purified soluble NgAgo variants, Lane #1: whole cell lysate; Lane #2: soluble fraction; Lane #3: unbound soluble fraction; Lane #4: washed fraction; Lanes #5-8: eluted fraction 1-4. Conditions: GST-tagged NgAgo variants were transformed into BL21 (DE3) electrocompetent cells and were plated on agar plates containing ampicillin (100 μg/ml) at 37° C. for 16 hours. A single colony was inoculated in LB with ampicillin for 16 hours and then diluted with 100-fold of LB containing ampicillin. IPTG was added to the liquid culture when the OD600 reached 0.5 with 0.1 mM final concentration. After 4 hours incubation at 37° C., cells were collected by centrifuge 7500 rpm at 4° C. for 5 minutes. Pellet was resuspended in TN buffer (10 mM Tris and 100 mM NaCl, pH 7.5). Sonication was carried out with power of 5 for 5 cycles of ten seconds rest and ten seconds sonication to lyse the cells. Cell lysates were centrifuged 12000 rpm at 4° C. for 30 minutes. The supernatant was collected as a soluble protein fraction and purified via glutathione agarose (Thermo Fisher Scientific, Waltham, MA. Cat. No: 16100) according to the manufacturer protocol. Whole cell lysates, soluble fractions, unbound soluble fractions, washed fractions, and eluted fractions from NgAgo variants were generated and analyzed via SDS-PAGE.

FIG. 12A shows SDS-PAGE analysis of GST-tag purified wildtype NgAgo. FIG. 12B shows SDS-PAGE analysis of GST-tag purified D663A/D738A. FIG. 12C shows SDS-PAGE analysis of GST-tag purified N-del. FIG. 12D shows SDS-PAGE analysis of GST-tag purified N-del/D663A/D738A. For FIGS. 12A-12D of SDS-PAGE analysis of GST-tag purified soluble NgAgo variants, Lane #1: whole cell lysate; Lane #2: soluble fraction; Lane #3: unbound soluble fraction; Lane #4: washed fraction; Lanes #5-8: eluted fraction 1-4. Conditions: GST-tagged NgAgo variants were transformed into BL21 (DE3) electrocompetent cells and were plated on agar plates containing ampicillin (100 µg/ml) at 37 °C for 16 hours. A single colony was inoculated in LB with ampicillin for 16 hours and then diluted with 100-fold of LB containing ampicillin. IPTG was added to the liquid culture when the OD600 reached 0.5 with 0.1 mM final concentration. After 4 hours incubation at 37° C., cells were collected by centrifuge 7500 rpm at 4° C. for 5 minutes. Pellet was resuspended in TN buffer (10 mM Tris and 100 mM NaCl, pH 7.5). Sonication was carried out with power of 5 for 5 cycles of ten seconds rest and ten seconds sonication to lyse the cells. Cell lysates were centrifuged 12000 rpm at 4° C. for 30 minutes. The supernatant was collected as a soluble protein fraction and purified via glutathione agarose (Thermo Fisher Scientific, Waltham, MA. Cat. No: 16100) according to the manufacturer protocol. Whole cell lysates, soluble fractions, unbound soluble fractions, washed fractions, and eluted fractions from NgAgo variants were generated and analyzed via SDS-PAGE.

Figure 13:
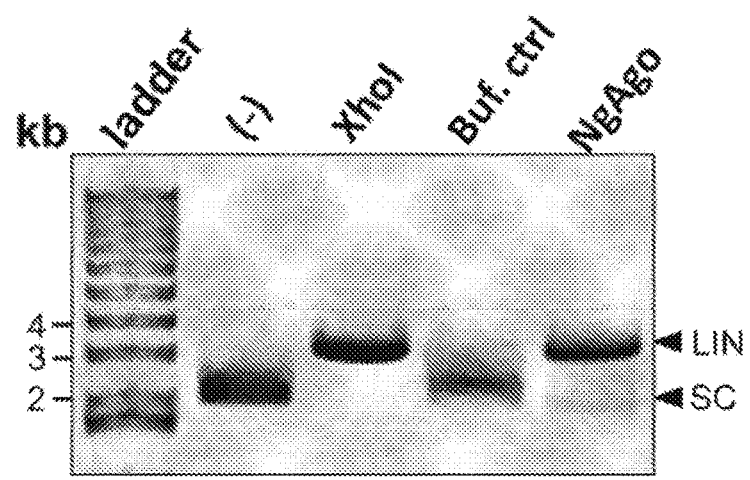
FIG. 13 demonstrates sNgAgo cuts unrelated plasmid DNA.

FIG. 13 demonstrates sNgAgo cuts unrelated plasmid DNA.

Figure 14:
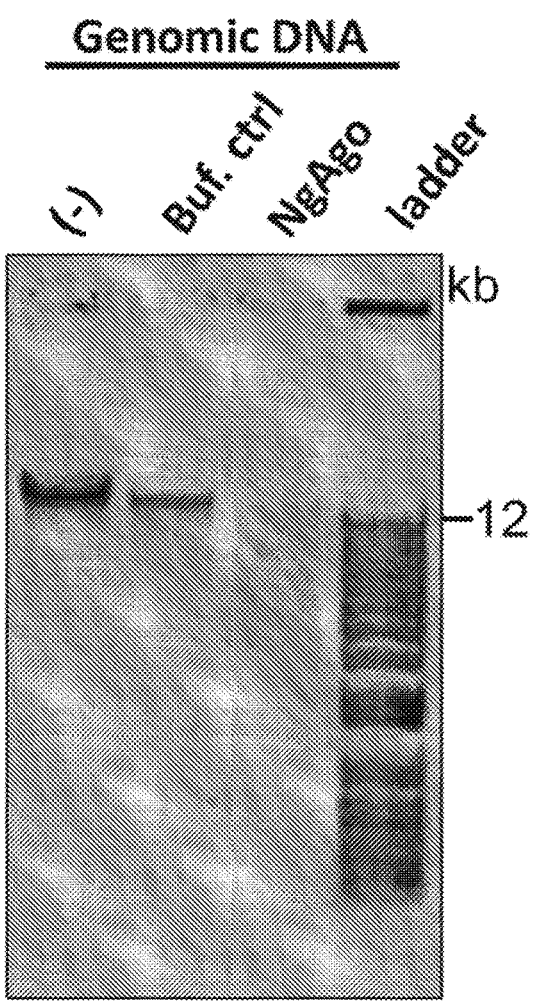
FIG. 14 shows sNgAgo cuts genomic DNA.

FIG. 14 shows sNgAgo cuts genomic DNA.

Figure 15:
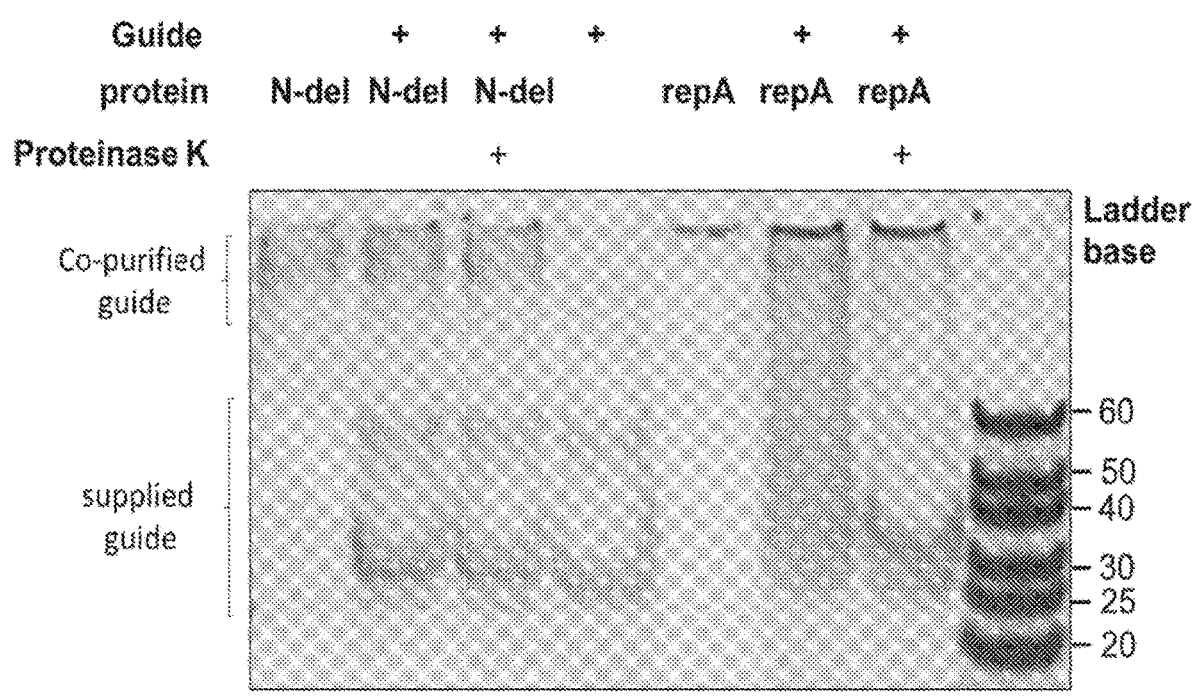
FIG. 15 shows repA binds single-stranded DNA. Electrophoretic mobility shift assay (EMSA) of N-del and repA domain with guides. N-del does not show band shifting while repA treatment shifts the bands, indicating ssDNA binding. Note N-del co-purified guides.

FIG. 15 shows repA binds single-stranded DNA. Electrophoretic mobility shift assay (EMSA) of N-del and repA domain with guides. N-del does not show band shifting while repA treatment shifts the bands, indicating ssDNA binding. Note N-del co-purified guides.

Figure 16:
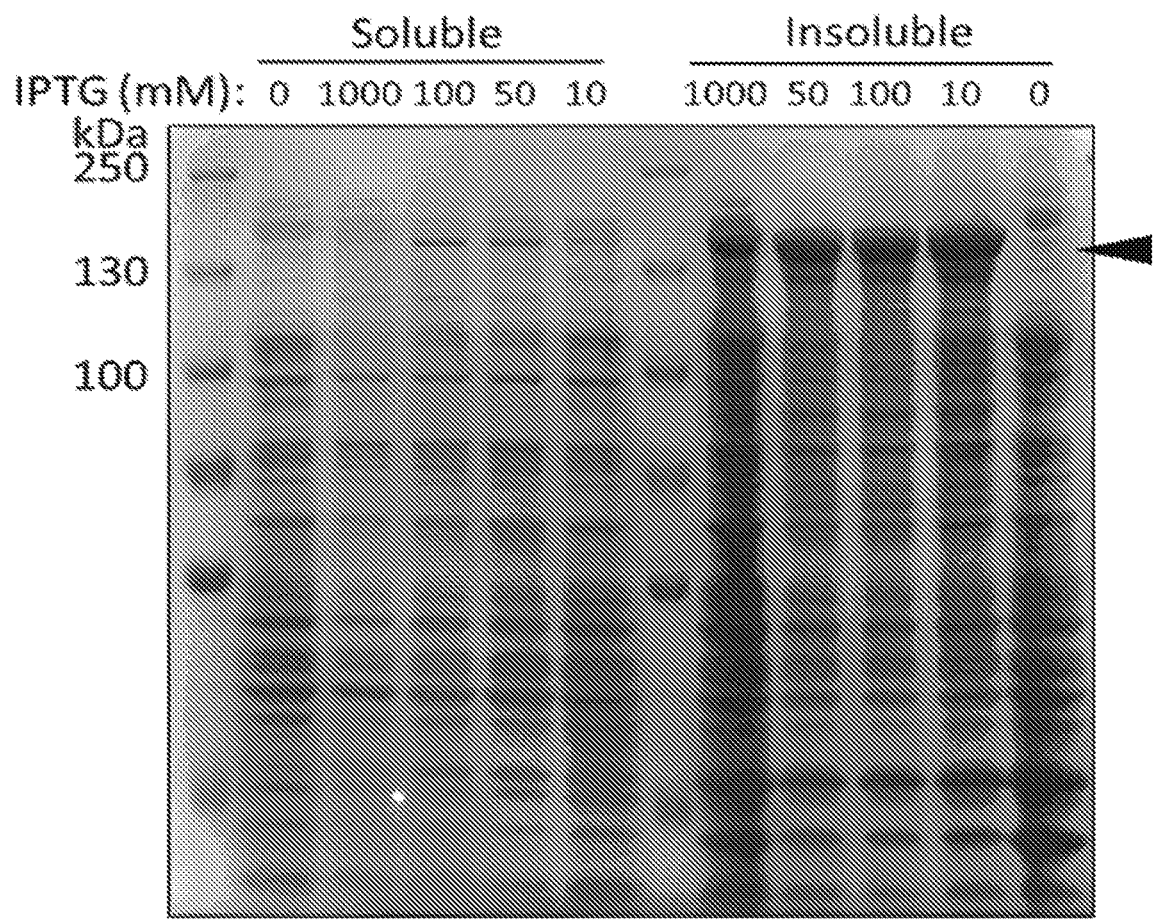
FIG. 16 shows optimization of soluble NgAgo protein expression. Different IPTG concentrations (1000 mM, 100 mM, 50 mM, and 10 mM) were used to induce GST-NgAgo expression. Soluble and insoluble protein fractions were analyzed by SDS-PAGE to determine the optimal conditions for soluble NgAgo expression.

FIG. 16 shows optimization of soluble NgAgo protein expression. Different IPTG concentrations (1000 mM, 100 mM, 50 mM, and 10 mM) were used to induce GST-NgAgo expression. Soluble and insoluble protein fractions were analyzed by SDS-PAGE to determine the optimal conditions for soluble NgAgo expression.

Figure 17A:
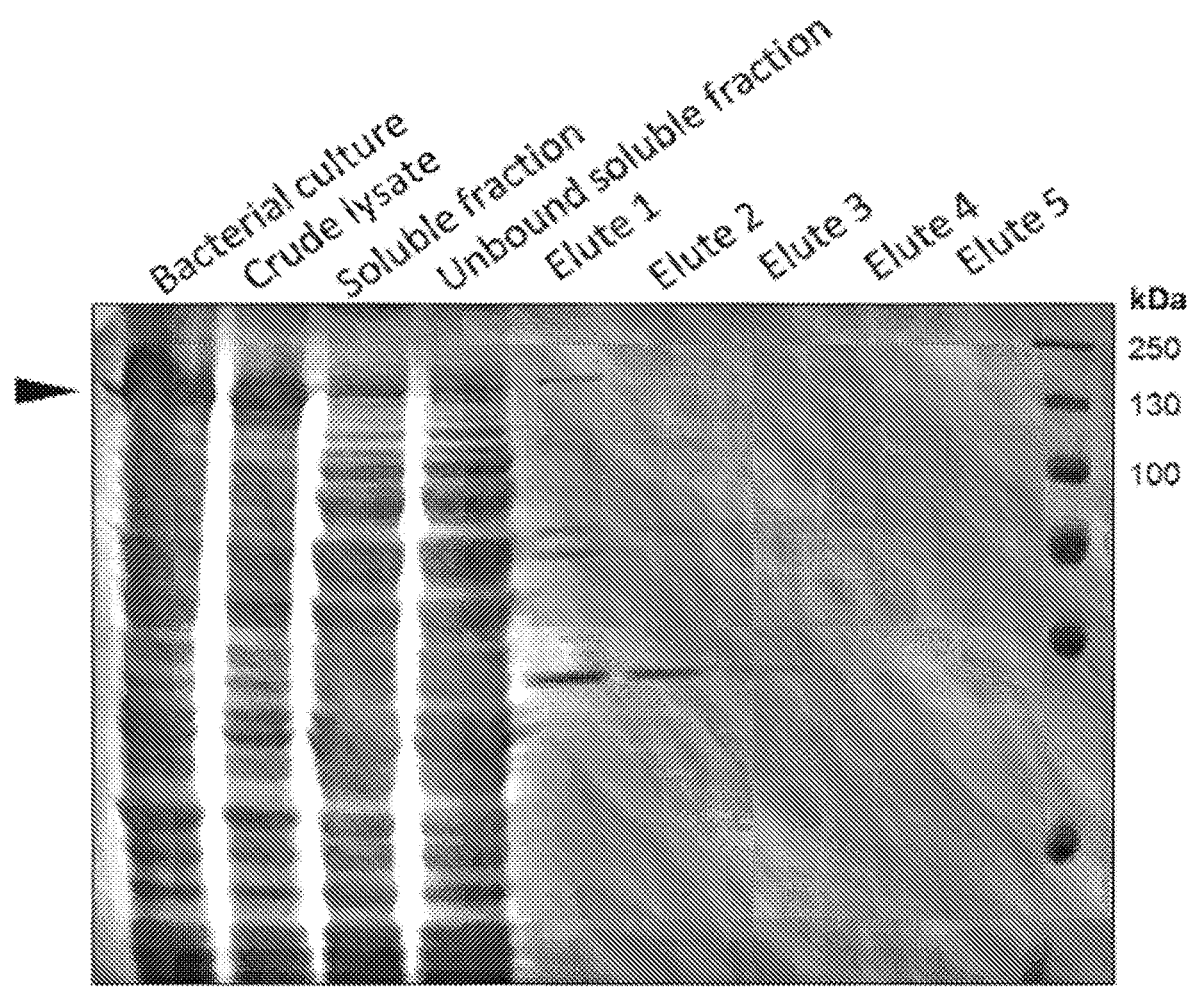
FIGS. 17A-17C depict SDS-PAGE analysis of His-tag purified NgAgo variants.
Figure 17B:
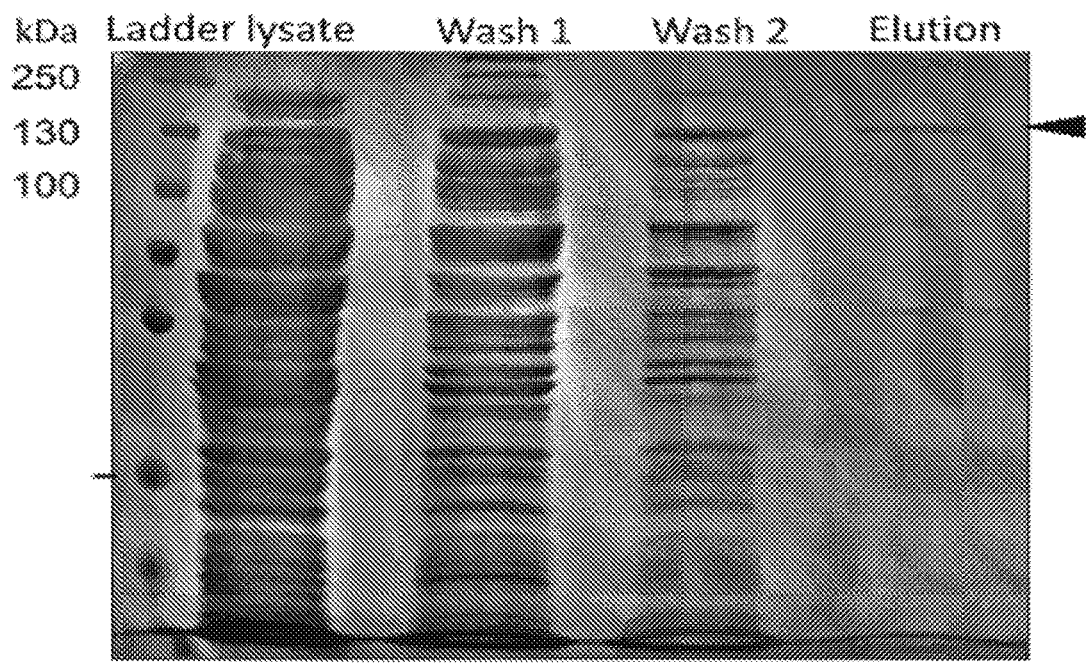
Figure 17C:
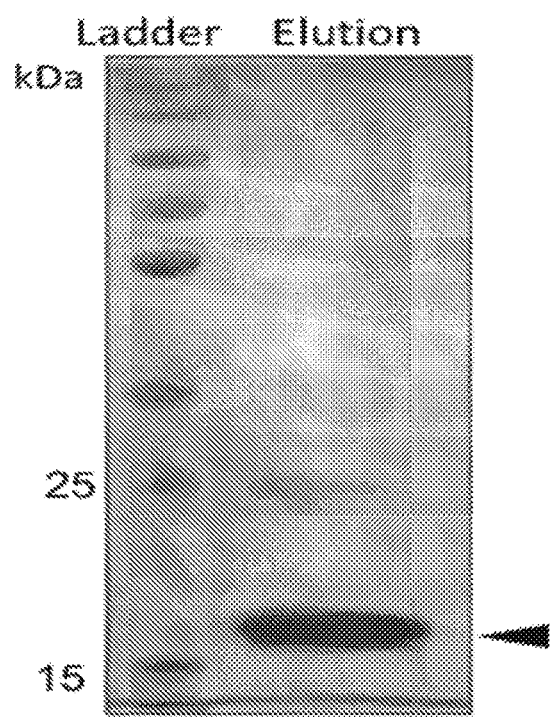

FIGS. 17A-17C depict SDS-PAGE analysis of His-tag purified NgAgo variants. FIG. 17A shows SDS-PAGE analysis of purified WT NgAgo from soluble fraction (sNgAgo). FIG. 17B shows SDS-PAGE analysis of purified WT NgAgo from insoluble fraction after refolding (rNgAgo). FIG. 17C shows SDS-PAGE analysis of purified repA.

Figure 18A:
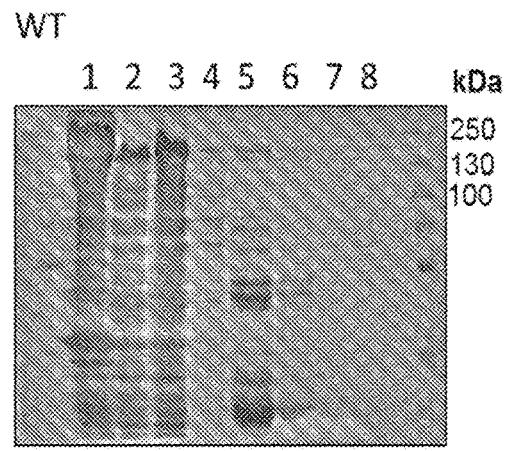
FIGS. 18A-18D depict SDS-PAGE analysis of GST-tag purified soluble NgAgo variants.
Figure 18B:
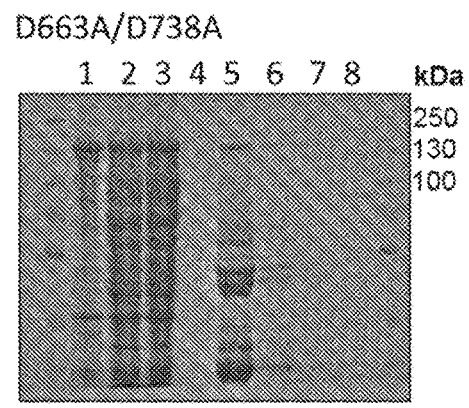
Figure 18C:
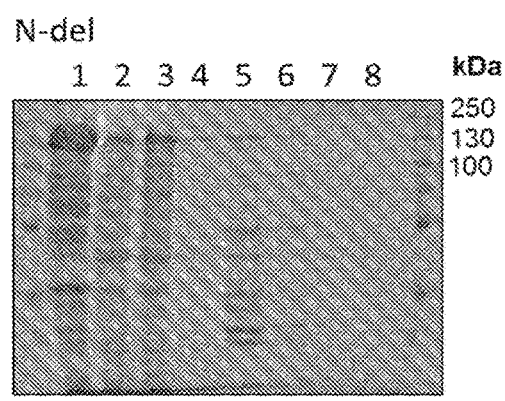
Figure 18D:
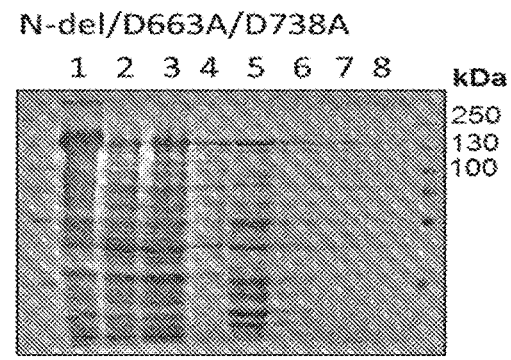

FIGS. 18A-18D depict SDS-PAGE analysis of GST-tag purified soluble NgAgo variants. FIG. 18A shows SDS-PAGE analysis of GST-tag purified WT NgAgo. FIG. 18B shows SDS-PAGE analysis of GST-tag purified D663A/D738A. FIG. 18C shows SDS-PAGE analysis of GST-tag purified N-del. FIG. 18D shows SDS-PAGE analysis of GST-tag purified N-del/D663A/D738A. Lane #1: whole cell lysate; Lane #2: soluble fraction; Lane #3: unbound soluble fraction; Lane #4 washed fraction; Lanes #5-8: eluted fraction 1-4.

N-Del Mutant Edits Target Gene in *E. coli* and Human Cells

We then use N-del mutant to perform the gene editing assay because the presence of repA domain induced DNA rearrangement. When provided with guides, the N-del mutant increased approximately 30% colony number in the selective plate (FIG. 6B), indicating specific editing ability of N-del mutant.

To further confirm the gene-editing ability of the N-del mutant, we targeted the endogenous lacZ and provided a donor template with a frameshifted lacZ as to repair (FIG. 6C). Since the lacZ product, β-galactosidase, catalyzes the conversion of colorless X-gal to a blue product, 5,5'-dibromo-4,4'-dichloro-indigo; successful recombination would inactivate β-galactosidase, resulting in the white color colonies. Blue-white colony ratio would reveal if N-del mutant capable of editing.

Why people fail to edit genomes with NgAgo? In this study, we have shown that NgAgo cuts DNA guide-independently and guide-dependently in vivo in *E. coli* and in vitro. The non-specific cleavage activity largely depends on the repA domain and the canonical catalytic tetrad site. To our knowledge, NgAgo is the first studied pAgo with an uncharacterized repA domain, indicating a new class of pAgos, as demonstrated by the phylogenetic tree analysis (FIG. 1E). Interestingly, all repA domain containing pAgos are from halophilic Archaea, indicating repA domain may be required for pAgos to function in the extreme environment. Heterologous expression of the repA domain induces plasmid degradation and upregulates several pathways involved. Despite the phenomena caused by repA domain in *E. coli*, this may not be true in the native host, Natronobacterium gregoryi. Nevertheless, these phenomena may explain why wild-type NgAgo cannot specifically edit genomes under the conditions previously examined in the literature. NgAgo is very insoluble in *E. coli*, all phenomena we have seen is due to a very small percent (less than 10%) of soluble protein. Excess ssDNA may saturate the minute concentration of soluble NgAgo for guide-dependent experiments (FIGS. 2C and 6A), preventing non-specific cleavage effect contributed by guide-independent cleavage and repA, which is a DNA binding domain. Additionally, exogeneous protein expression in Eukaryotes tends to be soluble because of the protein otherwise would be degraded. In this situation, the guides may not be enough to saturate the guide-binding site and repA, resulting in disastrous consequences by randomly cutting the plasmid and/or the genome of the host. As demonstrated by Javidi-Parsijani, transfection of NgAgo without guides restored frameshifted GFP expression, while no indel within the target site was detected. This may result from the repA-mediated DNA rearrangement effect, as demonstrated in our study.

Figure 4A:
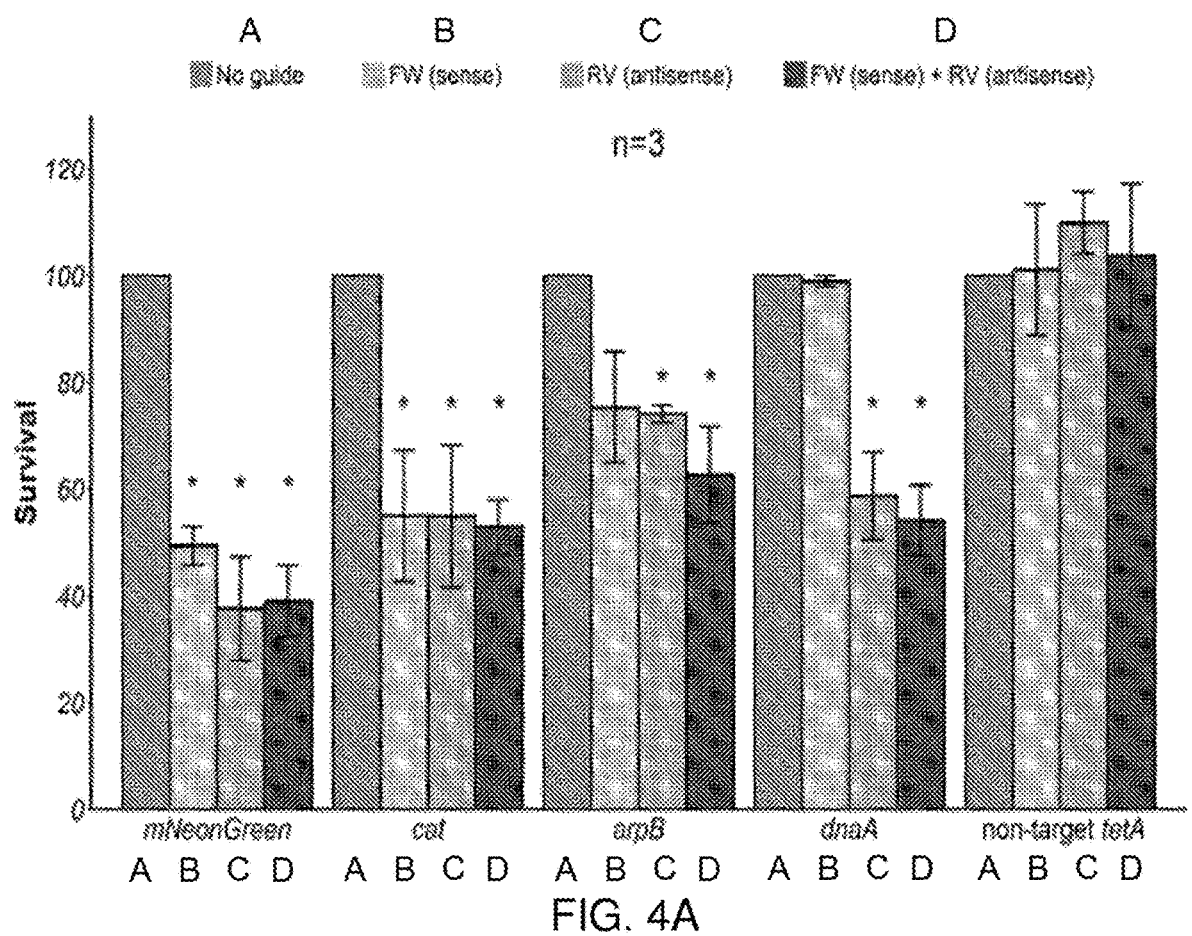
FIG. 4A shows wild-type NgAgo can be directed to cleave specific loci on the plasmid (mNeonGreen and cat) and in the genome (arpB and dnaA) of BL21 (DE3), resulting in cell death but have no effect on survival when the target, tetA, is absent at 37° C. after 16-20 hours incubation on agar plate containing ampicillin (100 µg/ml), chloramphenicol (25 µg/ml), and IPTG (0.1 mM)
Figure 4B:
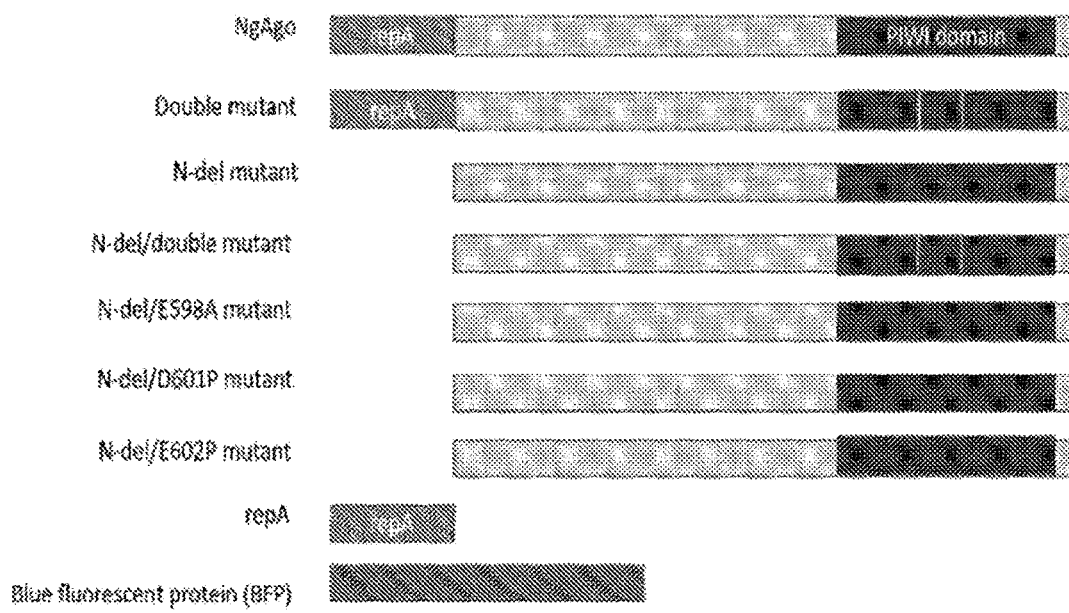
FIG. 4B shows the repA domain deletion of NgAgo (N-del) and other related mutants.
Figure 4C:
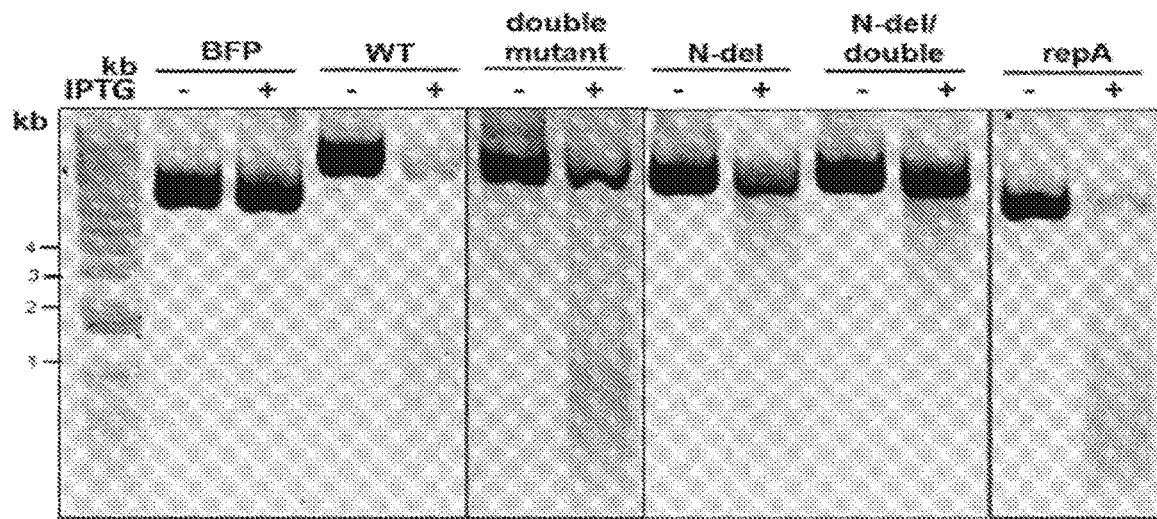
FIG. 4C shows deletions and mutations of NgAgo showed repA domain and catalytic tetrad contributes to random DNA cleavage activity.
Figure 4D:
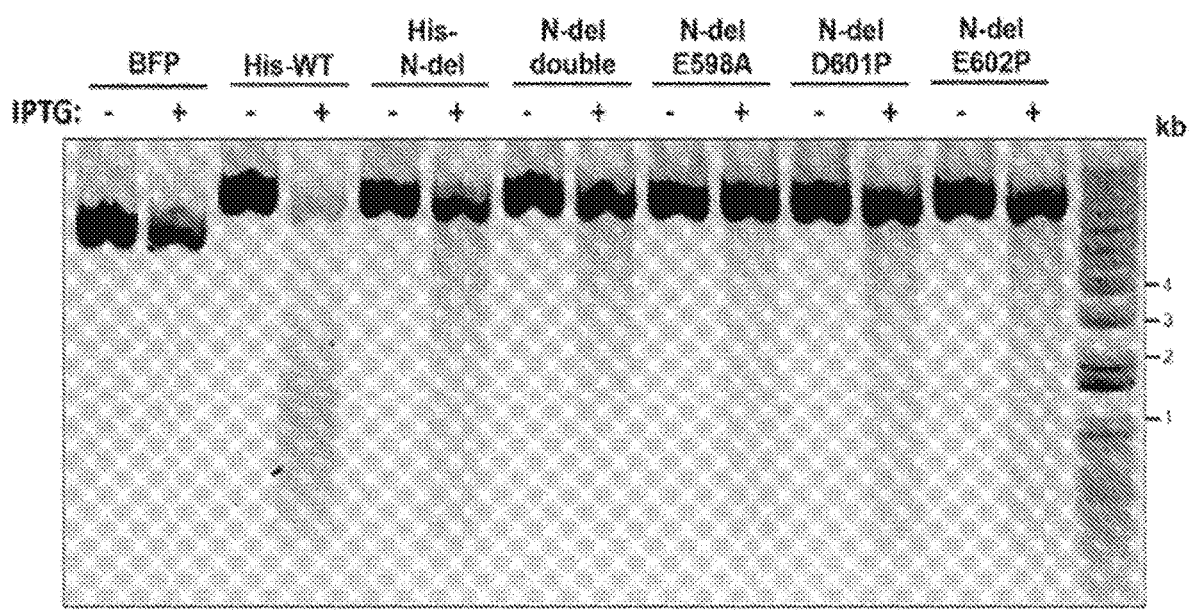
FIG. 4D shows BL21 (DE3) harboring repA domain deletion (N-del mutant) with other mutants (N-del/E598A, N-del/D601P, and N-del/E602P) were induced IPTG (0.1 mM) in the presence of ampicillin (100 µg/ml) at 37°C for four hours. Plasmids were then extracted for integrity visualization on gel-electrophoresis. N-del/E598A, N-del/D601P, and N-del/E602P showed reduced random DNA cleavage activities, which may serve as alternative mutants for gene-editing.
Figure 5A:
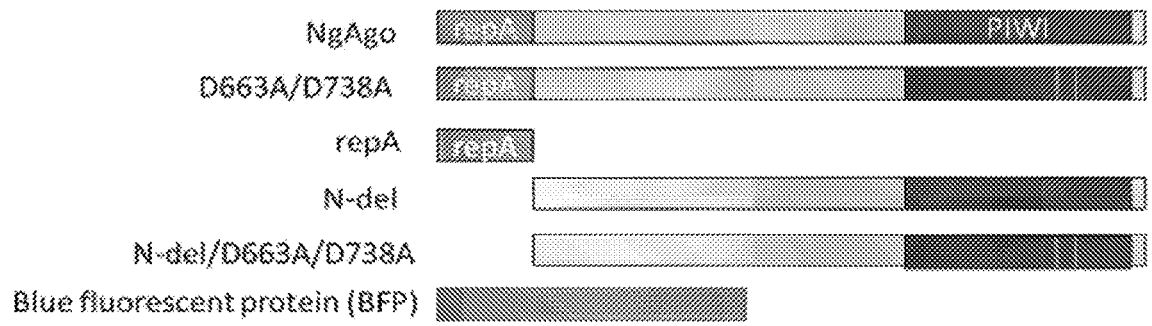
FIGS. 5A-5B demonstrates that NgAgo variants cut and nick plasmid DNA.
Figure 5B:
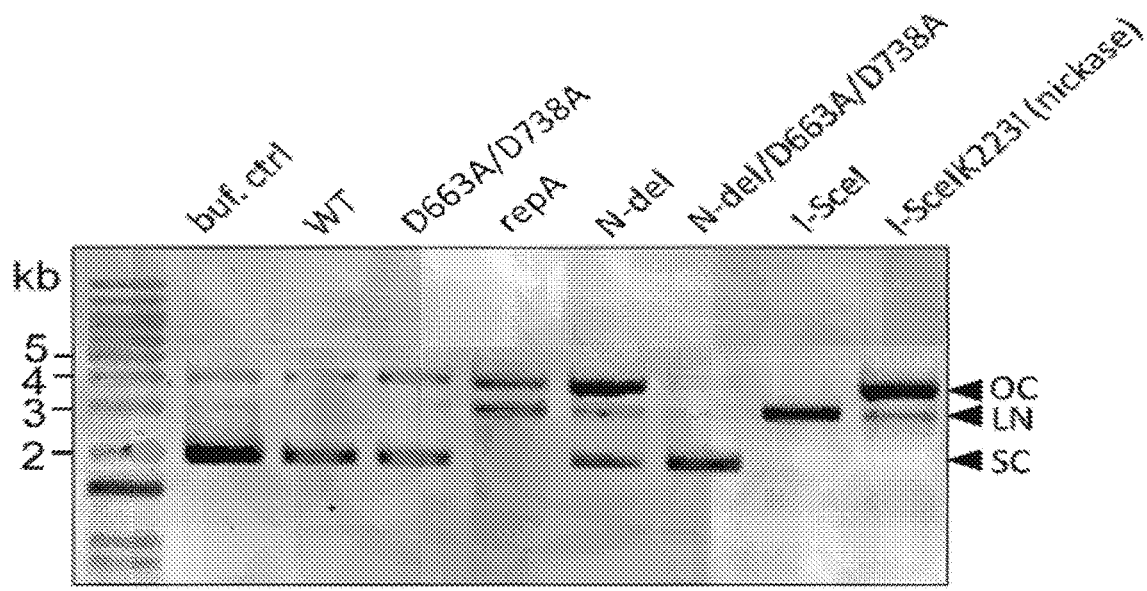

Why does repA only found in halophilic pAgos? We also found that the repA domain contributes to non-specific DNA cleavage activity (FIG. 4A). Although a detailed mechanism in the native host is unknown, our current hypothesis is that the repA domain directly or indirectly helps to unwind dsDNA, enabling NgAgo to nick one strand of DNA. Since high salt conditions make dsDNA harder to unwind, the repA domain may help to stabilize unwound DNA, which may explain why the repA domain only occurs in halophilic pAgos. The repA domain of NgAgo does not contain an ATP binding domain, suggesting it does not have helicase activity. However, we cannot rule out that other host factors within the *E. coli* may interact with the repA domain, having some synergistic effect. Further research is needed to clarify the function of this repA domain.

NgAgo is a DNA-guided DNA endonuclease. Although work by Sunghyeok claimed that refolded NgAgo could not cut DNA in vitro (Sunghyeok, Y, et al., 2017), consistent with our observation with refolded NgAgo, we establish that soluble NgAgo can in fact cleave DNA in vitro and in vivo. This suggests the refolded NgAgo may not be fully functional. Despite cleaving RNA in a programmable manner, the reviewer argues that this may due to the contamination of RNase H (Sunghyeok, Y, et al., 2017). Although we could not prove if Rnase H is contaminated during purification, our in vivo data showed that RV (antisense) guide alone could repress gene expression without NgAgo expression (FIG. 2C), indicating endogenous RNase H may involve in DNA guide-mediated gene repression, which may explain why NgAgo catalytic mutant could not abolish the repression effect in zebrafish.

Also, the previous study also suggested other domains excluding catalytic tetrad may involve in cleavage activity as they demonstrated that all the mutants could not abolish RNA cleavage by Sunghyeok, Y, et al. (2017). In this study, we showed that the catalytic tetrad is required for DNA cleavage in the absence of the repA domain, providing solid evidence that the cleavage is dependent on NgAgo itself.

Challenge of NgAgo. In our study in *E. coli*, we observed the NgAgo is very insoluble, likely due to the structure of halophilic proteins and toxicity. Halophilic proteins adapt themselves in the high salt environment with features such as negative charges on the surface. These characteristics make the protein unstable when expressing the protein in the low salt environment. Despite fusion to a GST tag, we had only a small increase in soluble protein. As demonstrated in our study, native soluble protein, but not refolded protein, is critical for activity (FIGS. 3A and 3B). Also, the guide-independent cleavage activity may make it very insoluble because it may randomly cut the plasmid DNA and/or the genome. Though we showed that N-del mutant has modest gene-editing ability (FIG. 6A), further research is needed for improving the enzyme activity.

Overall, we discovered that an uncharacterized repA domain interferes with the DNA cleavage activity of NgAgo by degrading DNA and inducing DNA rearrangement. Deletion of repA enables programmable DNA cleavage activity and target gene editing in *E. coli* and human cells. Our work provided insight into poorly characterized NgAgo for subsequent gene-editing tool development, and shed new light on seemingly contradictory reports.

Advantages and Improvements over Existing Methods. Modification of specific genes is essential to engineering new capabilities in biological systems. Existing CRISPR technologies rely on a conserved adjacent motif to target DNA sequences for modification. Additionally, cleavage efficiency is sequence (target) dependent and can be quite low. Thus, the CRISPR is not universally functional across a genome. NgAgo does not require an adjacent motif and can thus be used at any specified gene sequence. Second, current CRISPR technologies (Cas9 and Cas12a) use RNA guides that comprise 100 nucleotides (Cas9) and 43 nucleotides (Cas12a) while this system uses smaller DNA guides (Lee, S H, et al., Nature Biotechnology, 2017, 35, 17-18). Short DNA guides are cheaper than long RNA guides, enabling cheaper functional genomics screens. Third, NgAgo protein (WT: 98 kDa; N-del: 87 kDa) is shorter compare to Cas9 (158 kDa) and Cas12a (152 kDa), which make NgAgo more efficient to deliver to the interest of organism.

Commercial applications. Engineering crops with desired behavior. Crops are essential for food production, bioprocessing, and pharmaceutical production. However, some crops may not perform at their optimal behaviors. With gene-editing tools, scientists can engineer the crops with desired behavior. The desired behavior includes but not limited to being resistant to pathogenic viruses and resistant to environmental stresses.

Optimizing microbial production. Microbes are versatile platforms for the production of stereospecific compounds in a sustainable manner. One such product is the billion-dollar anticancer drug Taxol, which is difficult to produce synthetically and is currently obtained from trees that are increasingly susceptible to climate change. Microbial production of Taxol (and other similar compounds) would be more sustainable. To enable cost-competitive production of these compounds in microbes, tools such as this invention are needed to optimize the engineered microbial pathways so that they attain maximum productivity (see analogous study with the production of ß-carotene.

Curing genetic diseases. Gene-editing tool can rectify mutations responsible for genetic diseases or mitigate the undesired conditions of genetic diseases. Some diseases have been successfully cured or mitigated the undesired phenotype in animal models by CRISPR technology. Biotech companies such as CRISPR Therapeutics, and Vertex Pharmaceuticals are moving sickle cell treatment to gene editing based clinical trials in 2018. Flexible NgAgo-based technology is needed to expand the list of curable diseases.

Methods and Materials. Plasmids construction. All of the primers used in this study are listed in Table 1. Phusion DNA polymerase (ThermoFisher Scientific, F530L) was used in all cloning procedures involving PCR. Standard cloning methods were used in all cloning procedures (Sambrook, J. et al., Molecular Cloning: a laboratory manual. Cold Spring Harbor Laboratory Press, 1989). To generate the NgAgo expression plasmid, NgAgo from the plasmid nls-NgAgo-GK (Addgene, plasmid #78253) was amplified by PCR using primers containing NotI and XhoI cut sites. PCR products were digested and ligated to pET32a-GST-ELP64 (Professor Julie Liu, Purdue University) digested with both NotI and XhoI cut sites, resulting in pET-GST-Ago-His. Site-directed mutagenesis was used to introduce a stop codon within the XhoI cut site, resulting in pET-GST-Agqc. Plasmid DNA nls-NgAgo-GK was amplified by PCR using primers containing NdeI and XhoI cut sites. PCR products were digested and ligated to pET32a-GST-ELP64 digested with both NdeI and XhoI cut sites, resulting in pET-His-Ago.

To generate the target site plasmid, fluorescent protein mNeonGreen (Allele Biotechnology) was digested with both BamHI and EcoRI from the pNCS-mNeonGreen and ligated to pCas9-CR4 digested with both BamHI and EcoRI, resulting in the p15-mNeonGreen plasmid. The intermediate p15-mNeonGreen plasmid was then digested with SpeI and XhoI and fragment carrying mNeonGreen was then ligated to pN565 digested with both SpeI and XhoI, resulting in pIncw-mNeonGreen.

Cloning of NgAgo mutants. For protein purification, NgAgo was N-terminally tagged with a 2×6×His purification tag on the pET32 expression plasmid. Mutants (D663A, E704A, D738A, and D863A) were cloned by site-directed mutagenesis using Phusion DNA polymerase according to manufacturer specifications. Double mutant (D663A/D738A) was made by subcloning via the XhoI and BsiWI restriction sites.

Generation of targeting and editing construct. To generate the targeting construct for recombineering, the fluorescent protein mNeonGreen (Allele Biotechnology) and the reporter gene KanR amplified from pTKIP-neo lacking promoter and RBS were cloned into pTKDP-hph plasmid (Kuhlman TE., et al, Nucleic Acids Research, 2010, 38, e92; Tas, H, et al, PloS One, 2015, 10, e0136963), resulting in pTKDP-KanR/mNeonGreen-hph.

To generate the donor plasmid for repair after DSB, the region after the target site of fluorescent protein mNeonGreen was amplified and ligated with PCR product of truncated KanR (amplified from pTKIP-neo) to p15-mNeonGreen digested with EcoRI and XhoI, resulting in p15-KanR. Tet promoter driven red recombinase was amplified from pTKRed and cloned to p15-KanR via XhoI site, resulting in p15-KanR-pTetRed.

Strain construction. To test the homologous recombination ability of NgAgo, a KanR-mNeonGreen target site flanked by two double terminators was introduced in the atpI locus of MG1655 (DE3) (20) via pTKDP-KanR/mNeonGreen-hph by recombineering (Tseng H. et al., Applied & Environmental Microbiology, 2009, 75, 3137-3145; Tas, H, et al, PloS One, 2015, 10, e0136963).

NgAgo expression and purification. All GST-NgAgo or His-NgAgo variants were transformed into BL21 (DE3) electrocompetent cells and were plated on agar plates containing ampicillin (100 μg/ml). A single colony was inoculated in LB with ampicillin for 16 hours and then cultured in 100 ml of LB containing ampicillin. IPTG with 0.2 mM IPTG final concentration was added to the liquid culture when the OD600 reached 0.5. After 4 hours incubation at 37° C. or 22° C. overnight, cells were collected by centrifuge 7500 rpm at 4 °C for 5 minutes. Pellet was resuspended in TN buffer (10 mM Tris and 100 mM NaCl, pH 7.5). Sonication was carried out with power of 5 for ten seconds rest and ten seconds sonication to lyse the cells. Cell lysates were centrifuged 12000 rpm at 4° C. for 30 minutes. The supernatant was collected as a soluble protein fraction and was purified via His-IDA nickel column (Clontech Laboratories, 635657) according to the manufacturer instructions.

In vitro activity assay. Purified NgAgo or RFP protein control were mixed with phosphorylated single-stranded DNA (P-ssDNA) targeting mNeonGreen (guides are listed in the Table 2) and incubated at 37° C. for 30 minutes. After pre-incubation, 200 ng of substrate plasmid DNA (pNCS-mNeonGreen or p15-KanR) were then added to the sample. The final volume of the reaction is 20 μl (20 mM Tris-Cl, 300 mM KCl, 10 μM $MnCl_2$, and 2 mM DTT). The sample was then incubated at 37 °C for an hour. Proteinase K was added to the sample to digest the protein for 10 minutes at 37° C. The nucleic acids were then cleaned up by DNA Clean & Concentrator™-5 (Zymo Research, D4003T) and loaded with loading dye containing SDS (Thermo Fisher, R1151) before gel electrophoresis. The gel containing Sybrsafe (ThermoFisher Scientific, S33102) was visualized by the imaging system (Azure Biosystems, Azure c400).

In vivo cleavage assay. BL21 (DE3) harboring NgAgo expression plasmid and target plasmid were made electrocompetent and transformed with 1 µg of P-ssDNA. Cells were resuspended with pre-warmed SOC after transformation and diluted to spread on pre-warmed plate containing antibiotics (Ampicillin: 100 µg/ml; Chloramphenicol: 25 µg/ml) and 0.1 mM IPTG by plating beads. X-gal (0.2 mg/ml) is also included in the plates when targeting lacZ. Plates were visualized by an imaging system (Azure c400) and analyzed after incubation for 16 hours at 37° C.

Phylogenetic analysis. BLAST was used to compare NgAgo protein sequence with all the isolates in the database via the Integrated Microbial Genomes and Microbiomes (IMG) server of the Office of Science for the U.S. Department of Energy. Argonautes with a repA domain were selected, while Argonautes from the substrains of the same species were only chosen once, and truncated Argonautes were discarded without further phylogenetic tree analysis. Selected pAgos with repA domains and some well-characterized pAgos were compared and the tree was generated via the Phylogenetic analysis pipeline by ETE3 server at GenomeNet. The tree was plotted in R using ggtree package.

TABLE 1

DNA primers and their SEQ ID NOs used in this study.

| SEQ ID NO: | Name | Sequences (5' > 3') | Template | Purpose of the primer |
|---|---|---|---|---|
| 1 | NdeI HIS-Ago 5 | TATACATATGGGTCACCATCATCATCACCATTCATCGCATCACCATCACCATCACGTGCCAAAAAAGAAGAG | Nls-NgAgo-GK | pET-His-Ago |
| 2 | XhoI rmNdeI Ago 3' | ATATCTCGAGTTACTTACTTACGTATGGATCCCGG | Nls-NgAgo-GK | pET-His-Ago |
| 3 | XhoI STOP repA 3' | CTAACTCGAGTTACTCGACGGTCGTCTGG | Nls-NgAgo-GK | pET-His-repA |
| 4 | E598A 5' | GCCAGTCCGACAGCGACGTACGACGAG | | pET-His-Ago NgAgo mutant |
| 5 | E598A 3' | CTCGTCGTACGTCGCTGTCGGACTGGC | | pET-His-Ago NgAgo mutant |
| 6 | D601P 5' | GTCCGACAGAGACGTACCCAGAGCTGAAGAAGGCGCT | | pET-His-Ago NgAgo mutant |
| 7 | D601P 3' | 7 | | pET-His-Ago NgAgo mutant |
| 8 | E602P 5' | CGACAGAGACGTACGACCCACTGAAGAAGGCGCTTGC | | pET-His-Ago NgAgo mutant |
| 9 | E602P 3' | GCAAGCGCCTTCTTCAGTGGGTCGTACGTCTCTGTCG | | pET-His-Ago NgAgo mutant |
| 10 | D663A 3' | CGGGGTAGCTCCGAGAGACCGCAATCCCAATGAACATATC | | pET-His-Ago NgAgo mutant |
| 11 | D663A 5' | GATATGTTCATTGGGATTGCGGTCTCTCGGAGCTACCCCG | | pET-His-Ago NgAgo mutant |
| 12 | E704A 5' | CCGCAGCTCGGGGCGAAACTACAGTCG | | pET-His-Ago NgAgo mutant |
| 13 | E704A 3' | CGACTGTAGTTTCGCCCCGAGCTGCGG | | pET-His-Ago NgAgo mutant |
| 14 | D738A 5' | CGACCCATATCGTCATCCACCGTGCGGGCTTCATGAACGAAGACCTCGAC | | pET-His-Ago NgAgo mutant |
| 15 | D738A 3' | GTCGAGGTCTTCGTTCATGAAGCCCGCACGGTGGATGACGATATGGGTCG | | pET-His-Ago NgAgo mutant |
| 16 | D863A 5' | CCACCGCATACGCCGCGCAGGCAAGTACTCAC | | pET-His-Ago NgAgo mutant |
| 17 | D863A 3' | GTGAGTACTTGCCTGCGCGGCGTATGCGGTGG | | pET-His-Ago NgAgo mutant |

TABLE 2

DNA guides used in this study.

| SEQ ID NO: | Real identity (RV or FW) | 5' phosphorylated guide DNA Original when order | Sequences (5' to 3') |
|---|---|---|---|
| 18 | FW p-tetA | FW TetA p-ssDNA | GGATTGGCCTTATCATGCCAGTCT |
| 19 | RV p-tetA | RV TetA p-ssDNA | AGACTGGCATGATAAGGCCAATCC |
| 20 | FW p-cat | FW Cam P-ssDNA | CAGCTGAACGGTCTGGTTATAGGT |
| 21 | RV p-cat | RV Cam P-ssDNA | ACCTATAACCAGACCGTTCAGCTG |
| 22 | RV p-mNeonGreen | RV p-mGreen Gdna | CCTCGTAGGTGTAGCGGTAGTTAA |
| 23 | FW p-mNeonGreen | RW p-mGreen Gdna | TTAACTACCGCTACACCTACGAGG |
| 24 | RV p-dnaA | RV p-DnaA gDNA | TGGCTGGTAACTCATCCTGCAATC |
| 25 | FW p-dnaA | FW p-DnaA gDNA | GATTGCAGGATGAGTTACCAGCCA |
| 26 | FW p-arpB | RV arpB ssDNA | ATACAGCAGCATGTCCCCTTAGTC |
| 27 | RV p-arpB | FW arpB ssDNA | GACTAAGGGGACATGCTGCTGTAT |
| 28 | FW p-lacZ | LacZ RV target | CAGGATATCCTGCTGATGAAGCAG |
| 29 | RV p-lacZ | LacZ FW target | CTGCTTCATCAGCAGGATATCCTG |

TABLE 3

Top 10 hits of NgAgo in Phyre 2 search.

| Ranking | Structure ID | Structure source | Protein | Probability | Identity with NgAgo |
|---|---|---|---|---|---|
| 1 | 5GUH | PDB | Silkworm PIWI-clade Argonaute Siwi | 100 | 15% |
| 2 | 4EI3 | PDB | Human Argonaute2 | 100 | 18% |
| 3 | 3HO1 | PDB | Thermus thermophilus Argonaute N546 mutant | 100 | 19% |
| 4 | 4F1N | PDB | Kluyveromyces polysporus Argonaute | 100 | 14% |
| 5 | 3DLB | PDB | Thermus thermophilus Argonaute | 100 | 19% |
| 6 | 2F8S | PDB | Aquifex aeolicus Argonaute | 100 | 16% |
| 7 | 5G5T | PDB | Methanocaldococcus janaschii Argonaute | 100 | 15% |
| 8 | 1U04 | PDB | Pyrococcus furiosus Argonaute | 100 | 12% |
| 9 | 5AWH | PDB | Rhodobacter sphaeroides Argonaute | 100 | 14% |
| 10 | d1yvua2 | SCOP | Aquifex aeolicus Argonaute | 100 | 19% |

TABLE 4

Top 10 hits of NgAgo in HHpred search.

| Ranking | Structure ID | Protein | Probability | E-value | Identity to NgAgo |
|---|---|---|---|---|---|
| 1 | 5GUH | silkworm PIWI-clade Argonaute Siwi | 100 | 1e-86 | 15% |
| 2 | 4Z4D | Homo sapiens Argonaute2 | 100 | 3.4e-77 | 16% |
| 3 | 4F1N | Kluyveromyces polysporus Argonaute | 100 | 3e-77 | 17% |
| 4 | 4NCB | Thermus thermophilus Argonaute | 100 | 2.5e-68 | 17% |
| 5 | 5G5S | Methanocaldococcus janaschii Argonaute | 100 | 2.6e-68 | 12% |
| 6 | 1YVU | Aquifex aeolicus Argonaute | 100 | 3.9e-68 | 16% |
| 7 | 1U04 | Pyrococcus furiosus Argonaute | 100 | 1.2e-66 | 14% |
| 8 | 5I4A | Marinitoga piezophila Argonaute | 100 | 8.1e-63 | 14% |
| 9 | 5AWH | Rhodobacter sphaeroides Argonaute | 100 | 2.3e-50 | 16% |
| 10 | 2W42 | Archaeoglobus fulgidus Argonaute | 100 | 1.2e-42 | 18% |

TABLE 5

Top 10 hits of repA domain of NgAgo in Phyre 2 search. A non-OB fold domain match was eliminated in this table.

| Ranking | Structure ID | Source | Protein | Probability |
|---|---|---|---|---|
| 32 | 2KEN | PDB | *Methanosarcina mazei* OB domain of MM0293 | 95.8 |
| 33 | 3DM3 | PDB | *Methanocaldococcus jannaschii* repA | 95.2 |
| 34 | 2K50 | PDB | *Methanobacterium thermoautotrophicum* repA-related protein | 94.6 |
| 35 | 1O7I | PDB | *Sulfolobus solfataricus* ssb | 94.4 |
| 36 | 1FGU | PDB | *Homo sapiens* REPA | 92.3 |
| 37 | d1jmca2 | SCOP | *Homo sapiens* RPA70 | 92 |
| 38 | 4OWX | PDB | *Homo sapiens* SOSS complex subunit B1 | 91.8 |
| 40 | 3E0E | PDB | *Methanococcus maripaludis* repA | 78.2 |
| 41 | 2K75 | PDB | *Thermoplasma acidophilum* OB domain of Ta0387 | 67.2 |
| 42 | d1wjja_ | SCOP | *Arabidopsis thaliana* hypothetical protein F20O9.120 | 66.0 |

TABLE 6

Top 10 hits of repA domain of NgAgo in HHpred search. A non-OB fold domain match was eliminated in this table.

| Ranking | Structure ID | Protein | Probability | E-value |
|---|---|---|---|---|
| 27 | 4OWT | *Homo sapiens* SOSS1 subunit B1 | 94.68 | 0.06 |
| 28 | 1WJJ | *Arabidopsis thaliana* hypothetical protein F20O9.120 | 94.65 | 0.086 |
| 29 | 1O7I | *Sulfolobus solfataricus* single stranded DNA binding protein chain B | 94.0 | 0.28 |
| 30 | 2K50 | *Methanobacterium thermoautotrophicum* repA | 92.46 | 0.036 |
| 31 | 3DM3 | *Methanocaldococcus jannaschii* repA | 91.96 | 0.65 |
| 33 | 3E0E | *Methanococcus maripaludis* repA | 88.18 | 2.5 |
| 34 | 1YNX | *Saccharomyces cerevisiae* repA | 87.6 | 1.3 |
| 35 | 5D8F | *Homo sapiens* SOSS complex subunit B1 | 84.78 | 6.7 |
| 36 | 1JMC | *Homo sapiens* RPA70 | 82.12 | 4.7 |
| 37 | 4HIK | *Schizosaccharomyces pombe* Pot1pC | 81.44 | 5.1 |

TABLE 7

Additional DNA and Protein Sequences Used in this Study

| SEQ ID NO: | Sequence Identity | note |
|---|---|---|
| 30 | Wild type of NgAgo from *Natronobaeterium gregoryi* | |
| 31 | Double mutant of wild type of NgAgo | |
| 32 | N-del mutant E598A | |
| 33 | N-del mutant D601P | |
| 34 | N-del mutant D602P | |
| 35 | N-del with double mutations | |
| 36 | repA | |
| 37 | P15-kanR-PtetRed | |
| 38 | N-del (NgAgo with N-terminal deletion of repA) | |
| 39 | kanR-GFP | |
| 40 | Protein sequence of lambda red recombinase | |
| 41 | Protein sequence of GST-tag NgAgo His-tag | |
| 42 | Protein sequence of GST-tag NgAgo/D663A/D738A His-tag | |
| 51 | Plasmid DNA pNCS-mNeonGreen | |

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:

1. A method for modifying a chromosomal or an extra-chromosomal genetic material of a prokaryotic host cell, comprising:
   providing a gene editing system comprising:
      a donor DNA;
      a plurality of designed DNA sequences each having about 15-30 nucleotides and 5' phosphorylation, wherein said DNA sequences are complementary to a target nucleic acid sequence in a prokaryotic host cell;
      a lambda red recombinase or other recombinase system, wherein the lambda red recombinase or other recombinase system is driven by an inducible promoter that is sufficient to induce homologous recombination; and
      an NgAgo enzyme or a mutant thereof, a DNA expression cassette encoding the NgAgo enzyme or mutant thereof, or an mRNA encoding the NgAgo enzyme or mutant thereof, wherein said NgAgo enzyme or a mutant thereof is capable of interacting with said designed DNA sequences in the prokaryotic host cell and is capable of nicking the target nucleic acid sequence in the cell through the guidance of said designed DNA sequences;
   introducing the gene editing system into the prokaryotic host cell;
   wherein said NgAgo or a mutant thereof forms complexes with the designed DNA sequences, directing the complexes to bind to and nick the target nucleic acid sequence; and
   wherein the plurality of designed DNA sequences are targeted to different regions of said target nucleic acid sequence in a site-specific manner.

2. The method of claim 1, wherein said donor DNA and the lambda red recombinase or other recombinase system are provided together and encoded by SEQ ID NO: 37.

3. The method of claim 1, wherein said donor DNA comprises at least 20 nucleotides of homology to flanking regions of the nicked target nucleic acid sequence so that the donor DNA is capable of recombining with the flanking regions to replace or edit the chromosomal or extrachromosomal genetic material.

4. The method of claim 3, wherein the donor DNA is used to introduce new sequences, delete sequences, create point mutations, or promote a DNA rearrangement.

5. The method of claim 1, wherein the host cell is an *Escherichia coli*.

6. The method of claim 1, wherein the DNA expression cassette encoding the NgAgo enzyme or mutant thereof comprises
   an inducible regulatory sequence linked to the nucleotide sequence of NgAgo.

7. A gene editing system in a prokaryotic host cell comprising:
   a donor DNA;
   a designed DNA sequence of about 15-30 nucleotides with 5' phosphorylation, wherein said DNA sequence is complementary to a gene of interest in the cell;
   a lambda red recombinase or other recombinase system, wherein the lambda red recombinase or other recombinase system is driven by an inducible promoter that is sufficient to induce homologous recombination; and
   an NgAgo enzyme or a mutant thereof, wherein said NgAgo enzyme or a mutant thereof is capable of interacting with said designed DNA in the prokaryotic host cell and is capable of nicking the gene of interest in the cell through the guidance of said designed DNA.

8. The gene editing system in a host cell according to claim 7, wherein said donor DNA comprises at least 20 nucleotides of homology to flanking regions of the gene of interest so that the donor DNA is capable of recombining with the flanking regions of the gene of interest to replace or edit the nicked gene of interest.

9. The gene editing system in a host cell according to claim 7, wherein said NgAgo enzyme or a mutant thereof is a full-length NgAgo or a mutant thereof or a repA-deletion NgAgo (N-del) or a mutant thereof, in the form of a protein product of a DNA expression cassette or a protein product of a messenger RNA.

10. The gene editing system in a host cell according to claim 9, wherein said N-Del is a mutant encoded by SEQ ID NO: 32, SEQ ID NO: 33, or SEQ ID NO: 34.

11. The gene editing system in a host cell according to claim 7, wherein said prokaryotic cell is *Escherichia coli*.

12. A method for modifying a chromosomal or an extra-chromosomal genetic material of a prokaryotic host cell, comprising:
   providing a gene editing system comprising:
      a donor DNA;
      a plurality of designed DNA sequences each having about 15-30 nucleotides and 5' phosphorylation, wherein said DNA sequences are complementary to a target nucleic acid sequence in a prokaryotic host cell;
      a recombinase system comprising a lambda red recombinase or other recombinase system, the recombinase system driven by an inducible promoter that is sufficient to induce homologous recombination; and
      an NgAgo enzyme or a mutant thereof, a DNA expression cassette encoding the NgAgo enzyme or mutant thereof, or an mRNA encoding the NgAgo enzyme or mutant thereof, wherein said NgAgo enzyme or a mutant thereof is:
         a full-length NgAgo, a repA-deletion NgAgo (N-del), or a mutant thereof, and capable of interacting with said designed DNA sequences in the prokaryotic host cell and is capable of nicking the target nucleic acid sequence in the cell through the guidance of said designed DNA;

introducing the gene editing system into the prokaryotic host cell;

wherein said NgAgo enzyme or a mutant thereof forms complexes with the designed DNA sequences, directing the complexes to bind to and nick the target nucleic acid sequence; and wherein the plurality of designed DNA sequences are targeted to different regions of said target nucleic acid sequence in a site-specific manner.

13. The method of claim 12, wherein said N-del mutant is N-del/E598A encoded by SEQ ID NO: 32, SEQ ID NO: 33, or SEQ ID NO: 34.

14. The method of claim 12 wherein said donor DNA comprises at least 20 nucleotides of homology to flanking regions of the nicked target nucleic acid sequence so that the donor DNA is capable of recombining with of the flanking regions to replace or edit the chromosomal or extrachromosomal genetic material.

15. The method of claim 14, wherein the donor DNA is used to introduce new sequences, delete sequences, create point mutations, or promote a general DNA rearrangement.

16. The method of claim 12, wherein the recombinase system comprises an exo, gam, and beta recombinase system.

17. The method of claim 12, wherein the DNA expression cassette encoding the NgAgo enzyme or mutant thereof comprises an inducible promoter sequence linked to the nucleotide sequence encoding the NgAgo.

* * * * *

SEQUENCE LISTING

<160> NUMBER OF SEQ ID NOS: 72

<210> SEQ ID NO 1
<211> LENGTH: 72
<212> TYPE: DNA

-continued

```
<213> ORGANISM: artificial sequence
<220> FEATURE:
<223> OTHER INFORMATION: DNA primer, pET-His-Ago

<400> SEQUENCE: 1
tatacatatg ggtcaccatc atcatcacca ttcatcgcat caccatcacc atcacgtgcc     60
aaaaaagaag ag                                                        72

<210> SEQ ID NO 2
<211> LENGTH: 35
<212> TYPE: DNA
<213> ORGANISM: artificial sequence
<220> FEATURE:
<223> OTHER INFORMATION: DNA primer, pET His-Ago

<400> SEQUENCE: 2
atatctcgag ttacttactt acgtatggat cccgg                               35

<210> SEQ ID NO 3
<211> LENGTH: 29
<212> TYPE: DNA
<213> ORGANISM: artificial sequence
<220> FEATURE:
<223> OTHER INFORMATION: DNA primer, pET His-repA

<400> SEQUENCE: 3
ctaactcgag ttactcgacg gtcgtctgg                                      29

<210> SEQ ID NO 4
<211> LENGTH: 27
<212> TYPE: DNA
<213> ORGANISM: Artificial sequence
<220> FEATURE:
<223> OTHER INFORMATION: NgAgo mutant, EE598A

<400> SEQUENCE: 4
gccagtccga cagcgacgta cgacgag                                        27

<210> SEQ ID NO 5
<211> LENGTH: 27
<212> TYPE: DNA
<213> ORGANISM: artificial sequence
<220> FEATURE:
<223> OTHER INFORMATION: NgAgo mutant primer E598A 3'

<400> SEQUENCE: 5
ctcgtcgtac gtcgctgtcg gactggc                                        27

<210> SEQ ID NO 6
<211> LENGTH: 37
<212> TYPE: DNA
<213> ORGANISM: artificial sequence
<220> FEATURE:
<223> OTHER INFORMATION: NgAgo mutant primer D601P 5'

<400> SEQUENCE: 6
gtccgacaga gacgtaccca gagctgaaga aggcgct                             37

<210> SEQ ID NO 7
<211> LENGTH: 37
<212> TYPE: DNA
<213> ORGANISM: artificial sequence
<220> FEATURE:
<223> OTHER INFORMATION: NgAgo mutant primer D601P, 3'

<400> SEQUENCE: 7
```
agcgccttct tcagctctgg gtacgtctct gtcggac                37

<210> SEQ ID NO 8
<211> LENGTH: 37
<212> TYPE: DNA
<213> ORGANISM: artificial sequence
<220> FEATURE:
<223> OTHER INFORMATION: NgAgo mutant primer E602P 5'

<400> SEQUENCE: 8
cgacagagac gtacgaccca ctgaagaagg cgcttgc                37

<210> SEQ ID NO 9
<211> LENGTH: 37
<212> TYPE: DNA
<213> ORGANISM: artificial sequence
<220> FEATURE:
<223> OTHER INFORMATION: NgAgo mutant primer E602P 3'

<400> SEQUENCE: 9
gcaagcgcct tcttcagtgg gtcgtacgtc tctgtcg                37

<210> SEQ ID NO 10
<211> LENGTH: 40
<212> TYPE: DNA
<213> ORGANISM: artificial sequence
<220> FEATURE:
<223> OTHER INFORMATION: NgAgo mutant primer D663A 3'

<400> SEQUENCE: 10
cggggtagct ccgagagacc gcaatcccaa tgaacatatc          40

<210> SEQ ID NO 11
<211> LENGTH: 40
<212> TYPE: DNA
<213> ORGANISM: artificial sequence
<220> FEATURE:
<223> OTHER INFORMATION: NgAgo mutant primer D663A 5'

<400> SEQUENCE: 11
gatatgttca ttgggattgc ggtctctcgg agctaccccg          40

<210> SEQ ID NO 12
<211> LENGTH: 27
<212> TYPE: DNA
<213> ORGANISM: artificial sequence
<220> FEATURE:
<223> OTHER INFORMATION: NgAgo mutant primer E704A5'

<400> SEQUENCE: 12
ccgcagctcg gggcgaaact acagtcg                       27

<210> SEQ ID NO 13
<211> LENGTH: 27
<212> TYPE: DNA
<213> ORGANISM: artificial sequence
<220> FEATURE:
<223> OTHER INFORMATION: NgAgo mutant primer E704A 3'

<400> SEQUENCE: 13
cgactgtagt ttcgccccga gctgcgg                       27

<210> SEQ ID NO 14
<211> LENGTH: 50
<212> TYPE: DNA

```
<213> ORGANISM: artificial sequence
<220> FEATURE:
<223> OTHER INFORMATION: NgAgo mutant primer D738A 5'

<400> SEQUENCE: 14
cgacccatat cgtcatccac cgtgcgggct tcatgaacga agacctcgac                50

<210> SEQ ID NO 15
<211> LENGTH: 50
<212> TYPE: DNA
<213> ORGANISM: artificial sequence
<220> FEATURE:
<223> OTHER INFORMATION: NgAgo mutant primer D738A 3'

<400> SEQUENCE: 15
gtcgaggtct tcgttcatga agcccgcacg gtggatgacg atatgggtcg                50

<210> SEQ ID NO 16
<211> LENGTH: 32
<212> TYPE: DNA
<213> ORGANISM: artificial sequence
<220> FEATURE:
<223> OTHER INFORMATION: NgAgo mutant primer D863A 5'

<400> SEQUENCE: 16
ccaccgcata cgccgcgcag gcaagtactc ac                                    32

<210> SEQ ID NO 17
<211> LENGTH: 32
<212> TYPE: DNA
<213> ORGANISM: artificial sequence
<220> FEATURE:
<223> OTHER INFORMATION: NgAgo mutant primer D863A 3'

<400> SEQUENCE: 17
gtgagtactt gcctgcgcgg cgtatgcggt gg                                    32

<210> SEQ ID NO 18
<211> LENGTH: 24
<212> TYPE: DNA
<213> ORGANISM: artificial sequence
<220> FEATURE:
<223> OTHER INFORMATION: DNA guide FW p-tetA

<400> SEQUENCE: 18
ggattggcct tatcatgcca gtct                                             24

<210> SEQ ID NO 19
<211> LENGTH: 24
<212> TYPE: DNA
<213> ORGANISM: artificial sequence
<220> FEATURE:
<223> OTHER INFORMATION: DNA guide RV p-tetA

<400> SEQUENCE: 19
agactggcat gataaggcca atcc                                             24

<210> SEQ ID NO 20
<211> LENGTH: 24
<212> TYPE: DNA
<213> ORGANISM: artificial sequence
<220> FEATURE:
<223> OTHER INFORMATION: DNA guide FW p-cat

<400> SEQUENCE: 20
cagctgaacg gtctggttat aggt                                             24
```

<210> SEQ ID NO 21
<211> LENGTH: 24
<212> TYPE: DNA
<213> ORGANISM: artificial sequence
<220> FEATURE:
<223> OTHER INFORMATION: DNA guide RV p-cat

<400> SEQUENCE: 21
acctataacc agaccgttca gctg                                            24

<210> SEQ ID NO 22
<211> LENGTH: 24
<212> TYPE: DNA
<213> ORGANISM: artificial sequence
<220> FEATURE:
<223> OTHER INFORMATION: DNA guide RV p-mNeonGreen

<400> SEQUENCE: 22
cctcgtaggt gtagcggtag ttaa                                            24

<210> SEQ ID NO 23
<211> LENGTH: 24
<212> TYPE: DNA
<213> ORGANISM: artificial sequence
<220> FEATURE:
<223> OTHER INFORMATION: DNA guide FW p-mNeonGreen

<400> SEQUENCE: 23
ttaactaccg ctacacctac gagg                                            24

<210> SEQ ID NO 24
<211> LENGTH: 24
<212> TYPE: DNA
<213> ORGANISM: artificial sequence
<220> FEATURE:
<223> OTHER INFORMATION: DNA guide RV p-dnaA

<400> SEQUENCE: 24
tggctggtaa ctcatcctgc aatc                                            24

<210> SEQ ID NO 25
<211> LENGTH: 24
<212> TYPE: DNA
<213> ORGANISM: artificial sequence
<220> FEATURE:
<223> OTHER INFORMATION: DNA guide FW p-dnaA

<400> SEQUENCE: 25
gattgcagga tgagttacca gcca                                            24

<210> SEQ ID NO 26
<211> LENGTH: 24
<212> TYPE: DNA
<213> ORGANISM: artificial sequence
<220> FEATURE:
<223> OTHER INFORMATION: DNA guide FW p-arpB

<400> SEQUENCE: 26
atacagcagc atgtcccctt agtc                                            24

<210> SEQ ID NO 27
<211> LENGTH: 24
<212> TYPE: DNA
<213> ORGANISM: artificial sequence
<220> FEATURE:

<223> OTHER INFORMATION: DNA guide RV p-arpB

<400> SEQUENCE: 27
gactaagggg acatgctgct gtat                                          24

<210> SEQ ID NO 28
<211> LENGTH: 24
<212> TYPE: DNA
<213> ORGANISM: artificial sequence
<220> FEATURE:
<223> OTHER INFORMATION: DNA guide FW p-lacZ

<400> SEQUENCE: 28
caggatatcc tgctgatgaa gcag                                          24

<210> SEQ ID NO 29
<211> LENGTH: 24
<212> TYPE: DNA
<213> ORGANISM: artificial sequence
<220> FEATURE:
<223> OTHER INFORMATION: DNA guide RV p-lacZ

<400> SEQUENCE: 29
ctgcttcatc agcaggatat cctg                                          24

<210> SEQ ID NO 30
<211> LENGTH: 8128
<212> TYPE: DNA
<213> ORGANISM: Natronobacterium gregoryi

<400> SEQUENCE: 30
ctttaatagt ggactcttgt tccaaactgg aacaacactc aaccctatct cggtctattc      60
ttttgattta agggatttt tgccgatttc ggcctattgg ttaaaaaatg agctgattta     120
acaaaaattt aacgcgaatt ttaacaaaat attaacgttt acaatttcag gtggcacttt     180
tcggggaaat gtgcgcggaa cccctatttg tttatttttc taaatacatt caaatatgta     240
tccgctcatg agacaataac cctgataaat gcttcaataa tattgaaaaa ggaagagtat     300
gagtattcaa catttccgtg tcgcccttat tccctttttt gcggcatttt gccttcctgt     360
ttttgctcac ccagaaacgc tggtgaaagt aaaagatgct gaagatcagt tgggtgcacg     420
agtgggttac atcgaactgg atctcaacag cggtaagatc cttgagagtt ttcgccccga     480
agaacgtttt ccaatgatga gcacttttaa agttctgcta tgtggcgcgg tattatcccg     540
tattgacgcc gggcaagagc aactcggtcg ccgcatacac tattctcaga atgacttggt     600
tgagtactca ccagtcacag aaaagcatct tacggatggc atgacagtaa gagaattatg     660
cagtgctgcc ataaccatga gtgataacac tgcggccaac ttacttctga caacgatcgg     720
aggaccgaag gagctaaccg cttttttgca acatggggg atcatgtaa ctcgccttga     780
tcgttgggaa ccggagctga atgaagccat accaaacgac gagcgtgaca ccacgatgcc     840
tgcagcaatg gcaacaacgt tgcgcaaact attaactggc gaactactta ctctagcttc     900
ccggcaacaa ttaatagact ggatggaggc ggataaagtt gcaggaccac ttctgcgctc     960
ggcccttccg gctggctggt ttattgctga taaatctgga gccggtgagc gtgggtctcg    1020
cggtatcatt gcagcactgg ggccagatgg taagccctcc cgtatcgtag ttatctacac    1080
gacggggagt caggcaacta tggatgaacg aaatagacag atcgctgaga taggtgcctc    1140
actgattaag cattggtaac tgtcagacca agtttactca tatatacttt agattgattt    1200
aaaacttcat ttttaattta aaaggatcta ggtgaagatc cttttttgata atctcatgac    1260

```
caaaatccct taacgtgagt tttcgttcca ctgagcgtca gacccgtag aaaagatcaa    1320 aggatcttct tgagatcctt ttttttctgcg cgtaatctgc tgcttgcaaa caaaaaaacc  1380
accgctacca gcggtggttt gtttgccgga tcaagagcta ccaactcttt ttccgaaggt   1440
aactggcttc agcagagcgc agataccaaa tactgtcctt ctagtgtagc cgtagttagg   1500
ccaccacttc aagaactctg tagcaccgcc tacatacctc gctctgctaa tcctgttacc   1560
agtggctgct gccagtggcg ataagtcgtg tcttaccggg ttggactcaa gacgatagtt   1620
accggataag gcgcagcggt cgggctgaac ggggggttcg tgcacacagc ccagcttgga   1680
gcgaacgacc tacaccgaac tgagatacct acagcgtgag ctatgagaaa gcgccacgct   1740
tcccgaaggg agaaaggcgg acaggtatcc ggtaagcggc agggtcggaa caggagagcg   1800
cacgagggag cttccagggg gaaacgcctg gtatctttat agtcctgtcg ggtttcgcca   1860
cctctgactt gagcgtcgat ttttgtgatg ctcgtcaggg gggcggagcc tatggaaaaa   1920
cgccagcaac gcggccttt tacgttcct ggccttttgc tggccttttg ctcacatgtt     1980
ctttcctgcg ttatcccctg attctgtgga taaccgtatt accgcctttg agtgagctga   2040
taccgctcgc cgcagccgaa cgaccgagcg cagcgagtca gtgagcgagg aagcggaaga   2100
gcgcctgatg cggtattttc tccttacgca tctgtgcggt atttcacacc gcatatatgg   2160
tgcactctca gtacaatctg ctctgatgcc gcatagttaa gccagtatac actccgctat   2220
cgctacgtga ctgggtcatg gctgcgcccc gacacccgcc aacacccgct gacgcgccct   2280
gacgggcttg tctgctcccg gcatccgctt acagacaagc tgtgaccgtc tccgggagct   2340
gcatgtgtca gaggttttca ccgtcatcac cgaaacgcgc gaggcagctg cggtaaagct   2400
catcagcgtg gtcgtgaagc gattcacaga tgtctgcctg ttcatccgcg tccagctcgt   2460
tgagtttctc cagaagcgtt aatgtctggc ttctgataaa gcgggccatg ttaagggcgg   2520
ttttttcctg tttggtcact gatgcctccg tgtaaggggg atttctgttc atggggtaa   2580 tgataccgat gaaacgagag aggatgctca cgatacgggt tactgatgat gaacatgccc   2640
ggttactgga acgttgtgag ggtaaacaac tggcggtatg gatgcggcgg gaccagagaa   2700
aaatcactca gggtcaatgc cagcgcttcg ttaatacaga tgtaggtgtt ccacagggta   2760
gccagcagca tcctgcgatg cagatccgga acataatggt gcagggcgct gacttccgcg   2820
tttccagact ttacgaaaca cggaaaccga agaccattca tgttgttgct caggtcgcag   2880
acgttttgca gcagcagtcg cttcacgttc gctcgcgtat cggtgattca ttctgctaac   2940
cagtaaggca accccgccag cctagccggg tcctcaacga caggagcacg atcatgcgca   3000
cccgtggggc cgccatgccg gcgataatgg cctgcttctc gccgaaacgt tggtggcgg    3060 gaccagtgac gaaggcttga gcgagggcgt gcaagattcc gaataccgca agcgacaggc   3120
cgatcatcgt cgcgctccag cgaaagcggt cctcgccgaa aatgacccag agcgctgccg   3180
gcacctgtcc tacgagttgc atgataaaga agacagtcat aagtgcgcg acgatagtca    3240 tgccccgcgc ccaccggaag gagctgactg ggttgaaggc tctcaagggc atcggtcgag   3300
atcccggtgc ctaatgagtg agctaactta cattaattgc gttgcgctca ctgcccgctt   3360
tccagtcggg aaacctgtcg tgccagctgc attaatgaat cggccaacgc gcggggagag   3420
gcggtttgcg tattgggcgc cagggtggtt tttcttttca ccagtgagac gggcaacagc   3480
tgattgccct tcaccgcctg gccctgagag agttgcagca agcggtccac gctggtttgc   3540
cccagcaggc gaaaatcctg tttgatggtg gttaacggcg ggatataaca tgagctgtct   3600
```

```
tcggtatcgt cgtatcccac taccgagatg tccgcaccaa cgcgcagccc ggactcggta    3660
atggcgcgca ttgcgcccag cgccatctga tcgttggcaa ccagcatcgc agtgggaacg    3720
atgccctcat tcagcatttg catggtttgt tgaaaaccgg acatggcact ccagtcgcct    3780
tcccgttccg ctatcggctg aatttgattg cgagtgagat atttatgcca gccagccaga    3840
cgcagacgcg ccgagacaga acttaatggg cccgctaaca gcgcgatttg ctggtgaccc    3900
aatgcgacca gatgctccac gcccagtcgc gtaccgtctt catgggagaa ataatactg     3960
ttgatgggtg tctggtcaga gacatcaaga ataacgccg gaacattagt gcaggcagct     4020
tccacagcaa tggcatcctg gtcatccagc ggatagttaa tgatcagccc actgacgcgt    4080
tgcgcgagaa gattgtgcac cgccgcttta caggcttcga cgccgcttcg ttctaccatc    4140
gacaccacca cgctggcacc cagttgatcg gcgcgagatt taatcgccgc gacaatttgc    4200
gacggcgcgt gcagggccag actggaggtg gcaacgccaa tcagcaacga ctgtttgccc    4260
gccagttgtt gtgccacgcg gttgggaatg taattcagct ccgccatcgc cgcttccact    4320
ttttcccgcg ttttcgcaga aacgtggctg gcctggttca ccacgcggga aacggtctga    4380
taagagacac cggcatactc tgcgacatcg tataacgtta ctggtttcac attcaccacc    4440
ctgaattgac tctcttccgg gcgctatcat gccataccgc gaaaggtttt gcgccattcg    4500
atggtgtccg ggatctcgac gctctccctt atgcgactcc tgcattagga agcagcccag    4560
tagtaggttg aggccgttga gcaccgccgc gcaaggaat ggtgcatgca aggagatggc     4620
gcccaacagt cccccggcca cggggcctgc caccataccc acgccgaaac aagcgctcat    4680
gagcccgaag tggcgagccc gatcttcccc atcggtgatg tcggcgatat aggcgccagc    4740
aaccgcacct gtggcgccgg tgatgccggc cacgatgcgt ccggcgtaga ggatcgagat    4800
cgatctcgat cccgcgaaat taatacgact cactataggg gaattgtgag cggataacaa    4860
ttcccctcta gaaataattt tgtttaactt taagaaggag atatacatat gggtcaccat    4920
catcatcacc attcatcgca tcaccatcac catcacgtgc caaaaaagaa gagaaaggta    4980
gccacagtga ttgacctcga ttcgaccacc accgcagacg aactgacatc gggacacacg    5040
tacgacatct cagtcacgct caccggtgtc tacgataaca ccgacgagca gcatcctcgc    5100
atgtctctcg cattcgagca ggacaacggc gagcggcgtt acattaccct gtggaagaac    5160
acgacaccca aggatgtctt tacatacgac tacgccacgg gctcgacgta catcttcact    5220
aacatcgact acgaagtgaa ggacggctac gagaatctga ctgcaacata ccagacgacc    5280
gtcgagaacg ctaccgctca ggaagtcggg acgactgacg aggacgaaac gttcgcgggc    5340
ggcgagccgc tcgaccatca cttggacgac gcgctcaatg agacgccaga cgacgcggag    5400
acagagagcg actcaggcca tgtgatgacc tcgttcgcct cccgcgacca actccctgag    5460
tggacgctgc atacgtatac gctaacagcc acagacggcg caaagacgga cacggagtac    5520
gcgcgacgaa ccctcgcata cacggtacgg caggaactct ataccgacca tgatgcgcct    5580
ccggttgcaa ctgacgggct aatgcttctc acgccgagc cgctcggcga ccccgcgctt     5640
gacctcgatt gcggtgtccg ggtcgaggcg gacgagactc ggacactcga ttacaccacg    5700
gccaaagacc ggttactcgc ccgcgaactc gtcgaagagg ggctcaaacg ctccctctgg    5760
gatgactacc tcgttcgcgg catcgatgaa gtcctctcaa aggagcctgt gctgacttgc    5820
gatgagttcg acctacatga gcggtatgac ctctctgtcg aagtcggtca cagtgggcgg    5880
gcgtaccttc acatcaactt ccgccaccgg ttcgtaccga agctgacgct cgcagacatc    5940
gatgatgaca acatctatcc tgggctccgg gtgaagacga cgtatcgccc ccggcgagga    6000
```

```
catatcgtct ggggtctgcg ggacgagtgc gccaccgact cgctcaacac gctgggaaac    6060
cagtccgtcg ttgcatacca ccgcaacaat cagacaccta ttaacactga cctcctcgac    6120
gctatcgagg ccgctgaccg gcgagtcgtc gaaaccccgac gtcaagggca cggcgatgat    6180
gctgtctcat tcccccaaga actgcttgcg gtcgaaccga atacgcacca aattaagcag    6240
ttcgcctccg acggattcca ccaacaggcc cgctcaaaga cgcgtctctc ggcctcccgc    6300
tgcagcgaga aagcgcaagc gttcgccgag cggcttgacc cggtgcgtct caatgggtcc    6360
acggtagagt tctcctcgga gtttttcacc gggaacaacg agcagcaact gcgcctcctc    6420
tacgagaacg gtgagtcggt tctgacgttc gcgacgggg gcgtggtgc gcaccccgac    6480 gagacattct cgaaaggtat cgtcaatcca ccagagtcgt tcgaggtggc cgtagtactg    6540
cccgagcagc aggcagatac ctgcaaagcg cagtgggaca cgatggctga cctcctcaac    6600
caagctggcg cgccaccgac acggagcgag accgtccaat atgatgcgtt ctcctcgcca    6660
gagagcatca gcctcaatgt ggctggagcc atcgaccccta gcgaggtaga cgcggcattc    6720
gtcgtactgc cgccggacca agaaggattc gcagacctcg ccagtccgac agagacgtac    6780
gacgagctga agaaggcgct tgccaacatg ggcatttaca gccagatggc gtacttcgac    6840
cggttccgcg acgcgaaaat attctatact cgtaacgtgg cactcgggct gctggcagcc    6900
gctggcggcg tcgcattcac aaccgaacat gcgatgcctg gggacgcaga tatgttcatt    6960
gggattgcgg tctctcggag ctaccccgag gacggtgcca gcggccagat aaacattgcc    7020
gcgacggcga ccgccgtcta caaggatgga actatcctcg gccactcgtc cacccgaccg    7080
cagctcgggg agaaactaca gtcgacggat gttcgtgaca ttatgaagaa tgccatcctc    7140
ggctaccagc aggtgaccgg tgagtcgccg acccatatcg tcatccaccg tgcgggcttc    7200
atgaacgaag acctcgaccc cgccacgaaa ttcctcaacg aacaaggcgt cgagtacgac    7260
atcgtcgaaa tccgcaagca gccccagaca cgcctgctgg cagtctccga tgtgcagtac    7320
gatacgcctg tgaagagcat cgccgctatc aaccagaacg agccacgggc aacggtcgcc    7380
accttcggcg cacccgaata cttagcgaca cgcgatggag gcggccttcc ccgcccaatc    7440
caaattgaac gagtcgccgg cgaaaccgac atcgagacgc tcactcgcca agtctatctg    7500
ctctcccagt cgcatatcca ggtccataac tcgactgcgc gcctacccat caccaccgca    7560
tacgccgacc aggcaagtac tcacgcgacc aagggttacc tcgtccagac cggagcgttc    7620
gagtctaatg tcggattcct ccgggatcca tacgtaagta agtaactcga gcaccaccac    7680
caccaccact gagatccggc tgctaacaaa gcccgaaagg aagctgagtt ggctgctgcc    7740
accgctgagc aataactagc ataaccccctt ggggcctcta aacgggtctt gaggggtttt    7800
ttgctgaaag gaggaactat atccggattg gcgaatggga cgcgccctgt agcggcgcat    7860
taagcgcggc gggtgtggtg gttacgcgca gcgtgaccgc tacacttgcc agcgccctag    7920
cgcccgctcc tttcgctttc ttcccttcct ttctcgccac gttcgccggc tttccccgtc    7980
aagctctaaa tcggggctc cctttagggt tccgatttag tgctttacgg cacctcgacc    8040
ccaaaaaact tgattaggg gatggttcac gtagtgggcc atcgccctga tagacggttt    8100
ttcgcccttt gacgttggag tccacgtt                                      8128

<210> SEQ ID NO 31
<211> LENGTH: 8128
<212> TYPE: DNA
<213> ORGANISM: artificial sequence
<220> FEATURE:
```

<223> OTHER INFORMATION: NaAgo double mutant

<400> SEQUENCE: 31

```
ctttaatagt ggactcttgt tccaaactgg aacaacactc aaccctatct cggtctattc      60
ttttgattta tagggatttt tgccgatttc ggcctattgg ttaaaaaatg agctgattta     120
acaaaaattt aacgcgaatt ttaacaaaat attaacgttt acaatttcag gtggcacttt     180
tcggggaaat gtgcgcggaa cccctatttg tttatttttc taaatacatt caaatatgta     240
tccgctcatg agacaataac cctgataaat gcttcaataa tattgaaaaa ggaagagtat     300
gagtattcaa catttccgtg tcgcccttat tcccttttt gcggcatttt gccttcctgt      360
ttttgctcac ccagaaacgc tggtgaaagt aaaagatgct gaagatcagt tgggtgcacg     420
agtgggttac atcgaactgg atctcaacag cggtaagatc cttgagagtt tcgccccga      480
agaacgtttt ccaatgatga gcacttttaa agttctgcta tgtggcgcgg tattatcccg     540
tattgacgcc gggcaagagc aactcggtcg ccgcatacac tattctcaga atgacttggt     600
tgagtactca ccagtcacag aaaagcatct tacggatggc atgacagtaa gagaattatg     660
cagtgctgcc ataaccatga gtgataaac tgcggccaac ttacttctga caacgatcgg     720
aggaccgaag gagctaaccg cttttttgca caacatgggg gatcatgtaa ctcgccttga     780
tcgttgggaa ccggagctga atgaagccat accaaacgac gagcgtgaca ccacgatgcc     840
tgcagcaatg gcaacaacgt tgcgcaaact attaactggc gaactactta ctctagcttc     900
ccggcaacaa ttaatagact ggatggaggc ggataaagtt gcaggaccac ttctgcgctc     960
ggcccttccg gctggctggt ttattgctga taaatctgga gccggtgagc gtgggtctcg    1020
cggtatcatt gcagcactgg ggccagatgg taagccctcc cgtatcgtag ttatctacac    1080
gacggggagt caggcaacta tggatgaacg aaatagacag atcgctgaga taggtgcctc    1140
actgattaag cattggtaac tgtcagacca gtttactca tatatacttt agattgattt    1200
aaaacttcat ttttaattta aaaggatcta ggtgaagatc ctttttgata atctcatgac    1260
caaaatccct taacgtgagt tttcgttcca ctgagcgtca gaccccgtag aaaagatcaa    1320
aggatcttct tgagatcctt ttttctgcg cgtaatctgc tgcttgcaaa caaaaaaacc    1380
accgctacca gcggtggttt gtttgccgga tcaagagcta ccaactcttt ttccgaaggt    1440
aactggcttc agcagagcgc agataccaaa tactgtcctt ctagtgtagc cgtagttagg    1500
ccaccacttc aagaactctg tagcaccgcc tacatacctc gctctgctaa tcctgttacc    1560
agtggctgct gccagtggcg ataagtcgtg tcttaccggg ttggactcaa gacgatagtt    1620
accggataag gcgcagcggt cgggctgaac ggggggttcg tgcacacagc ccagcttgga    1680
gcgaacgacc tacaccgaac tgagatacct acagcgtgag ctatgagaaa gcgccacgct    1740
tcccgaaggg agaaaggcgg acaggtatcc ggtaagcggc agggtcggaa caggagagcg    1800
cacgagggag cttccagggg gaaacgcctg gtatctttat agtcctgtcg gtttcgccca    1860
cctctgactt gagcgtcgat ttttgtgatg ctcgtcaggg gggcggagcc tatgaaaaa    1920
cgccagcaac gcggcctttt tacggttcct ggccttttgc tggccttttg ctcacatgtt    1980
ctttcctgcg ttatccctg attctgtgga taaccgtatt accgcctttg agtgagctga    2040
taccgctcgc cgcagccgaa cgaccgagcg cagcgagtca gtgagcgagg aagcggaaga    2100
gcgcctgatg cggtattttc tccttacgca tctgtgcggt atttcacacc gcatatatgg    2160
tgcactctca gtacaatctg ctctgatgcc gcatagttaa gccagtatac actccgctat    2220
cgctacgtga ctgggtcatg gctgcgcccc gacacccgcc aacacccgct gacgcgccct    2280
```

```
gacgggcttg tctgctcccg gcatccgctt acagacaagc tgtgaccgtc tccgggagct   2340
gcatgtgtca gaggttttca ccgtcatcac cgaaacgcgc gaggcagctg cggtaaagct   2400
catcagcgtg gtcgtgaagc gattcacaga tgtctgcctg ttcatccgcg tccagctcgt   2460
tgagtttctc cagaagcgtt aatgtctggc ttctgataaa gcgggccatg ttaagggcgg   2520 tttttttcctg tttggtcact gatgcctccg tgtaaggggg atttctgttc atggggtaa   2580 tgataccgat gaaacgagag aggatgctca cgatacgggt tactgatgat gaacatgccc   2640
ggttactgga acgttgtgag ggtaaacaac tggcggtatg gatgcggcgg gaccagagaa   2700
aaatcactca gggtcaatgc cagcgcttcg ttaatacaga tgtaggtgtt ccacagggta   2760
gccagcagca tcctgcgatg cagatccgga acataatggt gcagggcgct gacttccgcg   2820
tttccagact ttacgaaaca cggaaaccga agaccattca tgttgttgct caggtcgcag   2880
acgttttgca gcagcagtcg cttcacgttc gctcgcgtat cggtgattca ttctgctaac   2940
cagtaaggca accccgccag cctagccggg tcctcaacga caggagcacg atcatgcgca   3000
cccgtggggc cgccatgccg cgataatggg cctgcttctc gccgaaacgt ttggtggcgg   3060
gaccagtgac gaaggcttga gcgagggcgt gcaagattcc gaataccgca agcgacaggc   3120
cgatcatcgt cgcgctccag cgaaagcggt cctcgccgaa aatgacccag agcgctgccg   3180
gcacctgtcc tacgagttgc atgataaaga agacagtcat aagtgcggcg acgatagtca   3240
tgccccgcgc ccaccggaag gagctgactg ggttgaaggc tctcaagggc atcggtcgag   3300
atcccggtgc ctaatgagtg agctaactta cattaattgc gttgcgctca ctgcccgctt   3360
tccagtcggg aaacctgtcg tgccagctgc attaatgaat cggccaacgc gcggggagag   3420
gcggtttgcg tattgggcgc cagggtggtt tttcttttca ccagtgagac gggcaacagc   3480
tgattgccct tcaccgcctg gccctgagag agttgcagca agcggtccac gctggtttgc   3540
cccagcaggc gaaaatcctg tttgatggtg gttaacggcg ggatataaca tgagctgtct   3600
tcggtatcgt cgtatcccac taccgagatg tccgcaccaa cgcgcagccc ggactcggta   3660
atggcgcgca ttgcgcccag cgccatctga tcgttggcaa ccagcatcgc agtgggaacg   3720
atgccctcat tcagcatttg catggtttgt tgaaaaccgg acatggcact ccagtcgcct   3780
tcccgttccg ctatcggctg aatttgattg cgagtgagat atttatgcca gccagccaga   3840
cgcagacgcg ccgagacaga acttaatggg cccgctaaca gcgcgatttg ctggtgaccc   3900
aatgcgacca gatgctccac gcccagtcgc gtaccgtctt catgggagaa aataatactg   3960
ttgatgggtg tctggtcaga gacatcaaga ataacgccgg aacattagt gcaggcagct   4020 tccacagcaa tggcatcctg gtcatccagc ggatagttaa tgatcagccc actgacgcgt   4080
tgcgcgagaa gattgtgcac cgccgcttta caggcttcga cgccgcttcg ttctaccatc   4140
gacaccacca cgctggcacc cagttgatcg gcgcgagatt taatcgccgc gacaatttgc   4200
gacggcgcgt gcagggccag actggaggtg caacgccaa tcagcaacga ctgtttgccc   4260
gccagttgtt gtgccacgcg gttgggaatg taattcagct ccgccatcgc cgcttccact   4320
ttttcccgcg ttttcgcaga aacgtggctg gcctggttca ccacgcggga aacggtctga   4380
taagagacac cggcatactc tgcgacatcg tataacgtta ctggtttcac attcaccacc   4440
ctgaattgac tctcttccgg gcgctatcat gccataccgc gaaaggtttt gcgccattcg   4500
atggtgtccg ggatctcgac gctctccctt atgcgactcc tgcattagga agcagcccag   4560
tagtaggttg aggccgttga gcaccgccgc cgcaaggaat ggtgcatgca aggagatggc   4620
```

```
gcccaacagt cccccggcca cggggcctgc caccataccc acgccgaaac aagcgctcat    4680
gagcccgaag tggcgagccc gatcttcccc atcggtgatg tcggcgatat aggcgccagc    4740
aaccgcacct gtggcgccgg tgatgccggc cacgatgcgt ccggcgtaga ggatcgagat    4800
cgatctcgat cccgcgaaat taatacgact cactataggg gaattgtgag cggataacaa    4860
ttcccctcta gaaataattt tgtttaactt taagaaggag atatacatat gggtcaccat    4920
catcatcacc attcatcgca tcaccatcac catcacgtgc caaaaaagaa gagaaaggta    4980
gccacagtga ttgacctcga ttcgaccacc accgcagacg aactgacatc gggacacacg    5040
tacgacatct cagtcacgct caccggtgtc tacgataaca ccgacgagca gcatcctcgc    5100
atgtctctcg cattcgagca ggacaacggc gagcggcgtt acattaccct gtggaagaac    5160
acgacaccca aggatgtctt tacatacgac tacgccacgg gctcgacgta catcttcact    5220
aacatcgact acgaagtgaa ggacggctac gagaatctga ctgcaacata ccagacgacc    5280
gtcgagaacg ctaccgctca ggaagtcggg acgactgacg aggacgaaac gttcgcgggc    5340
ggcgagccgc tcgaccatca cttggacgac gcgctcaatg agacgccaga cgacgcggag    5400
acagagagcg actcaggcca tgtgatgacc tcgttcgcct cccgcgacca actccctgag    5460
tggacgctgc atacgtatac gctaacagcc acagacggcg caaagacgga cacggagtac    5520
gcgcgacgaa ccctcgcata cacggtacgg caggaactct ataccgacca tgatgcggct    5580
ccggttgcaa ctgacgggct aatgcttctc acgccagagc cgctcggcga accccgctt     5640
gacctcgatt gcggtgtccg ggtcgaggcg gacgagactc ggacactcga ttacaccacg    5700
gccaaagacc ggttactcgc ccgcgaactc gtcgaagagg ggctcaaacg ctccctctgg    5760
gatgactacc tcgttcgcgg catcgatgaa gtcctctcaa aggagcctgt gctgacttgc    5820
gatgagttcg acctacatga gcggtatgac ctctctgtcg aagtcggtca cagtgggcgg    5880
gcgtaccttc acatcaactt ccgccaccgg ttcgtaccga agctgacgct cgcagacatc    5940
gatgatgaca acatctatcc tgggctccgg gtgaagacga cgtatcgccc ccggcgagga    6000
catatcgtct ggggtctgcg ggacgagtgc gccaccgact cgctcaacac gctgggaaac    6060
cagtccgtcg ttgcatacca ccgcaacaat cagacaccta ttaacactga cctcctcgac    6120
gctatcgagg ccgctgaccg gcgagtcgtc gaaacccgac gtcaagggca cggcgatgat    6180
gctgtctcat tccccaaga actgcttgcg gtcgaaccga atacgcacca aattaagcag    6240
ttcgcctccg acggattcca ccaacaggcc cgctcaaaga cgcgtctctc ggcctcccgc    6300
tgcagcgaga aagcgcaagc gttcgccgag cggcttgacc cggtgcgtct caatgggtcc    6360
acggtagagt tctcctcgga gttttttcacc gggaacaacg agcagcaact gcgcctcctc    6420
tacgagaacg gtgagtcggt tctgacgttc cgcgacgggg cgcgtggtgc gcaccccgac    6480
gagacattct cgaaaggtat cgtcaatcca ccagagtcgt tcgaggtggc cgtagtactg    6540
cccgagcagc aggcagatac ctgcaaagcg cagtgggaca cgatggctga cctcctcaac    6600
caagctggcg cgccaccgac acggagcgag accgtccaat atgatgcgtt ctcctcgcca    6660
gagagcatca gcctcaatgt ggctggagcc atcgacccta gcgaggtaga cgcggcattc    6720
gtcgtactgc cgccggacca agaaggattc gcagacctcg ccagtccgac agagacgtac    6780
gacgagctga agaaggcgct tgccaacatg ggcatttaca gccagatggc gtacttcgac    6840
cggttccgcg acgcgaaaat attctatact cgtaacgtgg cactcgggct gctggcagcc    6900
gctggcggcg tcgcattcac aaccgaacat gcgatgcctg gggacgcaga tatgttcatt    6960
gggattgcgg tctctcggag ctaccccgag gacggtgcca gcggccagat aaacattgcc    7020
```

```
gcgacggcga ccgccgtcta caaggatgga actatcctcg ccactcgtc cacccgaccg    7080 cagctcgggg agaaactaca gtcgacggat gttcgtgaca ttatgaagaa tgccatcctc    7140
ggctaccagc aggtgaccgg tgagtcgccg acccatatcg tcatccaccg tgcgggcttc    7200
atgaacgaag acctcgaccc cgccacggaa ttcctcaacg aacaaggcgt cgagtacgac    7260
atcgtcgaaa tccgcaagca gccccagaca cgcctgctgg cagtctccga tgtgcagtac    7320
gatacgcctg tgaagagcat cgccgctatc aaccagaacg agccacgggc aacggtcgcc    7380
accttcggcg cacccgaata cttagcgaca cgcgatggag cggccttcc ccgcccaatc    7440 caaattgaac gagtcgccgg cgaaaccgac atcgagacgc tcactcgcca agtctatctg    7500
ctctcccagt cgcatatcca ggtccataac tcgactgcgc gcctacccat caccaccgca    7560
tacgccgacc aggcaagtac tcacgcgacc aagggttacc tcgtccagac cggagcgttc    7620
gagtctaatg tcggattcct ccgggatcca tacgtaagta agtaactcga gcaccaccac    7680
caccaccact gagatccggc tgctaacaaa gcccgaaagg aagctgagtt ggctgctgcc    7740
accgctgagc aataactagc ataaccccct tggggcctcta aacgggtctt gagggggttttt    7800 ttgctgaaag gaggaactat atccggattg gcgaatggga cgcgccctgt agcggcgcat    7860
taagcgcggc gggtgtggtg gttacgcgca gcgtgaccgc tacacttgcc agcgccctag    7920
cgcccgctcc tttcgctttc ttcccttcct ttctcgccac gttcgccggc tttccccgtc    7980
aagctctaaa tcggggggctc cctttagggt tccgatttag tgctttacgg cacctcgacc    8040
ccaaaaaact tgattagggt gatggttcac gtagtgggcc atcgccctga tagacggttt    8100
ttcgcccttt gacgttggag tccacgtt                                      8128

<210> SEQ ID NO 32
<211> LENGTH: 7792
<212> TYPE: DNA
<213> ORGANISM: artificial sequence
<220> FEATURE:
<223> OTHER INFORMATION: N-del, E598A mutation

<400> SEQUENCE: 32
ctgcttctcg ccgaaacgtt tggtggcggg accagtgacg aaggcttgag cgagggcgtg      60
caagattccg aataccgcaa gcgacaggcc gatcatcgtc gcgctccagc gaaagcggtc     120
ctcgccgaaa atgacccaga gcgctgccgg cacctgtcct acgagttgca tgataaagaa     180
gacagtcata agtgcggcga cgatagtcat gccccgcgcc caccggaagg agctgactgg     240
gttgaaggct ctcaagggca tcggtcgaga tcccggtgcc taatgagtga gctaacttac     300
attaattgcg ttgcgctcac tgcccgcttt ccagtcggga aacctgtcgt gccagctgca     360
ttaatgaatc ggccaacgcg cggggagagg cggtttgcgt attgggcgcc agggtggttt     420
ttcttttcac cagtgagacg ggcaacagct gattgcccctt caccgcctgg ccctgagaga     480
gttgcagcaa gcggtccacg ctggtttgcc ccagcaggcg aaaatcctgt ttgatggtgg     540
ttaacggcgg gatataacat gagctgtctt cggtatcgtc gtatcccact accgagatgt     600
ccgcaccaac gcgcagcccg gactcggtaa tggcgcgcat tgcgcccagc gccatctgat     660
cgttggcaac cagcatcgca gtgggaacga tgccctcatt cagcatttgc atggtttgtt     720
gaaaaccgga catggcactc cagtcgcctt cccgttccgc tatcggctga atttgattgc     780
gagtgagata tttatgccag ccagccagac gcagacgcgc cgagacagaa cttaatgggc     840
ccgctaacag cgcgatttgc tggtgaccca atgcgaccag atgctccacg cccagtcgcg     900
```

```
taccgtcttc atgggagaaa ataatactgt tgatgggtgt ctggtcagag acatcaagaa    960
ataacgccgg aacattagtg caggcagctt ccacagcaat ggcatcctgg tcatccagcg   1020
gatagttaat gatcagccca ctgacgcgtt gcgcgagaag attgtgcacc gccgctttac   1080
aggcttcgac gccgcttcgt tctaccatcg acaccaccac gctggcaccc agttgatcgg   1140
cgcgagattt aatcgccgcg acaatttgcg acggcgcgtg cagggccaga ctggaggtgg   1200
caacgccaat cagcaacgac tgtttgcccg ccagttgttg tgccacgcgg ttgggaatgt   1260
aattcagctc cgccatcgcc gcttccactt tttcccgcgt tttcgcagaa acgtggctgg   1320
cctggttcac cacgcgggaa acggtctgat aagagacacc ggcatactct gcgacatcgt   1380
ataacgttac tggttttcaca ttcaccaccc tgaattgact ctcttccggg cgctatcatg   1440
ccataccgcg aaaggttttg cgccattcga tggtgtccgg gatctcgacg ctctccctta   1500
tgcgactcct gcattaggaa gcagcccagt agtaggttga ggccgttgag caccgccgcc   1560
gcaaggaatg gtgcatgcaa ggagatggcc cccaacagtc ccccggccac ggggcctgcc   1620
accataccca cgccgaaaca agcgctcatg agcccgaagt ggcgagcccg atcttcccca   1680
tcggtgatgt cggcgatata ggcgccagca accgcacctg tggcgccggt gatgccggcc   1740
acgatgcgtc cggcgtagag gatcgagatc gatctcgatc ccgcgaaatt aatacgactc   1800
actataggg aattgtgagc ggataacaat tcccctctag aaataatttt gtttaacttt   1860
aagaaggaga tatacatatg ggtcaccatc atcatcacca ttcatcgcat caccatcacc   1920
atcacaccgc tcaggaagtc gggacgactg acgaggacga aacgttcgcg ggcggcgagc   1980
cgctcgacca tcacttggac gacgcgctca atgagacgcc agacgacgcg gagacagaga   2040
gcgactcagg ccatgtgatg acctcgttcg cctcccgcga ccaactccct gagtggacgc   2100
tgcatacgta tacgctaaca gccacagacg gcgcaaagac ggacacggag tacgcgcgac   2160
gaaccctcgc atacacggta cggcaggaac tctataccga ccatgatgcg gctccggttg   2220
caactgacgg gctaatgctt ctcacgccag agccgctcgg cgagacccg cttgacctcg   2280
attgcggtgt ccgggtcgag gcggacgaga ctcggacact cgattacacc acggccaaag   2340
accggttact cgcccgcgaa ctcgtcgaag aggggctcaa acgctccctc tgggatgact   2400
acctcgttcg cggcatcgat gaagtcctct caaaggagcc tgtgctgact tgcgatgagt   2460
tcgacctaca tgagcggtat gacctctctg tcgaagtcgg tcacagtggg cgggcgtacc   2520
ttcacatcaa cttccgccac cggttcgtac cgaagctgac gctcgcagac atcgatgatg   2580
acaacatcta tcctgggctc cgggtgaaga cgacgtatcg ccccggcga ggacatatcg   2640
tctggggtct gcgggacgag tgcgccaccg actcgctcaa cacgctggga aaccagtccg   2700
tcgttgcata ccaccgcaac aatcagacac ctattaacac tgacctcctc gacgctatcg   2760
aggccgctga ccggcgagtc gtcgaaaccc gacgtcaagg gcacggcgat gatgctgtct   2820
cattccccca agaactgctt gcggtcgaac cgaatacgca ccaaattaag cagttcgcct   2880
ccgacggatt ccaccaacag gcccgctcaa agacgcgtct ctcggcctcc cgctgcagcg   2940
agaaagcgca agcgttcgcc gagcggcttg accggtgcg tctcaatggg tccacggtag   3000
agttctcctc ggagttttc accgggaaca acgagcagca actgcgcctc ctctacgaga   3060
acggtgagtc ggttctgacg ttccgcgacg gggcgcgtgg tgcgcacccc gacgagacat   3120
tctcgaaagg tatcgtcaat ccaccagagt cgttcgaggt ggccgtagta ctgcccgagc   3180
agcaggcaga tacctgcaaa gcgcagtggg acacgatggc tgacctcctc aaccaagctg   3240
gcgcgccacc gacacggagc gagaccgtcc aatatgatgc gttctcctcg ccagagagca   3300
```

```
tcagcctcaa tgtggctgga gccatcgacc ctagcgaggt agacgcggca ttcgtcgtac   3360
tgccgccgga ccaagaagga ttcgcagacc tcgccagtcc gacagcgacg tacgacgagc   3420
tgaagaaggc gcttgccaac atgggcattt acagccagat ggcgtacttc gaccggttcc   3480
gcgacgcgaa aatattctat actcgtaacg tggcactcgg gctgctggca gccgctggcg   3540
gcgtcgcatt cacaaccgaa catgcgatgc ctggggacgc agatatgttc attgggattg   3600
atgtctctcg gagctacccc gaggacggtg ccagcggcca gataaacatt gccgcgacgg   3660
cgaccgccgt ctacaaggat ggaactatcc tcggccactc gtccacccga ccgcagctcg   3720
gggagaaact acagtcgacg gatgttcgtg acattatgaa gaatgccatc ctcggctacc   3780
agcaggtgac cggtgagtcg ccgacccata tcgtcatcca ccgtgatggc ttcatgaacg   3840
aagacctcga ccccgccacg gaattcctca acgaacaagg cgtcgagtac gacatcgtcg   3900
aaatccgcaa gcagccccag acacgcctgc tggcagtctc cgatgtgcag tacgatacgc   3960
ctgtgaagag catcgccgct atcaaccaga acgagccacg ggcaacggtc gccaccttcg   4020
gcgcacccga atacttagcg acacgcgatg gaggcggcct tccccgccca atccaaattg   4080
aacgagtcgc cggcgaaacc gacatcgaga cgctcactcg ccaagtctat ctgctctccc   4140
agtcgcatat ccaggtccat aactcgactg cgcgcctacc catcaccacc gcatacgccg   4200
accaggcaag tactcacgcg accaagggtt acctcgtcca gaccggagcg ttcgagtcta   4260
atgtcggatt cctccgggat ccatacgtaa gtaagtaact cgagcaccac caccaccacc   4320
actgagatcc ggctgctaac aaagcccgaa aggaagctga gttggctgct gccaccgctg   4380
agcaataact agcataaccc cttggggcct ctaaacgggt cttgaggggt ttttgctga   4440 aaggaggaac tatatccgga ttggcgaatg ggacgcgccc tgtagcggcg cattaagcgc   4500
ggcgggtgtg gtggttacgc gcagcgtgac cgctacactt gccagcgccc tagcgcccgc   4560
tcctttcgct ttcttccctt cctttctcgc cacgttcgcc ggctttcccc gtcaagctct   4620
aaatcggggg ctcccttag ggttccgatt tagtgcttta cggcacctcg accccaaaaa   4680
acttgattag ggtgatggtt cacgtagtgg gccatcgccc tgatagacgg ttttcgccc   4740 tttgacgttg gagtccacgt tctttaatag tggactcttg ttccaaactg gaacaacact   4800
caaccctatc tcggtctatt cttttgattt ataagggatt ttgccgattt cggcctattg   4860
gttaaaaaat gagctgattt aacaaaaatt taacgcgaat tttaacaaaa tattaacgtt   4920
tacaatttca ggtggcactt tcggggaaa tgtgcgcgga acccctattt gtttatttt   4980 ctaaatacat tcaaatatgt atccgctcat gagacaataa ccctgataaa tgcttcaata   5040
atattgaaaa aggaagagta tgagtattca acatttccgt gtcgccctta ttcccttttt   5100
tgcggcattt tgccttcctg ttttgctca cccagaaacg ctggtgaaag taaagatgc   5160 tgaagatcag ttgggtgcac gagtgggtta catcgaactg gatctcaaca gcggtaagat   5220
ccttgagagt tttcgccccg aagaacgttt tccaatgatg agcactttta aagttctgct   5280
atgtggcgcg gtattatccc gtattgacgc cgggcaagag caactcggtc gccgcataca   5340
ctattctcag aatgacttgg ttgagtactc accagtcaca gaaaagcatc ttacggatgg   5400
catgacagta agagaattat gcagtgctgc cataaccatg agtgataaca ctgcggccaa   5460
cttacttctg acaacgatcg gaggaccgaa ggagctaacc gcttttttgc acaacatggg   5520
ggatcatgta actcgccttg atcgttggga accggagctg aatgaagcca taccaaacga   5580
cgagcgtgac accacgatgc ctgcagcaat ggcaacaacg ttgcgcaaac tattaactgg   5640
```

-continued

```
cgaactactt actctagctt cccggcaaca attaatagac tggatggagg cggataaagt    5700
tgcaggacca cttctgcgct cggcccttcc ggctggctgg tttattgctg ataaatctgg    5760
agccggtgag cgtgggtctc gcggtatcat tgcagcactg gggccagatg gtaagccctc    5820
ccgtatcgta gttatctaca cgacggggag tcaggcaact atggatgaac gaaatagaca    5880
gatcgctgag ataggtgcct cactgattaa gcattggtaa ctgtcagacc aagtttactc    5940
atatatactt tagattgatt taaaacttca ttttaatttt aaaaggatct aggtgaagat    6000
cctttttgat aatctcatga ccaaaatccc ttaacgtgag ttttcgttcc actgagcgtc    6060
agaccccgta gaaaagatca aaggatcttc ttgagatcct ttttttctgc gcgtaatctg    6120
ctgcttgcaa acaaaaaaac caccgctacc agcggtggtt tgtttgccgg atcaagagct    6180
accaactctt tttccgaagg taactggctt cagcagagcg cagataccaa atactgtcct    6240
tctagtgtag ccgtagttag gccaccactt caagaactct gtagcaccgc ctacatacct    6300
cgctctgcta atcctgttac cagtggctgc tgccagtggc gataagtcgt gtcttaccgg    6360
gttggactca agacgatagt taccggataa ggcgcagcgg tcgggctgaa cggggggttc    6420
gtgcacacag cccagcttgg agcgaacgac ctacaccgaa ctgagatacc tacagcgtga    6480
gctatgagaa agcgccacgc ttcccgaagg agaaaggcg acaggtatc cggtaagcgg    6540
cagggtcgga acaggagagc gcacgaggga gcttccaggg ggaaacgcct ggtatcttta    6600
tagtcctgtc gggtttcgcc acctctgact tgagcgtcga ttttgtgat gctcgtcagg    6660
ggggcggagc ctatggaaaa acgccagcaa cgcggccttt ttacggttcc tggccttttg    6720
ctggcctttt gctcacatgt tctttcctgc gttatcccct gattctgtgg ataaccgtat    6780
taccgccttt gagtgagctg ataccgctcg ccgcagccga acgaccgagc gcagcgagtc    6840
agtgagcgag gaagcggaag agcgcctgat gcggtatttt ctccttacgc atctgtgcgg    6900
tatttcacac cgcatatatg gtgcactctc agtacaatct gctctgatgc cgcatagtta    6960
agccagtata cactccgcta tcgctacgtg actgggtcat ggctgcgccc cgacacccgc    7020
caacacccgc tgacgcgccc tgacgggctt gtctgctccc ggcatccgct tacagacaag    7080
ctgtgaccgt ctccgggagc tgcatgtgtc agaggttttc accgtcatca ccgaaacgcg    7140
cgaggcagct gcggtaaagc tcatcagcgt ggtcgtgaag cgattcacag atgtctgcct    7200
gttcatccgc gtccagctcg ttgagtttct ccagaagcgt taatgtctgg cttctgataa    7260
agcgggccat gttaagggcg gttttttcct gtttggtcac tgatgcctcc gtgtaagggg    7320
gatttctgtt catggggta atgataccga tgaaacgaga gaggatgctc acgatacggg    7380
ttactgatga tgaacatgcc cggttactgg aacgttgtga gggtaaacaa ctggcggtat    7440
ggatgcggcg gaccagaga aaatcactc agggtcaatg ccagcgcttc gttaatacag    7500
atgtaggtgt tccacagggt agccagcagc atcctgcgat gcagatccgg aacataatgg    7560
tgcagggcgc tgacttccgc gtttccagac tttacgaaac acggaaaccg aagaccattc    7620
atgttgttgc tcaggtcgca gacgttttgc agcagcagtc gcttcacgtt cgctcgcgta    7680
tcggtgattc attctgctaa ccagtaaggc aaccccgcca gcctagccgg gtcctcaacg    7740
acaggagcac gatcatgcgc acccgtgggg ccgccatgcc ggcgataatg gc          7792
```

<210> SEQ ID NO 33
<211> LENGTH: 7792
<212> TYPE: DNA
<213> ORGANISM: artificial sequence
<220> FEATURE:
<223> OTHER INFORMATION: N-del/D601P

<400> SEQUENCE: 33

```
ctgcttctcg ccgaaacgtt tggtggcggg accagtgacg aaggcttgag cgagggcgtg      60
caagattccg aataccgcaa gcgacaggcc gatcatcgtc gcgctccagc gaaagcggtc     120
ctcgccgaaa atgacccaga gcgctgccgg cacctgtcct acgagttgca tgataaagaa     180
gacagtcata agtgcggcga cgatagtcat gccccgcgcc caccggaagg agctgactgg     240
gttgaaggct ctcaagggca tcggtcgaga tcccggtgcc taatgagtga gctaacttac     300
attaattgcg ttgcgctcac tgcccgcttt ccagtcggga aacctgtcgt gccagctgca     360
ttaatgaatc ggccaacgcg cggggagagg cggtttgcgt attgggcgcc agggtggttt     420
ttcttttcac cagtgagacg ggcaacagct gattgccctt caccgcctgg ccctgagaga     480
gttgcagcaa gcggtccacg ctggtttgcc ccagcaggcg aaaatcctgt ttgatggtgg     540
ttaacggcgg gatataacat gagctgtctt cggtatcgtc gtatcccact accgagatgt     600
ccgcaccaac gcgcagcccg gactcggtaa tggcgcgcat tgcgcccagc gccatctgat     660
cgttggcaac cagcatcgca gtgggaacga tgccctcatt cagcatttgc atggtttgtt     720
gaaaaccgga catggcactc cagtcgcctt cccgttccgc tatcggctga atttgattgc     780
gagtgagata tttatgccag ccagccagac gcagacgcgc cgagacagaa cttaatgggc     840
ccgctaacag cgcgatttgc tggtgaccca atgcgaccag atgctccacg cccagtcgcg     900
taccgtcttc atgggagaaa ataatactgt tgatgggtgt ctggtcagag acatcaagaa     960
ataacgccgg aacattagtg caggcagctt ccacagcaat ggcatcctgg tcatccagcg    1020
gatagttaat gatcagccca ctgacgcgtt gcgcgagaag attgtgcacc gccgctttac    1080
aggcttcgac gccgcttcgt tctaccatcg acaccaccac gctggcaccc agttgatcgg    1140
cgcgagattt aatcgccgcg acaatttgcg acggcgcgtg cagggccaga ctggaggtgg    1200
caacgccaat cagcaacgac tgtttgcccg ccagttgttg tgccacgcgg ttgggaatgt    1260
aattcagctc cgccatcgcc gcttccactt ttttcccgcgt tttcgcagaa acgtggctgg    1320
cctggttcac cacgcgggaa acggtctgat aagagacacc ggcatactct gcgacatcgt    1380
ataacgttac tggtttcaca ttcaccaccc tgaattgact ctcttccggg cgctatcatg    1440
ccataccgcg aaaggttttg cgccattcga tggtgtccgg gatctcgacg ctctccctta    1500
tgcgactcct gcattaggaa gcagcccagt agtaggttga ggccgttgag caccgccgcc    1560
gcaaggaatg gtgcatgcaa ggagatggcg cccaacagtc ccccggccac ggggcctgcc    1620
accatacccca cgccgaaaca agcgctcatg agcccgaagt ggcgagcccg atcttcccca    1680
tcggtgatgt cggcgatata ggcgccagca accgcacctg tggcgccggt gatgccggcc    1740
acgatgcgtc cggcgtagag gatcgagatc gatctcgatc ccgcgaaatt aatacgactc    1800
actataggg aattgtgagc ggataacaat tcccctctag aaataatttt gtttaacttt    1860
aagaaggaga tatacatatg ggtcaccatc atcatcacca ttcatcgcat caccatcacc    1920
atcacaccgc tcaggaagtc gggacgactg acgaggacga aacgttcgcg ggcggcgagc    1980
cgctcgacca tcacttggac gacgcgctca atgagacgcc agacgacgcg gagacagaga    2040
gcgactcagg ccatgtgatg acctcgttcg cctcccgcga ccaactccct gagtggacgc    2100
tgcatacgta tacgctaaca gccacagacg gcgcaaagac ggacacggag tacgcgcgac    2160
gaaccctcgc atacacggta cggcaggaac tctataccga ccatgatgcg gctccggttg    2220
caactgacgg gctaatgctt ctcacgccag agccgctcgg cgagacccccg cttgacctcg    2280
```

```
attgcggtgt ccgggtcgag gcggacgaga ctcggacact cgattacacc acggccaaag    2340
accggttact cgcccgcgaa ctcgtcgaag aggggctcaa acgctccctc tgggatgact    2400
acctcgttcg cggcatcgat gaagtcctct caaaggagcc tgtgctgact tgcgatgagt    2460
tcgacctaca tgagcggtat gacctctctg tcgaagtcgg tcacagtggg cgggcgtacc    2520
ttcacatcaa cttccgccac cggttcgtac cgaagctgac gctcgcagac atcgatgatg    2580
acaacatcta tcctgggctc cgggtgaaga cgacgtatcg cccccggcga ggacatatcg    2640
tctggggtct gcgggacgag tgcgccaccg actcgctcaa cacgctggga aaccagtccg    2700
tcgttgcata ccaccgcaac aatcagacac ctattaacac tgacctcctc gacgctatcg    2760
aggccgctga ccggcgagtc gtcgaaaccc gacgtcaagg gcacggcgat gatgctgtct    2820
cattccccca agaactgctt gcggtcgaac cgaatacgca ccaaattaag cagttcgcct    2880
ccgacggatt ccaccaacag gcccgctcaa agacgcgtct ctcggcctcc cgctgcagcg    2940
agaaagcgca agcgttcgcc gagcggcttg acccggtgcg tctcaatggg tccacggtag    3000
agttctcctc ggagtttttc accggaaaca acgagcagca actgcgcctc ctctacgaga    3060
acggtgagtc ggttctgacg ttccgcgacg gggcgcgtgg tgcgcacccc gacgagacat    3120
tctcgaaagg tatcgtcaat ccaccagagt cgttcgaggt ggccgtagta ctgcccgagc    3180
agcaggcaga tacctgcaaa gcgcagtggg acacgatggc tgacctcctc aaccaagctg    3240
gcgcgccacc gacacggagc gagaccgtcc aatatgatgc gttctcctcg ccagagagca    3300
tcagcctcaa tgtggctgga gccatcgacc ctagcgaggt agacgcggca ttcgtcgtac    3360
tgccgccgga ccaagaagga ttcgcagacc tcgccagtcc gacagagacg tacccagagc    3420
tgaagaaggc gcttgccaac atgggcattt acagccagat ggcgtacttc gaccggttcc    3480
gcgacgcgaa aatattctat actcgtaacg tggcactcgg gctgctggca gccgctggcg    3540
gcgtcgcatt cacaaccgaa catgcgatgc ctggggacgc agatatgttc attgggattg    3600
atgtctctcg gagctacccc gaggacggtg ccagcggcca gataaacatt gccgcgacgg    3660
cgaccgccgt ctacaaggat ggaactatcc tcggccactc gtccacccga ccgcagctcg    3720
gggagaaact acagtcgacg gatgttcgtg acattatgaa gaatgccatc ctcggctacc    3780
agcaggtgac cggtgagtcg ccgacccata tcgtcatcca ccgtgatggc ttcatgaacg    3840
aagacctcga ccccgccacg gaattcctca acgaacaagg cgtcgagtac gacatcgtcg    3900
aaatccgcaa gcagcgccag acacgcctgc tggcagtctc cgatgtgcag tacgatacgc    3960
ctgtgaagag catcgccgct atcaaccaga acgagccacg ggcaacggtc gccaccttcg    4020
gcgcacccga atacttagcg acacgcgatg gaggcggcct tccccgccca atccaaattg    4080
aacgagtcgc cggcgaaacc gacatcgaga cgctcactcg ccaagtctat ctgctctccc    4140
agtcgcatat ccaggtccat aactcgactg cgcgcctacc catcaccacc gcatacgccg    4200
accaggcaag tactcacgcg accaagggtt acctcgtcca gaccgagcg ttcgagtcta    4260
atgtcggatt cctccgggat ccatacgtaa gtaagtaact cgagcaccac caccaccacc    4320
actgagatcc ggctgctaac aaagcccgaa aggaagctga gttggctgct gccaccgctg    4380
agcaataact agcataaccc cttggggcct ctaaacgggt cttgaggggt ttttgctga    4440
aaggaggaac tatatccgga ttggcgaatg ggacgcgccc tgtagcggcg cattaagcgc    4500
ggcgggtgtg gtggttacgc gcagcgtgac cgctacactt gccagcgccc tagcgcccgc    4560
tcctttcgct ttcttccctt cctttctcgc cacgttcgcc ggcttccccc gtcaagctct    4620
aaatcggggg ctcccttag ggttccgatt tagtgcttta cggcacctcg accccaaaaa    4680
```

```
acttgattag ggtgatggtt cacgtagtgg gccatcgccc tgatagacgg tttttcgccc    4740
tttgacgttg gagtccacgt tctttaatag tggactcttg ttccaaactg gaacaacact    4800
caaccctatc tcggtctatt cttttgattt ataagggatt ttgccgattt cggcctattg    4860
gttaaaaaat gagctgattt aacaaaaatt taacgcgaat tttaacaaaa tattaacgtt    4920
tacaatttca ggtggcactt ttcggggaaa tgtgcgcgga acccctattt gtttattttt    4980
ctaaatacat tcaaatatgt atccgctcat gagacaataa ccctgataaa tgcttcaata    5040
atattgaaaa aggaagagta tgagtattca acatttccgt gtcgccctta ttcccttttt    5100
tgcggcattt tgccttcctg ttttgctca cccagaaacg ctggtgaaag taaaagatgc     5160
tgaagatcag ttgggtgcac gagtgggtta catcgaactg gatctcaaca gcggtaagat    5220
ccttgagagt tttcgccccg aagaacgttt tccaatgatg agcactttta aagttctgct    5280
atgtggcgcg gtattatccc gtattgacgc cgggcaagag caactcggtc gccgcataca    5340
ctattctcag aatgacttgg ttgagtactc accagtcaca gaaaagcatc ttacggatgg    5400
catgacagta agagaattat gcagtgctgc cataaccatg agtgataaca ctgcggccaa    5460
cttacttctg acaacgatcg gaggaccgaa ggagctaacc gcttttttgc acaacatggg    5520
ggatcatgta actcgcctg atcgttggga accggagctg aatgaagcca taccaaacga    5580
cgagcgtgac accacgatgc ctgcagcaat ggcaacaacg ttgcgcaaac tattaactgg    5640
cgaactactt actctagctt cccggcaaca attaatagac tggatggagg cggataaagt    5700
tgcaggacca cttctgcgct cggcccttcc ggctggctgg tttattgctg ataaatctgg    5760
agccggtgag cgtgggtctc gcggtatcat tgcagcactg gggccagatg gtaagccctc    5820
ccgtatcgta gttatctaca cgacggggag tcaggcaact atggatgaac gaaatagaca    5880
gatcgctgag ataggtgcct cactgattaa gcattggtaa ctgtcagacc aagtttactc    5940
atatatactt tagattgatt taaaacttca tttttaattt aaaaggatct aggtgaagat    6000
ccttttttgat aatctcatga ccaaaatccc ttaacgtgag ttttcgttcc actgagcgtc    6060
agacccccgta gaaagatca aaggatcttc ttgagatcct ttttttctgc gcgtaatctg    6120
ctgcttgcaa acaaaaaaac caccgctacc agcggtggtt tgtttgccgg atcaagagct    6180
accaactctt tttccgaagg taactggctt cagcagagcg cagataccaa atactgtcct    6240
tctagtgtag ccgtagttag gccaccactt caagaactct gtagcaccgc ctacatacct    6300
cgctctgcta atcctgttac cagtggctgc tgccagtggc gataagtcgt gtcttaccgg    6360
gttggactca agacgatagt taccggataa ggcgcagcgg tcgggctgaa cggggggttc    6420
gtgcacacag cccagcttgg agcgaacgac ctacaccgaa ctgagatacc tacagcgtga    6480
gctatgagaa agcgccacgc ttcccgaagg agaaaggcg acaggtatc cggtaagcgg     6540
cagggtcgga acaggagagc gcacgaggga gcttccaggg ggaaacgcct ggtatcttta    6600
tagtcctgtc gggtttcgcc acctctgact tgagcgtcga ttttgtgat gctcgtcagg     6660
ggggcggagc ctatggaaaa acgccagcaa cgcggccttt ttacggttcc tggccttttg    6720
ctggcctttt gctcacatgt tctttcctgc gttatcccct gattctgtgg ataaccgtat    6780
taccgccttt gagtgagctg ataccgctcg ccgcagccga acgaccgagc gcagcgagtc    6840
agtgagcgag gaagcggaag agcgcctgat gcggtatttt ctccttacgc atctgtgcgg    6900
tatttcacac cgcatatatg gtgcactctc agtacaatct gctctgatgc cgcatagtta    6960
agccagtata cactccgcta tcgctacgtg actgggtcat ggctgcgccc cgacacccgc    7020
```

-continued

```
caacacccgc tgacgcgccc tgacgggctt gtctgctccc ggcatccgct tacagacaag    7080
ctgtgaccgt ctccgggagc tgcatgtgtc agaggttttc accgtcatca ccgaaacgcg    7140
cgaggcagct gcggtaaagc tcatcagcgt ggtcgtgaag cgattcacag atgtctgcct    7200
gttcatccgc gtccagctcg ttgagttttct ccagaagcgt taatgtctgg cttctgataa   7260
agcgggccat gttaagggcg gttttttcct gtttggtcac tgatgcctcc gtgtaagggg    7320
gatttctgtt catgggggta atgataccga tgaaacgaga gaggatgctc acgatacggg    7380
ttactgatga tgaacatgcc cggttactgg aacgttgtga gggtaaacaa ctggcggtat    7440
ggatgcggcg ggaccagaga aaaatcactc agggtcaatg ccagcgcttc gttaatacag    7500
atgtaggtgt tccacagggt agccagcagc atcctgcgat gcagatccgg aacataatgg    7560
tgcagggcgc tgacttccgc gtttccgac tttacgaaac acggaaaccg aagaccattc     7620
atgttgttgc tcaggtcgca gacgttttgc agcagcagtc gcttcacgtt cgctcgcgta    7680
tcggtgattc attctgctaa ccagtaaggc aaccccgcca gcctagcgg gtcctcaacg     7740 acaggagcac gatcatgcgc acccgtgggg ccgccatgcc ggcgataatg gc            7792
```

<210> SEQ ID NO 34
<211> LENGTH: 7792
<212> TYPE: DNA
<213> ORGANISM: artificial sequence
<220> FEATURE:
<223> OTHER INFORMATION: N-del/E602P

<400> SEQUENCE: 34

```
ctgcttctcg ccgaaacgtt tggtggcggg accagtgacg aaggcttgag cgagggcgtg      60
caagattccg aataccgcaa gcgacaggcc gatcatcgtc gcgctccagc gaaagcggtc     120
ctcgccgaaa atgacccaga gcgctgccgg cacctgtcct acgagttgca tgataaagaa     180
gacagtcata agtgcggcga cgatagtcat gccccgcgcc caccggaagg agctgactgg     240
gttgaaggct ctcaagggca tcggtcgaga tcccggtgcc taatgagtga gctaacttac     300
attaattgcg ttgcgctcac tgcccgcttt ccagtcggga aacctgtcgt gccagctgca     360
ttaatgaatc ggccaacgcg cggggagagg cggtttgcgt attgggcgcc agggtggttt     420
ttcttttcac cagtgagacg ggcaacagct gattgcccctt caccgcctgg ccctgagaga    480
gttgcagcaa gcggtccacg ctggtttgcc ccagcaggcg aaaatcctgt ttgatggtgg    540
ttaacggcgg gatataacat gagctgtctt cggtatcgtc gtatcccact accgagatgt    600
ccgcaccaac gcgcagcccg gactcggtaa tggcgcgcat tgcgcccagc gccatctgat    660
cgttggcaac cagcatcgca gtgggaacga tgccctcatt cagcatttgc atggtttgtt    720
gaaaaccgga catggcactc cagtcgcctt cccgttccgc tatcggctga atttgattgc    780
gagtgagata tttatgccag ccagccagac gcagacgcgc cgagacagaa cttaatgggc    840
ccgctaacag cgcgatttgc tggtgaccca atgcgaccag atgctccacg cccagtcgcg    900
taccgtcttc atgggagaaa ataatactgt tgatgggtgt ctggtcagag acatcaagaa    960
ataacgccgg aacattagtg caggcagctt ccacagcaat ggcatcctgg tcatccagcg   1020
gatagttaat gatcagccca ctgacgcgtt gcgcgagaag attgtgcacc gccgctttac   1080
aggcttcgac gccgcttcgt tctaccatcg acaccaccac gctggcaccc agttgatcgg   1140
cgcgagattt aatcgccgcg acaatttgcg acggcgcgtg cagggccaga ctggaggtgg   1200
caacgccaat cagcaacgac tgtttgcccg ccagttgttg tgccacgcgg ttgggaatgt   1260
aattcagctc cgccatcgcc gcttccactt tttcccgcgt tttcgcagaa acgtggctgg   1320
```

```
cctggttcac cacgcgggaa acggtctgat aagagacacc ggcatactct gcgacatcgt    1380
ataacgttac tggtttcaca ttcaccaccc tgaattgact ctcttccggg cgctatcatg    1440
ccataccgcg aaaggttttg cgccattcga tggtgtccgg gatctcgacg ctctccctta    1500
tgcgactcct gcattaggaa gcagcccagt agtaggttga ggccgttgag caccgccgcc    1560
gcaaggaatg gtgcatgcaa ggagatggcg cccaacagtc ccccggccac ggggcctgcc    1620
accataccca cgccgaaaca agcgctcatg agcccgaagt ggcgagcccg atcttcccca    1680
tcggtgatgt cggcgatata ggcgccagca accgcacctg tggcgccggt gatgccggcc    1740
acgatgcgtc cggcgtagag gatcgagatc gatctcgatc ccgcgaaatt aatacgactc    1800
actatagggg aattgtgagc ggataacaat tcccctctag aaataatttt gtttaacttt    1860
aagaaggaga tatacatatg ggtcaccatc atcatcacca ttcatcgcat caccatcacc    1920
atcacaccgc tcaggaagtc gggacgactg acgaggacga aacgttcgcg ggcggcgagc    1980
cgctcgacca tcacttggac gacgcgctca atgagacgcc agacgacgcg gagacagaga    2040
gcgactcagg ccatgtgatg acctcgttcg cctcccgcga ccaactccct gagtggacgc    2100
tgcatacgta tacgctaaca gccacagacg gcgcaaagac ggacacggag tacgcgcgac    2160
gaaccctcgc atacacggta cggcaggaac tctataccga ccatgatgcg gctccggttg    2220
caactgacgg gctaatgctt ctcacgccag agcgctcgg cgagaccccg cttgacctcg    2280
attgcggtgt ccgggtcgag gcggacgaga ctcggacact cgattacacc acggccaaag    2340
accggttact cgcccgcgaa ctcgtcgaag aggggctcaa acgctccctc tgggatgact    2400
acctcgttcg cggcatcgat gaagtcctct caaaggagcc tgtgctgact tgcgatgagt    2460
tcgacctaca tgagcggtat gacctctctg tcgaagtcgg tcacagtggg cgggcgtacc    2520
ttcacatcaa cttccgccac cggttcgtac cgaagctgac gctcgcagac atcgatgatg    2580
acaacatcta tcctgggctc cgggtgaaga cgacgtatcg cccccggcga ggacatatcg    2640 tctgggtct gcgggacgag tgcgccaccg actcgctcaa cacgctggga aaccagtccg    2700
tcgttgcata ccaccgcaac aatcagacac ctattaacac tgacctcctc gacgctatcg    2760
aggccgctga ccggcgagtc gtcgaaaccc gacgtcaagg gcacggcgat gatgctgtct    2820
cattccccca agaactgctt gcggtcgaac cgaatacgca ccaaattaag cagttcgcct    2880
ccgacggatt ccaccaacag gcccgctcaa agacgcgtct ctcggcctcc cgctgcagcg    2940
agaaagcgca agcgttcgcc gagcggcttg acccggtgcg tctcaatggg tccacggtag    3000
agttctcctc ggagttttc accgggaaca acgagcagca actgcgcctc ctctacgaga    3060
acggtgagtc ggttctgacg ttccgcgacg gggcgcgtgg tgcgcacccc gacgagacat    3120
tctcgaaagg tatcgtcaat ccaccagagt cgttcgaggt ggccgtagta ctgcccgagc    3180
agcaggcaga tacctgcaaa gcgcagtggg acacgatggc tgacctcctc aaccaagctg    3240
gcgcgccacc gacacggagc gagaccgtcc aatatgatgc gttctcctcg ccagagagca    3300
tcagcctcaa tgtggctgga gccatcgacc ctagcgaggt agacgcggca ttcgtcgtac    3360
tgccgccgga ccaagaagga ttcgcagacc tcgccagtcc gacagagacg tacgacccac    3420
tgaagaaggc gcttgccaac atgggcattt acagccagat ggcgtacttc gaccggttcc    3480
gcgacgcgaa aatattctat actcgtaacg tggcactcgg gctgctggca gccgctggcg    3540
gcgtcgcatt cacaaccgaa catgcgatgc ctggggacgc agatatgttc attgggattg    3600
atgtctctcg gagctacccc gaggacggtg ccagcggcca gataaacatt gccgcgacgg    3660
```

```
cgaccgccgt ctacaaggat ggaactatcc tcggccactc gtccacccga ccgcagctcg   3720
gggagaaact acagtcgacg gatgttcgtg acattatgaa gaatgccatc ctcggctacc   3780
agcaggtgac cggtgagtcg ccgacccata tcgtcatcca ccgtgatggc ttcatgaacg   3840
aagacctcga ccccgccacg gaattcctca cgaacaagg cgtcgagtac gacatcgtcg   3900
aaatccgcaa gcagccccag acacgcctgc tggcagtctc cgatgtgcag tacgatacgc   3960
ctgtgaagag catcgccgct atcaaccaga acgagccacg ggcaacggtc gccaccttcg   4020
gcgcacccga atacttagcg acacgcgatg gaggcggcct tccccgccca atccaaattg   4080
aacgagtcgc cggcgaaacc gacatcgaga cgctcactcg ccaagtctat ctgctctccc   4140
agtcgcatat ccaggtccat aactcgactg cgcgcctacc catcaccacc gcatacgccg   4200
accaggcaag tactcacgcg accaagggtt acctcgtcca gaccggagcg ttcgagtcta   4260
atgtcggatt cctccgggat ccatacgtaa gtaagtaact cgagcaccac caccaccacc   4320
actgagatcc ggctgctaac aaagcccgaa aggaagctga gttggctgct gccaccgctg   4380
agcaataact agcataaccc cttggggcct ctaaacgggt cttgagagggt tttttgctga   4440
aaggaggaac tatatccgga ttggcgaatg ggacgcgccc tgtagcggcg cattaagcgc   4500
ggcgggtgtg gtggttacgc gcagcgtgac cgctacactt gccagcgccc tagcgcccgc   4560
tcctttcgct ttcttccctt cctttctcgc cacgttcgcc ggctttcccc gtcaagctct   4620
aaatcggggg ctccctttag ggttccgatt tagtgcttta cggcacctcg accccaaaaa   4680
acttgattag ggtgatggtt cacgtagtgg gccatcgccc tgatagacgg ttttcgccc   4740
tttgacgttg gagtccacgt tctttaatag tggactcttg ttccaaactg gaacaacact   4800
caaccctatc tcggtctatt cttttgattt ataagggatt ttgccgattt cggcctattg   4860
gttaaaaaat gagctgattt aacaaaaatt taacgcgaat tttaacaaaa tattaacgtt   4920
tacaatttca ggtggcactt ttcggggaaa tgtgcgcgga accccctattt gtttatttt   4980
ctaaatacat tcaaatatgt atccgctcat gagacaataa ccctgataaa tgcttcaata   5040
atattgaaaa aggaagagta tgagtattca acatttccgt gtcgccctta ttcccttttt   5100
tgcggcattt tgccttcctg ttttttgctca cccagaaacg ctggtgaaag taaaagatgc   5160
tgaagatcag ttgggtgcac gagtgggtta catcgaactg gatctcaaca gcggtaagat   5220
ccttgagagt tttcgccccg aagaacgttt tccaatgatg agcacttta aagttctgct   5280
atgtggcgcg gtattatccc gtattgacgc cgggcaagag caactcggtc gccgcataca   5340
ctattctcag aatgacttgg ttgagtactc accagtcaca gaaaagcatc ttacggatgg   5400
catgacagta agagaattat gcagtgctgc cataaccatg agtgataaca ctgcggccaa   5460
cttacttctg acaacgatcg gaggaccgaa ggagctaacc gcttttttgc acaacatggg   5520
ggatcatgta actcgccttg atcgttggga accggagctg aatgaagcca taccaaacga   5580
cgagcgtgac accacgatgc ctgcagcaat ggcaacaacg ttgcgcaaac tattaactgg   5640
cgaactactt actctagctt cccggcaaca attaatagac tggatggagg cggataaagt   5700
tgcaggacca cttctgcgct cggcccttcc ggctggctgg tttattgctg ataaatctgg   5760
agccggtgag cgtgggtctc gcggtatcat tgcagcactg gggccagatg gtaagccctc   5820
ccgtatcgta gttatctaca cgacggggag tcaggcaact atggatgaac gaaatagaca   5880
gatcgctgag ataggtgcct cactgattaa gcattggtaa ctgtcagacc aagtttactc   5940
atatatactt tagattgatt taaaacttca ttttaatttt aaaaggatct aggtgaagat   6000
cctttttgat aatctcatga ccaaaatccc ttaacgtgag ttttcgttcc actgagcgtc   6060
```

```
agaccccgta gaaaagatca aaggatcttc ttgagatcct tttttctgc gcgtaatctg    6120 ctgcttgcaa acaaaaaaac caccgctacc agcggtggtt tgtttgccgg atcaagagct    6180
accaactctt tttccgaagg taactggctt cagcagagcg cagataccaa atactgtcct    6240
tctagtgtag ccgtagttag gccaccactt caagaactct gtagcaccgc ctacatacct    6300
cgctctgcta atcctgttac cagtggctgc tgccagtggc gataagtcgt gtcttaccgg    6360
gttggactca agacgatagt taccggataa ggcgcagcgg tcgggctgaa cggggggttc    6420
gtgcacacag cccagcttgg agcgaacgac ctacaccgaa ctgagatacc tacagcgtga    6480
gctatgagaa agcgccacgc ttcccgaagg gagaaaggcg gacaggtatc cggtaagcgg    6540
cagggtcgga acaggagagc gcacgaggga gcttccaggg ggaaacgcct ggtatcttta    6600
tagtcctgtc gggtttcgcc acctctgact tgagcgtcga ttttgtgat gctcgtcagg    6660 ggggcggagc ctatggaaaa acgccagcaa cgcggccttt ttacggttcc tggccttttg    6720
ctggcctttt gctcacatgt tctttcctgc gttatcccct gattctgtgg ataaccgtat    6780
taccgccttt gagtgagctg ataccgctcg ccgcagccga acgaccgagc gcagcgagtc    6840
agtgagcgag gaagcggaag agcgcctgat gcggtatttt ctccttacgc atctgtgcgg    6900
tatttcacac cgcatatatg gtgcactctc agtacaatct gctctgatgc cgcatagtta    6960
agccagtata cactccgcta tcgctacgtg actgggtcat ggctgcgccc gacacccgc    7020 caacacccgc tgacgcgccc tgacgggctt gtctgctccc ggcatccgct tacagacaag    7080
ctgtgaccgt ctccgggagc tgcatgtgtc agaggttttc accgtcatca ccgaaacgcg    7140
cgaggcagct gcggtaaagc tcatcagcgt ggtcgtgaag cgattcacag atgtctgcct    7200
gttcatccgc gtccagctcg ttgagtttct ccagaagcgt taatgtctgg cttctgataa    7260
agcgggccat gttaagggcg gttttttcct gtttggtcac tgatgcctcc gtgtaagggg    7320
gatttctgtt catgggggta atgataccga tgaaacgaga gaggatgctc acgatacggg    7380
ttactgatga tgaacatgcc cggttactgg aacgttgtga gggtaaacaa ctggcggtat    7440
ggatgcggcg ggaccagaga aaaatcactc agggtcaatg ccagcgcttc gttaatacag    7500
atgtaggtgt tccacagggt agccagcagc atcctgcgat gcagatccgg aacataatgg    7560
tgcagggcgc tgacttccgc gtttccagac tttacgaaac acggaaaccg aagaccattc    7620
atgttgttgc tcaggtcgca gacgttttgc agcagcagtc gcttcacgtt cgctcgcgta    7680
tcggtgattc attctgctaa ccagtaaggc aaccccgcca gcctagccgg gtcctcaacg    7740
acaggagcac gatcatgcgc acccgtgggg ccgccatgcc ggcgataatg gc           7792
```

<210> SEQ ID NO 35
<211> LENGTH: 7792
<212> TYPE: DNA
<213> ORGANISM: artificial sequence
<220> FEATURE:
<223> OTHER INFORMATION: N-del/double mutations

<400> SEQUENCE: 35

```
ctgcttctcg ccgaaacgtt tggtggcggg accagtgacg aaggcttgag cgagggcgtg     60
caagattccg aataccgcaa gcgacaggcc gatcatcgtc gcgctccagc gaaagcggtc    120
ctcgccgaaa atgacccaga gcgctgccgg cacctgtcct acgagttgca tgataaagaa    180
gacagtcata agtgcggcga cgatagtcat gccccgcgcc caccggaagg agctgactgg    240
gttgaaggct ctcaagggca tcggtcgaga tcccggtgcc taatgagtga gctaacttac    300
```

```
attaattgcg ttgcgctcac tgcccgcttt ccagtcggga aacctgtcgt gccagctgca    360
ttaatgaatc ggccaacgcg cggggagagg cggtttgcgt attgggcgcc agggtggttt    420
ttcttttcac cagtgagacg ggcaacagct gattgccctt caccgcctgg ccctgagaga    480
gttgcagcaa gcggtccacg ctggtttgcc ccagcaggcg aaaatcctgt ttgatggtgg    540
ttaacggcgg gatataacat gagctgtctt cggtatcgtc gtatcccact accgagatgt    600
ccgcaccaac gcgcagcccg gactcggtaa tggcgcgcat tgcgcccagc gccatctgat    660
cgttggcaac cagcatcgca gtgggaacga tgccctcatt cagcatttgc atggtttgtt    720
gaaaaccgga catggcactc cagtcgcctt cccgttccgc tatcggctga atttgattgc    780
gagtgagata tttatgccag ccagccagac gcagacgcgc cgagacagaa cttaatgggc    840
ccgctaacag cgcgatttgc tggtgaccca atgcgaccag atgctccacg cccagtcgcg    900
taccgtcttc atgggagaaa ataatactgt tgatgggtgt ctggtcagag acatcaagaa    960
ataacgccgg aacattagtg caggcagctt ccacagcaat ggcatcctgg tcatccagcg   1020
gatagttaat gatcagccca ctgacgcgtt gcgcgagaag attgtgcacc gccgctttac   1080
aggcttcgac gccgcttcgt tctaccatcg acaccaccac gctggcaccc agttgatcgg   1140
cgcgagattt aatcgccgcg acaatttgcg acggcgcgtg cagggccaga ctggaggtgg   1200
caacgccaat cagcaacgac tgtttgcccg ccagttgttg tgccacgcgg ttgggaatgt   1260
aattcagctc cgccatcgcc gcttccactt tttcccgcgt tttcgcagaa acgtggctgg   1320
cctggttcac cacgcgggaa acggtctgat aagagacacc ggcatactct gcgacatcgt   1380
ataacgttac tggtttcaca ttcaccaccc tgaattgact ctcttccggg cgctatcatg   1440
ccataccgcg aaaggttttg cgccattcga tggtgtccgg gatctcgacg ctctccctta   1500
tgcgactcct gcattaggaa gcagcccagt agtaggttga ggccgttgag caccgccgcc   1560
gcaaggaatg gtgcatgcaa ggagatggcg cccaacagtc ccccggccac ggggcctgcc   1620
accataccca cgccgaaaca agcgctcatg agcccgaagt ggcgagcccg atcttcccca   1680
tcggtgatgt cggcgatata ggcgccagca accgcacctg tggcgccggt gatgccggcc   1740
acgatgcgtc cggcgtagag gatcgagatc gatctcgatc ccgcgaaatt aatacgactc   1800 actataggg aattgtgagc ggataacaat tcccctctag aaataatttt gtttaacttt   1860
aagaaggaga tatacatatg ggtcaccatc atcatcacca ttcatcgcat caccatcacc   1920
atcacaccgc tcaggaagtc gggacgactg acgaggacga aacgttcgcg ggcggcgagc   1980
cgctcgacca tcacttggac gacgcgctca atgagacgcc agacgacgcg gagacagaga   2040
gcgactcagg ccatgtgatg acctcgttcg cctcccgcga ccaactccct gagtggacgc   2100
tgcatacgta tacgctaaca gccacagacg gcgcaaagac ggacacggag tacgcgcgac   2160
gaaccctcgc atacacggta cggcaggaac tctataccga ccatgatgcg gctccggttg   2220
caactgacgg gctaatgctt ctcacgccag agccgctcgg cgagacccg cttgacctcg   2280 attgcggtgt ccgggtcgag gcggacgaga ctcggacact cgattacacc acggccaaag   2340
accggttact cgcccgcgaa ctcgtcgaag aggggctcaa acgctccctc tgggatgact   2400
acctcgttcg cggcatcgat gaagtcctct caaaggagcc tgtgctgact tgcgatgagt   2460
tcgacctaca tgagcggtat gacctctctg tcgaagtcgg tcacagtggg cgggcgtacc   2520
ttcacatcaa cttccgccac cggttcgtac cgaagctgac gctcgcagac atcgatgatg   2580
acaacatcta tcctgggctc cggggtgaaga cgacgtatcg ccccggcga ggacatatcg   2640 tctggggtct gcgggacgag tgcgccaccg actcgctcaa cacgctggga aaccagtccg   2700
```

-continued

```
tcgttgcata ccaccgcaac aatcagacac ctattaacac tgacctcctc gacgctatcg    2760
aggccgctga ccggcgagtc gtcgaaaccc gacgtcaagg gcacggcgat gatgctgtct    2820
cattccccca agaactgctt gcggtcgaac cgaatacgca ccaaattaag cagttcgcct    2880
ccgacggatt ccaccaacag gcccgctcaa agacgcgtct ctcggcctcc cgctgcagcg    2940
agaaagcgca agcgttcgcc gagcggcttg acccggtgcg tctcaatggg tccacggtag    3000
agttctcctc ggagtttttc accgggaaca acgagcagca actgcgcctc ctctacgaga    3060
acggtgagtc ggttctgacg ttccgcgacg gggcgcgtgg tgcgcacccc gacgagacat    3120
tctcgaaagg tatcgtcaat ccaccagagt cgttcgaggt ggccgtagta ctgcccgagc    3180
agcaggcaga tacctgcaaa gcgcagtggg acacgatggc tgacctcctc aaccaagctg    3240
gcgcgccacc gacacggagc gagaccgtcc aatatgatgc gttctcctcg ccagagagca    3300
tcagcctcaa tgtggctgga gccatcgacc ctagcgaggt agacgcggca ttcgtcgtac    3360
tgccgccgga ccaagaagga ttcgcagacc tcgccagtcc gacagagacg tacgacgagc    3420
tgaagaaggc gcttgccaac atgggcattt acagccagat ggcgtacttc gaccggttcc    3480
gcgacgcgaa aatattctat actcgtaacg tggcactcgg gctgctggca gccgctggcg    3540
gcgtcgcatt cacaaccgaa catgcgatgc ctggggacgc agatatgttc attgggattg    3600
cggtctctcg gagctacccc gaggacggtg ccagcggcca gataaacatt gccgcgacgg    3660
cgaccgccgt ctacaaggat ggaactatcc tcggccactc gtccacccga ccgcagctcg    3720
gggagaaact acagtcgacg gatgttcgtg acattatgaa gaatgccatc ctcggctacc    3780
agcaggtgac cggtgagtcg ccgacccata tcgtcatcca ccgtgcgggc ttcatgaacg    3840
aagacctcga ccccgccacg gaattcctca cgaacaaagg cgtcgagtac gacatcgtcg    3900
aaatccgcaa gcagccccag acacgcctgc tggcagtctc cgatgtgcag tacgatacgc    3960
ctgtgaagag catcgccgct atcaaccaga acgagccacg ggcaacggtc gccaccttcg    4020
gcgcacccga atacttagcg acacgcgatg gaggcggcct tccccgccca atccaaattg    4080
aacgagtcgc cggcgaaacc gacatcgaga cgctcactcg ccaagtctat ctgctctccc    4140
agtcgcatat ccaggtccat aactcgactg cgcgcctacc catcaccacc gcatacgccg    4200
accaggcaag tactcacgcg accaagggtt accctcgtcca gaccggagcg ttcgagtcta    4260
atgtcggatt cctccgggat ccatacgtaa gtaagtaact cgagcaccac caccaccacc    4320
actgagatcc ggctgctaac aaagcccgaa aggaagctga gttggctgct gccaccgctg    4380
agcaataact agcataaccc cttggggcct ctaaacgggt cttgaggggt ttttgctga    4440 aaggaggaac tatatccgga ttggcgaatg ggacgcgccc tgtagcggcg cattaagcgc    4500
ggcgggtgtg gtggttacgc gcagcgtgac cgctacactt gccagcgccc tagcgcccgc    4560
tcctttcgct ttcttccctt cctttctcgc cacgttcgcc ggctttcccc gtcaagctct    4620
aaatcggggg ctccctttag ggttccgatt tagtgcttta cggcacctcg accccaaaaa    4680
acttgattag ggtgatggtt cacgtagtgg gccatcgccc tgatagacgg ttttttcgccc    4740 tttgacgttg gagtccacgt tctttaatag tggactcttg ttccaaactg gaacaacact    4800
caaccctatc tcggtctatt cttttgattt ataaggggatt ttgccgattt cggcctattg    4860
gttaaaaaat gagctgattt aacaaaaatt taacgcgaat tttaacaaaa tattaacgtt    4920
tacaatttca ggtggcactt ttcggggaaa tgtgcgcgga accctatttt gtttattttt    4980
ctaaatacat tcaaatatgt atccgctcat gagacaataa ccctgataaa tgcttcaata    5040
```

-continued

```
atattgaaaa aggaagagta tgagtattca acatttccgt gtcgcccttg ttccctttt      5100
tgcggcattt tgccttcctg tttttgctca cccagaaacg ctggtgaaag taaaagatgc    5160
tgaagatcag ttgggtgcac gagtgggtta catcgaactg gatctcaaca gcggtaagat    5220
ccttgagagt tttcgccccg aagaacgttt tccaatgatg agcactttta aagttctgct    5280
atgtggcgcg gtattatccc gtattgacgc cgggcaagag caactcggtc gccgcataca    5340
ctattctcag aatgacttgg ttgagtactc accagtcaca gaaaagcatc ttacggatgg    5400
catgacagta agagaattat gcagtgctgc cataaccatg agtgataaca ctgcggccaa    5460
cttacttctg acaacgatcg gaggaccgaa ggagctaacc gcttttttgc acaacatggg    5520
ggatcatgta actcgccttg atcgttggga accggagctg aatgaagcca taccaaacga    5580
cgagcgtgac accacgatgc ctgcagcaat ggcaacaacg ttgcgcaaac tattaactgg    5640
cgaactactt actctagctt cccggcaaca attaatagac tggatggagg cggataaagt    5700
tgcaggacca cttctgcgct cggcccttcc ggctggctgg tttattgctg ataaatctgg    5760
agccggtgag cgtgggtctc gcggtatcat tgcagcactg gggccagatg gtaagccctc    5820
ccgtatcgta gttatctaca cgacggggag tcaggcaact atggatgaac gaaatagaca    5880
gatcgctgag ataggtgcct cactgattaa gcattggtaa ctgtcagacc aagtttactc    5940
atatatactt tagattgatt taaaacttca tttttaattt aaaaggatct aggtgaagat    6000
cctttttgat aatctcatga ccaaaatccc ttaacgtgag ttttcgttcc actgagcgtc    6060
agaccccgta gaaaagatca aaggatcttc ttgagatcct tttttctgc gcgtaatctg    6120
ctgcttgcaa acaaaaaaac caccgctacc agcggtggtt tgtttgccgg atcaagagct    6180
accaactctt tttccgaagg taactggctt cagcagagcg cagataccaa atactgtcct    6240
tctagtgtag ccgtagttag gccaccactt caagaactct gtagcaccgc ctacatacct    6300
cgctctgcta atcctgttac cagtggctgc tgccagtggc gataagtcgt gtcttaccgg    6360
gttggactca agacgatagt taccggataa ggcgcagcgg tcgggctgaa cggggggttc    6420
gtgcacacag cccagcttgg agcgaacgac ctacaccgaa ctgagatacc tacagcgtga    6480
gctatgagaa agcgccacgc ttcccgaagg gagaaaggcg gacaggtatc cggtaagcgg    6540
cagggtcgga acaggagagc gcacgaggga gcttccaggg ggaaacgcct ggtatcttta    6600
tagtcctgtc gggtttcgcc acctctgact tgagcgtcga ttttgtgat gctcgtcagg    6660
ggggcggagc ctatggaaaa acgccagcaa cgcggccttt ttacggttcc tggccttttg    6720
ctggcctttt gctcacatgt tctttcctgc gttatcccct gattctgtgg ataaccgtat    6780
taccgccttt gagtgagctg ataccgctcg ccgcagccga acgaccgagc gcagcgagtc    6840
agtgagcgag gaagcggaag agcgcctgat gcggtatttt ctccttacgc atctgtgcgg    6900
tatttcacac cgcatatatg gtgcactctc agtacaatct gctctgatgc cgcatagtta    6960
agccagtata cactccgcta tcgctacgtg actgggtcat ggctgcgccc cgacacccgc    7020
caacacccgc tgacgcgccc tgacgggctt gtctgctccc ggcatccgct tacagacaag    7080
ctgtgaccgt ctccgggagc tgcatgtgtc agaggttttc accgtcatca ccgaaacgcg    7140
cgaggcagct gcggtaaagc tcatcagcgt ggtcgtgaag cgattcacag atgtctgcct    7200
gttcatccgc gtccagctcg ttgagtttct ccagaagcgt taatgtctgg cttctgataa    7260
agcgggccat gttaagggcg gttttttcct gtttggtcac tgatgcctcc gtgtaagggg    7320
gatttctgtt catgggggta atgataccga tgaaacgaga gaggatgctc acgatacggg    7380
ttactgatga tgaacatgcc cggttactgg aacgttgtga gggtaaacaa ctggcggtat    7440
```

| | | | | |
|---|---|---|---|---|
| ggatgcggcg | ggaccagaga | aaaatcactc | agggtcaatg | ccagcgcttc gttaatacag | 7500 |
| atgtaggtgt | tccacagggt | agccagcagc | atcctgcgat | gcagatccgg aacataatgg | 7560 |
| tgcagggcgc | tgacttccgc | gtttccagac | tttacgaaac | acggaaaccg aagaccattc | 7620 |
| atgttgttgc | tcaggtcgca | gacgttttgc | agcagcagtc | gcttcacgtt cgctcgcgta | 7680 |
| tcggtgattc | attctgctaa | ccagtaaggc | aaccccgcca | gcctagccgg gtcctcaacg | 7740 |
| acaggagcac | gatcatgcgc | acccgtgggg | ccgccatgcc | ggcgataatg gc | 7792 |

<210> SEQ ID NO 36
<211> LENGTH: 5752
<212> TYPE: DNA
<213> ORGANISM: artificial sequence
<220> FEATURE:
<223> OTHER INFORMATION: repA

<400> SEQUENCE: 36

| | | | | | |
|---|---|---|---|---|---|
| catgacagta | agagaattat | gcagtgctgc | cataaccatg | agtgataaca ctgcggccaa | 60 |
| cttacttctg | acaacgatcg | gaggaccgaa | ggagctaacc | gcttttttgc acaacatggg | 120 |
| ggatcatgta | actcgccttg | atcgttggga | accggagctg | aatgaagcca taccaaacga | 180 |
| cgagcgtgac | accacgatgc | ctgcagcaat | ggcaacaacg | ttgcgcaaac tattaactgg | 240 |
| cgaactactt | actctagctt | cccggcaaca | attaatagac | tggatggagg cggataaagt | 300 |
| tgcaggacca | cttctgcgct | cggcccttcc | ggctggctgg | tttattgctg ataaatctgg | 360 |
| agccggtgag | cgtgggtctc | gcggtatcat | tgcagcactg | gggccagatg gtaagccctc | 420 |
| ccgtatcgta | gttatctaca | cgacggggag | tcaggcaact | atggatgaac gaaatagaca | 480 |
| gatcgctgag | ataggtgcct | cactgattaa | gcattggtaa | ctgtcagacc aagtttactc | 540 |
| atatatactt | tagattgatt | taaaacttca | tttttaattt | aaaaggatct aggtgaagat | 600 |
| cctttttgat | aatctcatga | ccaaaatccc | ttaacgtgag | ttttcgttcc actgagcgtc | 660 |
| agaccccgta | gaaaagatca | aaggatcttc | ttgagatcct | ttttttctgc gcgtaatctg | 720 |
| ctgcttgcaa | acaaaaaaac | caccgctacc | agcggtggtt | tgtttgccgg atcaagagct | 780 |
| accaactctt | tttccgaagg | taactggctt | cagcagagcg | cagataccaa atactgtcct | 840 |
| tctagtgtag | ccgtagttag | gccaccactt | caagaactct | gtagcaccgc ctacatacct | 900 |
| cgctctgcta | atcctgttac | cagtggctgc | tgccagtggc | gataagtcgt gtcttaccgg | 960 |
| gttggactca | agacgatagt | taccggataa | ggcgcagcgg | tcgggctgaa cggggggttc | 1020 |
| gtgcacacag | cccagcttgg | agcgaacgac | ctacaccgaa | ctgagatacc tacagcgtga | 1080 |
| gctatgagaa | agcgccacgc | ttcccgaagg | gagaaaggcg | gacaggtatc cggtaagcgg | 1140 |
| cagggtcgga | acaggagagc | gcacgaggga | gcttccaggg | ggaaacgcct ggtatcttta | 1200 |
| tagtcctgtc | gggtttcgcc | acctctgact | tgagcgtcga | ttttgtgat gctcgtcagg | 1260 |
| ggggcggagc | ctatgaaaa | acgccagcaa | cgcggccttt | ttacggttcc tggccttttg | 1320 |
| ctggcctttt | gctcacatgt | tctttcctgc | gttatcccct | gattctgtgg ataaccgtat | 1380 |
| taccgccttt | gagtgagctg | ataccgctcg | ccgcagccga | acgaccgagc gcagcgagtc | 1440 |
| agtgagcgag | gaagcggaag | agcgcctgat | gcggtatttt | ctccttacgc atctgtgcgg | 1500 |
| tatttcacac | cgcatatatg | gtgcactctc | agtacaatct | gctctgatgc cgcatagtta | 1560 |
| agccagtata | cactccgcta | tcgctacgtg | actgggtcat | ggctgcgccc cgacacccgc | 1620 |
| caacacccgc | tgacgcgccc | tgacgggctt | gtctgctccc | ggcatccgct tacagacaag | 1680 |

-continued

| | |
|---|---|
| ctgtgaccgt ctccgggagc tgcatgtgtc agaggttttc accgtcatca ccgaaacgcg | 1740 |
| cgaggcagct gcggtaaagc tcatcagcgt ggtcgtgaag cgattcacag atgtctgcct | 1800 |
| gttcatccgc gtccagctcg ttgagtttct ccagaagcgt taatgtctgg cttctgataa | 1860 |
| agcgggccat gttaagggcg gttttttcct gtttggtcac tgatgcctcc gtgtaagggg | 1920 |
| gatttctgtt catgggggta atgataccga tgaaacgaga gaggatgctc acgatacggg | 1980 |
| ttactgatga tgaacatgcc cggttactgg aacgttgtga gggtaaacaa ctggcggtat | 2040 |
| ggatgcggcg ggaccagaga aaaatcactc agggtcaatg ccagcgcttc gttaatacag | 2100 |
| atgtaggtgt tccacagggt agccagcagc atcctgcgat gcagatccgg aacataatgg | 2160 |
| tgcagggcgc tgacttccgc gtttccagac tttacgaaac acggaaaccg aagaccattc | 2220 |
| atgttgttgc tcaggtcgca gacgttttgc agcagcagtc gcttcacgtt cgctcgcgta | 2280 |
| tcggtgattc attctgctaa ccagtaaggc aaccccgcca gcctagccgg gtcctcaacg | 2340 |
| acaggagcac gatcatgcgc acccgtgggg ccgccatgcc ggcgataatg gcctgcttct | 2400 |
| cgccgaaacg tttggtggcg ggaccagtga cgaaggcttg agcgagggcg tgcaagattc | 2460 |
| cgaataccgc aagcgacagg ccgatcatcg tcgcgctcca gcgaaagcgg tcctcgccga | 2520 |
| aaaatgaccca gagcgctgcc ggcacctgtc ctacgagttg catgataaag aagacagtca | 2580 |
| taagtgcggc gacgatagtc atgccccgcg cccaccggaa ggagctgact gggttgaagg | 2640 |
| ctctcaaggg catcggtcga gatcccggtg cctaatgagt gagctaactt acattaattg | 2700 |
| cgttgcgctc actgcccgct ttccagtcgg gaaacctgtc gtgccagctg cattaatgaa | 2760 |
| tcggccaacg cgcggggaga ggcggtttgc gtattgggcg ccagggtggt ttttcttttc | 2820 |
| accagtgaga cgggcaacag ctgattgccc ttcaccgcct ggccctgaga gagttgcagc | 2880 |
| aagcggtcca cgctggtttg ccccagcagg cgaaaatcct gtttgatggt ggttaacggc | 2940 |
| gggatataac atgagctgtc ttcggtatcg tcgtatccca ctaccgagat gtccgcacca | 3000 |
| acgcgcagcc cggactcggt aatggcgcgc attgcgccca cgccatctg atcgttggca | 3060 |
| accagcatcg cagtgggaac gatgccctca ttcagcattt gcatggtttg ttgaaaaccg | 3120 |
| gacatggcac tccagtcgcc ttcccgttcc gctatcggct gaatttgatt gcgagtgaga | 3180 |
| tatttatgcc agccagccag acgcagacgc gccgagacag aacttaatgg gcccgctaac | 3240 |
| agcgcgattt gctggtgacc caatgcgacc agatgctcca cgcccagtcg cgtaccgtct | 3300 |
| tcatgggaga aaataatact gttgatgggt gtctggtcag agacatcaag aaataacgcc | 3360 |
| ggaacattag tgcaggcagc ttccacagca atggcatcct ggtcatccag cggatagtta | 3420 |
| atgatcagcc cactgacgcg ttgcgcgaga agattgtgca ccgccgcttt acaggcttcg | 3480 |
| acgccgcttc gttctaccat cgacaccacc acgctggcac ccagttgatc ggcgcgagat | 3540 |
| ttaatcgccg cgacaatttg cgacggcgcg tgcagggcca gactggaggt ggcaacgcca | 3600 |
| atcagcaacg actgtttgcc cgccagttgt tgtgccacgc ggttgggaat gtaattcagc | 3660 |
| tccgccatcg ccgcttccac ttttcccgc gttttcgcag aaacgtggct ggcctggttc | 3720 |
| accacgcggg aaacggtctg ataagagaca ccggcatact ctgcgacatc gtataacgtt | 3780 |
| actggtttca cattcaccac cctgaattga ctctcttccg ggcgctatca tgccataccg | 3840 |
| cgaaaggttt tgcgccattc gatggtgtcc gggatctcga cgctctccct tatgcgactc | 3900 |
| ctgcattagg aagcagccca gtagtaggtt gaggccgttg agcaccgccg ccgcaaggaa | 3960 |
| tggtgcatgc aaggagatgg cgcccaacag tcccccggcc acgggcctg ccaccatacc | 4020 |
| cacgccgaaa caagcgctca tgagcccgaa gtggcgagcc cgatcttccc catcggtgat | 4080 |

```
gtcggcgata taggcgccag caaccgcacc tgtggcgccg gtgatgccgg ccacgatgcg      4140
tccggcgtag aggatcgaga tcgatctcga tcccgcgaaa ttaatacgac tcactatagg      4200
ggaattgtga gcggataaca attcccctct agaaataatt ttgtttaact ttaagaagga      4260
gatatacata tgggtcacca tcatcatcac cattcatcgc atcaccatca ccatcacgtg      4320
ccaaaaaaga agagaaaggt agccacagtg attgacctcg attcgaccac caccgcagac      4380
gaactgacat cgggacacac gtacgacatc tcagtcacgc tcaccggtgt ctacgataac      4440
accgacgagc agcatcctcg catgtctctc gcattcgagc aggacaacgg cgagcggcgt      4500
tacattaccc tgtggaagaa cacgacaccc aaggatgtct ttacatacga ctacgccacg      4560
ggctcgacgt acatcttcac taacatcgac tacgaagtga aggacggcta cgagaatctg      4620
actgcaacat accagacgac cgtcgagtaa ctcgagcacc accaccacca ccactgagat      4680
ccggctgcta acaaagcccg aaaggaagct gagttggctg ctgccaccgc tgagcaataa      4740
ctagcataac cccttggggc ctctaaacgg gtcttgaggg gttttttgct gaaaggagga      4800
actatatccg gattggcgaa tgggacgcgc cctgtagcgg cgcattaagc gcggcgggtg      4860
tggtggttac gcgcagcgtg accgctacac ttgccagcgc cctagcgccc gctcctttcg      4920
ctttcttccc ttcctttctc gccacgttcg ccggctttcc ccgtcaagct ctaaatcggg      4980
ggctcccttt agggttccga tttagtgctt tacggcacct cgaccccaaa aaacttgatt      5040
agggtgatgg ttcacgtagt gggccatcgc cctgatagac ggtttttcgc cctttgacgt      5100
tggagtccac gttctttaat agtggactct tgttccaaac tggaacaaca ctcaaccct a     5160 tctcggtcta ttcttttgat ttataaggga ttttgccgat ttcggcctat tggttaaaaa      5220
atgagctgat ttaacaaaaa tttaacgcga attttaacaa atattaacg tttacaattt       5280 caggtggcac ttttcgggga aatgtgcgcg gaacccctat ttgtttattt ttctaaatac      5340
attcaaatat gtatccgctc atgagacaat aaccctgata aatgcttcaa taatattgaa      5400
aaaggaagag tatgagtatt caacatttcc gtgtcgccct tattccctt tttgcggcat       5460 tttgccttcc tgttttgct cacccagaaa cgctggtgaa agtaaaagat gctgaagatc       5520
agttgggtgc acgagtgggt tacatcgaac tggatctcaa cagcggtaag atccttgaga      5580
gttttcgccc cgaagaacgt tttccaatga tgagcacttt taaagttctg ctatgtggcg      5640
cggtattatc ccgtattgac gccgggcaag agcaactcgg tcgccgcata cactattctc      5700
agaatgactt ggttgagtac tcaccagtca cagaaaagca tcttacggat gg              5752
```

<210> SEQ ID NO 37
<211> LENGTH: 5428
<212> TYPE: DNA
<213> ORGANISM: artificial sequence
<220> FEATURE:
<223> OTHER INFORMATION: p15-kanR-PtetRed

<400> SEQUENCE: 37

```
gacgtcttaa gacccacttt cacatttaag ttgttttct aatccgcata tgatcaattc        60
aaggccgaat aagaaggctg gctctgcacc ttggtgatca ataattcga tagcttgtcg       120 taataatggc ggcatactat cagtagtagg tgtttccctt tcttctttag cgacttgatg      180
ctcttgatct tccaatacgc aacctaaagt aaaatgcccc acagcgctga gtgcatataa      240
tgcattctct agtgaaaaac cttgttggca taaaaaggct aattgatttt cgagagtttc      300
atactgtttt tctgtaggcc gtgtacctaa atgtactttt gctccatcgc gatgacttag      360
```

```
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600 aatcactta cttttatcta atctagacat cattaattcc taattgctag cattgtacct    660
aggactgagc tagccataaa gttgacactc tatcgttgat agagttattt taccactccc    720
tatcagtgat agagaaaaga attcgatact ttctcggcag gagcaaggtg agatgacagg    780
agatcctgcc ccggcacttc gcccaatagc agccagtccc ttcccgcttc agtgacaacg    840
tcgagcacag ctgcgcaagg aacgcccgtc gtggccagcc acgatagccg cgctgcctcg    900
tcctgcagtt cattcagggc accggacagg tcggtcttga caaaaagaac cgggcgcccc    960
tgcgctgaca gccggaacac ggcggcatca gagcagccga ttgtctgttg tgcccagtca   1020
tagccgaata gcctctccac ccaagcggcc ggagaacctg cgtgcaatcc atcttgttca   1080
atggccgatc ccatctagta tttctcctct ttctctagag ctagcactgt acctaggact   1140
gagctagccg tcaaccatgg gaagccacat caaggagag gcccaggtga aggggactgg    1200
tttccctgct gacggtcctg tgatgaccaa ctcgctgacc gctgcggact ggtgcaggtc   1260
gaagaagact accccaacg acaaaaccat catcagtacc tttaagtgga gttacaccac    1320
tggaaatggc aagcgctacc ggagcactgc gcggaccacc tacacctttg ccaagccaat   1380
ggcggctaac tatctgaaga accagccgat gtacgtgttc cgtaagacgg agctcaagca   1440
ctccaagacc gagctcaact tcaaggagtg caaaaggcc tttaccgatg tgatgggcat    1500
ggacgagctg tacaagtaaa aataataaaa aagccggatt aataatctgg ctttttatat   1560
tctctctcga gtccctatca gtgatagaga ttgacatccc tatcagtgat agagatactg   1620
agcactctag agaaagagga gaaatactag atggatatta atactgaaac tgagatcaag   1680
caaaagcatt cactaacccc ctttcctgtt tccctaatca gcccggcatt tcgcgggcga   1740
tattttcaca gctatttcag gagttcagcc atgaacgctt attacattca ggatcgtctt   1800
gaggctcaga gctgggcgcg tcactaccag cagctcgccc gtgaagagaa agaggcagaa   1860
ctggcagacg acatggaaaa aggcctgccc cagcacctgt ttgaatcgct atgcatcgat   1920
catttgcaac gccacggggc cagcaaaaaa tccattaccc gtgcgtttga tgacgatgtt   1980
gagtttcagg agcgcatggc agaacacatc cggtacatgg ttgaaaccat tgctcaccac   2040
caggttgata ttgattcaga ggtataaaac gaatgagtac tgcactcgca acgctggctg   2100
ggaagctggc tgaacgtgtc ggcatggatt ctgtcgaccc acaggaactg atcaccactc   2160
ttcgccagac ggcatttaaa ggtgatgcca gcgatgcgca gttcatcgca ttactgatcg   2220
ttgccaacca gtacggcctt aatccgtgga cgaaagaaat ttacgccttt cctgataagc   2280
agaatggcat cgttccggtg gtgggcgttg atgctggtc ccgcatcatc aatgaaaacc    2340
agcagtttga tggcatggac tttgagcagg acaatgaatc ctgtacatgc cggatttacc   2400
gcaaggaccg taatcatccg atctgcgtta ccgaatggat ggatgaatgc gccgcgaac    2460 cattcaaaac tcgcgaaggc agagaaatca cggggccgtg gcagtcgcat cccaaacgga   2520
tgttacgtca taaagccatg attcagtgtg cccgtctggc cttcggattt gctggtatct   2580
atgacaagga tgaagccgag cgcattgtcg aaaatactgc atacactgca gaacgtcagc   2640
cggaacgcga catcactccg gttaacgatg aaaccatgca ggagattaac actctgctga   2700
tcgccctgga taaaacatgg gatgacgact tattgccgct ctgttccag atatttcgcc    2760
```

```
gcgacattcg tgcatcgtca gaactgacac aggccgaagc agtaaaagct cttggattcc    2820
tgaaacagaa agccgcagag cagaaggtgg cagcatgaca ccggacatta tcctgcagcg    2880
taccgggatc gatgtgagag ctgtcgaaca gggggatgat gcgtggcaca aattacggct    2940
cggcgtcatc accgcttcag aagttcacaa cgtgatagca aaaccccgct ccggaaagaa    3000
gtggcctgac atgaaaatgt cctacttcca caccctgctt gctgaggttt gcaccggtgt    3060
ggctccggaa gttaacgcta aagcactggc ctggggaaaa cagtacgaga acgacgccag    3120
aaccctgttt gaattcactt ccggcgtgaa tgttactgaa tccccgatca tctatcgcga    3180
cgaaagtatg cgtaccgcct gctctcccga tggtttatgc agtgacgcca acggccttga    3240
actgaaatgc ccgtttacct cccgggattt catgaagttc cggctcggtg ttcgaggc     3300
cataaagtca gcttacatgg cccaggtgca gtacagcatg tgggtgacgc gaaaaaatgc    3360
ctggtacttt gccaactatg acccgcgtat gaagcgtgaa ggcctgcatt atgtcgtgat    3420
tgagcgggat gaaaagtaca tggcgagttt gacgagatc gtgccggagt tcatcgaaaa    3480
aatggacgag cactggctg aaattggttt tgtatttggg gagcaatggc gatgaaaaaa    3540
aaaaccccgc ttcggcgggg ttttttttc tcgagtaagg atctccaggc atcaaataaa    3600
acgaaaggct cagtcgaaag actgggcctt tcgttttatc tgttgtttgt cggtgaacgc    3660
tctctactag agtcacactg gctcaccttc gggtgggcct ttctgcgttt ataccctaggg   3720
atatattccg cttcctcgct cactgactcg ctacgctcgg tcgttcgact gcggcgagcg    3780
gaaatggctt acgaacgggg cggagatttc ctggaagatg ccaggaagat acttaacagg    3840
gaagtgagag ggccgcggca aagccgtttt tccataggct ccgcccccct gacaagcatc    3900
acgaaatctg acgctcaaat cagtggtggc gaaacccgac aggactataa agataccagg    3960
cgtttccccc tggcggctcc ctcgtgcgct ctcctgttcc tgcctttcgg tttaccggtg    4020
tcattccgct gttatggccg cgtttgtctc attccacgcc tgacactcag ttccgggtag    4080
gcagttcgct ccaagctgga ctgtatgcac gaaccccccg ttcagtccga ccgctgcgcc    4140
ttatccggta actatcgtct tgagtccaac ccggaaagac atgcaaaagc accactggca    4200
gcagccactg gtaattgatt tagaggagtt agtcttgaag tcatgcgccg gttaaggcta    4260
aactgaaagg acaagttttg gtgactgcgc tcctccaagc cagttacctc ggttcaaaga    4320
gttggtagct cagagaacct tcgaaaaacc gccctgcaag gcggttttt cgttttcaga    4380
gcaagagatt acgcgcagac caaaacgatc tcaagaagat catcttatta atcagataaa    4440
atatttctag atttcagtgc aatttatctc ttcaaatgta gcacctgaag tcagccccat    4500
acgatataag ttgttactag tgcttggatt ctcaccaata aaaaacgccc ggcggcaacc    4560
gagcgttctg aacaaatcca gatggagttc tgaggtcatt actggatcta tcaacaggag    4620
tccaagcgag ctcgatatca aattacgccc cgccctgcca ctcatcgcag tactgttgta    4680
attcattaag cattctgccg acatggaagc catcacaaac ggcatgatga acctgaatcg    4740
ccagcggcat cagcaccttg tcgccttgcg tataatattt gcccatggtg aaaacggggg    4800
cgaagaagtt gtccatattg gccacgttta aatcaaaact ggtgaaactc acccagggat    4860
tggctgagac gaaaaacata ttctcaataa acccttagg gaataggcc aggttttcac     4920
cgtaacacgc cacatcttgc gaatatatgt gtagaaactg ccggaaatcg tcgtggtatt    4980
cactccagag cgatgaaaac gtttcagttt gctcatggaa acggtgtaa caagggtgaa    5040
cactatccca tatcaccagc tcaccgtctt tcattgccat acgaaattcc ggatgagcat    5100
```

-continued

| | |
|---|---|
| tcatcaggcg ggcaagaatg tgaataaagg ccggataaaa cttgtgctta ttttcttta | 5160 |
| cggtctttaa aaaggccgta atatccagct gaacggtctg gttataggta cattgagcaa | 5220 |
| ctgactgaaa tgcctcaaaa tgttctttac gatgccattg ggatatatca acggtggtat | 5280 |
| atccagtgat ttttttctcc atttttagctt ccttagctcc tgaaaatctc gataactcaa | 5340 |
| aaaatacgcc cggtagtgat cttatttcat tatggtgaaa gttggaacct cttacgtgcc | 5400 |
| gatcaacgtc tcattttcgc cagatatc | 5428 |

```
<210> SEQ ID NO 38
<211> LENGTH: 7792
<212> TYPE: DNA
<213> ORGANISM: artificial sequence
<220> FEATURE:
<223> OTHER INFORMATION: N-del

<400> SEQUENCE: 38
```

| | |
|---|---|
| ctgcttctcg ccgaaacgtt tggtggcggg accagtgacg aaggcttgag cgagggcgtg | 60 |
| caagattccg aataccgcaa gcgacaggcc gatcatcgtc gcgctccagc gaaagcggtc | 120 |
| ctcgccgaaa atgacccaga gcgctgccgg cacctgtcct acgagttgca tgataaagaa | 180 |
| gacagtcata agtgcggcga cgatagtcat gccccgcgcc accggaagg agctgactgg | 240 |
| gttgaaggct ctcaagggca tcggtcgaga tcccggtgcc taatgagtga gctaacttac | 300 |
| attaattgcg ttgcgctcac tgcccgcttt ccagtcggga aacctgtcgt gccagctgca | 360 |
| ttaatgaatc ggccaacgcg cggggagagg cggtttgcgt attgggcgcc agggtggttt | 420 |
| ttcttttcac cagtgagacg ggcaacagct gattgccctt caccgcctgg ccctgagaga | 480 |
| gttgcagcaa gcggtccacg ctggtttgcc ccagcaggcg aaaatcctgt ttgatggtgg | 540 |
| ttaacgcgg gatataacat gagctgtctt cggtatcgtc gtatcccact accgagatgt | 600 |
| ccgcaccaac gcgcagcccg gactcggtaa tggcgcgcat tgcgcccagc gccatctgat | 660 |
| cgttggcaac cagcatcgca gtgggaacga tgccctcatt cagcatttgc atggtttgtt | 720 |
| gaaaaccgga catggcactc cagtcgcctt cccgttccgc tatcggctga atttgattgc | 780 |
| gagtgagata tttatgccag ccagccagac gcagacgcgc cgagacagaa cttaatgggc | 840 |
| ccgctaacag cgcgatttgc tggtgaccca atgcgaccag atgctccacg cccagtcgcg | 900 |
| taccgtcttc atgggagaaa ataatactgt tgatgggtgt ctggtcagag acatcaagaa | 960 |
| ataacgccgg aacattagtg caggcagctt ccacagcaat ggcatcctgg tcatccagcg | 1020 |
| gatagttaat gatcagccca ctgacgcgtt gcgcgagaag attgtgcacc gccgctttac | 1080 |
| aggcttcgac gccgcttcgt tctaccatcg acaccaccac gctggcaccc agttgatcgg | 1140 |
| cgcgagattt aatcgccgcg acaatttgcg acggcgcgtg cagggccaga ctggaggtgg | 1200 |
| caacgccaat cagcaacgac tgtttgcccg ccagttgttg tgccacgcgg ttgggaatgt | 1260 |
| aattcagctc cgccatcgcc gcttccactt ttcccgcgt tttcgcagaa acgtggctgg | 1320 |
| cctggttcac cacgcgggaa acggtctgat aagagacacc ggcatactct gcgacatcgt | 1380 |
| ataacgttac tggtttcaca ttcaccaccc tgaattgact ctcttccggg cgctatcatg | 1440 |
| ccataccgcg aaaggttttg cgccattcga tggtgtccgg gatctcgacg ctctccctta | 1500 |
| tgcgactcct gcattaggaa gcagcccagt agtaggttga ggccgttgag caccgccgcc | 1560 |
| gcaaggaatg gtgcatgcaa ggagatggcg cccaacagtc cccggccac ggggcctgcc | 1620 |
| accatacccca cgccgaaaca agcgctcatg agcccgaagt ggcgagcccg atcttcccca | 1680 |
| tcggtgatgt cggcgatata ggcgccagca accgcacctg tggcgccggt gatgccggcc | 1740 |

```
acgatgcgtc cggcgtagag gatcgagatc gatctcgatc ccgcgaaatt aatacgactc    1800
actatagggg aattgtgagc ggataacaat tcccctctag aaataatttt gtttaacttt    1860
aagaaggaga tatacatatg ggtcaccatc atcatcacca ttcatcgcat caccatcacc    1920
atcacaccgc tcaggaagtc gggacgactg acgaggacga aacgttcgcg ggcggcgagc    1980
cgctcgacca tcacttggac gacgcgctca atgagacgcc agacgacgcg gagacagaga    2040
gcgactcagg ccatgtgatg acctcgttcg cctcccgcga ccaactccct gagtggacgc    2100
tgcatacgta tacgctaaca gccacagacg gcgcaaagac ggacacggag tacgcgcgac    2160
gaaccctcgc atacacgtta cggcaggaac tctataccga ccatgatgcg gctccggttg    2220
caactgacgg gctaatgctt ctcacgccag agccgctcgg cgagaccccg cttgacctcg    2280
attgcggtgt ccgggtcgag gcggacgaga ctcggacact cgattacacc acggccaaag    2340
accggttact cgcccgcgaa ctcgtcgaag aggggctcaa acgctccctc tgggatgact    2400
acctcgttcg cggcatcgat gaagtcctct caaaggagcc tgtgctgact tgcgatgagt    2460
tcgacctaca tgagcggtat gacctctctg tcgaagtcgg tcacagtggg cgggcgtacc    2520
ttcacatcaa cttccgccac cggttcgtac cgaagctgac gctcgcagac atcgatgatg    2580
acaacatcta tcctgggctc cgggtgaaga cgacgtatcg cccccggcga ggacatatcg    2640 tctgggtct gcgggacgag tgcgccaccg actcgctcaa cacgctggga aaccagtccg    2700
tcgttgcata ccaccgcaac aatcagacac ctattaacac tgacctcctc gacgctatcg    2760
aggccgctga ccgcgagtc gtcgaaaccc gacgtcaagg gcacggcgat gatgctgtct    2820
cattccccca agaactgctt gcggtcgaac cgaatacgca ccaaattaag cagttcgcct    2880
ccgacggatt ccaccaacag gcccgctcaa agacgcgtct ctcggcctcc cgctgcagcg    2940
agaaagcgca agcgttcgcc gagcggcttg acccggtgcg tctcaatggg tccacggtag    3000
agttctcctc ggagttttc accgggaaca acgagcagca actgcgcctc ctctacgaga    3060
acggtgagtc ggttctgacg ttccgcgacg gggcgcgtgg tgcgcacccc gacgagacat    3120
tctcgaaagg tatcgtcaat ccaccagagt cgttcgaggt ggccgtagta ctgcccgagc    3180
agcaggcaga tacctgcaaa gcgcagtggg acacgatggc tgacctcctc aaccaagctg    3240
gcgcgccacc gacacggagc gagaccgtcc aatatgatgc gttctcctcg ccagagagca    3300
tcagcctcaa tgtggctgga gccatcgacc ctagcgaggt agacgcggca ttcgtcgtac    3360
tgccgccgga ccaagaagga ttcgcagacc tcgccagtcc gacagagacg tacgacgagc    3420
tgaagaaggc gcttgccaac atgggcattt acagccagat ggcgtacttc gaccggttcc    3480
gcgacgcgaa aatattctat actcgtaacg tggcactcgg gctgctggca gccgctggcg    3540
gcgtcgcatt cacaaccgaa catgcgatgc ctggggacgc agatatgttc attgggattg    3600
atgtctctcg gagctacccc gaggacggtg ccagcggcca gataaacatt gccgcgacgg    3660
cgaccgccgt ctacaaggat ggaactatcc tcggccactc gtccacccga ccgcagctcg    3720
gggagaaact acagtcgacg gatgttcgtg acattatgaa gaatgccatc ctcggctacc    3780
agcaggtgac cggtgagtcg ccgacccata tcgtcatcca ccgtgatggc ttcatgaacg    3840
aagacctcga ccccgccacg gaattcctca acgaacaagg cgtcgagtac gacatcgtcg    3900
aaatccgcaa gcagccccag acacgcctgc tggcagtctc cgatgtgcag tacgatacgc    3960
ctgtgaagag catcgccgct atcaaccaga acgagccacg ggcaacgtc gccaccttcg    4020 gcgcacccga atacttagcg acacgcgatg gaggcggcct tccccgccca atccaaattg    4080
```

```
aacgagtcgc cggcgaaacc gacatcgaga cgctcactcg ccaagtctat ctgctctccc    4140
agtcgcatat ccaggtccat aactcgactg cgcgcctacc catcaccacc gcatacgccg    4200
accaggcaag tactcacgcg accaagggtt acctcgtcca gaccggagcg ttcgagtcta    4260
atgtcggatt cctccgggat ccatacgtaa gtaagtaact cgagcaccac caccaccacc    4320
actgagatcc ggctgctaac aaagcccgaa aggaagctga gttggctgct gccaccgctg    4380
agcaataact agcataaccc cttggggcct ctaaacgggt cttgaggggt tttttgctga    4440
aaggaggaac tatatccgga ttggcgaatg ggacgcgccc tgtagcggcg cattaagcgc    4500
ggcgggtgtg gtggttacgc gcagcgtgac cgctacactt gccagcgccc tagcgcccgc    4560
tcctttcgct ttcttccctt cctttctcgc cacgttcgcc ggctttcccc gtcaagctct    4620
aaatcggggg ctcccttag ggttccgatt tagtgcttta cggcacctcg accccaaaaa    4680
acttgattag ggtgatggtt cacgtagtgg gccatcgccc tgatagacgg ttttttcgccc   4740
tttgacgttg gagtccacgt tctttaatag tggactcttg ttccaaactg gaacaacact    4800
caaccctatc tcggtctatt cttttgattt ataaggatt ttgccgattt cggcctattg     4860
gttaaaaaat gagctgattt aacaaaaatt taacgcgaat tttaacaaaa tattaacgtt    4920
tacaatttca ggtggcactt tcggggaaa tgtgcgcgga accctatt gtttattttt       4980
ctaaatacat tcaaatatgt atccgctcat gagacaataa ccctgataaa tgcttcaata    5040
atattgaaaa aggaagagta tgagtattca acatttccgt gtcgcccta ttcccttttt     5100
tgcggcattt tgccttcctg ttttgctca cccagaaacg ctggtgaaag taaaagatgc     5160
tgaagatcag ttgggtgcac gagtgggtta catcgaactg gatctcaaca gcggtaagat    5220
ccttgagagt tttcgccccg aagaacgttt tccaatgatg agcacttta aagttctgct     5280
atgtggcgcg gtattatccc gtattgacgc cgggcaagag caactcggtc gccgcataca    5340
ctattctcag aatgacttgg ttgagtactc accagtcaca gaaaagcatc ttacggatgg    5400
catgacagta agagaattat gcagtgctgc cataaccatg agtgataaca ctgcggccaa    5460
cttacttctg acaacgatcg gaggaccgaa ggagctaacc gcttttttgc acaacatggg    5520
ggatcatgta actcgccttg atcgttggga accggagctg aatgaagcca taccaaacga    5580
cgagcgtgac accacgatgc ctgcagcaat ggcaacaacg ttgcgcaaac tattaactgg    5640
cgaactactt actctagctt cccggcaaca attaatagac tggatggagg cggataaagt    5700
tgcaggacca cttctgcgct cggcccttcc ggctggctgg tttattgctg ataaatctgg    5760
agccggtgag cgtgggtctc gcggtatcat tgcagcactg gggccagatg gtaagccctc    5820
ccgtatcgta gttatctaca cgacggggag tcaggcaact atggatgaac gaaatagaca    5880
gatcgctgag ataggtgcct cactgattaa gcattggtaa ctgtcagacc aagtttactc    5940
atatatactt tagattgatt taaaacttca ttttaattt aaaaggatct aggtgaagat     6000
ccttttgat aatctcatga ccaaaatccc ttaacgtgag ttttcgttcc actgagcgtc     6060
agaccccgta gaaaagatca aggatcttc ttgagatcct ttttttctgc gcgtaatctg     6120
ctgcttgcaa acaaaaaaac caccgctacc agcggtggtt tgtttgccgg atcaagagct    6180
accaactctt tttccgaagg taactggctt cagcagagcg cagataccaa atactgtcct    6240
tctagtgtag ccgtagttag gccaccactt caagaactct gtagcaccgc ctacatacct    6300
cgctctgcta atcctgttac cagtggctgc tgccagtggc gataagtcgt gtcttaccgg    6360
gttggactca agacgatagt taccggataa ggcgcagcgg tcgggctgaa cggggggttc    6420
gtgcacacag cccagcttgg agcgaacgac ctacaccgaa ctgagatacc tacagcgtga    6480
```

```
gctatgagaa agcgccacgc ttcccgaagg gagaaaggcg gacaggtatc cggtaagcgg    6540
cagggtcgga acaggagagc gcacgaggga gcttccaggg ggaaacgcct ggtatcttta    6600
tagtcctgtc gggtttcgcc acctctgact tgagcgtcga ttttgtgat gctcgtcagg     6660 ggggcggagc ctatggaaaa acgccagcaa cgcggccttt ttacggttcc tggccttttg    6720
ctggcctttt gctcacatgt tctttcctgc gttatcccct gattctgtgg ataaccgtat    6780
taccgccttt gagtgagctg ataccgctcg ccgcagccga acgaccgagc gcagcgagtc    6840
agtgagcgag gaagcggaag agcgcctgat gcggtatttt ctccttacgc atctgtgcgg    6900
tatttcacac cgcatatatg gtgcactctc agtacaatct gctctgatgc cgcatagtta    6960
agccagtata cactccgcta tcgctacgtg actgggtcat ggctgcgccc cgacacccgc    7020
caacacccgc tgacgcgccc tgacgggctt gtctgctccc ggcatccgct tacagacaag    7080
ctgtgaccgt ctccgggagc tgcatgtgtc agaggttttc accgtcatca ccgaaacgcg    7140
cgaggcagct gcggtaaagc tcatcagcgt ggtcgtgaag cgattcacag atgtctgcct    7200
gttcatccgc gtccagctcg ttgagtttct ccagaagcgt taatgtctgg cttctgataa    7260
agcgggccat gttaagggcg gttttttcct gtttggtcac tgatgcctcc gtgtaagggg    7320
gatttctgtt catgggggta atgataccga tgaaacgaga gaggatgctc acgatacggg    7380
ttactgatga tgaacatgcc cggttactgg aacgttgtga gggtaaacaa ctggcggtat    7440
ggatgcggcg ggaccagaga aaaatcactc agggtcaatg ccagcgcttc gttaatacag    7500
atgtaggtgt tccacagggt agccagcagc atcctgcgat gcagatccgg aacataatgg    7560
tgcagggcgc tgacttccgc gtttccagac tttacgaaac acggaaaccg aagaccattc    7620
atgttgttgc tcaggtcgca gacgttttgc agcagcagtc gcttcacgtt cgctcgcgta    7680
tcggtgattc attctgctaa ccagtaaggc aaccccgcca gcctagccgg gtcctcaacg    7740
acaggagcac gatcatgcgc acccgtgggg ccgccatgcc ggcgataatg gc           7792
```

<210> SEQ ID NO 39
<211> LENGTH: 1360
<212> TYPE: DNA
<213> ORGANISM: artificial sequence
<220> FEATURE:
<223> OTHER INFORMATION: KanR-GFP

<400> SEQUENCE: 39

```
agagaatata aaaagccaga ttattaatcc ggcttttta ttattttac ttgtacagct       60 cgtccatgcc catcacatcg gtaaaggcct tttgccactc cttgaagttg agctcggtct    120
tggagtgctt gagctccgtc ttacggaaca cgtacatcgg ctggttcttc agatagttag    180
ccgccattgg cttggcaaag gtgtaggtgg tccgcgcagt gctccggtag cgcttgccat    240
ttccagtggt gtaactccac ttaaaggtac tgatgatggt tttgtcgttg gggtaagtct    300
tcttcgacct gcaccagtcc gcagcggtca gcgagttggt catcacagga ccgtcagcag    360
ggaaaccagt ccccttcacc tgggcctctc ctttgatgtg gcttccctcg taggtgtagc    420
ggtagttaac agtaagggag gcaccatctt caaactgcat tgtgcgatgg acttggtatc    480
cggagccatc taccatggtc tagaatggga tcggccattg aacaagatgg attgcacgca    540
ggttctccgg ccgcttgggt ggagaggcta ttcggctatg actgggcaca acagacaatc    600
ggctgctctg atgccgccgt gttccggctg tcagcgcagg ggcgcccggt tcttttgtc    660 aagaccgacc tgtccggtgc cctgaatgaa ctgcaggacg aggcagcgcg gctatcgtgg    720
```

| | |
|---|---|
| ctggccacga cgggcgttcc ttgcgcagct gtgctcgacg ttgtcactga agcgggaagg | 780 |
| gactggctgc tattgggcga agtgccgggg caggatctcc tgtcatctca ccttgctcct | 840 |
| gccgagaaag tatccatcat ggctgatgca atgcggcggc tgcatacgct tgatccggct | 900 |
| acctgcccat tcgaccacca agcgaaacat cgcatcgagc gagcacgtac tcggatggaa | 960 |
| gccggtcttg tcgatcagga tgatctggac gaagagcatc aggggctcgc gccagccgaa | 1020 |
| ctgttcgcca ggctcaaggc gcgcatgccc gacggcgatg atctcgtcgt gacccatggc | 1080 |
| gatgcctgct tgccgaatat catggtggaa aatggccgct tttctggatt catcgactgt | 1140 |
| ggccggctgg gtgtggcgga ccgctatcag gacatagcgt tggctacccg tgatattgct | 1200 |
| gaagagcttg gcggcgaatg ggctgaccgc ttcctcgtgc tttacggtat cgccgctccc | 1260 |
| gattcgcagc gcatcgcctt ctatcgcctt cttgacgagt tcttctaagg atccaaataa | 1320 |
| taaaaaagcc ggattaataa tctggctttt tatattctct | 1360 |

<210> SEQ ID NO 40
<211> LENGTH: 2976
<212> TYPE: DNA
<213> ORGANISM: artificial sequence
<220> FEATURE:
<223> OTHER INFORMATION: pBSI-SceI (E/H) plasmid DNA

<400> SEQUENCE: 40

| | |
|---|---|
| aaattgtaaa cgttaatatt ttgttaaaat tcgcgttaaa ttttttgttaa atcagctcat | 60 |
| tttttaacca ataggccgaa atcggcaaaa tcccttataa atcaaaagaa tagaccgaga | 120 |
| tagggttgag tgttgttcca gtttggaaca agagtccact attaaagaac gtggactcca | 180 |
| acgtcaaagg gcgaaaaacc gtctatcagg gcgatggccc actacgtgaa ccatcaccct | 240 |
| aatcaagttt ttggggtcg aggtgccgta agcactaaa tcggaacccct aaagggagcc | 300 |
| cccgatttag agcttgacgg ggaaagccgg cgaacgtggc gagaaaggaa gggaagaaag | 360 |
| cgaaaggagc gggcgctagg gcgctggcaa gtgtagcggt cacgctgcgc gtaaccacca | 420 |
| cacccgccgc gcttaatgcg ccgctacagg gcgcgtccca ttcgccattc aggctacgca | 480 |
| actgttggga agggcgatcg gtgcgggcct cttcgctatt acgccagctg gcgaagggg | 540 |
| gatgtgctgc aaggcgatta agttgggtaa cgccagggtt ttcccagtca cgacgttgta | 600 |
| aaacgacggc cagtgaattg taatacgact cactataggg cgaattggag ctccaccgcg | 660 |
| gtggcggccg ctctagaact agtggatccc ccgggctgca ggaattacgc tagggataac | 720 |
| agggtaatac agctttatcg ataccgtcga cctcgagggg gggcccggta cccagctttt | 780 |
| gttcccttta gtgagggtta attccgagct tggcgtaatc atggtcatag ctgtttcctg | 840 |
| tgtgaaattg ttatccgctc acaattccac acaacatagg agccgaagc ataaagtgta | 900 |
| aagcctgggg tgcctaatga gtgaggtaac tcacattaat tgcgttgcgc tcactgcccg | 960 |
| ctttccagtc gggaaacctg tcgtgccagc tgcattaatg aatcggccaa cgcgcgggga | 1020 |
| gaggcggttt gcgtattggg cgctcttccg cttcctcgct cactgactcg ctgcgctcgg | 1080 |
| tcgttcggct gcggcgagcg gtatcagctc actcaaaggc ggtaatacgg ttatccacag | 1140 |
| aatcagggga taacgcagga aagaacatgt gagcaaaagg ccagcaaaag gccaggaacc | 1200 |
| gtaaaaaggc cgcgttgctg gcgtttttcc ataggctcgg ccccctgac gagcatcaca | 1260 |
| aaaatcgacg ctcaagtcag aggtggcgaa acccgacagg actataaaga taccaggcgt | 1320 |
| tccccctgg aagctccctc gtgcgctctc ctgttccgac cctgccgctt accggatacc | 1380 |
| tgtccgcctt tctcccttcg ggaagcgtgg cgctttctca atgctcacgc tgtaggtatc | 1440 |

```
tcagttcggt gtaggtcgtt cgctccaagc tgggctgtgt gcacgaaccc cccgttcagc    1500
ccgaccgctg cgccttatcc ggtaactatc gtcttgagtc caacccggta agacacgact    1560
tatcgccact ggcagcagcc actggtaaca ggattagcag agcgaggtat gtaggcggtg    1620
ctacagagtt cttgaagtgg tggcctaact acggctacac tagaaggaca gtatttggta    1680
tctgcgctct gctgaagcca gttaccttcg gaaaagagt  tggtagctct tgatccggca    1740
aacaaaccac cgctggtagc ggtggttttt ttgtttgcaa gcagcagatt acgcgcagaa    1800
aaaaaggatc tcaagaagat cctttgatct tttctacggg gtctgacgct cagtggaacg    1860
aaaactcacg ttaagggatt ttggtcatga gattatcaaa aaggatcttc acctagatcc    1920
ttttaaatta aaaatgaagt tttaaatcaa tctaaagtat atatgagtaa acttggtctg    1980
acagttacca atgcttaatc agtgaggcac ctatctcagc gatctgtcta tttcgttcat    2040
ccatagttgc ctgactcccc gtcgtgtaga taactacgat acgggagggc ttaccatctg    2100
gccccagtgt tgcaatgata ccgcgagacc cacgctcacc ggctccagat ttatcagcaa    2160
taaaccagcc agccggaagg gccgagcgca gaagtggtcc tgcaacttta tccgcctcca    2220
tccagtctat taattgttgc cgggaagcta gagtaagtag ttcgccagtt aatagtttgc    2280
gcaacgttgt tgccattgct acaggcatcg tggtgtcacg ctcgtcgttt ggtatggctt    2340
cattcagctc cggttcccaa cgatcaaggc gagttacatg atcccccatg ttgtgaaaaa    2400
aagcggttag ctccttcggt cctccgatcg ttgtcagaag taagttggcc gcagtgttat    2460
cactcatgct tatggcagca ctgcataatt ctcttactgt catgccatcc gtaagatgct    2520
tttctgtgac tggtgagtac tcaaccaagt cattctgaga atagtgtatg cggcgaccga    2580
gttgctcttg cccggcgtca atacgggata taccgcgcc  acatagcaga actttaaaag    2640
tgctcatcat tggaaaacgt tcttcgggc  gaaaactctc aaggatctta ccgctgttga    2700
gatccagttc gatgtaaccc actcgtgcac ccaactgatc ttcagcatct tttactttca    2760
ccagcgtttc tgggtgagca aaaacaggaa ggcaaaatgc cgcaaaaaag ggaataaggg    2820
cgacacggaa atgttgaata ctcatactct ccttttttca atattattga agcatttatc    2880
agggttattg tctcatgagc ggatacatat ttgaatgtat ttagaaaaat aaacaaatag    2940
gggttccgcg cacatttccc cgaaaagtgc cacctg                              2976
```

<210> SEQ ID NO 41
<211> LENGTH: 1137
<212> TYPE: PRT
<213> ORGANISM: artificial sequence
<220> FEATURE:
<223> OTHER INFORMATION: GST-tag-NgAgo-His tag

<400> SEQUENCE: 41

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu

-continued

```
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Ala Met Gly Gly
            210                 215                 220
Gly Met Val Pro Lys Lys Lys Arg Lys Val Ala Thr Val Ile Asp Leu
225                 230                 235                 240
Asp Ser Thr Thr Thr Ala Asp Glu Leu Thr Ser Gly His Thr Tyr Asp
                245                 250                 255
Ile Ser Val Thr Leu Thr Gly Val Tyr Asp Asn Thr Asp Glu Gln His
            260                 265                 270
Pro Arg Met Ser Leu Ala Phe Glu Gln Asp Asn Gly Glu Arg Arg Tyr
            275                 280                 285
Ile Thr Leu Trp Lys Asn Thr Thr Pro Lys Asp Val Phe Thr Tyr Asp
            290                 295                 300
Tyr Ala Thr Gly Ser Thr Tyr Ile Phe Thr Asn Ile Asp Tyr Glu Val
305                 310                 315                 320
Lys Asp Gly Tyr Glu Asn Leu Thr Ala Thr Tyr Gln Thr Thr Val Glu
                325                 330                 335
Asn Ala Thr Ala Gln Glu Val Gly Thr Thr Asp Glu Asp Glu Thr Phe
            340                 345                 350
Ala Gly Gly Glu Pro Leu Asp His His Leu Asp Asp Ala Leu Asn Glu
            355                 360                 365
Thr Pro Asp Asp Ala Glu Thr Glu Ser Asp Ser Gly His Val Met Thr
            370                 375                 380
Ser Phe Ala Ser Arg Asp Gln Leu Pro Glu Trp Thr Leu His Thr Tyr
385                 390                 395                 400
Thr Leu Thr Ala Thr Asp Gly Ala Lys Thr Asp Thr Glu Tyr Ala Arg
                405                 410                 415
Arg Thr Leu Ala Tyr Thr Val Arg Gln Glu Leu Tyr Thr Asp His Asp
            420                 425                 430
Ala Ala Pro Val Ala Thr Asp Gly Leu Met Leu Leu Thr Pro Glu Pro
            435                 440                 445
Leu Gly Glu Thr Pro Leu Asp Leu Asp Cys Gly Val Arg Val Glu Ala
            450                 455                 460
Asp Glu Thr Arg Thr Leu Asp Tyr Thr Thr Ala Lys Asp Arg Leu Leu
465                 470                 475                 480
Ala Arg Glu Leu Val Glu Glu Gly Leu Lys Arg Ser Leu Trp Asp Asp
                485                 490                 495
Tyr Leu Val Arg Gly Ile Asp Glu Val Leu Ser Lys Glu Pro Val Leu
            500                 505                 510
```

```
Thr Cys Asp Glu Phe Asp Leu His Glu Arg Tyr Asp Leu Ser Val Glu
        515                 520                 525

Val Gly His Ser Gly Arg Ala Tyr Leu His Ile Asn Phe Arg His Arg
        530                 535                 540

Phe Val Pro Lys Leu Thr Leu Ala Asp Ile Asp Asp Asn Ile Tyr
545                 550                 555                 560

Pro Gly Leu Arg Val Lys Thr Thr Tyr Arg Pro Arg Arg Gly His Ile
                    565                 570                 575

Val Trp Gly Leu Arg Asp Glu Cys Ala Thr Asp Ser Leu Asn Thr Leu
                580                 585                 590

Gly Asn Gln Ser Val Val Ala Tyr His Arg Asn Asn Gln Thr Pro Ile
            595                 600                 605

Asn Thr Asp Leu Leu Asp Ala Ile Glu Ala Ala Asp Arg Arg Val Val
        610                 615                 620

Glu Thr Arg Arg Gln Gly His Gly Asp Asp Ala Val Ser Phe Pro Gln
625                 630                 635                 640

Glu Leu Leu Ala Val Glu Pro Asn Thr His Gln Ile Lys Gln Phe Ala
                    645                 650                 655

Ser Asp Gly Phe His Gln Gln Ala Arg Ser Lys Thr Arg Leu Ser Ala
                660                 665                 670

Ser Arg Cys Ser Glu Lys Ala Gln Ala Phe Ala Glu Arg Leu Asp Pro
            675                 680                 685

Val Arg Leu Asn Gly Ser Thr Val Glu Phe Ser Glu Phe Phe Thr
        690                 695                 700

Gly Asn Asn Glu Gln Gln Leu Arg Leu Leu Tyr Glu Asn Gly Glu Ser
705                 710                 715                 720

Val Leu Thr Phe Arg Asp Gly Ala Arg Gly Ala His Pro Asp Glu Thr
                    725                 730                 735

Phe Ser Lys Gly Ile Val Asn Pro Pro Glu Ser Phe Glu Val Ala Val
                740                 745                 750

Val Leu Pro Glu Gln Gln Ala Asp Thr Cys Lys Ala Gln Trp Asp Thr
            755                 760                 765

Met Ala Asp Leu Leu Asn Gln Ala Gly Ala Pro Pro Thr Arg Ser Glu
        770                 775                 780

Thr Val Gln Tyr Asp Ala Phe Ser Ser Pro Glu Ser Ile Ser Leu Asn
785                 790                 795                 800

Val Ala Gly Ala Ile Asp Pro Ser Glu Val Asp Ala Ala Phe Val Val
                    805                 810                 815

Leu Pro Pro Asp Gln Glu Gly Phe Ala Asp Leu Ala Ser Pro Thr Glu
                820                 825                 830

Thr Tyr Asp Glu Leu Lys Lys Ala Leu Ala Asn Met Gly Ile Tyr Ser
            835                 840                 845

Gln Met Ala Tyr Phe Asp Arg Phe Arg Asp Ala Lys Ile Phe Tyr Thr
        850                 855                 860

Arg Asn Val Ala Leu Gly Leu Leu Ala Ala Gly Gly Val Ala Phe
865                 870                 875                 880

Thr Thr Glu His Ala Met Pro Gly Asp Ala Asp Met Phe Ile Gly Ile
                    885                 890                 895

Asp Val Ser Arg Ser Tyr Pro Glu Asp Gly Ala Ser Gly Gln Ile Asn
                900                 905                 910

Ile Ala Ala Thr Ala Thr Ala Val Tyr Lys Asp Gly Thr Ile Leu Gly
            915                 920                 925
```

-continued

His Ser Ser Thr Arg Pro Gln Leu Gly Glu Lys Leu Gln Ser Thr Asp
    930                 935                 940

Val Arg Asp Ile Met Lys Asn Ala Ile Leu Gly Tyr Gln Gln Val Thr
945                 950                 955                 960

Gly Glu Ser Pro Thr His Ile Val Ile His Arg Asp Gly Phe Met Asn
                965                 970                 975

Glu Asp Leu Asp Pro Ala Thr Glu Phe Leu Asn Glu Gln Gly Val Glu
            980                 985                 990

Tyr Asp Ile Val Glu Ile Arg Lys Gln Pro Gln Thr Arg Leu Leu Ala
        995                 1000                1005

Val Ser Asp Val Gln Tyr Asp Thr Pro Val Lys Ser Ile Ala Ala
    1010                1015                1020

Ile Asn Gln Asn Glu Pro Arg Ala Thr Val Ala Thr Phe Gly Ala
    1025                1030                1035

Pro Glu Tyr Leu Ala Thr Arg Asp Gly Gly Leu Pro Arg Pro
    1040                1045                1050

Ile Gln Ile Glu Arg Val Ala Gly Glu Thr Asp Ile Glu Thr Leu
    1055                1060                1065

Thr Arg Gln Val Tyr Leu Leu Ser Gln Ser His Ile Gln Val His
    1070                1075                1080

Asn Ser Thr Ala Arg Leu Pro Ile Thr Thr Ala Tyr Ala Asp Gln
    1085                1090                1095

Ala Ser Thr His Ala Thr Lys Gly Tyr Leu Val Gln Thr Gly Ala
    1100                1105                1110

Phe Glu Ser Asn Val Gly Phe Leu Arg Asp Pro Tyr Val Ser Lys
    1115                1120                1125

Leu Leu Glu His His His His His His
    1130                1135

<210> SEQ ID NO 42
<211> LENGTH: 1137
<212> TYPE: PRT
<213> ORGANISM: artificial sequence
<220> FEATURE:
<223> OTHER INFORMATION: GST-tag-NgAgo/D663A/D738A-His-tag

<400> SEQUENCE: 42

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Ala Met Gly Gly
            210                 215                 220

Gly Met Val Pro Lys Lys Arg Lys Val Ala Thr Val Ile Asp Leu
225                 230                 235                 240

Asp Ser Thr Thr Thr Ala Asp Glu Leu Thr Ser Gly His Thr Tyr Asp
            245                 250                 255

Ile Ser Val Thr Leu Thr Gly Val Tyr Asp Asn Thr Asp Glu Gln His
            260                 265                 270

Pro Arg Met Ser Leu Ala Phe Glu Gln Asp Asn Gly Glu Arg Arg Tyr
            275                 280                 285

Ile Thr Leu Trp Lys Asn Thr Thr Pro Lys Asp Val Phe Thr Tyr Asp
290                 295                 300

Tyr Ala Thr Gly Ser Thr Tyr Ile Phe Thr Asn Ile Asp Tyr Glu Val
305                 310                 315                 320

Lys Asp Gly Tyr Glu Asn Leu Thr Ala Thr Tyr Gln Thr Thr Val Glu
            325                 330                 335

Asn Ala Thr Ala Gln Glu Val Gly Thr Thr Asp Glu Asp Glu Thr Phe
            340                 345                 350

Ala Gly Gly Glu Pro Leu Asp His His Leu Asp Asp Ala Leu Asn Glu
            355                 360                 365

Thr Pro Asp Asp Ala Glu Thr Glu Ser Asp Ser Gly His Val Met Thr
            370                 375                 380

Ser Phe Ala Ser Arg Asp Gln Leu Pro Glu Trp Thr Leu His Thr Tyr
385                 390                 395                 400

Thr Leu Thr Ala Thr Asp Gly Ala Lys Thr Asp Thr Glu Tyr Ala Arg
            405                 410                 415

Arg Thr Leu Ala Tyr Thr Val Arg Gln Glu Leu Tyr Thr Asp His Asp
            420                 425                 430

Ala Ala Pro Val Ala Thr Asp Gly Leu Met Leu Leu Thr Pro Glu Pro
            435                 440                 445

Leu Gly Glu Thr Pro Leu Asp Leu Asp Cys Gly Val Arg Val Glu Ala
450                 455                 460

Asp Glu Thr Arg Thr Leu Asp Tyr Thr Thr Ala Lys Asp Arg Leu Leu
465                 470                 475                 480

Ala Arg Glu Leu Val Glu Glu Gly Leu Lys Arg Ser Leu Trp Asp Asp
            485                 490                 495

Tyr Leu Val Arg Gly Ile Asp Glu Val Leu Ser Lys Glu Pro Val Leu
            500                 505                 510

Thr Cys Asp Glu Phe Asp Leu His Glu Arg Tyr Asp Leu Ser Val Glu
            515                 520                 525

Val Gly His Ser Gly Arg Ala Tyr Leu His Ile Asn Phe Arg His Arg
            530                 535                 540

Phe Val Pro Lys Leu Thr Leu Ala Asp Ile Asp Asp Asp Asn Ile Tyr
545                 550                 555                 560

Pro Gly Leu Arg Val Lys Thr Thr Tyr Arg Pro Arg Arg Gly His Ile
```

```
            565                 570                 575
Val Trp Gly Leu Arg Asp Glu Cys Ala Thr Asp Ser Leu Asn Thr Leu
            580                 585                 590

Gly Asn Gln Ser Val Val Ala Tyr His Arg Asn Asn Gln Thr Pro Ile
            595                 600                 605

Asn Thr Asp Leu Leu Asp Ala Ile Glu Ala Ala Asp Arg Arg Val Val
610                 615                 620

Glu Thr Arg Arg Gln Gly His Gly Asp Ala Val Ser Phe Pro Gln
625                 630                 635                 640

Glu Leu Leu Ala Val Glu Pro Asn Thr His Gln Ile Lys Gln Phe Ala
                645                 650                 655

Ser Asp Gly Phe His Gln Gln Ala Arg Ser Lys Thr Arg Leu Ser Ala
                660                 665                 670

Ser Arg Cys Ser Glu Lys Ala Gln Ala Phe Ala Glu Arg Leu Asp Pro
                675                 680                 685

Val Arg Leu Asn Gly Ser Thr Val Glu Phe Ser Ser Glu Phe Phe Thr
            690                 695                 700

Gly Asn Asn Glu Gln Gln Leu Arg Leu Leu Tyr Glu Asn Gly Glu Ser
705                 710                 715                 720

Val Leu Thr Phe Arg Asp Gly Ala Arg Gly Ala His Pro Asp Glu Thr
                725                 730                 735

Phe Ser Lys Gly Ile Val Asn Pro Pro Glu Ser Phe Glu Val Ala Val
                740                 745                 750

Val Leu Pro Glu Gln Gln Ala Asp Thr Cys Lys Ala Gln Trp Asp Thr
                755                 760                 765

Met Ala Asp Leu Leu Asn Gln Ala Gly Ala Pro Pro Thr Arg Ser Glu
770                 775                 780

Thr Val Gln Tyr Asp Ala Phe Ser Ser Pro Glu Ser Ile Ser Leu Asn
785                 790                 795                 800

Val Ala Gly Ala Ile Asp Pro Ser Glu Val Asp Ala Ala Phe Val Val
                805                 810                 815

Leu Pro Pro Asp Gln Glu Gly Phe Ala Asp Leu Ala Ser Pro Thr Glu
                820                 825                 830

Thr Tyr Asp Glu Leu Lys Lys Ala Leu Ala Asn Met Gly Ile Tyr Ser
                835                 840                 845

Gln Met Ala Tyr Phe Asp Arg Phe Arg Asp Ala Lys Ile Phe Tyr Thr
                850                 855                 860

Arg Asn Val Ala Leu Gly Leu Leu Ala Ala Gly Gly Val Ala Phe
865                 870                 875                 880

Thr Thr Glu His Ala Met Pro Gly Asp Ala Asp Met Phe Ile Gly Ile
                885                 890                 895

Ala Val Ser Arg Ser Tyr Pro Glu Asp Gly Ala Ser Gly Gln Ile Asn
                900                 905                 910

Ile Ala Ala Thr Ala Thr Ala Val Tyr Lys Asp Gly Thr Ile Leu Gly
                915                 920                 925

His Ser Ser Thr Arg Pro Gln Leu Gly Glu Lys Leu Gln Ser Thr Asp
                930                 935                 940

Val Arg Asp Ile Met Lys Asn Ala Ile Leu Gly Tyr Gln Gln Val Thr
945                 950                 955                 960

Gly Glu Ser Pro Thr His Ile Val Ile His Arg Ala Gly Phe Met Asn
                965                 970                 975

Glu Asp Leu Asp Pro Ala Thr Glu Phe Leu Asn Glu Gln Gly Val Glu
                980                 985                 990
```

-continued

Tyr Asp Ile Val Glu Ile Arg Lys Gln Pro Gln Thr Arg Leu Leu Ala
        995                 1000                1005

Val Ser Asp Val Gln Tyr Asp Thr Pro Val Lys Ser Ile Ala Ala
    1010                1015                1020

Ile Asn Gln Asn Glu Pro Arg Ala Thr Val Ala Thr Phe Gly Ala
    1025                1030                1035

Pro Glu Tyr Leu Ala Thr Arg Asp Gly Gly Leu Pro Arg Pro
    1040                1045                1050

Ile Gln Ile Glu Arg Val Ala Gly Glu Thr Asp Ile Glu Thr Leu
    1055                1060                1065

Thr Arg Gln Val Tyr Leu Leu Ser Gln Ser His Ile Gln Val His
    1070                1075                1080

Asn Ser Thr Ala Arg Leu Pro Ile Thr Thr Ala Tyr Ala Asp Gln
    1085                1090                1095

Ala Ser Thr His Ala Thr Lys Gly Tyr Leu Val Gln Thr Gly Ala
    1100                1105                1110

Phe Glu Ser Asn Val Gly Phe Leu Arg Asp Pro Tyr Val Ser Lys
    1115                1120                1125

Leu Leu Glu His His His His His His
    1130                1135

<210> SEQ ID NO 43
<211> LENGTH: 1016
<212> TYPE: PRT
<213> ORGANISM: artificial sequence
<220> FEATURE:
<223> OTHER INFORMATION: GDT-tag-N-del-His-tag

<400> SEQUENCE: 43

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

```
Thr Phe Gly Gly Gly Asp His Pro Pro Lys Thr Ala Gln Glu Val Gly
    210                 215                 220

Thr Thr Asp Glu Asp Glu Thr Phe Ala Gly Gly Glu Pro Leu Asp His
225                 230                 235                 240

His Leu Asp Asp Ala Leu Asn Glu Thr Pro Asp Asp Ala Glu Thr Glu
                245                 250                 255

Ser Asp Ser Gly His Val Met Thr Ser Phe Ala Ser Arg Asp Gln Leu
            260                 265                 270

Pro Glu Trp Thr Leu His Thr Tyr Thr Leu Thr Ala Thr Asp Gly Ala
        275                 280                 285

Lys Thr Asp Thr Glu Tyr Ala Arg Arg Thr Leu Ala Tyr Thr Val Arg
    290                 295                 300

Gln Glu Leu Tyr Thr Asp His Asp Ala Ala Pro Val Ala Thr Asp Gly
305                 310                 315                 320

Leu Met Leu Leu Thr Pro Glu Pro Leu Gly Glu Thr Pro Leu Asp Leu
                325                 330                 335

Asp Cys Gly Val Arg Val Glu Ala Asp Glu Thr Arg Thr Leu Asp Tyr
            340                 345                 350

Thr Thr Ala Lys Asp Arg Leu Leu Ala Arg Glu Leu Val Glu Glu Gly
        355                 360                 365

Leu Lys Arg Ser Leu Trp Asp Asp Tyr Leu Val Arg Gly Ile Asp Glu
    370                 375                 380

Val Leu Ser Lys Glu Pro Val Leu Thr Cys Asp Glu Phe Asp Leu His
385                 390                 395                 400

Glu Arg Tyr Asp Leu Ser Val Glu Val Gly His Ser Gly Arg Ala Tyr
                405                 410                 415

Leu His Ile Asn Phe Arg His Arg Phe Val Pro Lys Leu Thr Leu Ala
            420                 425                 430

Asp Ile Asp Asp Asp Asn Ile Tyr Pro Gly Leu Arg Val Lys Thr Thr
        435                 440                 445

Tyr Arg Pro Arg Arg Gly His Ile Val Trp Gly Leu Arg Asp Glu Cys
    450                 455                 460

Ala Thr Asp Ser Leu Asn Thr Leu Gly Asn Gln Ser Val Val Ala Tyr
465                 470                 475                 480

His Arg Asn Asn Gln Thr Pro Ile Asn Thr Asp Leu Leu Asp Ala Ile
                485                 490                 495

Glu Ala Ala Asp Arg Arg Val Val Thr Arg Arg Gln Gly His Gly
            500                 505                 510

Asp Asp Ala Val Ser Phe Pro Gln Glu Leu Leu Ala Val Glu Pro Asn
        515                 520                 525

Thr His Gln Ile Lys Gln Phe Ala Ser Asp Gly Phe His Gln Ala
    530                 535                 540

Arg Ser Lys Thr Arg Leu Ser Ala Ser Arg Cys Ser Glu Lys Ala Gln
545                 550                 555                 560

Ala Phe Ala Glu Arg Leu Asp Pro Val Arg Leu Asn Gly Ser Thr Val
                565                 570                 575

Glu Phe Ser Ser Glu Phe Phe Thr Gly Asn Asn Glu Gln Gln Leu Arg
            580                 585                 590

Leu Leu Tyr Glu Asn Gly Glu Ser Val Leu Thr Phe Arg Asp Gly Ala
        595                 600                 605

Arg Gly Ala His Pro Asp Glu Thr Phe Ser Lys Gly Ile Val Asn Pro
610                 615                 620
```

```
Pro Glu Ser Phe Glu Val Ala Val Val Leu Pro Gln Gln Ala Asp
625                 630                 635                 640

Thr Cys Lys Ala Gln Trp Asp Thr Met Ala Asp Leu Leu Asn Gln Ala
                645                 650                 655

Gly Ala Pro Pro Thr Arg Ser Glu Thr Val Gln Tyr Asp Ala Phe Ser
            660                 665                 670

Ser Pro Glu Ser Ile Ser Leu Asn Val Ala Gly Ala Ile Asp Pro Ser
        675                 680                 685

Glu Val Asp Ala Ala Phe Val Leu Pro Pro Asp Gln Glu Gly Phe
    690                 695                 700

Ala Asp Leu Ala Ser Pro Thr Glu Thr Tyr Asp Glu Leu Lys Lys Ala
705                 710                 715                 720

Leu Ala Asn Met Gly Ile Tyr Ser Gln Met Ala Tyr Phe Asp Arg Phe
                725                 730                 735

Arg Asp Ala Lys Ile Phe Tyr Thr Arg Asn Val Ala Leu Gly Leu Leu
            740                 745                 750

Ala Ala Ala Gly Gly Val Ala Phe Thr Thr Glu His Ala Met Pro Gly
        755                 760                 765

Asp Ala Asp Met Phe Ile Gly Ile Asp Val Ser Arg Ser Tyr Pro Glu
770                 775                 780

Asp Gly Ala Ser Gly Gln Ile Asn Ile Ala Ala Thr Ala Thr Ala Val
785                 790                 795                 800

Tyr Lys Asp Gly Thr Ile Leu Gly His Ser Ser Thr Arg Pro Gln Leu
                805                 810                 815

Gly Glu Lys Leu Gln Ser Thr Asp Val Arg Asp Ile Met Lys Asn Ala
            820                 825                 830

Ile Leu Gly Tyr Gln Gln Val Thr Gly Glu Ser Pro Thr His Ile Val
        835                 840                 845

Ile His Arg Asp Gly Phe Met Asn Glu Asp Leu Asp Pro Ala Thr Glu
850                 855                 860

Phe Leu Asn Glu Gln Gly Val Glu Tyr Asp Ile Val Glu Ile Arg Lys
865                 870                 875                 880

Gln Pro Gln Thr Arg Leu Leu Ala Val Ser Asp Val Gln Tyr Asp Thr
                885                 890                 895

Pro Val Lys Ser Ile Ala Ala Ile Asn Gln Asn Glu Pro Arg Ala Thr
            900                 905                 910

Val Ala Thr Phe Gly Ala Pro Glu Tyr Leu Ala Thr Arg Asp Gly Gly
        915                 920                 925

Gly Leu Pro Arg Pro Ile Gln Ile Glu Arg Val Ala Gly Glu Thr Asp
930                 935                 940

Ile Glu Thr Leu Thr Arg Gln Val Tyr Leu Leu Ser Gln Ser His Ile
945                 950                 955                 960

Gln Val His Asn Ser Thr Ala Arg Leu Pro Ile Thr Thr Ala Tyr Ala
                965                 970                 975

Asp Gln Ala Ser Thr His Ala Thr Lys Gly Tyr Leu Val Gln Thr Gly
            980                 985                 990

Ala Phe Glu Ser Asn Val Gly Phe Leu Arg Asp Pro Tyr Val Ser Lys
        995                 1000                1005

Leu Glu His His His His His His
    1010                1015

<210> SEQ ID NO 44
<211> LENGTH: 1016
<212> TYPE: PRT
```

<213> ORGANISM: artificial sequence
<220> FEATURE:
<223> OTHER INFORMATION: GST-tag-N-del/D663A/D738A-His-tag

<400> SEQUENCE: 44

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Thr Ala Gln Glu Val Gly
    210                 215                 220

Thr Thr Asp Glu Asp Glu Thr Phe Ala Gly Gly Glu Pro Leu Asp His
225                 230                 235                 240

His Leu Asp Asp Ala Leu Asn Glu Thr Pro Asp Asp Ala Glu Thr Glu
                245                 250                 255

Ser Asp Ser Gly His Val Met Thr Ser Phe Ala Ser Arg Asp Gln Leu
            260                 265                 270

Pro Glu Trp Thr Leu His Thr Tyr Thr Leu Thr Ala Thr Asp Gly Ala
        275                 280                 285

Lys Thr Asp Thr Glu Tyr Ala Arg Arg Thr Leu Ala Tyr Thr Val Arg
    290                 295                 300

Gln Glu Leu Tyr Thr Asp His Asp Ala Ala Pro Val Ala Thr Asp Gly
305                 310                 315                 320

Leu Met Leu Leu Thr Pro Glu Pro Leu Gly Glu Thr Pro Leu Asp Leu
                325                 330                 335

Asp Cys Gly Val Arg Val Glu Ala Asp Glu Thr Arg Thr Leu Asp Tyr
            340                 345                 350

Thr Thr Ala Lys Asp Arg Leu Leu Ala Arg Glu Leu Val Glu Glu Gly
        355                 360                 365

Leu Lys Arg Ser Leu Trp Asp Asp Tyr Leu Val Arg Gly Ile Asp Glu
    370                 375                 380

Val Leu Ser Lys Glu Pro Val Leu Thr Cys Asp Glu Phe Asp Leu His
```

-continued

| | | | |
|---|---|---|---|
| 385 | 390 | 395 | 400 |

Glu Arg Tyr Asp Leu Ser Val Glu Val Gly His Ser Gly Arg Ala Tyr
            405                 410                 415

Leu His Ile Asn Phe Arg His Arg Phe Val Pro Lys Leu Thr Leu Ala
            420                 425                 430

Asp Ile Asp Asp Asn Ile Tyr Pro Gly Leu Arg Val Lys Thr Thr
            435                 440                 445

Tyr Arg Pro Arg Gly His Ile Val Trp Gly Leu Arg Asp Glu Cys
450                 455                 460

Ala Thr Asp Ser Leu Asn Thr Leu Gly Asn Gln Ser Val Val Ala Tyr
465                 470                 475                 480

His Arg Asn Asn Gln Thr Pro Ile Asn Thr Asp Leu Leu Asp Ala Ile
            485                 490                 495

Glu Ala Ala Asp Arg Arg Val Val Glu Thr Arg Arg Gln Gly His Gly
            500                 505                 510

Asp Asp Ala Val Ser Phe Pro Gln Glu Leu Leu Ala Val Glu Pro Asn
            515                 520                 525

Thr His Gln Ile Lys Gln Phe Ala Ser Asp Gly Phe His Gln Gln Ala
530                 535                 540

Arg Ser Lys Thr Arg Leu Ser Ala Ser Arg Cys Ser Glu Lys Ala Gln
545                 550                 555                 560

Ala Phe Ala Glu Arg Leu Asp Pro Val Arg Leu Asn Gly Ser Thr Val
            565                 570                 575

Glu Phe Ser Ser Glu Phe Phe Thr Gly Asn Asn Glu Gln Gln Leu Arg
            580                 585                 590

Leu Leu Tyr Glu Asn Gly Glu Ser Val Leu Thr Phe Arg Asp Gly Ala
            595                 600                 605

Arg Gly Ala His Pro Asp Glu Thr Phe Ser Lys Gly Ile Val Asn Pro
610                 615                 620

Pro Glu Ser Phe Glu Val Ala Val Leu Pro Glu Gln Gln Ala Asp
625                 630                 635                 640

Thr Cys Lys Ala Gln Trp Asp Thr Met Ala Asp Leu Leu Asn Gln Ala
            645                 650                 655

Gly Ala Pro Pro Thr Arg Ser Glu Thr Val Gln Tyr Asp Ala Phe Ser
            660                 665                 670

Ser Pro Glu Ser Ile Ser Leu Asn Val Ala Gly Ala Ile Asp Pro Ser
            675                 680                 685

Glu Val Asp Ala Ala Phe Val Val Leu Pro Pro Asp Gln Glu Gly Phe
            690                 695                 700

Ala Asp Leu Ala Ser Pro Thr Glu Thr Tyr Asp Glu Leu Lys Lys Ala
705                 710                 715                 720

Leu Ala Asn Met Gly Ile Tyr Ser Gln Met Ala Tyr Phe Asp Arg Phe
            725                 730                 735

Arg Asp Ala Lys Ile Phe Tyr Thr Arg Asn Val Ala Leu Gly Leu Leu
            740                 745                 750

Ala Ala Ala Gly Gly Val Ala Phe Thr Thr Glu His Ala Met Pro Gly
            755                 760                 765

Asp Ala Asp Met Phe Ile Gly Ile Ala Val Ser Arg Ser Tyr Pro Glu
            770                 775                 780

Asp Gly Ala Ser Gly Gln Ile Asn Ile Ala Ala Thr Ala Thr Ala Val
785                 790                 795                 800

Tyr Lys Asp Gly Thr Ile Leu Gly His Ser Ser Thr Arg Pro Gln Leu
            805                 810                 815

```
Gly Glu Lys Leu Gln Ser Thr Asp Val Arg Asp Ile Met Lys Asn Ala
            820                 825                 830

Ile Leu Gly Tyr Gln Gln Val Thr Gly Glu Ser Pro Thr His Ile Val
            835                 840                 845

Ile His Arg Ala Gly Phe Met Asn Glu Asp Leu Asp Pro Ala Thr Glu
        850                 855                 860

Phe Leu Asn Glu Gln Gly Val Glu Tyr Asp Ile Val Glu Ile Arg Lys
865                 870                 875                 880

Gln Pro Gln Thr Arg Leu Leu Ala Val Ser Asp Val Gln Tyr Asp Thr
                885                 890                 895

Pro Val Lys Ser Ile Ala Ala Ile Asn Gln Asn Glu Pro Arg Ala Thr
            900                 905                 910

Val Ala Thr Phe Gly Ala Pro Glu Tyr Leu Ala Thr Arg Asp Gly Gly
            915                 920                 925

Gly Leu Pro Arg Pro Ile Gln Ile Glu Arg Val Ala Gly Glu Thr Asp
        930                 935                 940

Ile Glu Thr Leu Thr Arg Gln Val Tyr Leu Leu Ser Gln Ser His Ile
945                 950                 955                 960

Gln Val His Asn Ser Thr Ala Arg Leu Pro Ile Thr Thr Ala Tyr Ala
                965                 970                 975

Asp Gln Ala Ser Thr His Ala Thr Lys Gly Tyr Leu Val Gln Thr Gly
            980                 985                 990

Ala Phe Glu Ser Asn Val Gly Phe Leu Arg Asp Pro Tyr Val Ser Lys
        995                 1000                1005

Leu Glu His His His His His His
    1010                1015

<210> SEQ ID NO 45
<211> LENGTH: 918
<212> TYPE: PRT
<213> ORGANISM: artificial sequence
<220> FEATURE:
<223> OTHER INFORMATION: His-tag NgAgo

<400> SEQUENCE: 45

Met Gly His His His His His Ser Ser His His His His His His
1               5                   10                  15

Val Pro Lys Lys Arg Lys Val Ala Thr Val Ile Asp Leu Asp Ser
            20                  25                  30

Thr Thr Thr Ala Asp Glu Leu Thr Ser Gly His Thr Tyr Asp Ile Ser
        35                  40                  45

Val Thr Leu Thr Gly Val Tyr Asp Asn Thr Asp Glu Gln His Pro Arg
50                  55                  60

Met Ser Leu Ala Phe Glu Gln Asp Asn Gly Glu Arg Arg Tyr Ile Thr
65                  70                  75                  80

Leu Trp Lys Asn Thr Thr Pro Lys Asp Val Phe Thr Tyr Asp Tyr Ala
                85                  90                  95

Thr Gly Ser Thr Tyr Ile Phe Thr Asn Ile Asp Tyr Glu Val Lys Asp
            100                 105                 110

Gly Tyr Glu Asn Leu Thr Ala Thr Tyr Gln Thr Thr Val Glu Asn Ala
        115                 120                 125

Thr Ala Gln Glu Val Gly Thr Thr Asp Glu Asp Glu Thr Phe Ala Gly
    130                 135                 140

Gly Glu Pro Leu Asp His His Leu Asp Asp Ala Leu Asn Glu Thr Pro
145                 150                 155                 160
```

Asp Asp Ala Glu Thr Glu Ser Asp Ser Gly His Val Met Thr Ser Phe
            165                 170                 175

Ala Ser Arg Asp Gln Leu Pro Glu Trp Thr Leu His Thr Tyr Thr Leu
            180                 185                 190

Thr Ala Thr Asp Gly Ala Lys Thr Asp Thr Glu Tyr Ala Arg Arg Thr
            195                 200                 205

Leu Ala Tyr Thr Val Arg Gln Glu Leu Tyr Thr Asp His Asp Ala Ala
            210                 215                 220

Pro Val Ala Thr Asp Gly Leu Met Leu Leu Thr Pro Glu Pro Leu Gly
225                 230                 235                 240

Glu Thr Pro Leu Asp Leu Asp Cys Gly Val Arg Val Glu Ala Asp Glu
            245                 250                 255

Thr Arg Thr Leu Asp Tyr Thr Thr Ala Lys Asp Arg Leu Leu Ala Arg
            260                 265                 270

Glu Leu Val Glu Glu Gly Leu Lys Arg Ser Leu Trp Asp Asp Tyr Leu
            275                 280                 285

Val Arg Gly Ile Asp Glu Val Leu Ser Lys Glu Pro Val Leu Thr Cys
            290                 295                 300

Asp Glu Phe Asp Leu His Glu Arg Tyr Asp Leu Ser Val Glu Val Gly
305                 310                 315                 320

His Ser Gly Arg Ala Tyr Leu His Ile Asn Phe Arg His Arg Phe Val
            325                 330                 335

Pro Lys Leu Thr Leu Ala Asp Ile Asp Asp Asn Ile Tyr Pro Gly
            340                 345                 350

Leu Arg Val Lys Thr Thr Tyr Arg Pro Arg Arg Gly His Ile Val Trp
            355                 360                 365

Gly Leu Arg Asp Glu Cys Ala Thr Asp Ser Leu Asn Thr Leu Gly Asn
370                 375                 380

Gln Ser Val Val Ala Tyr His Arg Asn Asn Gln Thr Pro Ile Asn Thr
385                 390                 395                 400

Asp Leu Leu Asp Ala Ile Glu Ala Ala Asp Arg Arg Val Val Glu Thr
            405                 410                 415

Arg Arg Gln Gly His Gly Asp Asp Ala Val Ser Phe Pro Gln Glu Leu
            420                 425                 430

Leu Ala Val Glu Pro Asn Thr His Gln Ile Lys Gln Phe Ala Ser Asp
            435                 440                 445

Gly Phe His Gln Gln Ala Arg Ser Lys Thr Arg Leu Ser Ala Ser Arg
            450                 455                 460

Cys Ser Glu Lys Ala Gln Ala Phe Ala Glu Arg Leu Asp Pro Val Arg
465                 470                 475                 480

Leu Asn Gly Ser Thr Val Glu Phe Ser Ser Glu Phe Phe Thr Gly Asn
            485                 490                 495

Asn Glu Gln Gln Leu Arg Leu Leu Tyr Glu Asn Gly Glu Ser Val Leu
            500                 505                 510

Thr Phe Arg Asp Gly Ala Arg Gly Ala His Pro Asp Gly Thr Phe Ser
            515                 520                 525

Lys Gly Ile Val Asn Pro Pro Glu Ser Phe Glu Val Ala Val Val Leu
            530                 535                 540

Pro Glu Gln Gln Ala Asp Thr Cys Lys Ala Gln Trp Asp Thr Met Ala
545                 550                 555                 560

Asp Leu Leu Asn Gln Ala Gly Ala Pro Pro Thr Arg Ser Glu Thr Val
            565                 570                 575

```
Gln Tyr Asp Ala Phe Ser Ser Pro Glu Ser Ile Ser Leu Asn Val Ala
            580                 585                 590

Gly Ala Ile Asp Pro Ser Glu Val Asp Ala Ala Phe Val Val Leu Pro
        595                 600                 605

Pro Asp Gln Glu Gly Phe Ala Asp Leu Ala Ser Pro Thr Glu Thr Tyr
    610                 615                 620

Asp Glu Leu Lys Lys Ala Leu Ala Asn Met Gly Ile Tyr Ser Gln Met
625                 630                 635                 640

Ala Tyr Phe Asp Arg Phe Arg Asp Ala Lys Ile Phe Tyr Thr Arg Asn
                645                 650                 655

Val Ala Leu Gly Leu Leu Ala Ala Gly Gly Val Ala Phe Thr Thr
            660                 665                 670

Glu His Ala Met Pro Gly Asp Ala Asp Met Phe Ile Gly Ile Asp Val
            675                 680                 685

Ser Arg Ser Tyr Pro Glu Asp Gly Ala Ser Gly Gln Ile Asn Ile Ala
        690                 695                 700

Ala Thr Ala Thr Ala Val Tyr Lys Asp Gly Thr Ile Leu Gly His Ser
705                 710                 715                 720

Ser Thr Arg Pro Gln Leu Gly Glu Lys Leu Gln Ser Thr Asp Val Arg
                725                 730                 735

Asp Ile Met Lys Asn Ala Ile Leu Gly Tyr Gln Gln Val Thr Gly Glu
            740                 745                 750

Ser Pro Thr His Ile Val Ile His Arg Asp Gly Phe Met Asn Glu Asp
        755                 760                 765

Leu Asp Pro Ala Thr Glu Phe Leu Asn Glu Gln Gly Val Glu Tyr Asp
770                 775                 780

Ile Val Glu Ile Arg Lys Gln Pro Gln Thr Arg Leu Leu Ala Val Ser
785                 790                 795                 800

Asp Val Gln Tyr Asp Thr Pro Val Lys Ser Ile Ala Ala Ile Asn Gln
                805                 810                 815

Asn Glu Pro Arg Ala Thr Val Ala Thr Phe Gly Ala Pro Glu Tyr Leu
            820                 825                 830

Ala Thr Arg Asp Gly Gly Gly Leu Pro Arg Pro Ile Gln Ile Glu Arg
            835                 840                 845

Val Ala Gly Glu Thr Asp Ile Glu Thr Leu Thr Arg Gln Val Tyr Leu
850                 855                 860

Leu Ser Gln Ser His Ile Gln Val His Asn Ser Thr Ala Arg Leu Pro
865                 870                 875                 880

Ile Thr Thr Ala Tyr Ala Asp Gln Ala Ser Thr His Ala Thr Lys Gly
                885                 890                 895

Tyr Leu Val Gln Thr Gly Ala Phe Glu Ser Asn Val Gly Phe Leu Arg
            900                 905                 910

Asp Pro Tyr Val Ser Lys
            915

<210> SEQ ID NO 46
<211> LENGTH: 806
<212> TYPE: PRT
<213> ORGANISM: artificial sequence
<220> FEATURE:
<223> OTHER INFORMATION: His-tag-N-del

<400> SEQUENCE: 46

Met Gly His His His His His Ser Ser His His His His
1               5                   10                  15
```

-continued

```
Thr Ala Gln Glu Val Gly Thr Thr Asp Glu Asp Thr Phe Ala Gly
             20                  25                  30

Gly Glu Pro Leu Asp His His Leu Asp Asp Ala Leu Asn Glu Thr Pro
         35                  40                  45

Asp Asp Ala Glu Thr Glu Ser Asp Ser Gly His Val Met Thr Ser Phe
 50                  55                  60

Ala Ser Arg Asp Gln Leu Pro Glu Trp Thr Leu His Thr Tyr Thr Leu
 65                  70                  75                  80

Thr Ala Thr Asp Gly Ala Lys Thr Asp Thr Glu Tyr Ala Arg Arg Thr
                 85                  90                  95

Leu Ala Tyr Thr Val Arg Gln Glu Leu Tyr Thr Asp His Asp Ala Ala
             100                 105                 110

Pro Val Ala Thr Asp Gly Leu Met Leu Leu Thr Pro Glu Pro Leu Gly
         115                 120                 125

Glu Thr Pro Leu Asp Leu Asp Cys Gly Val Arg Val Glu Ala Asp Glu
 130                 135                 140

Thr Arg Thr Leu Asp Tyr Thr Thr Ala Lys Asp Arg Leu Leu Ala Arg
145                 150                 155                 160

Glu Leu Val Glu Glu Gly Leu Lys Arg Ser Leu Trp Asp Asp Tyr Leu
                165                 170                 175

Val Arg Gly Ile Asp Glu Val Leu Ser Lys Glu Pro Val Leu Thr Cys
            180                 185                 190

Asp Glu Phe Asp Leu His Glu Arg Tyr Asp Leu Ser Val Glu Val Gly
        195                 200                 205

His Ser Gly Arg Ala Tyr Leu His Ile Asn Phe Arg His Arg Phe Val
210                 215                 220

Pro Lys Leu Thr Leu Ala Asp Ile Asp Asp Asn Ile Tyr Pro Gly
225                 230                 235                 240

Leu Arg Val Lys Thr Thr Tyr Arg Pro Arg Gly His Ile Val Trp
                245                 250                 255

Gly Leu Arg Asp Glu Cys Ala Thr Asp Ser Leu Asn Thr Leu Gly Asn
            260                 265                 270

Gln Ser Val Val Ala Tyr His Arg Asn Asn Gln Thr Pro Ile Asn Thr
        275                 280                 285

Asp Leu Leu Asp Ala Ile Glu Ala Ala Asp Arg Arg Val Val Glu Thr
290                 295                 300

Arg Arg Gln Gly His Gly Asp Asp Ala Val Ser Phe Pro Gln Glu Leu
305                 310                 315                 320

Leu Ala Val Glu Pro Asn Thr His Gln Ile Lys Gln Phe Ala Ser Asp
                325                 330                 335

Gly Phe His Gln Gln Ala Arg Ser Lys Thr Arg Leu Ser Ala Ser Arg
            340                 345                 350

Cys Ser Glu Lys Ala Gln Ala Phe Ala Glu Arg Leu Asp Pro Val Arg
        355                 360                 365

Leu Asn Gly Ser Thr Val Glu Phe Ser Ser Glu Phe Thr Gly Asn
370                 375                 380

Asn Glu Gln Gln Leu Arg Leu Leu Tyr Glu Asn Gly Glu Ser Val Leu
385                 390                 395                 400

Thr Phe Arg Asp Gly Ala Arg Gly Ala His Pro Asp Glu Thr Phe Ser
                405                 410                 415

Lys Gly Ile Val Asn Pro Pro Glu Ser Phe Glu Val Ala Val Val Leu
            420                 425                 430

Pro Glu Gln Gln Ala Asp Thr Cys Lys Ala Gln Trp Asp Thr Met Ala
```

```
                435                 440                 445
Asp Leu Leu Asn Gln Ala Gly Ala Pro Pro Thr Arg Ser Glu Thr Val
450                 455                 460

Gln Tyr Asp Ala Phe Ser Ser Pro Glu Ser Ile Ser Leu Asn Val Ala
465                 470                 475                 480

Gly Ala Ile Asp Pro Ser Glu Val Asp Ala Phe Val Val Leu Pro
                485                 490                 495

Pro Asp Gln Glu Gly Phe Ala Asp Leu Ala Ser Pro Thr Glu Thr Tyr
                500                 505                 510

Asp Glu Leu Lys Lys Ala Leu Ala Asn Met Gly Ile Tyr Ser Gln Met
                515                 520                 525

Ala Tyr Phe Asp Arg Phe Arg Asp Ala Lys Ile Phe Tyr Thr Arg Asn
                530                 535                 540

Val Ala Leu Gly Leu Leu Ala Ala Gly Gly Val Ala Phe Thr Thr
545                 550                 555                 560

Glu His Ala Met Pro Gly Asp Ala Asp Met Phe Ile Gly Ile Asp Val
                565                 570                 575

Ser Arg Ser Tyr Pro Glu Asp Gly Ala Ser Gly Gln Ile Asn Ile Ala
                580                 585                 590

Ala Thr Ala Thr Ala Val Tyr Lys Asp Gly Thr Ile Leu Gly His Ser
                595                 600                 605

Ser Thr Arg Pro Gln Leu Gly Glu Lys Leu Gln Ser Thr Asp Val Arg
                610                 615                 620

Asp Ile Met Lys Asn Ala Ile Leu Gly Tyr Gln Gln Val Thr Gly Glu
625                 630                 635                 640

Ser Pro Thr His Ile Val Ile His Arg Asp Gly Phe Met Asn Glu Asp
                645                 650                 655

Leu Asp Pro Ala Thr Glu Phe Leu Asn Glu Gln Gly Val Glu Tyr Asp
                660                 665                 670

Ile Val Glu Ile Arg Lys Gln Pro Gln Thr Arg Leu Leu Ala Val Ser
                675                 680                 685

Asp Val Gln Tyr Asp Thr Pro Val Lys Ser Ile Ala Ala Ile Asn Gln
                690                 695                 700

Asn Glu Pro Arg Ala Thr Val Ala Thr Phe Gly Ala Pro Glu Tyr Leu
705                 710                 715                 720

Ala Thr Arg Asp Gly Gly Leu Pro Arg Pro Ile Gln Ile Glu Arg
                725                 730                 735

Val Ala Gly Glu Thr Asp Ile Glu Thr Leu Thr Arg Gln Val Tyr Leu
                740                 745                 750

Leu Ser Gln Ser His Ile Gln Val His Asn Ser Thr Ala Arg Leu Pro
                755                 760                 765

Ile Thr Thr Ala Tyr Ala Asp Gln Ala Ser Thr His Ala Thr Lys Gly
                770                 775                 780

Tyr Leu Val Gln Thr Gly Ala Phe Glu Ser Asn Val Gly Phe Leu Arg
785                 790                 795                 800

Asp Pro Tyr Val Ser Lys
                805
```

<210> SEQ ID NO 47
<211> LENGTH: 126
<212> TYPE: PRT
<213> ORGANISM: artificial sequence
<220> FEATURE:
<223> OTHER INFORMATION: His-tag repA

<400> SEQUENCE: 47

```
Met Gly His His His His His Ser Ser His His His His
1               5                   10                  15

Val Pro Lys Lys Arg Lys Val Ala Thr Val Ile Asp Leu Asp Ser
                20                  25                  30

Thr Thr Thr Ala Asp Glu Leu Thr Ser Gly His Thr Tyr Asp Ile Ser
            35                  40                  45

Val Thr Leu Thr Gly Val Tyr Asp Asn Thr Asp Glu Gln His Pro Arg
50                  55                  60

Met Ser Leu Ala Phe Glu Gln Asp Asn Gly Glu Arg Arg Tyr Ile Thr
65                  70                  75                  80

Leu Trp Lys Asn Thr Thr Pro Lys Asp Val Phe Thr Tyr Asp Tyr Ala
                85                  90                  95

Thr Gly Ser Thr Tyr Ile Phe Thr Asn Ile Asp Tyr Glu Val Lys Asp
                100                 105                 110

Gly Tyr Glu Asn Leu Thr Ala Thr Tyr Gln Thr Thr Val Glu
                115                 120                 125
```

<210> SEQ ID NO 48
<211> LENGTH: 806
<212> TYPE: PRT
<213> ORGANISM: artificial sequence
<220> FEATURE:
<223> OTHER INFORMATION: His-tag N-del/E598A

<400> SEQUENCE: 48

```
Met Gly His His His His His Ser Ser His His His His
1               5                   10                  15

Thr Ala Gln Glu Val Gly Thr Thr Asp Glu Asp Glu Thr Phe Ala Gly
                20                  25                  30

Gly Glu Pro Leu Asp His His Leu Asp Asp Ala Leu Asn Glu Thr Pro
            35                  40                  45

Asp Asp Ala Glu Thr Glu Ser Asp Ser Gly His Val Met Thr Ser Phe
50                  55                  60

Ala Ser Arg Asp Gln Leu Pro Glu Trp Thr Leu His Thr Tyr Thr Leu
65                  70                  75                  80

Thr Ala Thr Asp Gly Ala Lys Thr Asp Thr Glu Tyr Ala Arg Arg Thr
                85                  90                  95

Leu Ala Tyr Thr Val Arg Gln Glu Leu Tyr Thr Asp His Asp Ala Ala
                100                 105                 110

Pro Val Ala Thr Asp Gly Leu Met Leu Leu Thr Pro Glu Pro Leu Gly
                115                 120                 125

Glu Thr Pro Leu Asp Leu Asp Cys Gly Val Arg Val Glu Ala Asp Glu
130                 135                 140

Thr Arg Thr Leu Asp Tyr Thr Thr Ala Lys Asp Arg Leu Leu Ala Arg
145                 150                 155                 160

Glu Leu Val Glu Glu Gly Leu Lys Arg Ser Leu Trp Asp Asp Tyr Leu
                165                 170                 175

Val Arg Gly Ile Asp Glu Val Leu Ser Lys Glu Pro Val Leu Thr Cys
                180                 185                 190

Asp Glu Phe Asp Leu His Glu Arg Tyr Asp Leu Ser Val Glu Val Gly
                195                 200                 205

His Ser Gly Arg Ala Tyr Leu His Ile Asn Phe Arg His Arg Phe Val
210                 215                 220

Pro Lys Leu Thr Leu Ala Asp Ile Asp Asp Asp Asn Ile Tyr Pro Gly
```

-continued

```
            225                 230                 235                 240
        Leu Arg Val Lys Thr Thr Tyr Arg Pro Arg Gly His Ile Val Trp
                        245                 250                 255
        Gly Leu Arg Asp Glu Cys Ala Thr Asp Ser Leu Asn Thr Leu Gly Asn
                        260                 265                 270
        Gln Ser Val Val Ala Tyr His Arg Asn Asn Gln Thr Pro Ile Asn Thr
                        275                 280                 285
        Asp Leu Leu Asp Ala Ile Glu Ala Ala Asp Arg Val Val Glu Thr
                        290                 295                 300
        Arg Arg Gln Gly His Gly Asp Asp Ala Val Ser Phe Pro Gln Glu Leu
        305                 310                 315                 320
        Leu Ala Val Glu Pro Asn Thr His Gln Ile Lys Gln Phe Ala Ser Asp
                        325                 330                 335
        Gly Phe His Gln Gln Ala Arg Ser Lys Thr Arg Leu Ser Ala Ser Arg
                        340                 345                 350
        Cys Ser Glu Lys Ala Gln Ala Phe Ala Glu Arg Leu Asp Pro Val Arg
                        355                 360                 365
        Leu Asn Gly Ser Thr Val Glu Phe Ser Ser Glu Phe Thr Gly Asn
                        370                 375                 380
        Asn Glu Gln Gln Leu Arg Leu Leu Tyr Glu Asn Gly Glu Ser Val Leu
        385                 390                 395                 400
        Thr Phe Arg Asp Gly Ala Arg Gly Ala His Pro Asp Glu Thr Phe Ser
                        405                 410                 415
        Lys Gly Ile Val Asn Pro Pro Glu Ser Phe Glu Val Ala Val Val Leu
                        420                 425                 430
        Pro Glu Gln Gln Ala Asp Thr Cys Lys Ala Gln Trp Asp Thr Met Ala
                        435                 440                 445
        Asp Leu Leu Asn Gln Ala Gly Ala Pro Pro Thr Arg Ser Glu Thr Val
                        450                 455                 460
        Gln Tyr Asp Ala Phe Ser Ser Pro Glu Ser Ile Ser Leu Asn Val Ala
        465                 470                 475                 480
        Gly Ala Ile Asp Pro Ser Glu Val Asp Ala Ala Phe Val Val Leu Pro
                        485                 490                 495
        Pro Asp Gln Glu Gly Phe Ala Asp Leu Ala Ser Pro Thr Ala Thr Tyr
                        500                 505                 510
        Asp Glu Leu Lys Lys Ala Leu Ala Asn Met Gly Ile Tyr Ser Gln Met
                        515                 520                 525
        Ala Tyr Phe Asp Arg Phe Arg Asp Ala Lys Ile Phe Tyr Thr Arg Asn
                        530                 535                 540
        Val Ala Leu Gly Leu Leu Ala Ala Ala Gly Gly Val Ala Phe Thr Thr
        545                 550                 555                 560
        Glu His Ala Met Pro Gly Asp Ala Asp Met Phe Ile Gly Ile Asp Val
                        565                 570                 575
        Ser Arg Ser Tyr Pro Glu Asp Gly Ala Ser Gly Gln Ile Asn Ile Ala
                        580                 585                 590
        Ala Thr Ala Thr Ala Val Tyr Lys Asp Gly Thr Ile Leu Gly His Ser
                        595                 600                 605
        Ser Thr Arg Pro Gln Leu Gly Glu Lys Leu Gln Ser Thr Asp Val Arg
                        610                 615                 620
        Asp Ile Met Lys Asn Ala Ile Leu Gly Tyr Gln Gln Val Thr Gly Glu
        625                 630                 635                 640
        Ser Pro Thr His Ile Val Ile His Arg Asp Gly Phe Met Asn Glu Asp
                        645                 650                 655
```

-continued

```
Leu Asp Pro Ala Thr Glu Phe Leu Asn Glu Gln Gly Val Glu Tyr Asp
            660                 665                 670

Ile Val Glu Ile Arg Lys Gln Pro Gln Thr Arg Leu Leu Ala Val Ser
        675                 680                 685

Asp Val Gln Tyr Asp Thr Pro Val Lys Ser Ile Ala Ala Ile Asn Gln
690                 695                 700

Asn Glu Pro Arg Ala Thr Val Ala Thr Phe Gly Ala Pro Glu Tyr Leu
705                 710                 715                 720

Ala Thr Arg Asp Gly Gly Leu Pro Arg Pro Ile Gln Ile Glu Arg
                725                 730                 735

Val Ala Gly Glu Thr Asp Ile Glu Thr Leu Thr Arg Gln Val Tyr Leu
            740                 745                 750

Leu Ser Gln Ser His Ile Gln Val His Asn Ser Thr Ala Arg Leu Pro
        755                 760                 765

Ile Thr Thr Ala Tyr Ala Asp Gln Ala Ser Thr His Ala Thr Lys Gly
770                 775                 780

Tyr Leu Val Gln Thr Gly Ala Phe Glu Ser Asn Val Gly Phe Leu Arg
785                 790                 795                 800

Asp Pro Tyr Val Ser Lys
                805

<210> SEQ ID NO 49
<211> LENGTH: 806
<212> TYPE: PRT
<213> ORGANISM: artificial sequence
<220> FEATURE:
<223> OTHER INFORMATION: His-tag N-del/D601P

<400> SEQUENCE: 49

Met Gly His His His His His Ser Ser His His His His His
1               5                   10                  15

Thr Ala Gln Glu Val Gly Thr Thr Asp Glu Asp Glu Thr Phe Ala Gly
            20                  25                  30

Gly Glu Pro Leu Asp His His Leu Asp Asp Ala Leu Asn Glu Thr Pro
        35                  40                  45

Asp Asp Ala Glu Thr Glu Ser Asp Ser Gly His Val Met Thr Ser Phe
50                  55                  60

Ala Ser Arg Asp Gln Leu Pro Glu Trp Thr Leu His Thr Tyr Thr Leu
65                  70                  75                  80

Thr Ala Thr Asp Gly Ala Lys Thr Asp Thr Glu Tyr Ala Arg Arg Thr
                85                  90                  95

Leu Ala Tyr Thr Val Arg Gln Glu Leu Tyr Thr Asp His Asp Ala Ala
            100                 105                 110

Pro Val Ala Thr Asp Gly Leu Met Leu Leu Thr Pro Glu Pro Leu Gly
        115                 120                 125

Glu Thr Pro Leu Asp Leu Asp Cys Gly Val Arg Val Glu Ala Asp Glu
130                 135                 140

Thr Arg Thr Leu Asp Tyr Thr Thr Ala Lys Asp Arg Leu Leu Ala Arg
145                 150                 155                 160

Glu Leu Val Glu Glu Gly Leu Lys Arg Ser Leu Trp Asp Asp Tyr Leu
                165                 170                 175

Val Arg Gly Ile Asp Glu Val Leu Ser Lys Glu Pro Val Leu Thr Cys
            180                 185                 190

Asp Glu Phe Asp Leu His Glu Arg Tyr Asp Leu Ser Val Glu Val Gly
        195                 200                 205
```

-continued

```
His Ser Gly Arg Ala Tyr Leu His Ile Asn Phe Arg His Arg Phe Val
    210                 215                 220
Pro Lys Leu Thr Leu Ala Asp Ile Asp Asp Asp Asn Ile Tyr Pro Gly
225                 230                 235                 240
Leu Arg Val Lys Thr Thr Tyr Arg Pro Arg Arg Gly His Ile Val Trp
                245                 250                 255
Gly Leu Arg Asp Glu Cys Ala Thr Asp Ser Leu Asn Thr Leu Gly Asn
            260                 265                 270
Gln Ser Val Val Ala Tyr His Arg Asn Asn Gln Thr Pro Ile Asn Thr
        275                 280                 285
Asp Leu Leu Asp Ala Ile Glu Ala Ala Asp Arg Val Val Glu Thr
    290                 295                 300
Arg Arg Gln Gly His Gly Asp Asp Ala Val Ser Phe Pro Gln Glu Leu
305                 310                 315                 320
Leu Ala Val Glu Pro Asn Thr His Gln Ile Lys Gln Phe Ala Ser Asp
                325                 330                 335
Gly Phe His Gln Gln Ala Arg Ser Lys Thr Arg Leu Ser Ala Ser Arg
            340                 345                 350
Cys Ser Glu Lys Ala Gln Ala Phe Ala Glu Arg Leu Asp Pro Val Arg
        355                 360                 365
Leu Asn Gly Ser Thr Val Glu Phe Ser Ser Glu Phe Phe Thr Gly Asn
    370                 375                 380
Asn Glu Gln Gln Leu Arg Leu Leu Tyr Glu Asn Gly Glu Ser Val Leu
385                 390                 395                 400
Thr Phe Arg Asp Gly Ala Arg Gly Ala His Pro Asp Glu Thr Phe Ser
                405                 410                 415
Lys Gly Ile Val Asn Pro Pro Glu Ser Phe Glu Val Ala Val Val Leu
            420                 425                 430
Pro Glu Gln Gln Ala Asp Thr Cys Lys Ala Gln Trp Asp Thr Met Ala
        435                 440                 445
Asp Leu Leu Asn Gln Ala Gly Ala Pro Pro Thr Arg Ser Glu Thr Val
    450                 455                 460
Gln Tyr Asp Ala Phe Ser Ser Pro Glu Ser Ile Ser Leu Asn Val Ala
465                 470                 475                 480
Gly Ala Ile Asp Pro Ser Glu Val Asp Ala Ala Phe Val Val Leu Pro
                485                 490                 495
Pro Asp Gln Glu Gly Phe Ala Asp Leu Ala Ser Pro Thr Glu Thr Tyr
            500                 505                 510
Pro Glu Leu Lys Lys Ala Leu Ala Asn Met Gly Ile Tyr Ser Gln Met
        515                 520                 525
Ala Tyr Phe Asp Arg Phe Arg Asp Ala Lys Ile Phe Tyr Thr Arg Asn
    530                 535                 540
Val Ala Leu Gly Leu Leu Ala Ala Gly Gly Val Ala Phe Thr Thr
545                 550                 555                 560
Glu His Ala Met Pro Gly Asp Ala Asp Met Phe Ile Gly Ile Asp Val
                565                 570                 575
Ser Arg Ser Tyr Pro Glu Asp Gly Ala Ser Gly Gln Ile Asn Ile Ala
            580                 585                 590
Ala Thr Ala Thr Ala Val Tyr Lys Asp Gly Thr Ile Leu Gly His Ser
        595                 600                 605
Ser Thr Arg Pro Gln Leu Gly Glu Lys Leu Gln Ser Thr Asp Val Arg
    610                 615                 620
```

-continued

Asp Ile Met Lys Asn Ala Ile Leu Gly Tyr Gln Gln Val Thr Gly Glu
625                 630                 635                 640

Ser Pro Thr His Ile Val Ile His Arg Asp Gly Phe Met Asn Glu Asp
            645                 650                 655

Leu Asp Pro Ala Thr Glu Phe Leu Asn Glu Gln Gly Val Glu Tyr Asp
        660                 665                 670

Ile Val Glu Ile Arg Lys Gln Pro Gln Thr Arg Leu Leu Ala Val Ser
                675                 680                 685

Asp Val Gln Tyr Asp Thr Pro Val Lys Ser Ile Ala Ala Ile Asn Gln
690                 695                 700

Asn Glu Pro Arg Ala Thr Val Ala Thr Phe Gly Ala Pro Glu Tyr Leu
705                 710                 715                 720

Ala Thr Arg Asp Gly Gly Leu Pro Arg Pro Ile Gln Ile Glu Arg
            725                 730                 735

Val Ala Gly Glu Thr Asp Ile Glu Thr Leu Thr Arg Gln Val Tyr Leu
                740                 745                 750

Leu Ser Gln Ser His Ile Gln Val His Asn Ser Thr Ala Arg Leu Pro
            755                 760                 765

Ile Thr Thr Ala Tyr Ala Asp Gln Ala Ser Thr His Ala Thr Lys Gly
770                 775                 780

Tyr Leu Val Gln Thr Gly Ala Phe Glu Ser Asn Val Gly Phe Leu Arg
785                 790                 795                 800

Asp Pro Tyr Val Ser Lys
            805

<210> SEQ ID NO 50
<211> LENGTH: 806
<212> TYPE: PRT
<213> ORGANISM: artificial sequence
<220> FEATURE:
<223> OTHER INFORMATION: His-tag N-del/E602P

<400> SEQUENCE: 50

Met Gly His His His His His His Ser Ser His His His His His His
1               5                   10                  15

Thr Ala Gln Glu Val Gly Thr Thr Asp Glu Asp Glu Thr Phe Ala Gly
            20                  25                  30

Gly Glu Pro Leu Asp His Leu Asp Asp Ala Leu Asn Glu Thr Pro
        35                  40                  45

Asp Asp Ala Glu Thr Glu Ser Asp Ser Gly His Val Met Thr Ser Phe
50                  55                  60

Ala Ser Arg Asp Gln Leu Pro Glu Trp Thr Leu His Thr Tyr Thr Leu
65                  70                  75                  80

Thr Ala Thr Asp Gly Ala Lys Thr Asp Thr Glu Tyr Ala Arg Arg Thr
                85                  90                  95

Leu Ala Tyr Thr Val Arg Gln Glu Leu Tyr Thr Asp His Asp Ala Ala
            100                 105                 110

Pro Val Ala Thr Asp Gly Leu Met Leu Leu Thr Pro Glu Pro Leu Gly
        115                 120                 125

Glu Thr Pro Leu Asp Leu Asp Cys Gly Val Arg Val Glu Ala Asp Glu
130                 135                 140

Thr Arg Thr Leu Asp Tyr Thr Thr Ala Lys Asp Arg Leu Leu Ala Arg
145                 150                 155                 160

Glu Leu Val Glu Glu Gly Leu Lys Arg Ser Leu Trp Asp Asp Tyr Leu
                165                 170                 175

```
Val Arg Gly Ile Asp Glu Val Leu Ser Lys Glu Pro Val Leu Thr Cys
            180                 185                 190

Asp Glu Phe Asp Leu His Glu Arg Tyr Asp Leu Ser Val Glu Val Gly
        195                 200                 205

His Ser Gly Arg Ala Tyr Leu His Ile Asn Phe Arg His Arg Phe Val
    210                 215                 220

Pro Lys Leu Thr Leu Ala Asp Ile Asp Asp Asn Ile Tyr Pro Gly
225                 230                 235                 240

Leu Arg Val Lys Thr Thr Tyr Arg Pro Arg Gly His Ile Val Trp
                245                 250                 255

Gly Leu Arg Asp Glu Cys Ala Thr Asp Ser Leu Asn Thr Leu Gly Asn
            260                 265                 270

Gln Ser Val Val Ala Tyr His Arg Asn Asn Gln Thr Pro Ile Asn Thr
        275                 280                 285

Asp Leu Leu Asp Ala Ile Glu Ala Ala Asp Arg Arg Val Val Glu Thr
        290                 295                 300

Arg Arg Gln Gly His Gly Asp Asp Ala Val Ser Phe Pro Gln Glu Leu
305                 310                 315                 320

Leu Ala Val Glu Pro Asn Thr His Gln Ile Lys Gln Phe Ala Ser Asp
            325                 330                 335

Gly Phe His Gln Gln Ala Arg Ser Lys Thr Arg Leu Ser Ala Ser Arg
            340                 345                 350

Cys Ser Glu Lys Ala Gln Ala Phe Ala Glu Arg Leu Asp Pro Val Arg
        355                 360                 365

Leu Asn Gly Ser Thr Val Glu Phe Ser Ser Glu Phe Phe Thr Gly Asn
370                 375                 380

Asn Glu Gln Gln Leu Arg Leu Leu Tyr Glu Asn Gly Glu Ser Val Leu
385                 390                 395                 400

Thr Phe Arg Asp Gly Ala Arg Gly Ala His Pro Asp Glu Thr Phe Ser
            405                 410                 415

Lys Gly Ile Val Asn Pro Pro Glu Ser Phe Glu Val Ala Val Val Leu
            420                 425                 430

Pro Glu Gln Gln Ala Asp Thr Cys Lys Ala Gln Trp Asp Thr Met Ala
        435                 440                 445

Asp Leu Leu Asn Gln Ala Gly Ala Pro Pro Thr Arg Ser Glu Thr Val
450                 455                 460

Gln Tyr Asp Ala Phe Ser Ser Pro Glu Ser Ile Ser Leu Asn Val Ala
465                 470                 475                 480

Gly Ala Ile Asp Pro Ser Glu Val Asp Ala Ala Phe Val Leu Pro
            485                 490                 495

Pro Asp Gln Glu Gly Phe Ala Asp Leu Ala Ser Pro Thr Glu Thr Tyr
        500                 505                 510

Asp Pro Leu Lys Lys Ala Leu Ala Asn Met Gly Ile Tyr Ser Gln Met
        515                 520                 525

Ala Tyr Phe Asp Arg Phe Arg Asp Ala Lys Ile Phe Tyr Thr Arg Asn
        530                 535                 540

Val Ala Leu Gly Leu Leu Ala Ala Ala Gly Val Ala Phe Thr Thr
545                 550                 555                 560

Glu His Ala Met Pro Gly Asp Ala Asp Met Phe Ile Gly Ile Asp Val
            565                 570                 575

Ser Arg Ser Tyr Pro Glu Asp Gly Ala Ser Gly Gln Ile Asn Ile Ala
        580                 585                 590

Ala Thr Ala Thr Ala Val Tyr Lys Asp Gly Thr Ile Leu Gly His Ser
```

-continued

```
            595                 600                 605
Ser Thr Arg Pro Gln Leu Gly Glu Lys Leu Gln Ser Thr Asp Val Arg
    610                 615                 620

Asp Ile Met Lys Asn Ala Ile Leu Gly Tyr Gln Gln Val Thr Gly Glu
625                 630                 635                 640

Ser Pro Thr His Ile Val Ile His Arg Asp Gly Phe Met Asn Glu Asp
                645                 650                 655

Leu Asp Pro Ala Thr Glu Phe Leu Asn Glu Gln Gly Val Glu Tyr Asp
                660                 665                 670

Ile Val Glu Ile Arg Lys Gln Pro Gln Thr Arg Leu Leu Ala Val Ser
            675                 680                 685

Asp Val Gln Tyr Asp Thr Pro Val Lys Ser Ile Ala Ala Ile Asn Gln
        690                 695                 700

Asn Glu Pro Arg Ala Thr Val Ala Thr Phe Gly Ala Pro Glu Tyr Leu
705                 710                 715                 720

Ala Thr Arg Asp Gly Gly Gly Leu Pro Arg Pro Ile Gln Ile Glu Arg
                725                 730                 735

Val Ala Gly Glu Thr Asp Ile Glu Thr Leu Thr Arg Gln Val Tyr Leu
                740                 745                 750

Leu Ser Gln Ser His Ile Gln Val His Asn Ser Thr Ala Arg Leu Pro
            755                 760                 765

Ile Thr Thr Ala Tyr Ala Asp Gln Ala Ser Thr His Ala Thr Lys Gly
        770                 775                 780

Tyr Leu Val Gln Thr Gly Ala Phe Glu Ser Asn Val Gly Phe Leu Arg
785                 790                 795                 800

Asp Pro Tyr Val Ser Lys
                805
```

<210> SEQ ID NO 51
<211> LENGTH: 3637
<212> TYPE: DNA
<213> ORGANISM: artificial sequence
<220> FEATURE:
<223> OTHER INFORMATION: pNCS-mNeonGreen plasmid

<400> SEQUENCE: 51

```
gatctcgatc ccgcgaaatt aatacgactc actataggga gaccacaacg gtttccctct    60
agaatcaccg agtttattct tgacacctga tgcgatgaat gatataatag gaaagtactg   120
ttttgtttaa ctttaagaag gagatataca tatgcggggt tctcatcatc atcatcatca   180
tggtatggct agcatgactg gtggacagca aatgggtcgg gatctgtacg acgatgacga   240
taaggatccg ctcgagatgg tgagcaaggg cgaggaggat aacatggcct ctctcccagc   300
gacacatgag ttacacatct ttggctccat caacggtgtg gactttgaca tggtgggtca   360
gggcaccggc aatccaaatg atggttatga ggagttaaac ctgaagtcca ccaagggtga   420
cctccagttc tcccctggat tctggtccc tcatatcggg tatggcttcc atcagtacct   480
gccctaccct gacgggatgt cgcctttcca ggccgccatg gtagatggct ccggatacca   540
agtccatcgc acaatgcagt ttgaagatgg tgcctccctt actgttaact accgctacac   600
ctacgaggga agccacatca aggagaggc ccaggtgaag gggactggtt tccctgctga   660
cggtcctgtg atgaccaact cgctgaccgc tgcggactgg tgcaggtcga agaagactta   720
ccccaacgac aaaaccatca tcagtacctt taagtgagt tacaccactg gaaatggcaa   780
gcgctaccgg agcactgcgc ggaccaccta caccttgcc aagccaatgg cggctaacta   840
```

```
tctgaagaac cagccgatgt acgtgttccg taagacggag ctcaagcact ccaagaccga    900
gctcaacttc aaggagtggc aaaaggcctt taccgatgtg atgggcatgg acgagctgta    960
caagtaagcg gccgcgaatt cgaagcttga tccggctgct aacaaagccc gaaaggaagc   1020
tgagttggct gctgccaccg ctgagcaata actagcataa ccccttgggg cctctaaacg   1080
ggtcttgagg ggttttttgc tgaaaggagg aactatatcc ggatctggcg taatagcgaa   1140
gaggcccgca ccgatcgccc ttcccaacag ttgcgcagcc tgaatggcga atggacgcg    1200 ccctgtagcg gcgcattaag cgcggcgggt gtggtggtta cgcgcagcgt gaccgctaca   1260
cttgccagcg ccctagcgcc cgctcctttc gctttcttcc cttcctttct cgccacgttc   1320
gccggctttc cccgtcaagc tctaaatcgg gggctccctt tagggttccg atttagtgct   1380
ttacggcacc tcgaccccaa aaaacttgat tagggtgatg gttcacgtag tgggccatcg   1440
ccctgataga cggtttttcg ccctttgacg ttggagtcca cgttctttaa tagtggactc   1500
ttgttccaaa ctggaacaac actcaaccct atctcggtct attctttga tttataaggg    1560 attttgccga tttcggccta ttggttaaaa aatgagctga tttaacaaaa atttaacgcg   1620
aattttaaca aaatattaac gcttacaatt taggtggcac ttttcgggga aatgtgcgcg   1680
gaacccctat ttgtttattt ttctaaatac attcaaatat gtatccgctc atgagacaat   1740
aaccctgata aatgcttcaa taatattgaa aaaggaagag tatgagtatt caacatttcc   1800
gtgtcgccct tattccctt ttttgcggcat tttgccttcc tgtttttgct cacccagaaa   1860
cgctggtgaa agtaaaagat gctgaagatc agttgggtgc acgagtgggt tacatcgaac   1920
tggatctcaa cagcggtaag atccttgaga gttttcgccc cgaagaacgt tttccaatga   1980
tgagcacttt taaagttctg ctatgtggcg cggtattatc ccgtattgac gccgggcaag   2040
agcaactcgg tcgccgcata cactattctc agaatgactt ggttgagtac tcaccagtca   2100
cagaaaagca tcttacggat ggcatgacag taagagaatt atgcagtgct gccataacca   2160
tgagtgataa cactgcggcc aacttacttc tgacaacgat cggaggaccg aaggagctaa   2220 ccgcttttt gcacaacatg ggggatcatg taactcgcct tgatcgttgg aaccggagc    2280 tgaatgaagc cataccaaac gacgagcgtg acaccacgat gcctgtagca atggcaacaa   2340
cgttgcgcaa actattaact ggcgaactac ttactctagc ttcccggcaa caattaatag   2400
actggatgga ggcggataaa gttgcaggac cacttctgcg ctcggccctt ccggctggct   2460
ggtttattgc tgataaatct ggagccggtg agcgtgggtc tcgcggtatc attgcagcac   2520
tggggccaga tggtaagccc tcccgtatcg tagttatcta cacgacgggg agtcaggcaa   2580
ctatggatga acgaaataga cagatcgctg agataggtgc ctcactgatt aagcattggt   2640
aactgtcaga ccaagtttac tcatatatac tttagattga tttaaaactt catttttaat   2700
ttaaaaggat ctaggtgaag atcctttttg ataatctcat gaccaaaatc ccttaacgtg   2760
agttttcgtt ccactgagcg tcagaccccg tagaaaagat caaaggatct tcttgagatc   2820 cttttttct gcgcgtaatc tgctgcttgc aaacaaaaaa accaccgcta ccagcggtgg   2880
tttgtttgcc ggatcaagag ctaccaactc tttttccgaa ggtaactggc ttcagcagag   2940
cgcagatacc aaatactgtt cttctagtgt agccgtagtt aggccaccac ttcaagaact   3000
ctgtagcacc gcctacatac ctcgctctgc taatcctgtt accagtggct gctgccagtg   3060
gcgataagtc gtgtcttacc gggttggact caagacgata gttaccggat aaggcgcagc   3120
ggtcgggctg aacggggggt tcgtgcacac agcccagctt ggagcgaacg acctacaccg   3180
aactgagata cctacagcgt gagctatgag aaagcgccac gcttcccgaa gggagaaagg   3240
```

```
cggacaggta tccggtaagc ggcagggtcg gaacaggaga gcgcacgagg gagcttccag   3300
ggggaaacgc ctggtatctt tatagtcctg tcgggtttcg ccacctctga cttgagcgtc   3360 gattttttgtg atgctcgtca ggggggcgga gcctatggaa aaacgccagc aacgcggcct   3420
ttttacggtt cctggccttt tgctggcctt ttgctcacat gttctttcct gcgttatccc   3480
ctgattctgt ggataaccgt attaccgcct ttgagtgagc tgataccgct cgccgcagcc   3540
gaacgaccga gcgcagcgag tcagtgagcg aggaagcgga agagcgccca atacgcaaac   3600
cgcctctccc cgcgcgttgg ccgattcatt aatgcag                            3637
```

<210> SEQ ID NO 52
<211> LENGTH: 7
<212> TYPE: PRT
<213> ORGANISM: Natrobacterium gregoryi

<400> SEQUENCE: 52

Ile Gly Ile Glu Val Ser Arg
1               5

<210> SEQ ID NO 53
<211> LENGTH: 7
<212> TYPE: PRT
<213> ORGANISM: Natronbacterium gregoryi

<400> SEQUENCE: 53

Gln Leu Gly Glu Lys Leu Gln
1               5

<210> SEQ ID NO 54
<211> LENGTH: 7
<212> TYPE: PRT
<213> ORGANISM: Natronbacterium gregoryi

<400> SEQUENCE: 54

Ile His Arg Asp Gly Phe Met
1               5

<210> SEQ ID NO 55
<211> LENGTH: 7
<212> TYPE: PRT
<213> ORGANISM: Natronbacterium gregoryi

<400> SEQUENCE: 55

Ala Tyr Ala Asp Gln Ala Ser
1               5

<210> SEQ ID NO 56
<211> LENGTH: 7
<212> TYPE: PRT
<213> ORGANISM: Methanococcus jannaschii

<400> SEQUENCE: 56

Met Gly Leu Leu Thr Gly Leu
1               5

<210> SEQ ID NO 57
<211> LENGTH: 5
<212> TYPE: PRT
<213> ORGANISM: Methanocaldococcus jannaschii

<400> SEQUENCE: 57

Gly Glu Arg Leu His

```
1               5

<210> SEQ ID NO 58
<211> LENGTH: 7
<212> TYPE: PRT
<213> ORGANISM: Methanocaldococcus jannaschii

<400> SEQUENCE: 58

Phe Leu Arg Asp Gly Phe Ile
1               5

<210> SEQ ID NO 59
<211> LENGTH: 7
<212> TYPE: PRT
<213> ORGANISM: Methanocaldococcus jannaschii

<400> SEQUENCE: 59

His Tyr Ala Asp Lys Phe Val
1               5

<210> SEQ ID NO 60
<211> LENGTH: 7
<212> TYPE: PRT
<213> ORGANISM: Pyrococcus furiosus

<400> SEQUENCE: 60

Ile Gly Ile Leu Val Ala Pro
1               5

<210> SEQ ID NO 61
<211> LENGTH: 7
<212> TYPE: PRT
<213> ORGANISM: Pyrococcus furiosus

<400> SEQUENCE: 61

Gln Arg Gly Glu Ser Val Asp
1               5

<210> SEQ ID NO 62
<211> LENGTH: 7
<212> TYPE: PRT
<213> ORGANISM: Pyrococcus furiosus

<400> SEQUENCE: 62

Leu Leu Arg Asp Gly Arg Ile
1               5

<210> SEQ ID NO 63
<211> LENGTH: 7
<212> TYPE: PRT
<213> ORGANISM: Pyrococcus furiosus

<400> SEQUENCE: 63

His Tyr Ala His Lys Phe Ala
1               5

<210> SEQ ID NO 64
<211> LENGTH: 7
<212> TYPE: PRT
<213> ORGANISM: Marinitoga piezophila

<400> SEQUENCE: 64

Ile Gly Ile Leu Leu Ser His
1               5
```

```
<210> SEQ ID NO 65
<211> LENGTH: 7
<212> TYPE: PRT
<213> ORGANISM: Marinitoga piezophila

<400> SEQUENCE: 65

Lys Met Asn Leu Asp Ile Leu
1               5

<210> SEQ ID NO 66
<211> LENGTH: 7
<212> TYPE: PRT
<213> ORGANISM: Marinitoga piezophila

<400> SEQUENCE: 66

Ile Leu Arg Asp Gly Arg Phe
1               5

<210> SEQ ID NO 67
<211> LENGTH: 7
<212> TYPE: PRT
<213> ORGANISM: Marinitoga piezophila

<400> SEQUENCE: 67

His Ile Ala Asn Lys Val Ala
1               5

<210> SEQ ID NO 68
<211> LENGTH: 7
<212> TYPE: PRT
<213> ORGANISM: Thermus thermophilus

<400> SEQUENCE: 68

Val Gly Phe Leu Ala Gly Gly
1               5

<210> SEQ ID NO 69
<211> LENGTH: 7
<212> TYPE: PRT
<213> ORGANISM: Thermus thermophilus

<400> SEQUENCE: 69

Gln Ala Gly Glu Arg Ile Pro
1               5

<210> SEQ ID NO 70
<211> LENGTH: 7
<212> TYPE: PRT
<213> ORGANISM: Thermus thermophilus

<400> SEQUENCE: 70

Leu Leu Arg Asp Gly Arg Val
1               5

<210> SEQ ID NO 71
<211> LENGTH: 7
<212> TYPE: PRT
<213> ORGANISM: Thermus thermophilus

<400> SEQUENCE: 71

His Leu Ala Asp Arg Leu Val
1               5

<210> SEQ ID NO 72
```

```
<211> LENGTH: 24
<212> TYPE: DNA
<213> ORGANISM: Artificial Sequence
<220> FEATURE:
<223> OTHER INFORMATION: target region of the target plasmid
      pIncW-mNeonGreen, mNeonGreen

<400> SEQUENCE: 72
ggagcatcca catcgccatc aatt                                          24
```